US007524503B2

(12) United States Patent
Khanna et al.

(10) Patent No.: US 7,524,503 B2
(45) Date of Patent: Apr. 28, 2009

(54) HUMAN CYTOMEGALOVIRUS (HCMV) CYTOTOXIC T CELL EPITOPES, POLYEPITOPES COMPOSITIONS COMPRISING SAME AND DIAGNOSTIC AND PROPHYLACTIC AND THERAPEUTIC USES THEREFOR

(75) Inventors: Rajiv Khanna, Herston (AU); Rebecca Ann Elkington, Manly (AU); Susan Jennifer Walker, Taringa (AU)

(73) Assignee: The Council of the Queensland Institute of Medical Research, Herston, Queensland (AU)

( * ) Notice: Subject to any disclaimer, the term of this patent is extended or adjusted under 35 U.S.C. 154(b) by 323 days.

(21) Appl. No.: 10/482,284

(22) PCT Filed: Jun. 26, 2002

(86) PCT No.: PCT/AU02/00829

§ 371 (c)(1),
(2), (4) Date: Apr. 13, 2004

(87) PCT Pub. No.: WO03/000720

PCT Pub. Date: Jan. 3, 2003

(65) Prior Publication Data

US 2005/0019344 A1    Jan. 27, 2005

(30) Foreign Application Priority Data

Jun. 26, 2001    (AU) .................................. PR 5931

(51) Int. Cl.
*A61K 39/245* (2006.01)
*C07K 7/06* (2006.01)
*C12Q 1/70* (2006.01)

(52) U.S. Cl. ................. 424/186.1; 424/230.1; 530/328; 435/5

(58) Field of Classification Search .............. 424/186.1; 530/350

See application file for complete search history.

(56) References Cited

U.S. PATENT DOCUMENTS

| 6,074,645 A | 6/2000 | Diamond et al. | |
|---|---|---|---|
| 6,074,817 A * | 6/2000 | Landini et al. | ................. 435/5 |
| 6,242,567 B1 | 6/2001 | Pande et al. | |

FOREIGN PATENT DOCUMENTS

| DE | 199 19 121 A1 | 11/2000 |
|---|---|---|
| WO | WO 94/23744 | 10/1994 |
| WO | WO 96/01321 | 1/1996 |
| WO | WO 98/02746 | 1/1998 |
| WO | WO 98/02746 A | 1/1998 |
| WO | WO 98/21233 | 5/1998 |
| WO | WO 01/72782 A2 | 10/2001 |

OTHER PUBLICATIONS

Pepperl et al., "Dense Bodies of Human Cytomegalovirus Induce both Humoral and Cellular Immune Responses in the Absence of Viral Gene Expression," Journal of Virology, vol. 74, No. 13, Jul. 2000, pp. 6132-6146.*
Boppana et al., "Recognition of Human Cytomegalovirus Gene Products by HCMV-Specific Cytotoxic T Cells," Virology 222, pp. 293-296 (1996).*
Schleiss, "Progress in Cytomegalovirus Vaccine Development," Herpes, 12:3 (2005).*
Schleiss et al., "Progess toward an elusive goal: current status of cytomegalovirus vaccines," Expert Rev. Vaccines 4(3), 381-406 (2005).*
Paston et al., "Progress Made Towards the Development of a CMV Peptide Vaccine," Human Immunology, 65, 544-549 (2004).*
"Vaccination and Enrollment are Discontinued in Phase II Trials of Merck's Investigational HIV Vaccine Candidate." Downloaded from the Internet on Sep. 25, 2007, <<http://www.merck.com/newsroom/press_releases/research_and_develpoment_2007_0921_print.html>>.*
Khanna et al., "Human cytomegalovirus vaccine: time to look for alternative options," Trends in Molecular Medicine, vol. 12, No. 1 (2006).
Chee et al. "Analysis of the Protein-Coding Content of the Sequence of Human Cytomegalovirus Strain AD169," Curr Top. Microbiol. Immunol, 154:125-169 (1990).
Results of SEQ ID No. 165 search, .rag. Oct. 19, 2006.
Results of SEQ ID No. 165 search, .rup. Oct. 19, 2006.
Ripalti, A et al.; *Journal of Clinical Microbioloty* , "Construction of Polyepitopes Fusion Antigens of Human Cytomegalovirus of ppUL32: Reactivity with Human Antibodies"; vol. 32, No. 2, Feb. 1994; pp. 358-363. See Abstract "Material and Methods".
Ripalti, A. et al; *Microbiologica* ; "Construction of a Polyepitope Fusion Antigen of Human Cytomegalovirus ppUL32 and Detection of Specific Antibodies by ELISA", vol. 18, 1995; pp. 1-12. See summary and "Materials and Methods".
Gyulai, Z. et al; *The Journal of Infectious Diseases*; "Cytotoxic T Lympocyte (CTL) Responses to Human Cytomegalovirus pp65, IEI-Exon4, gB, pp150, and pp28 in Healthy Individuals: Reevaluation of Prevelance of IEI-Specific CTLs"; vol. 181, 2000; pp. 1537-1546. See Abstract.
Greijer, A. et al; *Journal of Clinical Microbiology* ;"Molecular Fine-Specificity Analysis of Antibody Responses to Human Cytomegalovirus and Design of Novel Synthetic-Peptide-Based Serodiagnostic Assays", vol. 37, No. 1, Jan. 1999; pp. 179-188. See abstract and Table 1.

(Continued)

*Primary Examiner*—Mary E Mosher
(74) *Attorney, Agent, or Firm*—Nixon & Vanderhye

(57) ABSTRACT

The present invention provides CTL epitope peptides and polyepitope peptides from 14 distinct antigens of human cytomegalovirus (HCMV) that are restricted through HLA the most commonly prevalent class I alleles in different ethnic populations of the world. These epitopes provide an important platform for CTL epitope-based vaccines against HCMV. The present invention further provides vaccine compositions comprising the subject epitope and polyepitope peptides and methods for vaccination of humans and for the adoptive transfer of HCMV-specific T cells to human subjects. The present invention further provides reagents and methods for determining the HCMV status or level of HCMV-specific immunity of a subject.

10 Claims, 36 Drawing Sheets

OTHER PUBLICATIONS

GenBank CAA03097 Nov. 17, 2004 (1 pg).
Elkington, R., et al; *Journal of Virology*, vol. 77, No. 9; pp. 5226-5240 (2003).
Larosa, C., et al; *Blood*, vol. 97, No. 6; pp. 1776-1876 (2001).
Gonczol, E., et al; *Expert Opinion on Biological Therapy*, vol. 1, No. 3; pp. 401-412 (2001).
Plotkin, S.A., et al; *Pediatric Infectious Disease Journal*, vol. 18, No. 4, pp. 313-326 (1999).
Gavin, M.A., et al; *Journal of Immunology*, vol. 151, No. 8, pp. 3971-3980 (1993).
Wills, M.R., et al; *Journal of Virology*, vol. 70, No. 11; pp. 7569-7579 (1996).
Solache, A., et al; *Journal of Immunology*, vol. 163, pp. 5512-5518 (1999).
Diamond, D.J., et al; *Blood*, vol. 90, No. 5; pp. 1751-1767 (1997).
Kuzushima, K., et al; *Blood*, vol. 98, No. 6; pp. 1872-1881 (2001).
Retiere, C., et al; *Journal of Virology*, vol. 74, No. 9; pp. 3948-3952 (2000).
Saulquin, X., et al; *European Journal of Immunology*, vol. 30; pp. 2531-2539 (2000).
Gratama, J.W., et al; *Clinical and Applied Immunology Reviews*, vol. 2; pp. 17-32 (2001).
Longmate, J., et al; *Immunogenetics*, vol. 52, (3-4); pp. 165-173 (2001).
Engstrand, M., et al; *Transplantation*, vol. 69, No. 11; pp. 2243-2250 (2000).
Li, C., et al; *Chinese Medical Journal*, vol. 110, No. 5; pp. 397-400 (1997).
Khan, N., et al; *The Journal of Infectious Diseases*; vol. 185; pp. 1025-1034 (2002).
Zaia, J.A., et al; *Hematology*; pp. 339-355 (2000).
Stratton, et al; "*Appendix 4: Cytomegalovirus*" in Vaccines for the 21st Century, Institute of Medicine; pp. 165-171.
Sissons, J.G.P., et al; *Journal of Infection*; vol. 44; pp. 78-83 (2002).
Li, C.R., et al; *Blood*, vol. 83, No. 7; pp. 1971-1979 (1994).
Walkter, E.A., et al; *New England Journal of Medicine*; vol. 333, No. 16; pp. 1038-1044 (1995).
Petrovsky, N., et al; *Journal of Immunological Methods*; vol. 186; pp. 37-46 (1995).
Kern, F., et al; *Nature Medicine*, vol. 4, No. 8; pp. 975-978 (1998).
Weeks, M.P., et al; *Journal of Virology*, vol. 73, No. 3; pp. 2099-2108 (1999).
Bankier, A.T., et al; *DNA Sequence—I.DNA Sequencing and Mapping*, vol. 2, No. 1; pp. 1-12 1991).
Klenerman, P., et al; *Nature Reviews Immonology*; vol. 2; pp. 263-272 (2002).
Comoli, P., et al; *Herpes*, vol. 7, No. 1; pp. 9-12 (2000).
Sester, M., et al; *Transplantation*, vol. 71, No. 9; pp. 1287-1294 (2001).
Reddehase, M.J.; *Current Opinions in Immunology*, vol. 12, No. 4; pp. 390-396 (2000).
Kern, F., et al; *Journal of Virology*, vol. 73, No. 10; pp. 8179-8184 (1999).
Riddell, S.R., et al; *Science*, vol. 257; pp. 238-240 (1992).
June, C.H.; *Blood*, vol. 99, No. 11; p. 3883 (2002).
Einsele, H., et al; *Blood*, vol. 99, No. 11; pp. 3916-3922 (2002).
Gratama, J.W., et al; *Blood*, vol. 98, No. 5; pp. 1358-1364 (2001).
Jin, X., et al; *Journal of Infectious Diseases*, vol. 181, pp. 165-175 (2000).
Singhal, S., et al; *Transplantation*, vol. 69, No. 11; pp. 2251-2259 (2000).
Hassan-Walker, A.F., et al; *The Journal of Immunology*, vol. 183, pp. 835-843 (2001).
Gallot, G., et al; *Journal of Immunology*, vol. 167; pp. 4196-4206 (2001).
Plotkin, S.A., et al; *S.A. American Heart Journal*, vol. 138 (5, part 2), S484-S487 (1999).

* cited by examiner

HUMAN CYTOMEGALOVIRUS (HCMV) CYTOTOXIC T CELL EPITOPES, POLYEPITOPES COMPOSITIONS COMPRISING SAME AND DIAGNOSTIC AND PROPHYLACTIC AND THERAPEUTIC USES THEREFOR

This application is the U.S. National Phase of International Application PCT/AU02/00829, filed 26 Jun. 2002, which designated the U.S.

FIELD OF THE INVENTION

The present invention relates to isolated peptide epitopes and compositions comprising same for use in raising CTL responses against cytomegalovirus (CMV). In particular, the present invention relates to isolated peptides comprising one or more CTL epitopes from human cytomegalovirus (HCMV) and to vaccine compositions comprising same for use in the prophylactic or therapeutic treatment of humans against CMV infection. The present invention also provides methods for producing isolated T cells capable of recognizing HCMV peptide epitopes and methods for producing such T cells. The isolated peptide epitopes and T cells are particularly useful in monitoring immune repsonses in various clinical settings (eg. transplantation) and in the diagnosis of HCMV infection.

BACKGROUND TO THE INVENTION

1. General Information

This specification contains amino acid sequence information prepared using Patent in Version 3.1, presented herein after the Abstract. Each sequence is identified in the sequence listing by the numeric indicator <210> followed by the sequence identifier (e.g. <210>1, <210>2, etc). The length of each sequence and source organism are indicated by information provided in the numeric indicator fields <211> and <213>, respectively. Sequences referred to in the specification are defined by the term "SEQ ID NO:", followed by the sequence identifier (eg. SEQ ID NO: 1 refers to the sequence designated as <400>1).

As used herein the term "derived from" shall be taken to indicate that a specified integer may be obtained from a particular source albeit not necessarily directly from that source.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally-equivalent products, compositions and methods are clearly within the scope of the invention, as described herein.

All the references cited in this application are specifically incorporated by reference herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactiva, Germany);
10. Sakakibara, D., Teichman, J., Lien, E. Land Fenichel, R. L. (1976). Biochem. Biophys. Res. Commun. 73 336-342
11. Merrifield, R. B. (1963). J. Am. Chem. Soc. 85, 2149-2154.
12. Barany, G. and Merrifield, R. B. (1979) in The Peptides (Gross, E. and Meienhofer, J. eds.), vol. 2, pp. 1-284, Academic Press, New York.
13. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart.
14. Bodanszky, M. (1984) Principles of Peptide Synthesis, Springer-Verlag, Heidelberg.
15. Bodanszky, M. & Bodanszky, A. (1984) The Practice of Peptide Synthesis, Springer-Verilag, Heidelberg.
16. Bodanszky, M. (1985) Int. J. Peptide Protein Res. 25, 449-474.
17. Handbook of Experimental Immunology, Vols. I-IV (D. M. Weir and C. C. Blackwell, eds., 1986, Blackwell Scientific Publications).

2. Description of the Related Art

HCMV belongs to the θ-subfamily of the herpesvirus group, which are large strictly host-species specific DNA viruses encoding about 170-200 antigenically distinct polypeptides. HCMV is found universally throughout all geographic locations and socioeconomic groups, and infects between 50 and 85% of adults (Alford and Britt, In: Virology, $2^{nd}$ Edition, Fields et. al. eds, Raven Press, 1990).

For most healthy persons who acquire primary HCMV infection after birth, there are few symptoms and no long-term health consequences. Occasionally, some adults with primary HCMV infection display symptoms of a mononucleosis-like syndrome with prolonged fever, and a mild hepatitis. Once infected with HCMV, the virus remains dormant by establishing a reservoir of latently-infected cells from which chronic low-grade re-activation into virus productive (lytic) cycle occurs throughout life. Although the factors controlling latency and re-activation are not completely understood, impairment of the body's cell-mediated immune system either by drug-induced immunosuppression or infection by certain pathogens can consistently reactivate the virus (Zaia and Forman, *Infect Dis Clin North Am* 9, 879-900, 1995).

There are clinical situations where HCMV infection is a significant cause of morbidity and mortality. For example, HCMV infection carries significant health risks to a foetus in utero, to people who work with children, and to individuals having a compromised immune system, such as, for example, those infected with HIV-1 or having undergone organ transplantation (Britt, *Trends Microbiol* 4, 34-81, 1996; Plotkin, *Pediatr Infect Dis J* 18, 313-325, 1999).

With particular respect to the health risks to a foetus in utero, those risks appear to be almost exclusively associated with non-immune women who become infected during pregnancy (Fowler et. al, *New Engl J Med* 326, 663-667, 1992; Murph et. al., In: Epidemiology of congenital cytomegalovirus infection: maternal risk factors and molecular analysis cytomegalovirus strains. 1998). Epidemiological studies have shown that 80%-90% of developing unborn babies who acquire congenital HCMV infection display a variable pattern of pathological sequelae within the first few years of life that may include hearing loss, vision impairment and mental retardation. Another 5% to 10% of infants who are infected but without symptoms at birth will subsequently have a varying degrees of hearing and mental or coordination problems. In 1996 alone, more than 17,000 cases of HCMV-induced sequelae or death were estimated in Europe and the USA (Plotkin, *Pediatr Infect Dis J* 18, 313-325, 1999).

Additionally, recent studies suggest that HCMV seropositive individuals who have undergone coronary angioplasty develop restenosis more frequently than seronegative patients (Field, *Antivir Chem Chemother* 10, 219-232, 1999), although a causal relationship has yet to be shown.

There is also a likelihood that there is a significant therapeutic benefit to be derived for individuals belonging to these high-risk groups, by reducing their HCMV load.

Accordingly, there is a need for an effective vaccine to provide such a reduction in HCMV load.

There have been a number of attempts at designing a vaccine against HCMV (for review see Britt, *Trends Microbiol* 4, 34-81, 1996; Plotkin, *Pediatr Infect Dis J* 18, 313-325, 1999), using either attenuated HCMV strains or subunit vaccines.

The first vaccines against HCMV were based on immunization using attenuated strains of HCMV, such as, for example, the Towne strain and AD-169 strain (Elek and Stern, *Lancet* 1, 1-5, 1974; Neff et. al., *Proc Soc Exp Biol Med* 160, 32-37, 1979). Although both attenuated viruses were shown to elicit cellular and humoral responses, neither vaccine prevented foetal infection in pregnant women experiencing a primary HCMV infection. Furthermore, vaccinated normal volunteers showed limited protection from viral challenge using the HCMV Toledo strain (Quinnan et. al., *Ann Intern Med* 101, 478-483, 1984; Adler et. al., *Pediatr Infect Dis J.* 17, 200-206, 1998). Subunit vaccines have been based on single HCMV antigen formulations, such as, for example, the full-length glycoprotein B (gB) polypeptide in combination with MF59 adjuvant (Chiron), or alternatively, a recombinant full-length gB polypeptide expressed using a viral vector (Pass et. al., *J Infect Dis* 180, 970-975, 1999; Adler et. al. *J Infect Dis* 180, 843-846, 1999). Additionally, a canarypox virus expressing a full length recombinant HCMV pp65 polypeptide has recently been tested in a clinical trial and shown to elicit a strong CTL and antibody response to this antigen (Gyulai et. al., Proceedings of the Seventh International Cytomegalovirus Workshop, Brighton, UK, Mar. 7-9, 1999, abstract).

However, vaccine formulations based on one or more full-length HCMV antigens are likely to present a number of limitations. For example, the expression of HCMV proteins such as pp65 can inhibit proteasomal processing of IE-1 through an associated kinase activity (Gilbert et al., *Nature* 383, 720, 1996). Moreover, other genes associated with the early phase of HCMV infection are also known to interfere at various steps of the MHC class I processing pathway and presentation (Reddehase, *Curr. Opin. Immunol.* 12, 390-396, 2000).

CTL epitope-based vaccines provide an alternative technology for overcoming the potential limitations associated with use of full-length HCMV antigens. However, the large degree of HLA polymorphism in human populations presents a major obstacle for the practical application of defined CTL epitopes as vaccines. A vaccine based on a single HCMV pp65-specific CTL epitope (NLVPMVATV; SEQ ID NO: 5) linked to the pan-HLA-DR T-helper epitope and one or two palmitic acid molecules is under investigation (Zaia et al., *Hematol. (Am. Soc. Hematol. Educat. Program.)* 339-355, 2000; La Rosa et al., *Blood* 97, 1776-1786, 2001).

For any subunit vaccine against HCMV, protection against HCMV is assumed to be achievable by inducing cellular immunity against a single virion antigen. There is evidence that in healthy carriers of the HCMV virus, subdominant T cell responses are also directed against other virion antigens, such as, for example, pp150, IE-1, and gH, which may also play a crucial role in controlling HCMV reactivation (for review see Britt, *Trends Microbiol* 4, 34-38, 1996; Ito, *Nippon Rinsho* 56, 62-68, 1998).

Clearly, the development of an effective vaccine against HCMV requires the elucidation of viral antigens that activate a protective cytotoxic T-lymphocyte (CTL) response and the determination of immunodominant CTL epitopes within those antigens.

CTL epitopes have been described for two immunodominant HCMV polypeptides, in particular, pp65 and IE-1 (Borysiewicz et al., *J. Exp. Med.* 168, 919, 1988; Sissons, *J. Royal Coll. Phys., Lond.* 20, 40, 1986; Wills et al., *J. Virol.* 70, 7569, 1996; Kern et al., *Intervirology* 42, 322, 1999; Weekes et al., *J. Virol.* 73, 2099, 1999; Reddehase, *Curr. Opin. Immunol.* 12, 390.-396, 2000).

Exemplary known CTL epitopes derived from HCMV pp65 are described herein With reference to SEQ ID NOs: 1-17 and 55. Epitopes listed as SEQ ID NOs: 1-17 are described as having the following HLA restrictions:

1. SVLGPISGHVLK (SEQ ID NO: 1) is restricted to HLA A*11xx (Diamond, U.S. Pat. No. 6,074,645, Jun. 13, 2000);
2. FTSQYRIQGKL (SEQ ID NO: 2) is restricted to HLA A*2402 (Longmate et al., *Immunogenet.* 52, 165-173, 2000);
3. FVFPTKDVALR (SEQ ID NO: 3) is restricted to HLA A*68xx (Longmate et al., *Immunogenet.* 52, 165-173, 2000);
4. FPTKDVAL (SEQ ID NO: 4) is restricted to HLA B35xx (Diamond U.S. Pat. No. 6,074,645, Jun. 13, 2000);
5. NLVPMVATV (SEQ ID NO: 5) is restricted to HLA A*02xx (Wills et al., *J. Virol.* 70, 7569-7579, 1996);

6. MLNIPSINV (SEQ ID NO: 6) is restricted to HLA A*0201 (Solache et al., *J. Immunol.* 163, 5512-5518, 1999);
7. RIFAELEGV (SEQ ID NO: 7) is restricted to HLA A*0201 (Diamond et al., *Blood* 90, 1751-1767, 1997);
8. TPRVTGGGGAM (SEQ ID NO: 8) is restricted to HLA B*07xx (Wills et al., *J. Virol.* 70, 7569-7579, 1996; Kern et al., *Nature Med.* 4, 975-978, 1998; Diamond U.S. Pat. No. 6,074,645, Jun. 13, 2000);
9. RPHERNGFTVL (SEQ ID NO: 9) is restricted to HLA B*07xx (Weekes et al., *J. Virol.* 73, 2099-2108, 1999; Diamond U.S. Pat. No. 6,074,645, Jun. 13, 2000);
10. RLLQTGIHV (SEQ ID NO: 10) is restricted to HLA A*0201 (Solache et al., *J. Immunol.* 163, 5512-5518, 1999);
11. VIGDQYVKV (SEQ ID NO: 11) is restricted to HLA A*0201 (Solache et al., *J. Immunol.* 163, 5512-5518, 1999);
12. ALFFFDIDL (SEQ ID NO: 12) is restricted to HLA A*0201 (Solache et al., *J. Immunol.* 163, 5512-5518, 1999);
13. YSEHPTFTSQY (SEQ ID NO: 13) is restricted to HLA A*01xx (Diamond, U.S. Pat. No. 6,074,645, Jun. 13, 2000);
14. VLCPKNMII (SEQ ID NO: 14) is restricted to HLA A*0201 (Solache et al., *J. Immunol.* 163, 5512-5518, 1999);
15. DIYRIFAEL (SEQ ID NO: 15) is restricted to HLA A*0201 (Solache et al., *J. Immunol.* 163, 5512-5518, 1999);
16. ILARNLVPMV (SEQ ID NO: 16) is restricted to HLA A*0201 (Diamond et al., *Blood* 90, 1751-1767, 1997; Solache et al., *J. Immunol* 163, 5512-5518, 1999); and
17. EFFWDANDIY (SEQ ID NO: 17) is restricted to HLA B*44xx (Longmate et al., *Immunogenet.* 52, 165-173, 2000).

The epitope listed in SEQ ID NO: 55 (IPSINVHHY) was described by Gavin et al., *J. Immunol.* 151, 3971-3980, 1993.

Exemplary known CTL epitopes derived from HCMV IE-1 are described herein with reference to SEQ ID NOs: 18-20. Respectively, those epitopes are described as having the following HLA restrictions:
1. YILEETSVM (SEQ ID NO: 18) is restricted to HLA A*02xx (Retière et al., *J. Virol.* 74, 3948-3952, 2000);
2. CVETMCNEY (SEQ ID NO: 19) is restricted to HLA B*18xx (Retière et al., *J. Virol.* 74, 3948-3952, 2000); and
3. RRIEEICMK (SEQ ID NO: 20) is restricted to HLA B*27xx (Salquin et al., *Eur. J. Immunol.* 30, 2531-2539, 2000).

Although there is some evidence to suggest that HCMV antigens other than pp65 or IE-1 may also be useful for eliciting CTL control of HCMV infection, such as, for example, HCMV pp150 and HCMV gB, information on the utility of those antigens is limited (Gyulai et al., *J. Infect. Dis.* 181, 537-546, 2000). An exemplary known CTL epitope from HCMV pp150 is described herein with reference to SEQ ID NO: 21 having the following HLA restriction:
1. TTVYPPSSTAK (SEQ ID NO: 21) is restricted to HLA A*0301 (Longmate et al., *Immunogenet.* 52, 165-173, 2001).

SUMMARY OF THE INVENTION

In work leading up to the present invention, the inventors sought to comprehensively map CTL responses to a wide variety of HCMV antigens that are expressed at different stages of infection and play an important role in overall pathogenesis of HCMV-associated diseases, in particular pp28, pp50, pp65, pp150, pp71, gH, gB, IE-1, IE-2, US2, US3, US6, US11, and UL18.

A highly efficient and rapid strategy, based on the use of predictive algorithms, ELISPOT and cytotoxicity assays, was employed to comprehensively profile HLA class I-restricted CTL responses against HCMV in a cohort of twenty four healthy virus carriers. Preliminary analysis of these HCMV antigen sequences, using computer based algorithms and peptide stabilization assays, strongly suggested that these antigens contained CTL epitopes. Synthetic peptides were subsequently tested for their ability to induce CTL activity in peripheral blood T cells from seropositive donors, as measured by IFN-γ production in ELISPOT.

The present inventors also isolated both polyclonal and cloned CTLs from seropositive donors that showed strong responses in cytotoxicity assays, thereby confirming strong cytolytic activity toward target cells that were sensitized with synthetic peptides, or alternatively, infected with recombinant vaccinia encoding individual HCMV antigens.

Using the above approaches, the present inventors identified a large number of novel HCMV CTL epitopes having utility in the formulation of vaccines against HCMV or otherwise modulating HCMV immune control, or as diagnostic reagents for assaying HCMV or the recovery of HCMV-specific T-cell-mediated immunity following transplantation or during pregnancy. The identification of certain previously-described CTL epitopes was also confirmed by the inventors. The present inventors showed that CD8+ CTL responses to HCMV often contained multiple antigen-specific activities that were not merely constrained to pp65, IE-1, or pp150. In fact, more than 40% of the CTL epitopes are located in antigens other than pp65 and IE-1, which were previously considered to be the primary antigens for CTL control. A number of HCMV antigens were identified by the present inventors for the first time as targets for HCMV-specific cellular immunity. Interestingly, these activities also included subdominant T cell responses to HCMV-encoded immunomodulators, such as, for example, US2, US3, and UL18. Clonal analysis revealed novel individual responses to antigens such as, for example, pp28, pp50, pp65, pp150, gB, gH, US2, IE-1 and IE-2. The overall repertoire of HCMV-specific CTL responses from a spectrum of healthy virus carriers is distributed throughout most of the antigens tested.

Several HLA-restricting determinants recognized by the novel CTL epitopes have been defined, in addition to new HLA-restricting determinants for certain previously-described HCMV CTL epitopes.

The present inventors also designed novel polyepitopes comprising multiple HCMV epitopes for use in vaccine preparations.

The present inventors also designed vaccine preparations based upon the novel epitopes and polyepitopes of the invention. Preferably, an effective CTL epitope-based HCMV vaccine that provides widespread protection against HCMV in a human population comprises not only epitopes derived from pp65 and IE-1 proteins, but also other regions of the genome expressed during early, late and latent infection.

Accordingly, one aspect of the present invention relates to an immunologically active peptide comprising one or more CTL epitopes of a HCMV antigen or a derivative thereof or a functionally equivalent variant thereof, wherein said peptide is preferably capable of eliciting a cellular immune response to HCMV in a human subject. Preferably, the peptide directs CTLs of a human subject to recognize and lyse human cells infected with HCMV, thereby providing or enhancing cellular immunity against HCMV. Preferably, the immunologically active peptide, in association with an MHC Class I molecule, is recognized by the CTLs of a healthy HCMV seropositive subject, or a subject having a latent or inactive HCMV infection.

Preferably, the immunologically active peptide of the invention displays HLA supertype specificity. Such an epitope is clearly preferred for use in vaccine formulations, because it reduces the total number of epitopes required to cover a significant proportion of the population irrespective of ethnicity, thereby minimizing formulation difficulties.

Preferably, the immunologically active peptide of the invention additionally comprises one or more CD4+ determinants sufficient to facilitate a T-helper function in the context of an MHC class II molecule on the surface of an antigen presenting cell (APC) of a human subject infected with HCMV. For example, the present inventors provide herein several 20-mer peptides comprising contiguous or overlapping CTL epitopes and T-helper epitope functions as evidenced by their having the ability to bind to both $CD4^+$ and $CD8^+$ cells. Such a peptide has an advantage over a minimal CTL epitope of not necessarily requiring the inclusion of an exogenous T-helper epitope in a vaccine formulation.

In a second aspect, the present invention relates to an immunologically active peptide comprising a polyepitope (ie. two or more distinct epitopes) of a HCMV antigen or a derivative thereof or a functionally equivalent variant thereof, wherein said peptide is preferably capable of eliciting a cellular immune response to HCMV in a human subject.

Preferably, the polyepitope is not restricted to a single MHC Class I haplotype. Even more preferably, the polyepitope is specific for a sufficient number of MHC Class I molecules to provide coverage for at least about 35% of the general population, preferably at least about 55% of the general population, more preferably at least about 75% of the general population, and still more preferably at least about 95% of the general population, irrespective of racial origin or ethnicity. Those skilled in the art will readily be in a position to determine the number of individual HCMV CTL epitopes required to provide coverage of any given population from the HLA specificity data provided herein. As with single epitopes, the polyepitope of the invention preferably displays HLA supertype specificity and/or preferably comprise one or more CD4+ determinants sufficient to facilitate a T-helper function in a human subject infected with HCMV.

Another aspect of the invention relates to a prophylactic or therapeutic vaccine composition for eliciting a cellular immune response in a human subject against HCMV, said composition comprising an immunologically active peptide of the invention (ie. an epitope or polyepitope) in combination with a pharmaceutically acceptable carrier, excipient, diluent and/or an adjuvant. The vaccine composition may comprise more than one epitope or polyepitope. The vaccine composition of the invention may be a subunit vaccine comprising the immunologically active peptide(s) or a derivative thereof or a functionally equivalent variant thereof or alternatively, a nucleic acid-based vaccine that comprises nucleic acid, such as, for example, DNA or RNA, encoding the immunologically active peptide(s) or derivative or variant and cloned into a suitable vector (eg. vaccinia, canarypox, adenovirus, or other eukaryotic virus vector). Alternatively, the peptide or derivative or variant is formulated as a cellular vaccine via the administration of an autologous or allogeneic antigen presenting cell (APC) or a dendritic cell that has been treated in vitro so as to present the peptide on its surface.

In a related embodiment the present invention provides for the use of an immunologically active peptide of the invention or a variant or derivative thereof in the preparation of a vaccine composition for use in the prophylactic or therapeutic treatment of HCMV infection in a human subject, including the therapeutic treatment of a latent HCMV infection in a human subject.

In a related embodiment the present invention provides for the use of an immunologically active peptide of the invention or a variant or derivative thereof in the preparation of a vaccine composition for use in enhancing the immune function of a human subject before or during or after transplantation, wherein said subject carries a latent HCMV infection or is at risk of being infected with HCMV.

Another aspect of the present invention relates to a method of enhancing the immune system of a human subject comprising administering an immunologically active peptide comprising a CTL epitope of a HCMV antigen or a derivative or variant thereof or a vaccine composition comprising said peptide or derivative or variant for a time and under conditions sufficient to activate a CTL and/or a CTL precursor of said subject.

In a related embodiment, the invention relates to a method of enhancing the HCMV-specific cell mediated immunity of a human subject, said method comprising contacting ex vivo a T cell obtained from a human subject with an immunologically active peptide comprising a CTL epitope of a HCMV antigen or a derivative or variant thereof or a vaccine composition comprising said peptide or derivative or variant for a time and under conditions sufficient to confer HCMV activity on said T cells.

Another aspect of the invention relates to a method of providing or enhancing immunity against HCMV in an uninfected human subject comprising administering to said subject an immunologically active peptide comprising a CTL epitope of a HCMV antigen or a derivative or variant thereof or a vaccine composition comprising said peptide or derivative or variant for a time and under conditions sufficient to provide immunological memory against a future infection by HCMV.

Another aspect of the invention relates to a method of enhancing or conferring immunity against HCMV in an uninfected human subject comprising contacting ex vivo a T cell obtained from a human subject with an immunologically active peptide comprising a CTL epitope of a HCMV antigen or a derivative or variant thereof or a vaccine composition comprising said peptide or derivative or variant for a time and under conditions sufficient to confer HCMV activity on said T cells.

As will be apparent from the description herein, the immunologically active peptide of the invention or a derivative or variant thereof, or a vaccine composition comprising said peptide or derivative or variant, is useful for directly stimulating a CTL or a precursor CTL in vitro. Using appropriate assay technology known to the skilled artisan, the peptide of the invention or a derivative or functionally equivalent variant thereof, or a composition comprising said peptide or derivative or variant, is useful for determining the level of HCMV-specific immunity in a human subject who is either suffering from a primary HCMV infection or at risk of HCMV infection or the reactivation of HCMV infection, such as, for example, a transplant patient, HIV-infected individual, a female having reproductive capacity or a pregnant female. In a related embodiment, the peptide or composition of the invention is also useful for distinguishing an individual who is seropositive from an individual who has not been exposed to HCMV (ie. a seronegative individual).

Accordingly, another aspect of the invention relates to a diagnostic method for quantitively or qualitatively monitoring HCMV-specific T cell immunity in a human subject, said method comprising contacting ex vivo a T cell obtained from a human subject with an APC primed with an immunologically active peptide comprising a CTL epitope of a HCMV antigen or a derivative or variant thereof or a vaccine composition comprising said peptide or derivative or variant and determining the activation of a CTL or precursor CTL, wherein said activation of a CTL or precursor CTL indicates that the subject has been previously infected with HCMV.

Another aspect of the present invention relates to a method of producing an isolated CTL or precursor CTL capable of binding to or lyzing a human cell infected with HCMV said method comprising contacting a T cell with an isolated peptide of the present invention or an APC primed with an isolated peptide of the invention, culturing the T cell and selecting T cells that proliferate. Optionally, the T cell is contacted with peptide in the presence of a cytokine, such as, for example, IL-2.

The present invention clearly extends to the T cell clones produced using a novel immunologically active peptide described herein, and to the use of such T cell clones in any diagnostic, prophylactic or therapeutic procedures for monitoring HCMV infection, latency of HCMV infection, the likelihood of HCMV infection in a human subject, such as, for example, before, during or following organ transplantation (eg. BMT), or during pregnancy.

BRIEF DESCRIPTION OF THE DRAWINGS

FIG. 1b is graphical representation showing MHC stabilization on T2 cells for various HLA A2-binding peptides derived from the HCMV antigen pp71. Peptides tested had the amino acid sequences indicated at the right of the graph (i.e. SEQ ID NOs: 177, 176, 175, and 174 respectively, from top to bottom). T2 cells were incubated with peptide and HLA A2 expression on these cells analyzed by flow cytometry using B87.2 antibody as described in the legend to FIG. 1a. Fluorescence intensity is indicated as described in the legend to FIG. 1a.

FIG. 1c is graphical representation showing MHC stabilization on T2 cells for various HLA A2-binding peptides derived from the HCMV antigen pp150. Peptides tested had the amino acid sequences indicated at the right of the graph (i.e. SEQ ID NOs: 140, 141, 122, 138, 139, 142, 145, 144, and 143 respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1d is graphical representation showing MHC stabilization on T2 cells for various HLA A2-binding peptides derived from the HCMV antigen IE-1. Peptides tested had the amino acid sequences indicated at the right of the graph (i.e. SEQ ID NOs: 98, 102, 96, 101, 100, 103, 97, and 99 respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1e is graphical representation showing MHC stabilization on T2 cells for various HLA A2-binding peptides derived from the HCMV antigen gB. Peptides tested had the amino acid sequences indicated at the right of the graph (i.e. SEQ ID NOs: 183, 188, 181, 187, 186, 182, 185, and 184 respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1f is graphical representation showing MHC stabilization on T2 cells for various HLA A2-binding peptides derived from the HCMV antigens pp50 and pp28. Peptides tested had the amino acid sequences indicated at the right of the graph (i.e. SEQ ID Nos: 164 and 163 for pp50-derived peptides, respectively, from top to bottom; and SEQ ID NOs: 155, 154, 153, 152, 151 and 150 for pp28-derived peptides, respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1g is graphical representation showing MHC stabilization on T2 cells for various HLA A2-binding peptides derived from the HCMV antigen gH. Peptides tested had the amino acid sequences indicated at the right of the graph (i.e. SEQ ID NOs: 216, 206, 205, 201, 200, 204, 203, 198, 202, 197, 199, and 196 respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1h is graphical representation showing MHC stabilization on T2 cells for various HLA A2-binding peptides derived from the HCMV antigen IE-2. Peptides tested had the amino acid sequences indicated at the right of the graph (i.e. SEQ ID NOs: 256, 254, 253, 252, and 251 respectively, from top to bottom). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 1i is graphical representation showing MHC stabilization on T2 cells for various HLA A2-binding peptides derived from the HCMV antigens US3, US2, and UL18. Peptides tested had the amino acid sequences indicated at the right of the graph (i.e. SEQ ID NOs: 300, 298, and 299 for US3-derived peptides, respectively, from top to bottom; SEQ ID NOs: 296, 294 and 295 for US2-derived peptides respectively, from top to bottom; and SEQ ID NO: 293 for the UL18-derived peptide at the bottom of the graph). T2 cells were incubated with peptide and HLA A2 expression on these cells analyzed by flow cytometry using BB7.2 antibody as described in the legend to FIG. 1a. Fluorescence intensity is indicated as described in the legend to FIG. 1a.

FIG. 7b is a graphical representation showing ex vivo HCMV-specific T cell responses against overlapping sets of peptides derived from HCMV antigen pp65. A set of 56 overlapping peptides was tested as described in the legend to FIG. 7a.

FIG. 7c is a graphical representation showing ex vivo HCMV-specific T cell responses against overlapping sets of peptides derived from HCMV antigen IE-1. Sets of 49 overlapping peptides was tested as described in the legend to FIG. 7a.

FIG. 7d is a graphical representation showing ex vivo HCMV-specific T cell responses against overlapping sets of peptides derived from HCMV antigen IE-2. A set of 41 overlapping peptides was tested as described in the legend to FIG. 7a.

FIG. 7e is a graphical representation showing ex vivo HCMV-specific T cell responses against overlapping sets of peptides derived from HCMV antigen gH. A set of 74 overlapping peptides was tested as described in the legend to FIG. 7a.

FIG. 7f is a graphical representation showing ex vivo HCMV-specific T cell responses against overlapping sets of peptides derived from HCMV antigen pp150. A set of 104 overlapping peptides was tested as described in the legend to FIG. 7a.

DETAILED DESCRIPTION OF THE PREFERRED EMBODIMENTS

1. Isolated HCMV Epitopes

Figure 1A:
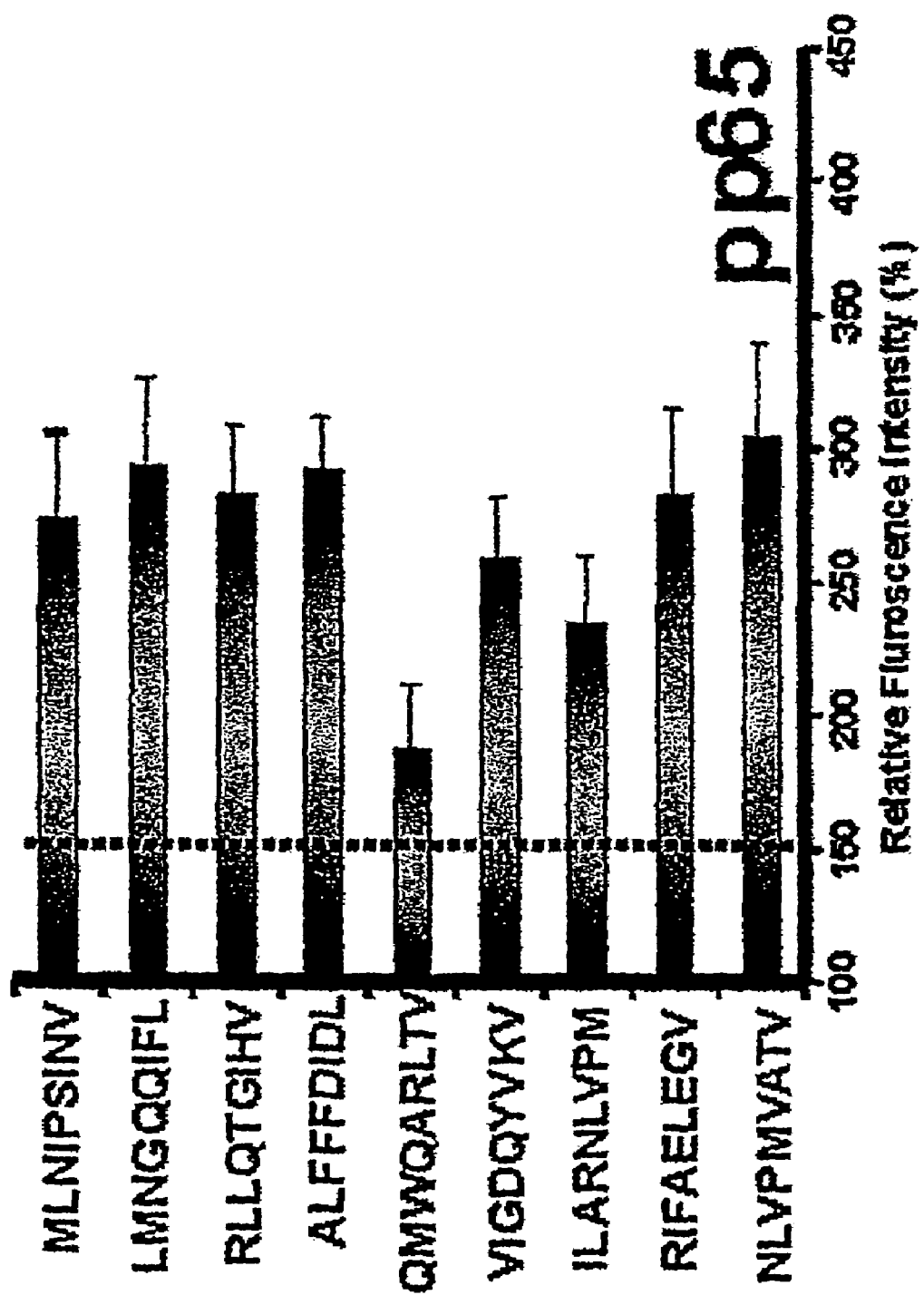
FIG. 1a is graphical representation showing MHC stabilization on T2 cells for various HLA A2-binding peptides derived from the HCMV antigen pp65. Peptides tested had the amino acid sequences indicated at the right of the graph (i.e. SEQ ID NOs: 6, 53, 10, 12, 52, 11, 54, 7, and 5, respectively, from top to bottom). T2 cells were initially incubated with 100 μl of each peptide (100 μg/ml) for 14-16 h at 26° C., followed by incubation at 37° C. for 2-3 h. HLA A2 expression on these cells was analyzed by flow cytometry using BB7.2 antibody. Fluorescence intensity is indicated as a percentage of the fluorescence intensity for HLA A2 on T2 cells incubated at 26° C. without peptide. The dotted line indicates the mean+3 S.E.M. of the fluorescence intensity for HLA A2 on T2 cells incubated at 26° C. without peptide.
Figure 1B:
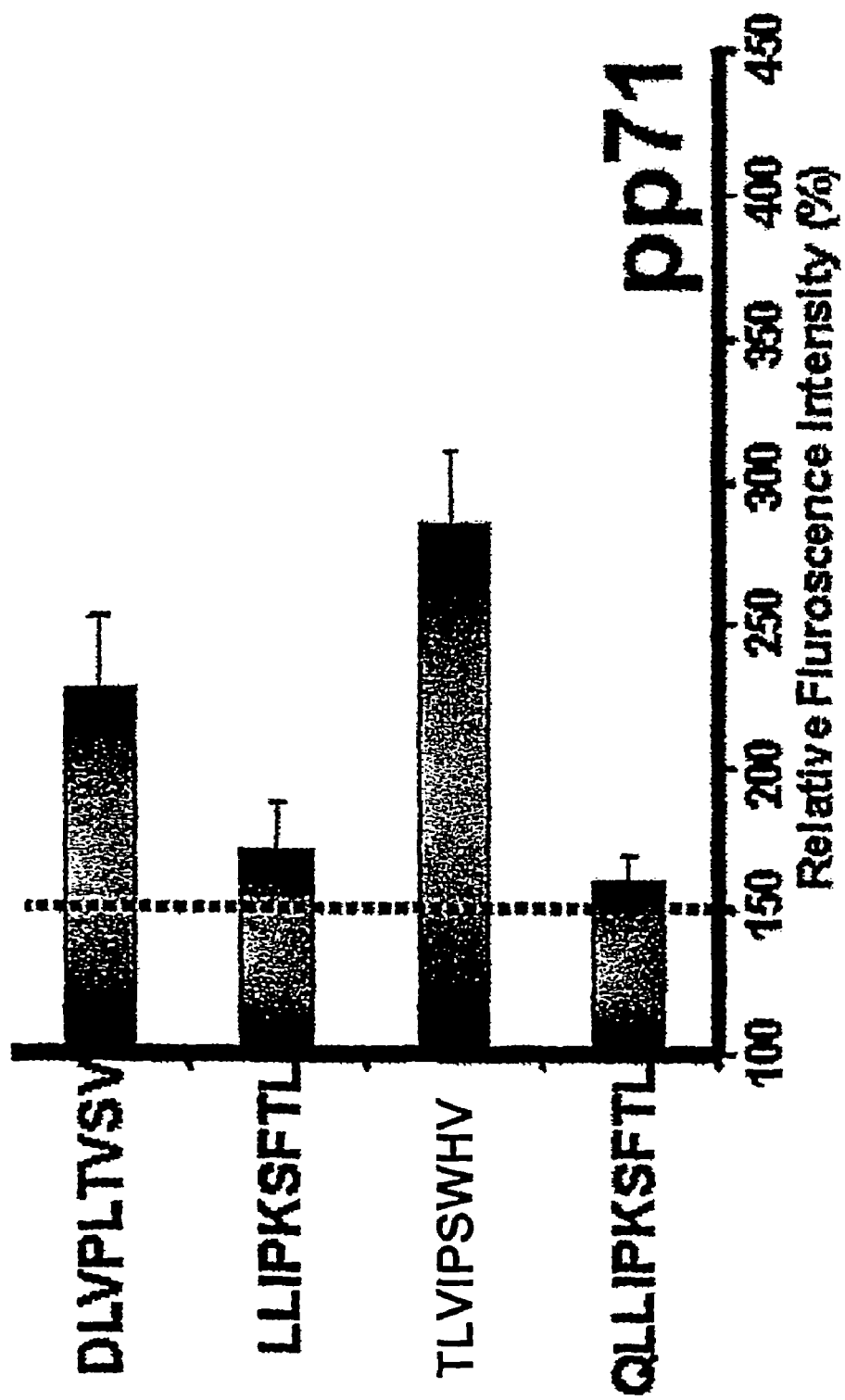
Figure 1C:
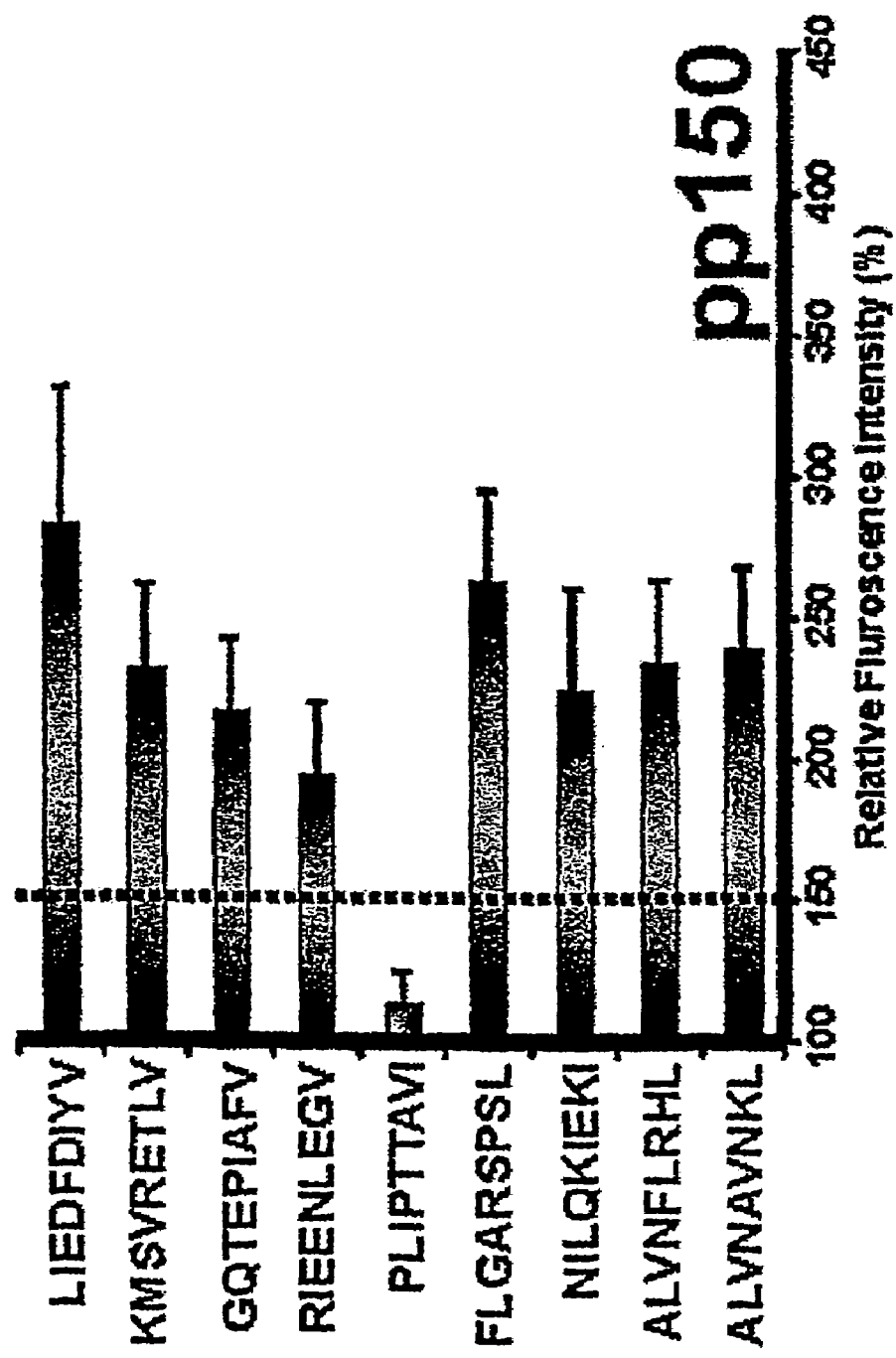
Figure 1D:
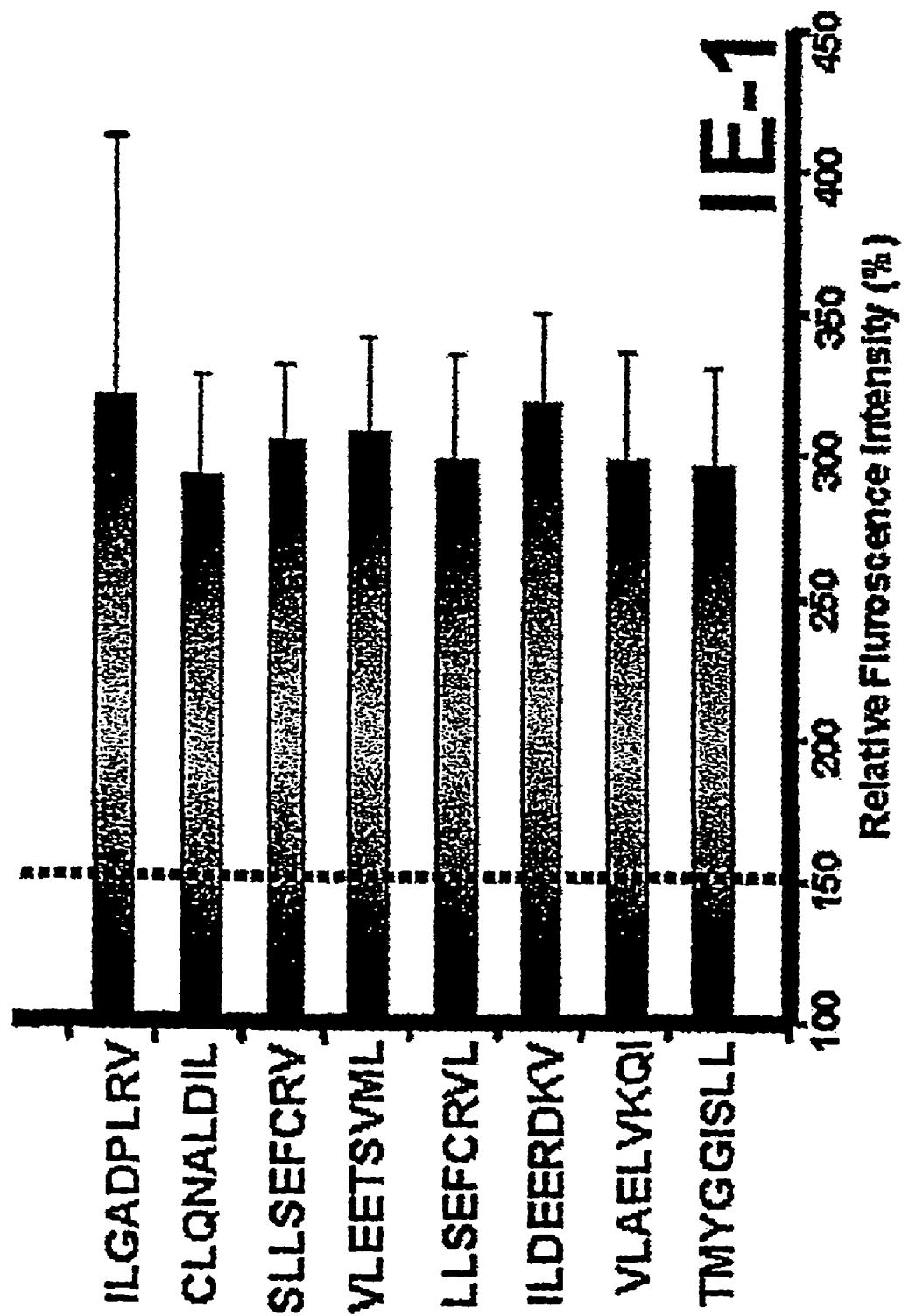
Figure 1E:
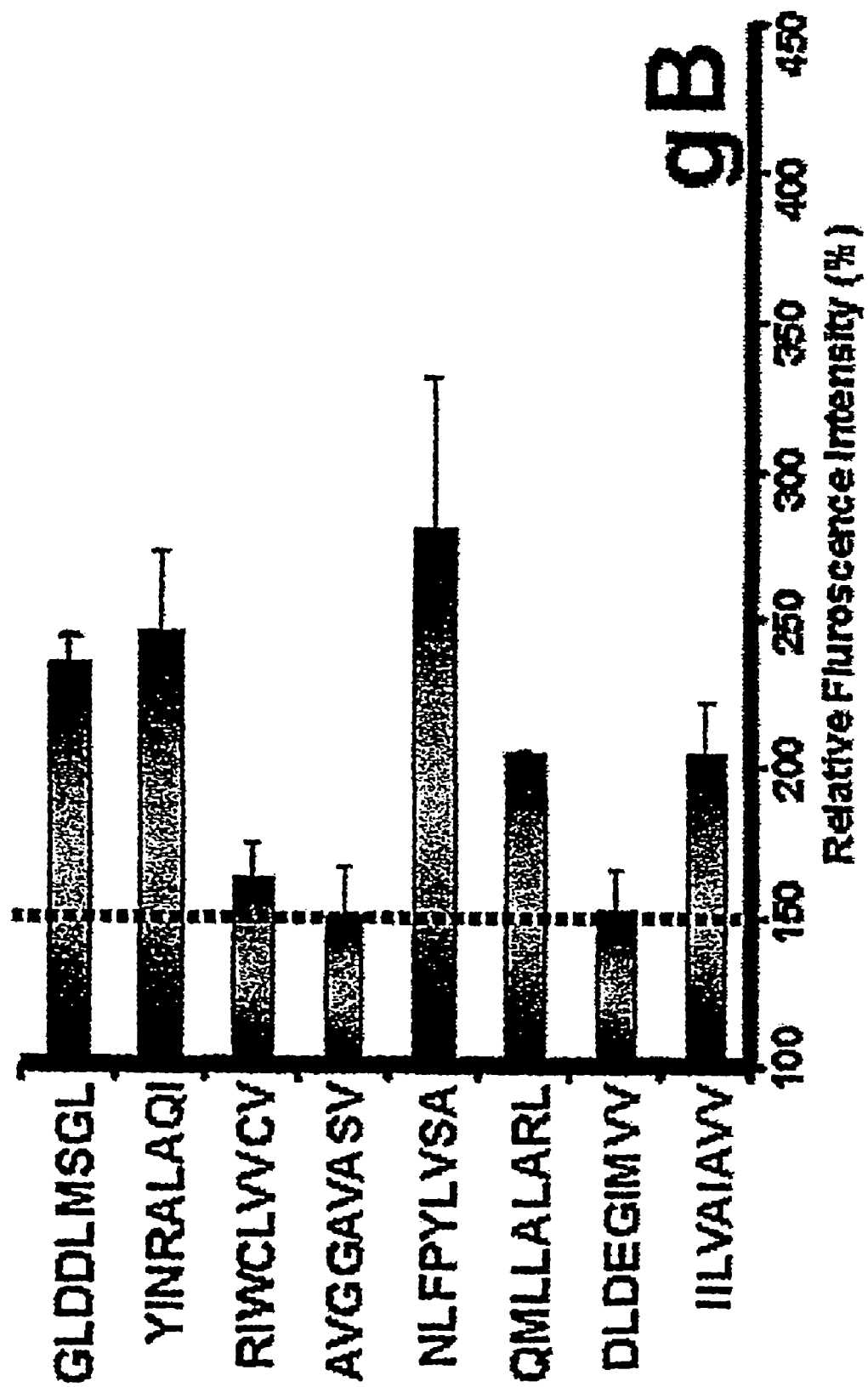
Figure 1F:
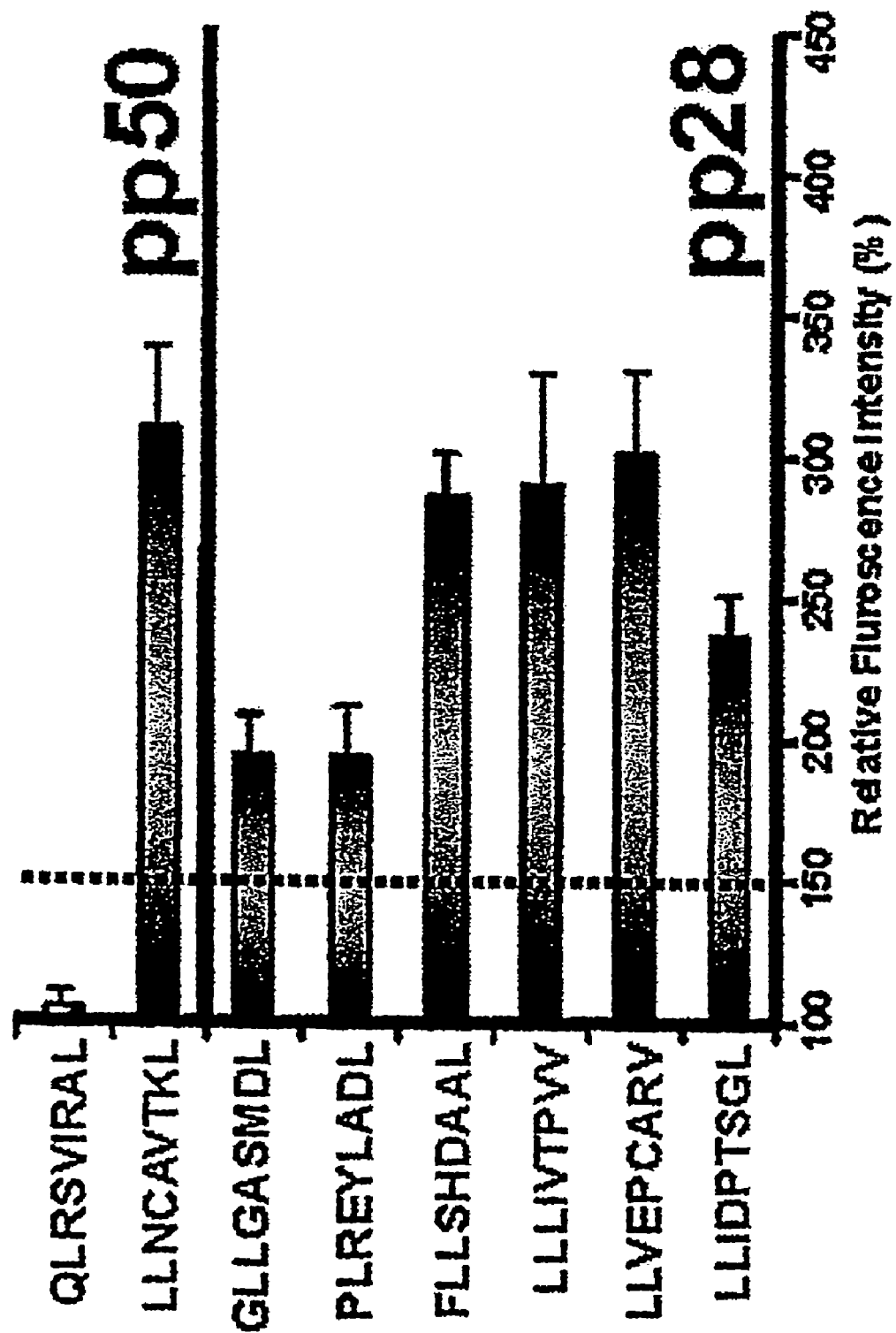
Figure 1G:
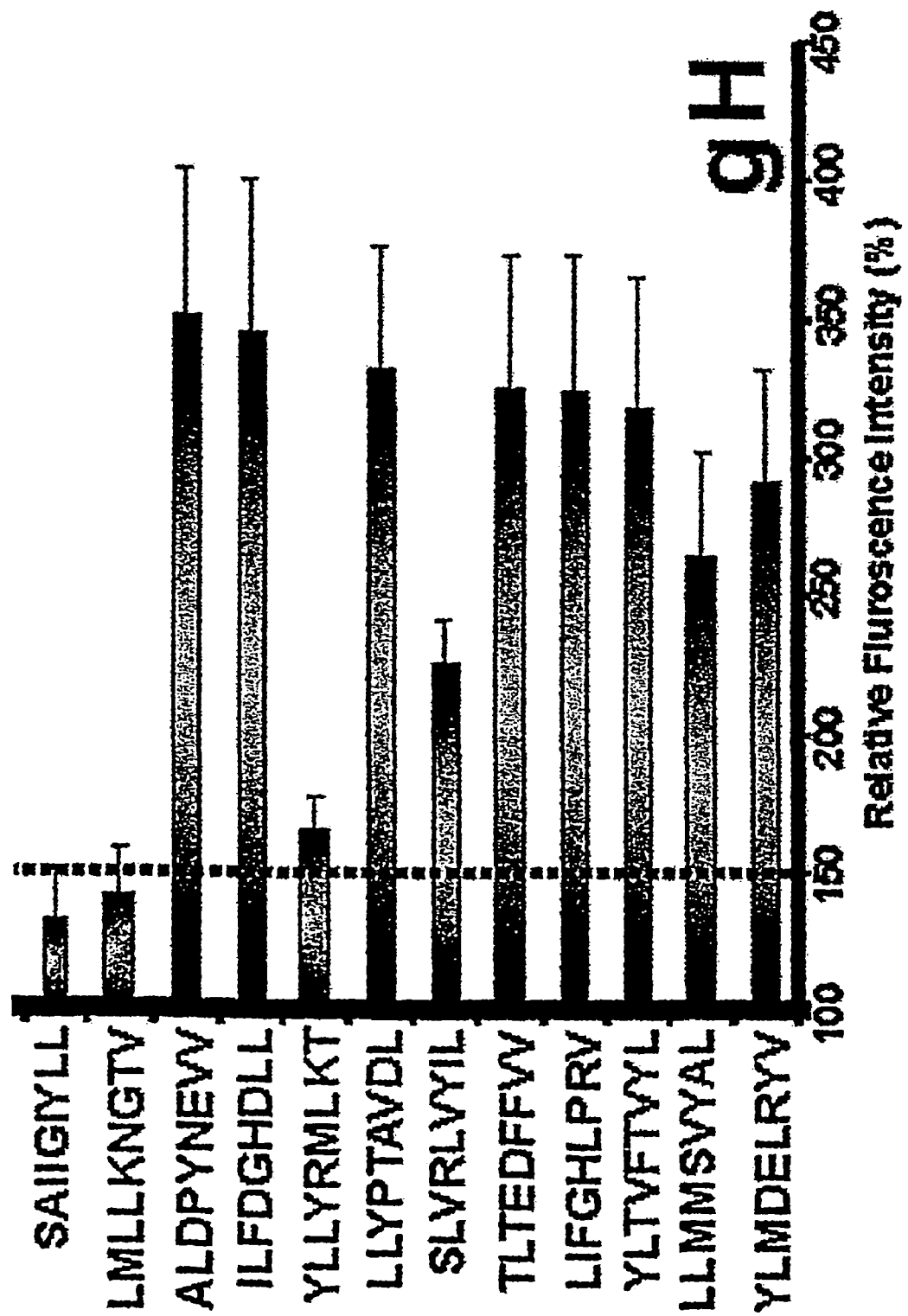
Figure 1H:
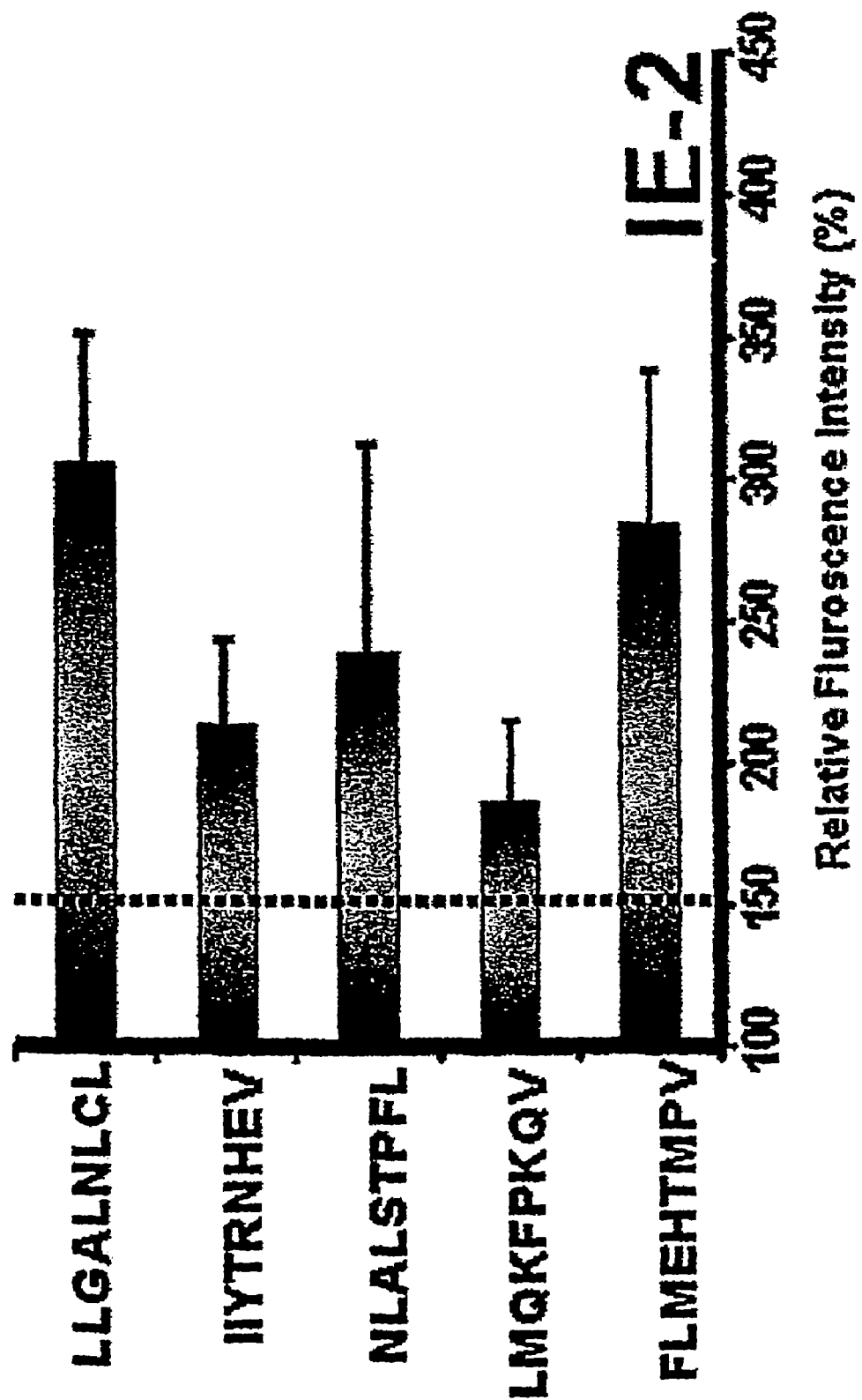
Figure 1I:
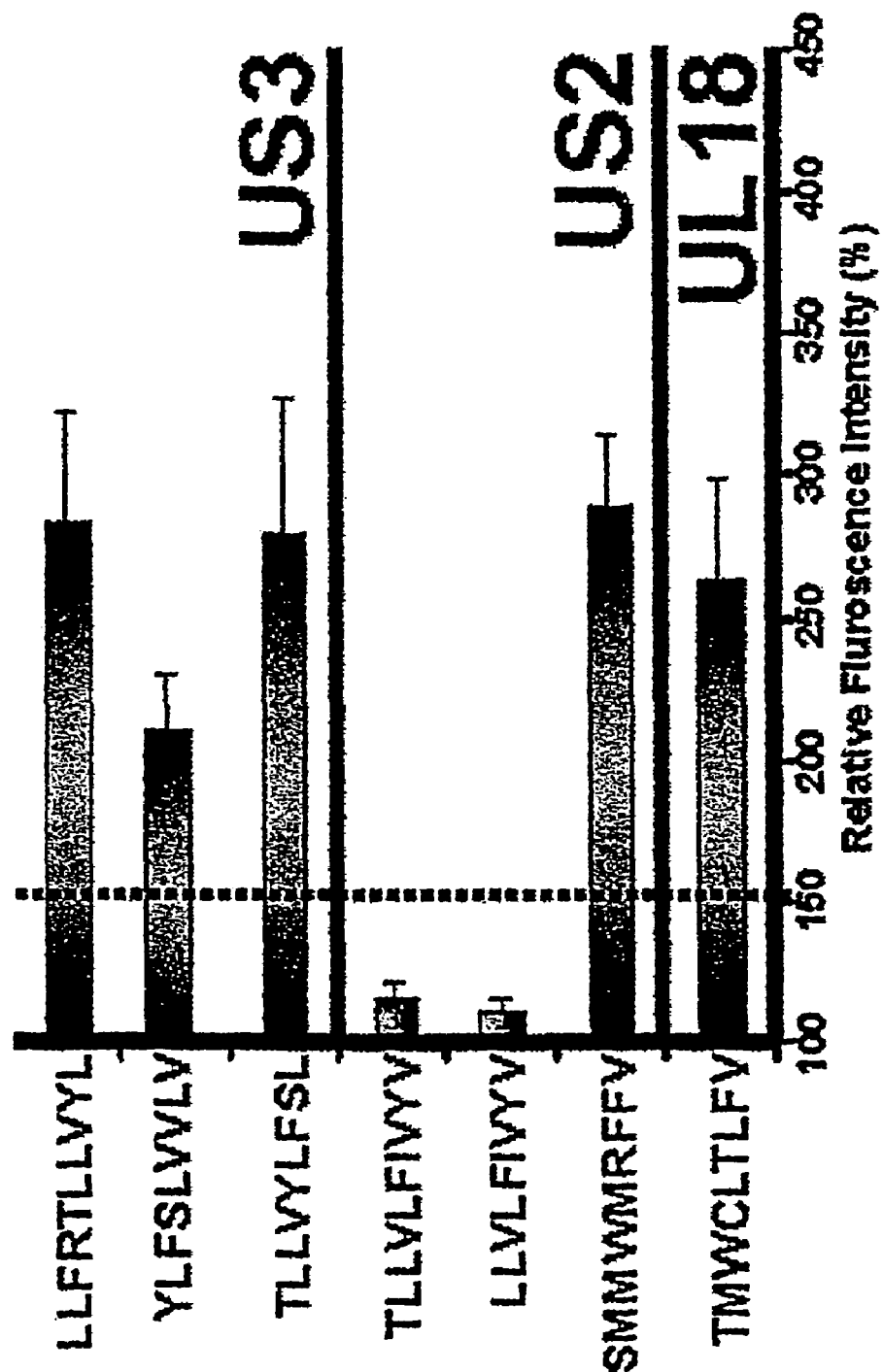

One aspect of the present invention provides an isolated peptide comprising a cytotoxic T-lymphocyte (CTL) epitope of an antigen of a cytomegalovirus of humans (HCMV) selected from the group consisting of pp28, pp50, pp65, pp71, pp150, gB, gH, IE-1, IE-2, US2, US3, US6, US11, and UL18 or a derivative or functionally equivalent variant of said peptide, wherein said peptide consists of an amino acid sequence having about 9 to about 20 contiguous amino acids of said antigen and wherein:

(i) said CTL epitope of pp65 consists of an amino acid sequence selected from the group consisting of SEQ ID NO: 22 (SQEPMSIYVY); SEQ ID NO: 23 (ATVQGQNLKY); SEQ ID NO: 24 (IRETVELRQY); SEQ ID NO: 25 (IGDQYVKVY); SEQ ID NO: 26 (TVQGQNLKY); SEQ ID NO: 27 (YRIQGKLEY); SEQ ID NO: 28 (QVIGDQYVK (SEQ ID NO: 29 (LLLQRGPQY); SEQ ID NO: 30 (RVTGGGAMA); SEQ ID NO: 31 (GVMTRGRLK); SEQ ID NO: 32 (VYALPLKML); SEQ ID NO: 33 (QYDPVAALF); SEQ ID NO: 34 (VYYTSAFVF); SEQ ID NO: 35 (DVPSGKLFM); SEQ ID NO: 36 (DIDLLLQRG); SEQ ID NO: 37 (YVKVYLESF); SEQ ID NO: 38 (TVQGQNLKY); SEQ ID NO: 39 (EPMSIYVYAL); SEQ ID NO: 40 (HVRVSQPSL); SEQ ID NO: 41 (QARLTVSGL); SEQ ID NO: 42 (RRRHRQDAL); SEQ ID NO: 43 (QPKRRRHRQ); SEQ ID NO: 44 (LCPKSIPGL); SEQ ID NO: 45 (YRIQGKLEY); SEQ ID NO: 46 (YSEHPTFTSQY); SEQ ID NO: 47 (SEHPTFTSQY); SEQ ID NO: 48 (CEDVPSGKLF); SEQ ID NO: 49 (NEIHNPAVF); SEQ ID NO: 50 (RETVELRQY); SEQ ID NO: 51 (QEPMSIYVY); SEQ ID NO: 52 (QMWQARLTV); SEQ ID NO: 53 (LMNGQQIFL); SEQ ID NO: 54 (ILARNLVPM); SEQ ID NO: 56 (QEFFWDANDIY); SEQ ID NO: 57 (QEFFWDANDI); SEQ ID NO: 58 (QYRIQGKLE); SEQ ID NO: 59 (RKHRHLPVADAV); SEQ ID NO: 60 (DPVAALFFF); SEQ ID NO: 61 (PGKISHIMLDVA); SEQ ID NO: 62 (TRATKMQVI); SEQ ID NO: 63 (QAIRETVEL); SEQ ID NO: 64 (YHRTWDRHEGA); SEQ ID NO: 65 (FMRPHERNGFTV); SEQ ID NO: 66 (CPSQEPMSIYVY); SEQ ID NO: 67 (LNIPSINVHHYPSMERKHR); SEQ ID NO: 68 (ATVQGQNLKYQEFFWDANDI); SEQ ID NO: 69 (QEFFWDANDIYRIFAELEGV); SEQ ID NO:70 (PQYSEHPTFTSQYRIQGKLE); SEQ ID NO:71 (SQYRIQGKLEYRHTWDRHDE); SEQ ID NO: 72 (VFTUVPPWQAGILARNLVPMV); SEQ ID NO: 73 (ILARNLVPMVATVQGQNLKY); SEQ ID NO: 74 (DQYVKVYLESFCEDVPSGKL); SEQ ID NO: 75

(YPSMERKHRHLPVADAV1H); SEQ ID NO: 76 (QYD-PVAALFFFDIDLLLQRG); SEQ ID NO: 77 (IIKPGK-ISHIMLDVAFTSHE); SEQ ID NO: 78 (AHELVCSMEN-TRATKMQVIG); SEQ ID NO: 79 (TRATKMQVIGDQYVKVYLES); SEQ ID NO: 80 (MNGQQIFLEVQAIRETVELR); SEQ ID NO: 81 (QAIRETVELRQYDPVAALFF); SEQ ID NO: 82 (LTVSGLAWTRQQNQWKEPDV); SEQ ID NO: 83 (WQPMQPKRRRHRQDALPGP); SEQ ID NO: 84 (YRHTWDRHDEGMQGDDDVVV); SEQ ID NO: 85 (TSAGRKRKSASSATACTSGV); SEQ ID NO: 86 (HRQDALPGPCIASTPKKHRG); SEQ ID NO: 87 (YYT-SAFVFPTKDVALRHWC); SEQ ID NO: 88 (VTTERK-TPRVTGGGAMAGAS); SEQ ID NO: 89 (QPFMR-PHERNGFTVLCPKNM); SEQ ID NO: 90 (SICPSQEPMSIYVYALPLKM); SEQ ID NO: 91 (IYVY-ALPLKMLNIPSINVHH); SEQ ID NO: 92 (QQN-QWKEPDVYYTSAFVFPT); SEQ ID NO: 93 (GAAQGDDDVWTSGSDSDEEL); SEQ ID NO: 94 (TGGGAMAGASTSAGRKRKSA); and SEQ ID NO: 95 (KDVALRHVVCAHELVCSMEN;

(ii) said CTL epitope of IE-1 consists of an amino acid sequence selected from the group consisting of: SEQ ID NO: 96 (SLLSEFCRV); SEQ ID NO: 97 (VLAELVKQI); SEQ ID NO: 98 (ILGADPLRV); SEQ ID NO: 99 (TMYG-GISLL); SEQ ID NO: 100 (LLSEFCRVL); SEQ ID NO: 101 (VLEETSVML); SEQ ID NO: 102 (CLQNALDIL); SEQ ID NO: 103 (ILDEERDKV); SEQ ID NO: 104 (IKE-HMLKKY); SEQ ID NO: 105 (DEEEAIVAY); SEQ ID NO: 106 (KLGGALQAK); SEQ ID NO: 107 (QYIL-GADPL); SEQ ID NO: 108 (KYTQTEEKF); SEQ ID NO: 109 (KARAKKDEL); SEQ ID NO: 110 (VMKRRIEEI); SEQ ID NO: 111 (RHRIKEHML); SEQ ID NO: 112 (EL-RRKMMYM); SEQ ID NO: 113 (QIKVRVDMV); SEQ ID NO: 114 (ELRKKMMYM); SEQ ID NO: 115 (RRK-MMYMCY); SEQ ID NO: 116 (AYAQKIFKIL); SEQ ID NO: 117 (CSPDEIMAYAQKIFKILDEE); SEQ ID NO: 118 (SEPVSEIEEVAPEEEEDGAE); SEQ ID NO: 119 (VLCCYVLEETSVMLAKRPLI); SEQ ID NO: 120 (RRKMMYMCYRNIEFFTKNSA); and SEQ ID NO: 121 (NIEFFTKNSAFPKTTNGCSQ); and (iii) said CTL epitope of pp150 consists of an amino acid sequence selected from the group consisting of SEQ ID NO: 122 (GQTEPIAFV); SEQ ID NO: 130 (RPST-PRAAV); SEQ ID NO: 131 (SPWAPTAPL); SEQ ID NO: 132 (KARDHLAVL); SEQ ID NO: 133 (WPRERAWAL); SEQ ID NO: 134 (NVRRSWEEL); SEQ ID NO: 138 (RIEENLEGV); SEQ ID NO: 139 (PLIPTTAVI); SEQ ID NO: 140 (LIEDFDIYV); SEQ ID NO: 141 (KMS-VRETLV); SEQ ID NO: 142 (FLGARSPSL); SEQ ID NO: 143 (ALVNAVNKL); SEQ ID NO: 144 (ALVNFLRHL); SEQ ID NO: 145 (NILQKIEKI); SEQ ID NO: 146 (ER-AWALKNPHLA); SEQ ID NO: 147 (WPRERAWALKN-PHLAYNPFR); SEQ ID NO: 148 (STSQKPVLGKRVAT-PHASAR); and SEQ ID NO: 149 (HANTALVNAVNKLVYTGRLI).

In a particularly preferred embodiment, the peptide of the invention consists of about 8-12 amino acids in length or about 19-21 amino acids in length, more preferably 9 or 10 or 11 or 20 residues in length.

As used herein, the term "CTL epitope" shall be taken to mean a non-naturally occurring peptide or polypeptide or antigen of at least about 9 amino acids in length and having an amino acid sequence selected from the group consisting of:

(i) a sequence that interacts at a significant level with a MHC Class I allele as determined using a predictive algorithm for determining MHC Class 1-binding epitopes, such as, for example, the SYFPEITHI algorithm of the University of Tuebingen, Germany, or the algorithm of the HLA Peptide Binding Predictions program of the BioInformatics and Molecular Analysis Section (BIMAS) of the National Institutes of Health of the Government of the United States of America;

(ii) a sequence that binds to and/or stabilizes an MHC Class I molecule on the surface of an antigen presenting cell (APC) irrespective of whether or not said APC is in a substantially isolated form, such as, for example in the PBMC fraction or buffy coat fraction of a sample obtained from a human subject, or alternatively, in its natural state;

(iii) a sequence that induces a memory CTL response or elicits IFN-γ expression by a T cell, such as, for example, CD8$^+$ T cell, cytotoxic T cell (CTL) or effector T cell or memory T cell, irrespective of whether or not said T cell is in a substantially isolated form, such as, for example in the PBMC fraction or buffy coat fraction of a sample obtained from a human subject, or alternatvely, in its natural state; and (iv) a sequence that stimulates CTL activity in a standard cytotoxicity assay.

Preferably, a CTL epitope as defined herein comprises a sequence that satisfies at least, preferably at least two and more preferably all three functional criteria recited at paragraphs (ii) through (iv) supra. Even more preferably, a CTL epitope as defined herein comprises a sequence that additionally satisfies criterion (i) supra.

Particularly preferred CTL epitopes of the invention are capable of eliciting a cellular immune response against intact HCMV in human cells or tissues, such as, for example, by recognizing and lyzing human cells infected with HCMV, thereby providing or enhancing cellular immunity against HCMV.

As used herein, the term "pp28" or "HCMV pp28" or "pp28 antigen" or similar term shall be taken to mean a polypeptide of HCMV having the publicly available amino acid sequence deposited under NCBI Accession No. NC 001347 (Chee et al., Curr. Top. Microbiol. Immunol 154, 125-169, 1990; and Bankier et al., DNA Seq 2, 1-12, 1991), and preferably having the function of a DNase, or a related polypeptide of HCMV or other β-herpesvirus of humans having at least about 80% amino acid sequence identity to said sequence. Those skilled in the art will be aware that the pp28 polypeptide of HCMV is also termed "UL98".

"NCBI" means the database of the National Center for Biotechnology Information at the National Library of Medicine at the National Institutes of Health of the Government of the United States of America, Bethesda, Md. 20894.

A preferred epitope of pp28 has an amino acid sequence selected from the group consisting of: SEQ ID NO: 150 (LLIDPTSGL); SEQ ID NO: 151 (LLVEPCARV); SEQ ID NO: 152 (LLLIVTPVV); SEQ ID NO: 153 (FLLSHDML); SEQ ID NO: 154 (PLREYLADL); SEQ ID NO: 155 (GLL-GASMDL); SEQ ID NO: 156 (LVEPCARVY); SEQ ID NO: 157 (GIKHEGLVK); SEQ ID NO: 158 (ELLAGGRVF); SEQ ID NO: 159 (RLLDLAPNY); SEQ ID NO: 160 (ELLGRLNVY); SEQ ID NO: 161 (CRYKYLRKK); and SEQ ID NO: 162 (ARVYEIKCR).

Even more preferably, a CTL epitope of pp28 has an amino acid sequence set forth in SEQ ID NO: 150 (LLIDPTSGL) or SEQ ID NO: 162 (ARVYEIKCR), and still more preferably has the amino acid sequence set forth in SEQ ID NO: 162.

As used herein, the term "pp50" or "HCMV pp50" or "pp50 antigen" or similar term shall be taken to mean a polypeptide of HCMV having the publicly available amino acid sequence deposited under NCBI Accession No.

QQBEV2 or P16790 (Chee et al., *Curr. Top. Microbiol. Immunol* 154, 125-169, 1990), and preferably having the function of a DNA polymerase processivity factor or polymerase accessory protein as described by Leach and Mocarski, J. Virol., 63, 1783-1791, 1989, or a related polypeptide of HCMV or other β-herpesvirus of humans having at least about 80% amino acid sequence identity to said sequence. Those skilled in the art will be aware that the pp50 polypeptide of HCMV is also termed "UL44".

A preferred epitope of pp50 has an amino acid sequence selected from the group consisting of: SEQ ID NO: 163 (LLNCAVTKL); SEQ ID NO: 164 (QLRSVIRAL); SEQ ID NO: 165 (VTEHDTLLY); SEQ ID NO: 166 (RGDPFDKNY); SEQ ID NO: 167 (GLDRNSGNY); SEQ ID NO: 168 (TLLNCAVTK); SEQ ID NO: 169 (TVRSHCVSK); SEQ ID NO: 170 (YEQHKITSY); SEQ ID NO: 171 (TRVKRNVKK); SEQ ID NO: 172 (SEDSVTFEF); and SEQ ID NO: 173 (TRLSEPPTL).

Even more preferably, the epitope of pp50 consists of an amino acid sequence selected from the group consisting of SEQ ID NO: 163 (LLNCAVTKL); SEQ ID NO: 165 (VTEHDTLLY); SEQ ID NO: 166 (RGDPFDKNY); SEQ ID NO: 167 (GLDRNSGNY); and SEQ ID NO: 170 (YEQHKITSY). Still more preferably, the epitope of pp50 has the amino acid sequence set forth in SEQ ID NO: 165.

As used herein, the term "pp65" or "HCMV pp65" or "pp65 antigen" or similar term shall be taken to mean a polypeptide of HCMV having the publicly available amino acid sequence deposited under NCBI Accession No. WMBETW (Chee et al., *Curr. Top. Microbiol. Immunol* 154, 125-169, 1990; and Pande et al., *Virol.*, 82, 220-228, 1991), and preferably having the function of a lower matrix phosphoprotein or tegument protein as described by Pande et al., *Virol.*, 82, 220-228, 1991, or a related polypeptide of HCMV or other β-herpesvirus of humans having at least about 80% amino acid sequence identity to said sequence.

Particularly preferred epitopes of pp65 will consist of an amino acid sequence listed herein above, and more preferably, and amino acid sequence selected from the group consisting of: SEQ ID NO: 25 (IGDQYVKVY); SEQ ID NO: 26 (TVQGQNLKY); SEQ ID NO: 27 (YRIQGKLEY); SEQ ID NO: 40 (HVRVSQPSL); SEQ ID NO: 41 (QARLTVSGL); SEQ ID NO: 42 (RRRHRQDAL); SEQ ID NO: 53 (LMNGQQIFL); SEQ ID NO: 54 (ILARNLVPM); SEQ ID NO: 56 (QEFFWDANDIY); SEQ ID NO: 57 (QEFFWDANDI); SEQ ID NO: 58 (QYRIQGKLE); SEQ ID NO: 59 (RKHRHLPVADAV); SEQ ID NO: 60 (DPVMLFFF); SEQ ID NO: 61 (PGKISHIMLDVA); SEQ ID NO: 63 (QAIRETVEL); SEQ ID NO: 66 (CPSQEPMSIYVY); SEQ ID NO: 67 (LNIPSINVHHYPSMERKHR); SEQ ID NO: 68 (ATVQGQNLKYQEFFWDANDI); SEQ ID NO: 69 (QEFFWDANDIYRIFAELEGV); SEQ ID NO:70 (PQYSEHPTFTSQYRIQGKLE); SEQ ID NO:71 (SQYRIQGKLEYRHTWDRHDE); SEQ ID NO: 72 (VFTWPPWQAGILARNLVPMV); SEQ ID NO: 73 (ILARNLVPMVATVQGQNLKY); SEQ ID NO: 75 (YPSAAERKHRHLPVADAV1H); SEQ ID NO: 76 (QYDPVMLFFFDIDLLLQRG); SEQ ID NO: 77 (IIKPGKISHIMLDVAFTSHE); SEQ ID NO: 80 (MNGQQIFLEVQAIRETVELR); SEQ ID NO: 81 (QAIRETVELRQYDPVMLFF); SEQ ID NO: 87 (YYTSAFVFPTKDVALRHWC); SEQ ID NO: 90 (SICPSQEPMSIYVYALPLKM); and SEQ ID NO: 92 (QQNQWKEPDVYYTSAFVFPT).

As used herein, the term "pp71" or "HCMV pp71" or "pp71 antigen" or similar term shall be taken to mean a polypeptide of HCMV having the publicly available amino acid sequence deposited under NCBI Accession Nos. NP 040017 or WMBES1 (Chee et al., *Curr. Top. Microbiol. Immunol* 154, 125-169, 1990; Ruger et al., *J Virol.*, 61, 446-453, 1987; and Bankier et al., *DNA Seq* 2, 1-12, 1991), and preferably having the function of an upper matrix phosphoprotein as described by Ruger et al., *J. Virol.*, 61, 446-453, 1987, or a related polypeptide of HCMV or other β-herpesvirus of humans having at least about 80% amino acid sequence identity to said sequence. Those skilled in the art will be aware that the pp71 polypeptide of HCMV is also termed "UL82".

A particularly preferred epitope of pp71 has an amino acid sequence selected from the group consisting of: SEQ ID NO: 174 (QLLIPKSFTL); SEQ ID NO: 175 (TLVIPSWHV); SEQ ID NO: 176 (LLIPKSFTL); SEQ ID NO: 177 (DLVPLTVSV); SEQ ID NO: 178 (CSDPNTYIHK); SEQ ID NO: 179 (EYIVQIQNAF); and SEQ ID NO: 180 (AEVVARHNPY).

As used herein, the term "pp150" or "HCMV pp150" or "pp150 antigen" or similar term shall be taken to mean a polypeptide of HCMV having the publicly available amino acid sequence deposited under NCBI Accession No. XPBEA9 (Chee et al., *Curr. Top. Microbiol. Immunol* 154, 125-169, 1990), and preferably having the function of a large (approximately 150 kDa) structural phosphoprotein as described by Jahn et al., *J. Virol.*, 61, 1358-1367, 1987, or a related polypeptide of HCMV or other β-herpesvirus of humans having at least about 80% amino acid sequence identity to said sequence.

Particularly preferred epitopes of pp150 will consist of an amino acid sequence listed herein above, and more preferably, the amino acid sequence set forth in SEQ ID NO: 146 (ERAWALKNPHLA) or SEQ ID NO: 147 (WPRERAWALKNPHLAYNPFR).

As used herein, the term "gB" or "HCMV gB" or "gB antigen" or similar term shall be taken to mean a polypeptide of HCMV having the publicly available amino acid sequence deposited under NCBI Accession No. $PO_{6473}$ (Chee et al., *Curr. Top. Microbiol. Immunol* 154, 125-169, 1990; Cranage et al., *EMBO J.* 5, 3057-3063, 1986; Kouzarides et al., *Viral.*, 157, 397413, 1987; Kouzarides et al., *J. Virol.*, 61, 125-133, 1987), and preferably having the function of a DNA polymerase or being a glycoprotein as described by; Kouzarides et al., *J. Virol.*, 61, 125-133, 1987, or a related polypeptide of HCMV or other β-herpesvirus of humans having at least about 80% amino acid sequence identity to said sequence. Those skilled in the art will be aware that the gB polypeptide of HCMV is also termed "UL55".

A particularly preferred epitope of gB has an amino acid sequence selected from the group consisting of: SEQ ID NO: 123 (AYEYVDYLF); SEQ ID NO: 124 (SYENKTMQL); SEQ ID NO: 125 (AYIYTTYLL); SEQ ID NO: 126 (NTDFRVLEL); SEQ ID NO: 127 (ATSTGDVVY); SEQ ID NO: 128 (LDEGIMVVY); SEQ ID NO: 129 (VKESPGRCY); SEQ ID NO: 135 (IMREFNSYK); SEQ ID NO: 136 (KMTATFLSK); SEQ ID NO: 137 (CYSRPWIF); SEQ ID NO: 181 (RIWCLWCV); SEQ ID NO: 182 (QMLLALARL); SEQ ID NO: 183 (GLDDLMSGL); SEQ ID NO: 184 (IILVAIAW); SEQ ID NO: 185 (DLDEGIMVV); SEQ ID NO: 186 (NLFPYLVSA); SEQ ID NO: 187 (AVGGAVASV); SEQ ID NO: 188 (YINRALAQI); SEQ ID NO: 189 (YAYIYTTYL); SEQ ID NO: 190 (VFETSGGLVV); SEQ ID NO: 191 (DDYSNTHSTRYV); SEQ ID NO: 192 (RSYAYIYTYLLGSNTEYVA); SEQ ID NO: 193 (TYEKYGNVSVFETSGGLWF); SEQ ID NO: 194 (FETSGGLWFWQGIKQKSLV); and SEQ ID NO: 195 (MQLIPDDYSNTHSTRYVTVK).

Even more preferably, the epitope of gB consists of an amino acid sequence selected from the group consisting of SEQ ID NO: 187 (AVGGAVASV); SEQ ID NO: 189 (YAYIYTTYL); SEQ ID NO: 190 (VFETSGGLW); SEQ ID NO: 191 (DDYSNTHSTRYV); SEQ ID NO: 192 (RSYAYIYTTYLLGSNTEYVA); SEQ ID NO: 193 (TYEKYGNVSVFETSGGLWF); and SEQ ID NO: 195 (MQLIPDDYSNTHSTRYVTVK).

As used herein, the term "gH" or "HCMV gH" or "gH antigen" or similar term shall be taken to mean a polypeptide of HCMV having the publicly available amino acid sequence deposited under NCBI Accession No. P12824 (Chee et al., Curr. Top. Microbiol. Immunol 154, 125-169, 1990; Cranage et al., J. Virol., 62, 1416-1422, 1988), and preferably being a glycoprotein as described by Cranage et al., J. Virol., 62, 1416-1422, 1988, or a related polypeptide of HCMV or other β-herpesvirus of humans having at least about 80% amino acid sequence identity to said sequence. Those skilled in the art will be aware that the gH polypeptide of HCMV is also termed "UL75".

A particularly preferred epitope of gH has an amino acid sequence selected from the group consisting of: SEQ ID NO: 196 (YLMDELRYV); SEQ ID NO: 197 (YLTVFTVYL); SEQ ID NO: 198 (TLTEDFFVV); SEQ ID NO: 199 (LLMMSVYAL); SEQ ID NO: 200 (YLLYRMLKT); SEQ ID NO: 201 (ILFDGHDLL); SEQ ID NO: 202 (LIFGHLPRV); SEQ ID NO: 203 (SLVRLVYIL); SEQ ID NO: 204 (LLYPTAVDL); SEQ ID NO: 205 (ALDPYNEW); SEQ ID NO: 206 (LMLLKNGTV); SEQ ID NO: 207 (SAIIGIYLL); SEQ ID NO: 208 (ITSLVRLVY); SEQ ID NO: 209 (HHEYLSDLY); SEQ ID NO: 210 (AIIGIYLLY); SEQ ID NO: 211 (QTEKHELLV); SEQ ID NO: 212 (ATDSRLLMM); SEQ ID NO: 213 (FLDAALDFNY); SEQ ID NO: 214 (DTQGVINIMY); SEQ ID NO: 215 (LRENTTQCTY); SEQ ID NO: 216 (SAIIGIYLLY); SEQ ID NO: 217 (SLRNSTVVR); SEQ ID NO: 218 (ALALFMAR); SEQ ID NO: 219 (QLNRHSYLK); SEQ ID NO: 220 (RLFPDATVP); SEQ ID NO: 221 (RLNTYALVSK); SEQ ID NO: 222 (LVRLVYILSK); SEQ ID NO: 223 (YLMDELRYVK); SEQ ID NO: 224 (ELYLMGSLVH); SEQ ID NO: 225 (ALTVSEHVSY); SEQ ID NO: 226 (NYLDLSALL); SEQ ID NO: 227 (SYVVTNQYL); SEQ ID NO: 228 (SYLKDSDFL); SEQ ID NO: 229 (TYALVSKDL); SEQ ID NO: 230 (SYRSFSQQL); SEQ ID NO: 231 (TYGRPIRFL); SEQ ID NO: 232 (YYVFHMPRCL); SEQ ID NO: 233 (MYMHDSDDVL); SEQ ID NO: 234 (ETFPDLFCL); SEQ ID NO: 235 (DLTETLERY); SEQ ID NO: 236 (SPRTHYLML); SEQ ID NO: 237 (FPDLFCLPL); SEQ ID NO: 238 (SPRTHYLMLL); SEQ ID NO: 239 (MPRCLFAGPL); SEQ ID NO: 240 (TPMLLIFGHL); SEQ ID NO: 241 (APYQRDNFIL); SEQ ID NO: 242 (GRCQMLDRR); SEQ ID NO: 243 (RRDHSLERL); SEQ ID NO: 244 (SEALDPHAF); SEQ ID NO: 245 (RENTTQCTY); SEQ ID NO: 246 (DDVLFALDPY); SEQ ID NO: 247 (HELLVLVKKAQL); SEQ ID NO: 248 (LTVSEHVSYVVT); SEQ ID NO: 249 (RQTEKHELLVLVKKAQLNRH); and SEQ ID NO: 250 (ALTVSEHVSYVVTNQYLIKG).

Even more preferably, the epitope of gH consists of the amino acid sequence set forth in SEQ ID NO: 247 (HELLVLVKKAQL) or SEQ ID NO: 249 (RQTEKHELLVLVKKAQLNRH).

As used herein, the term "IE-1" or "HCMV IE-1" or "IE-1 antigen" or similar term shall be taken to mean a polypeptide of HCMV having the publicly available amino acid sequence deposited under NCBI Accession No. EDBEM5 (Chee et al., Curr. Top. Microbiol. Immunol 154, 125-169, 1990), and preferably having the expression profile of an immediate-early HCMV protein, or a related polypeptide of HCMV or other β-herpesvirus of humans having at least about 80% amino acid sequence identity to said sequence. Those skilled in the art will be aware that the IE-1 polypeptide of HCMV is also termed "UL123".

Particularly preferred epitopes of IE-1 will consist of an amino acid sequence listed herein above, and more preferably, the amino acid sequence set forth in SEQ ID NO: 97 (VLAELVKQI); SEQ ID NO: 101 (VLEETSVML); SEQ ID NO: 112 (ELRRKMMYM); SEQ ID NO: 113 (QIKVRVDMV); SEQ ID NO: 114 (ELKRKMMYM); SEQ ID NO: 116 (AYAQKIFKIL); SEQ ID NO: 117 (CSPDEIMAYAQKIFKILDEE); SEQ ID NO: 118 (SEPVSEIEEVAPEEEEDGAE); and SEQ ID NO: 119 (VLCCYVLEETSVMLAKRPLI).

As used herein, the term "IE-2" or "HCMV IE-2" or "IE-2 antigen" or similar term shall be taken to mean a polypeptide of HCMV having the publicly available amino acid sequence deposited under NCBI Accession No. NC 001347 (Chee et al., Curr. Top. Microbiol. Immunol 154, 125-169, 1990; Bankier et al., DNA Seq 2, 1-12, 1991), and preferably having the expression profile of an immediate-early HCMV protein, or a related polypeptide of HCMV or other β-herpesvirus of humans having at least about 80% amino acid sequence identity to said sequence. Those skilled in the art will be aware that the IE-2 polypeptide of HCMV is also termed "UL122".

A particularly preferred epitope of IE-2 has an amino acid sequence selected from the group consisting of: SEQ ID NO: 251 (FLMEHTMPV); SEQ ID NO: 252 (LMQKFPKQV); SEQ ID NO: 253 (NLALSTPFL); SEQ ID NO: 254 (IIYTRNHEV); SEQ ID NO: 255 (IIYTRNHEVK); SEQ ID NO: 256 (LLGALNLCL); SEQ ID NO: 257 (KPEPDFTIQY); SEQ ID NO: 258 (IMKDKNTPF); SEQ ID NO: 259 (PRKKKSKRI); SEQ ID NO: 260 (FEQPTETPP); SEQ ID NO: 261 (FEQPTETP); SEQ ID NO: 262 (FEQPTETPPE); SEQ ID NO: 263 (EQPTETPPE); SEQ ID NO: 264 (QFEQPTETPPE); SEQ ID NO: 265 (SDYNMIIHA); SEQ ID NO: 266 (YRNMIIHAAT); SEQ ID NO: 267 (CLPLMQKFP); SEQ ID NO: 268 (IDEVSRMFRNTNRS); SEQ ID NO: 269 (TMKAYAVGQFEQPTETPPE); SEQ ID NO: 270 (FEQPTETPPEDLDTLSLAIE); SEQ ID NO: 271 (MLPLIKQEDIKPEPDFTIQY); SEQ ID NO: 272 (THQLCPRSSDYRNMIIHAAT); SEQ ID NO: 273 (YRNMIIHAATPVDLLGALNL); SEQ ID NO: 274 (TGPRKKKSKRISELDNEKVR); SEQ ID NO: 275 (PVDLLGALNLCLPLMQKFPK); SEQ ID NO: 276 (IQIIYTRNHEVKSEVDAVRC); SEQ ID NO: 277 (VKSEVDAVRCRLGTMCNLAL); SEQ ID NO: 278 (RVKIDEVSRMFRNTNRSLEY); SEQ ID NO: 279 (SSSSSSCSSASDSESESEEM); SEQ ID NO: 280 (ASSPSTGSGTPRBTSPTHPL); SEQ ID NO: 281 (PRVTSPTHPLSQMNHPPLPD); SEQ ID NO: 282 (PLGRPDEDSSSSSSSSCSSA); SEQ ID NO: 283 (SDSESESEEMKCSSGGGASV); SEQ ID NO: 284 (KCSSGGGASVTSSHHGRGGF); SEQ ID NO: 285 (CTPNVQTRRGRVKIDEVSRM); SEQ ID NO: 286 (FRNTNRSLEYKNLPFTIPSM); SEQ ID NO: 287 (HQVLDEAIKACKTMQVNNKG); SEQ ID NO: 288 (CKTMQVNNKGIQIIYTRNHE); SEQ ID NO: 289 (KAAWSLKELHTHQLCPRSSD); and SEQ ID NO: 290 (CLPLMQKFPKQVMVRIFSTN).

Even more preferably, the epitope of IE-2 consists of an amino acid sequence selected from the group consisting of: SEQ ID NO: 254 (IIYTRNHEV); SEQ ID NO: 255 (IIYTRNHEVK); SEQ ID NO: 260 (FEQPTETPP); SEQ ID NO: 261 (FEQPTETP); SEQ ID NO: 262 (FEQPTETPPE); SEQ ID NO: 263 (EQPTETPPE); SEQ ID NO: 264

(QFEQPTETPPE); SEQ ID NO: 269 (TAAKAYAVGQFEQPTETPPE); SEQ ID NO: 270 (FEQPTETPPEDLDTlSLAIE); and SEQ ID NO: 276 (IQI-IYTRNHEVKSEVDAVRC).

As used herein, the term "UL18" or "HCMV UL18" or "UL18 antigen" or similar term shall be taken to mean a polypeptide of HCMV having the publicly available amino acid sequence deposited under NCBI Accession No. P08560 (Chee et al., *Curr. Top. Microbiol. Immunol* 154, 125-169, 1990; Beck and Barrell, *Nature* 331, 269-272, 1988), and preferably being a glycoprotein having at least one transmembrane region, or a related polypeptide of HCMV or other β-herpesvirus of humans having at least about 80% amino acid sequence identity to said sequence.

A particularly preferred epitope of UL18 has an amino acid sequence selected from the group consisting of: SEQ ID NO: 291 (GEINITFIHY); SEQ ID NO: 292 (TENGSFVAGY); SEQ ID NO: 293 (TMWCLTLFV); and SEQ ID NO: 308 (LELEIALGY).

Even more preferably, the epitope of UL18 consists of the amino acid sequence set forth in SEQ ID NO: 292 (TENGSFVAGY).

As used herein, the term "US2" or "HCMV US2" or "US2 antigen" or similar term shall be taken to mean a polypeptide of HCMV having the publicly available amino acid sequence deposited under NCBI Accession No. QQBEC5 (Chee et al., *Curr. Top. Microbiol. Immunol* 154, 125-169, 1990; Weston and Barrell, J. Mol. Biol. 192, 177-208,1986), and preferably being a glycoprotein having at least one transmembrane region, or a related polypeptide of HCMV or other β-herpesvirus of humans having at least about 80% amino acid sequence identity to said sequence.

A particularly preferred epitope of US2 has an amino acid sequence selected from the group consisting of: SEQ ID NO: 294 (LLVLFIVYV); SEQ ID NO: 295 (SMMWMRFFV); SEQ ID NO: 296 (TLLVLFIVYV); and SEQ ID NO: 297 (VYVTVDCNL).

Even more preferably, the epitope of US2 consists of the amino acid sequence set forth in SEQ ID NO: 295 (SMMWMRFFV).

As used herein, the term "US3" or "HCMV US3" or "US3 antigen" or similar term shall be taken to mean a polypeptide of HCMV having the publicly available amino acid sequence deposited under NCBI Accession Nos. QQBEC6 or P09712 or AAA45955 (Chee et al., *Curr. Top. Microbiol. Immunol* 154, 125-169, 1990; Weston and Barrell, *J. Mol. Biol.* 192, 177-208, 1986; and *Weston Virol.* 162, 406-416, 1988), and preferably being a glycoprotein that is expressed early during infection, or a related polypeptide of HCMV or other β-herpesvirus of humans having at least about 80% amino acid sequence identity to said sequence.

A particularly preferred epitope of US3 has an amino acid sequence selected from the group consisting of: SEQ ID NO: 298 (YLFSLWLV); SEQ ID NO: 299 (TLLVYLFSL); SEQ ID NO: 300 (LLFRTLLVYL); and SEQ ID NO: 301 (VYLFSLVVL).

Even more preferably, the epitope of US3 consists of the amino acid sequence set forth in SEQ ID NO: 298 (YLFSLVVLV).

As used herein, the term "US6" or "HCMV US6" or "US6 antigen" or similar term shall be taken to mean a polypeptide of HCMV having the publicly available amino acid sequence deposited under NCBI Accession No. QQBEC7 (Chee et al., *Curr. Top. Microbiol. Immunol* 154, 125-169, 1990; Weston and Barrell, J. Mol. Biol. 192, 177-208, 1986), and preferably being a glycoprotein having at least one transmembrane region, or a related polypeptide of HCMV or other β-herpesvirus of humans having at least about 80% amino acid sequence identity to said sequence.

A particularly preferred epitope of US6 has an amino acid sequence set forth in SEQ ID NO: 303 (LYLCCGITL).

As used herein, the term "US11" or "HCMV US11" or "US11 antigen" or similar term shall be taken to mean a polypeptide of HCMV having the publicly available amino acid sequence deposited under NCBI Accession Nos. NC 001347 (Chee et al., *Curr. Top. Microbiol. Immunol* 154, 125-169, 1990; Bankier et al., *DNA Seq* 2, 1-12, 1991), or a related polypeptide of HCMV or other β-herpesvirus of humans having at least about 80% amino acid sequence identity to said sequence.

A particularly preferred epitope of US11 has an amino acid sequence selected from the group consisting of: SEQ ID NO: 302 (YYVECEPRC); SEQ ID NO: 304 (TLFDEPPPLV); SEQ ID NO: 305 (TPRVYYQTL); SEQ ID NO: 306 (APVAGSMPEL); and SEQ ID NO: 307 (SESLVAKRY).

As will be known to those skilled in the art, a minimum CTL epitope is restricted to CD8+ T cells expressing particular subsets of HLA Class I molecules. Preferably, the CTL epitope of the present invention is restricted to HLA alleles selected from the group consisting of: HLA A1, HLA A2, HLA A3, HLA A23, HLA A24, HLA A26, HLA A29, HLA A30, HLA B7, HLA B8, HLA B27, HLA B35, HLA B41, HLA B44, HLA B57, and HLA B58. The particular HLA restrictions for the epitopes of the invention are provided herein in Tables 1, 3 and 4.

In a particularly preferred embodiment, the pp28-derived epitope of the invention is restricted to an HLA allele selected from the group consisting of: HLA A1, HLA A2, HLA A3, and HLA B27.

In a particularly preferred embodiment, the pp50-derived epitope of the invention is restricted to an HLA allele selected from the group consisting of: HLA A1, HLA A2, HLA A3, HLA B27 and HLA B44.

In a particularly preferred embodiment, the pp65-derived epitope of the invention is restricted to an HLA allele selected from the group consisting of: HLA A1, HLA A2, HLA A3, HLA A24, HLA B7, HLA B8, HLA B27, HLA B35, HLA B44, HLA B57, and HLA B58.

In a particularly preferred embodiment, the pp71-derived epitope of the invention is restricted to an HLA allele selected from the group consisting of: HLA A1, HLA A2, HLA A24, and HLA B44.

In a particularly preferred embodiment, the pp150-derived epitope of the invention is restricted to an HLA allele selected from the group consisting of: HLA A1, HLA A2, HLA B7 and HLA B8.

In a particularly preferred embodiment, the gB-derived epitope of the invention is restricted to an HLA allele selected from the group consisting of: HLA A1, HLA A2, HLA A3, HLA A24, HLA A29, HLA B41, HLA DR7 and HLA DR*.

In a particularly preferred embodiment, the gH-derived epitope of the invention is restricted to an HLA allele selected from the group consisting of: HLA A1, HLA A2, HLA A3, HLA A24, HLA A26, HLA B7, HLA B27, and HLA B44.

In a particularly preferred embodiment, the IE-1-derived epitope of the invention is restricted to an HLA allele selected from the group consisting of: HLA A1, HLA A2, HLA A3, HLA A23, HLA A24, HLA A30, HLA B7, HLA B8 and HLA B27.

In a particularly preferred embodiment, the IE-2-derived epitope of the invention is restricted to an HLA allele selected from the group consisting of: HLA A1, HLA A2, HLA A3, HLA B8, HLA 835 and HLA B41.

In a particularly preferred embodiment, the UL18-derived epitope of the invention is restricted to an HLA allele selected from the group consisting of: HLA A2 and HLA B44.

In a particularly preferred embodiment, the US2-derived epitope of the invention is restricted to HLA A2 or HLA A24.

In a particularly preferred embodiment, the US3-derived epitope of the invention is restricted to HLA A2 or HLA A24.

In a particularly preferred embodiment, the US6-derived epitope of the invention is restricted to HLA A24.

In a particularly preferred embodiment, the US11-derived epitope of the invention is restricted to an HLA allele selected from the group consisting of: HLA A2, HLA A24, HLA B7, and HLA B44.

Preferably, the immunologically active peptides of the invention display HLA supertype specificity. Such epitopes are clearly preferred in vaccine formulations, because they reduce the total number of epitopes required to cover a significant proportion of the population irrespective of ethnicity, thereby minimizing formulation difficulties. For example, CTLs specific for the HLA A23-restricted epitope of HCMV IE-1 set forth in SEQ ID NOs: 116 or 117 recognizes peptide-sensitized target cells expressing HLA A23, HLA A24, and HLA A30. Additionally, the epitope from HCMV IE-1 set forth in SEQ ID NO: 109 is restricted to both HLA B7 and HLA B8. Additionally, CTLs specific for the epitope from HCMV pp65 set forth in SEQ ID NOs: 57 or 69 recognizes peptide-sensitized target cells expressing HLA A1 and HLA A24. Additionally, CTLs specific for the epitope from HCMV pp65 set forth in SEQ ID NOs: 63, 80 or 81 recognizes peptide-sensitized target cells expressing HLA B57 and HLA B58.

Preferably, the immunologically active peptide of the invention additionally comprises one or more CD4+determinants sufficient to facilitate a T-helper function in the context of an MHC class II molecule on the surface of an antigen presenting cell (APC) of a human subject infected with HCMV. For example, the present inventors provide herein several 20-mer peptides comprising contiguous or overlapping CTL epitopes and T-helper epitope functions as evidenced by their having the ability to bind to both CD4+ and CD8+ cells. Such a peptide has an advantage over a minimal CTL epitope of not necessarily requiring the inclusion of an exogenous T-helper epitope in a vaccine formulation.

For example, a preferred epitope of pp65 comprising both CTL and T-helper epitopes has an amino acid sequence selected from the group consisting of: SEQ ID NO:70 (PQYSEHPTFTSQYRIQGKLE); SEQ ID NO: 76 (QYDPVAALFFFDIDLLLQRG); SEQ ID NO: 77 (IIKPGKISHIMLDVAFTSHE); SEQ ID NO: 80 (MNGQQIFLEVQAIRETVELR); SEQ ID NO: 81 (QAIRETVELRQYDPVMLFF); SEQ ID NO: 87 (YYTSAFVFPTKDVALRHWC); SEQ ID NO: 88 (VTTERKTPRVTGGGAMAGAS); SEQ ID NO: 90 (SICPSQEPMSIYVYALPLKM); SEQ ID NO: 92 (QQNQWKEPDVYYTSAFVFPT); and SEQ ID NO: 94 (TGGGAMAGASTSAGRKRKSA).

A particularly preferred epitope of pp150 comprising both CTL and T-helper epitopes has the amino acid sequence set forth in SEQ ID NO: 147 (WPRERAWALKNPHLAYNPFR).

A particularly preferred epitope of gB comprising both CTL and T-helper epitopes has an amino acid sequence set forth in SEQ ID NO: 192 (RSYAYIYTTYLLGSNTEYVA) or SEQ ID NO: 195 (MQLIPDDYSNTHSTRYVTVK).

A particularly preferred epitope of gH comprising both CTL and T-helper epitopes has the amino acid sequence set forth in SEQ ID NO: 249 (RQTEKHELLVLVKKAQLNRH).

A particularly preferred epitope of IE-1 comprising both CTL and T-helper epitopes will consist of the amino acid sequence set forth in SEQ ID NO: 117 (CSPDEIMAYAQKIFKILDEE).

A particularly preferred epitope of IE-2 comprising both CTL and T-helper epitopes has an amino acid sequence selected from the group consisting of: SEQ ID NO: 269 (TAAKAYAVGQFEQPTETPPE); SEQ ID NO: 270 (FEQPTETPPEDLDTLSLAIE); SEQ ID NO: 279 (SSSSSSCSSASDSESESEEM); and SEQ ID NO: 283 (SDSESESEEMKCSSGGGASV).

By "functionally equivalent variant" of an epitope exemplified herein is meant a peptide of the same length as said epitope and like HLA specificity and having substantially the same amino acid sequence as said epitope. The peptide or the structural variants disclosed herein also can be a functional part of a longer peptide epitope which produces the immunological effects disclosed herein subject to the proviso that the longer peptide does not have a different HLA specificity to the base peptide from which it is derived and is not a previously known epitope.

Functionally equivalent sequence variants can be designed and/or constructed by those skilled in the art based upon the present disclosure without undue experimentation. For example, it has been established that individual MHC Class I molecules preferentially bind peptides having an amino acid sequence that includes one or more invariant "anchor positions" that allow the peptide to bind to MHC Class I molecules with high affinity (K. Falk et al., Nature 351, 290-296, 1991). Additionally, amino acids other than those at anchor positions also contribute to the specificity of peptide binding to MHC Class I molecules. Preferred variants of the exemplified peptides will retain such residues of the base peptides.

Preferably, the variant peptide, with the anchor positions of the base peptide intact will also consist of an amino acid sequence selected from the group consisting of:

(i) a sequence that interacts at a significant level with a MHC Class I allele as determined using a predictive algorithm for determining MHC Class I-binding epitopes, such as, for example, the SYFPEITHI algorithm of the University of Tuebingen, Germany, or the algorithm of the HLA Peptide Binding Predictions program of the BioInformatics and Molecular Analysis Section (BIMAS) of the National Institutes of Health of the Government of the United States of America;

(ii) a sequence that binds to and/or stabilizes an MHC Class I molecule on the surface of an APC irrespective of whether or not said T cell is in a substantially isolated form, such as, for example in the PBMC fraction or buffy coat fraction of a sample obtained from a human subject, or alternatively, in its natural state;

(iii) a sequence that induces a memory CTL response or elicits IFN-γ expression by a T cell, such as, for example, a CD8+ T cell, cytotoxic T cell (CTL) or effector T cell, irrespective of whether or not said T cell is in a substantially isolated form, such as, for example in the PBMC fraction or buffy coat fraction of a sample obtained from a human subject, or alternatively, in its natural state; and (iv) a sequence that stimulates CTL activity in a standard cytotoxicity assay.

The determination of such criteria is readily achievable from the disclosure provided herein.

Even more preferably, a functionally equivalent variant comprises a sequence that satisfies at least, preferably at least two and more preferably all three functional criteria recited at paragraphs (ii) through (iv) supra. Even more preferably, a CTL epitope as defined herein comprises a sequence that additionally satisfies criterion (i) supra.

Preferred variants will typically include conservative amino acid substitutions relative to the sequence of the base peptide, such as, for example, consisting of the substitution of one amino acid for another residue of like hydrophobicity, size, charge, antigenicity, etc. Particularly preferred conservative amino acid substitutions are selected from the group consisting of:

(i) a substitution involving any two of glycine, alanine and proline;
(ii) a substitution involving any two of isoleucine, leucine and valine;
(iii) a substitution involving any two of methionine, threonine, serine, and cystine;
(iv) a substitution involving asparagine and glutamine;
(v) a substitution involving aspartate and glutamate;
(vi) a substitution involving lysine and arginine; and
(vii) a substitution involving any two of histidine, phenylalanine, tryptophan and tyrosine.

It is also understood in the art that the substitution of like amino acids is made effectively on the basis of hydrophilicity, particularly where the biological functional equivalent protein or peptide thereby created is intended for use in immunological embodiments, as in the present case (e.g. U.S. Pat. No. 4,554,101), In fact, the greatest local average hydrophilicity of a protein, as governed by the hydrophilicity of its adjacent amino acids, correlates with its immunogenicity and antigenicity. As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05.

Preferred derivatives of the subject peptides include lipopeptides, wherein a lipid moiety is conjugated to the amino acid sequence, said lipid moiety known to act as an adjuvant (Jung et al., *Angew Chem, Int Ed Engl* 10, 872, 1985; Martinon et al., *J Immunol* 149, 3416, 1992; Toyokuni et al., *J Am Chem Soc* 116, 395, 1994; Deprez, et al., *J Med Chem* 38, 459, 1995; Sauzet et al., *Vaccine* 13, 1339, 1995; BenMohamed et al., *Eur. J. Immunol.* 27, 1242, 1997; Wiesmuller et al., *Vaccine* 7, 29, 1989; Nardin et al., *Vaccine* 16, 590, 1998; Benmohamed, et al. *Vaccine* 18, 2843, 2000; and Obert, et al., *Vaccine* 16, 161, 1998). Suitable lipopeptides show none of the harmful side effects associated with adjuvant formulations, and both antibody and cellular responses have been observed against lipopeptides. Several different lipid moieties are known for use in lipopeptide constructs. Exemplary lipid moieties include, but are not limited to, palmitoyl, myristoyl, stearoyl and decanoyl groups or, more generally, any $C_2$ to $C_{30}$ saturated, monounsaturated, or polyunsaturated fatty acyl group is thought to be useful.

The lipoamino acid S-[2,3-bis(palmitoyloxy)propyl]cysteine, also known as $Pam_3Cys$-OH (Wiesmuller et al., *Z. Physiol. Chem.* 364 593, 1983), is a synthetic version of the N-terminal moiety of Braun's lipoprotein that spans the inner and outer membranes of Gram negative bacteria. U.S. Pat. No. 5,700,910 to Metzger et al (*Dec.* 23, 1997) describes several N-acyl-S-(2-hydroxyalkyl)cysteines for use as intermediates in the preparation of lipopeptides that are used as synthetic adjuvants, B lymphocyte stimulants, macrophage stimulants, or synthetic vaccines. Metzger et al also teach the use of such compounds as intermediates in the synthesis of $Pam_3Cys$-OH (Wiesmuller et al., *Z. Physiol. Chem.* 364, 593, 1983), and of lipopeptides that comprise this lipoamino acid or an analog thereof at the N-terminus. According to Metzger et al., the peptide moiety of the lipopeptides are conjugated to the lipoamino acid moiety by removal of the C-terminal protective groups in the lipoamino acid, and then using the resultant compound as a substrate for lipopeptide synthesis, such as in solid phase peptide synthesis. $Pam_3Cys$ has been shown to be capable of stimulating virus-specific cytotoxic T lymphocyte (CTL) responses against influenza virus-infected cells (Deres et al., *Nature* 342, 561, 1989) and to elicit protective antibodies against foot-and-mouth disease (Wiesmuller et al., *Vaccine* 7, 29, 1989; U.S. Pat. No. 6,024,964 to Jung et al., *Feb.* 15, 2000) when coupled to the appropriate synthetic CTL epitopes. The advantage of using $Pam_3Cys$ in such vaccines is that the compound is a membrane anchor compound (i.e. it can penetrate into the plasma membrane of a cell to enhance the induction of cytotoxic T-lymphocytes in response to specific CTL epitopes attached via their N-termini to the lipoamino acid.

$Pam_2Cys$, a synthetic lipoamino acid comprising the lipid moiety of macrophage-activating lipopeptide (i.e. MALP-2), has been recently synthesized (Metzger et al., *J Pept. Sci* 1, 184, 1995). $Pam_2Cys$ is reported to be a more potent simulator of splenocytes and macrophages than $Pam_3Cys$ (Metzger et al., *J Pept. Sci* 1, 184, 1995; Muhlradt et al., *J Exp Med* 185, 1951, 1997; and Muhlradt et al., *Infect Immun* 66, 4804, 1998).

Alternatively, or in addition to the conjugation of one or more lipid moieties to the epitope of the invention, the epitopes are modified by the addition of one or more other epitopes, such as, for example, one or more HCMV B cell epitopes, HCMV T-helper epitopes or promiscuous/permissive T-helper epitopes. In this respect, the generation of an antibody response against a given antigen requires the generation of a strong T helper cell response (Vitiello et al., *J. Clin. Invest.* 95, 341-349, 1995; Livingston et al, *J. Immunol.* 159, 1383-1392, 1997). Accordingly, it is particularly preferred to derivatize the subject CTL epitopes in this manner. Alternatively, promiscuous or permissive T-helper epitope-containing peptides are administered in conjunction with the antigen. Examples of promiscuous or permissive T-helper epitopes are tetanus toxoid peptide, *Plasmodium falciparum* pfg27, lactate dehydrogenase, and HIVgp120 (Contreas et al., *Infect. Immun,* 66, 3579-3590, 1998; Gaudebout et al., *J. A.I.D.S. Human Retrovirol* 14, 91-101, 1997; Kaumaya et al, *J. Mol. Recog.* 6, 81-94, 1993; and Fem and Good *J. Immunol.* 148, 907-913, 1992). Ghosh et al., *Immunol* 104, 58-66, 2001 and International Patent Application No. PCT/AU00/00070 (WO 00/46390) also describe T-helper epitopes from the fusion protein of Canine Distemper Virus (CDV-F). Certain promiscuous T-helper epitopes induce strong B cell responses to a given antigen, and can bypass certain haplotype restricted immune responses (Kaumaya et al., *J. Mol. Recog.* 6, 81-94, 1993).

Alternatively, or in addition, the peptide is derivatized by covalent linkage to an adjuvant which is known for immunization purposes, such as, for example, muralydipeptide, lipid or lipopolysaccharide.

The peptide of the invention is readily synthesized using standard techniques, such as the Merrifield method of synthesis (Merrifield, *J Am Chem Soc,* 85:2149-2154, 1963) and the myriad of available improvements on that technology (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in The Peptides (Gross, E. and Meienhofer, J. eds.), vol. 2, pp. 1-284, Academic Press, New York; Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int J. Peptide Protein Res. 25, 449-474.

Preferably, the peptide is synthesized on a solid phase support, such as, for example, a polystyrene gel bead comprising polystyrene cross-linked with divinylbenzene, preferably 1% (w.w) divinylbenzene, which is further swollen using lipophilic solvent, such as, for example dichloromethane or dimethylformamide (DMF). The polystyrene can be functionalized by addition of chloromethane or amino methyl groups. Alternatively, cross-linked and functonalized polydimethyl-acrylamide gel can be used once swollen and solvated using DMF or dipolar aprotic solvent. Other solid phase supports known to those skilled in the art can also be used for peptide synthesis, such as, for example, polyethylene glycol-derived bead produced by grafting polyethylene glycol to the surface of inert polystyrene beads. Preferred commercially available solid phase supports include PAL-PEG-PS, PAC-PEG-PS, KA, KR, or TGR (Applied Biosystems, CA 94404, USA).

For solid phase peptide synthesis, blocking groups that are stable to the repeated treatments necessary for removal of the amino blocking group of the growing peptide chain and for repeated amino acid couplings, are used for protecting the amino acid side-chains during synthesis and for masking undesired reactivity of the α-amino, carboxyl or side chain functional groups. Blocking groups (also called protecting groups or masking groups) thus protect the amino group of the amino acid having an activated carboxyl group that is involved in the coupling reaction, or protect the carboxyl group of the amino acid having an acylated amino group that is involved in the coupling reaction.

During synthesis, coupling occurs following removal of a blocking group without the disruption of a peptide bond, or any protecting group attached to another part of the peptide. Additionally, the peptide-resin anchorage that protects the C-terminus of the peptide is protected throughout the synthetic process until cleavage from the resin is required. Accordingly, by the judicious selection of orthogonally protected α-amino acids, amino acids are added at desired locations to a growing peptide whilst it is still attached to the resin.

Preferred amino blocking groups are easily removable but sufficiently stable to survive conditions for the coupling reaction and other manipulations, such as, for example, modifications to the side-chain groups.

Preferred amino blocking groups are selected from the group consisting of: (i) a benzyloxycarbonyl group (Z or carbocenzoxy) that is removed easily by catalytic hydrogenation at room temperature and ordinary pressure, or using sodium in liquid ammonia and hydrobromic acid in acetic acid; (ii) a urethane derivative; (iii) a t-Butoxycarbonyl group (Boc) that is introduced using t-butoxycarbonyl azide or di-tert-butyidicarbonate and removed using mild acid such as, for example, trifluoroacetic acid (50% TFA in dichloromethane), or HCl in acetic acid/dioxane/ethylacetate; (iv) a 9-fluorenylmethyloxycarbonyl group (Fmoc) that is cleaved under mildly basic, non-hydrolytic conditions, such as, for example, using a primary or secondary amine (eg. 20% piperidine in dimethyl formamide); (v) a 2-(4-biphenylyl) propyl (2)oxycarbonyl group (Bpoc); (vi) a 2-nitro-phenylsulfenyl group (Nps); and (vii) a dithia-succionyl group (Dts).

Boc is widely used to protect the N-terminus in Fmoc chemistry, or Fmoc is widely used to protect the N-terminus in Boc chemistry.

Side chain-protecting groups will vary for the functional side chains of the amino acids forming the peptide being synthesized. Side-chain protecting groups are generally based on the Bzl group or the tBu group. Amino acids having alcohols or carboxylic acids in the side-chain are protected as Bzl ethers, Bzl esters, cHex esters, tBu ethers, or tBu esters. Side-chain protection of Fmoc amino acids requires blocking groups that are ideally base stable and weak acid (TFA) labile. For example, the epsilon-amino group of Lysine is protected using Mtt (eg. Fmoc-lysine(Mtt)-OH). Alternatively, a halogenated benzyl derivative such as CIZ is used to protect lysine is enhanced acid stability is required. The thiol group of Cystine, the imidazole of Histidine, or guanidino group of Arginine, generally require specialised protection. Many different protecting groups for peptide synthesis have been described (see The Peptides, Gross et al. eds., Vol. 3, Academic Press, New York, 1981). For example, the 4-methoxy-2,3,6-trimethylphenylsulfonyl (Nd-Mtr) group is useful for Arginine side-chain protection, however deprotection of Arg (Mtr) requires prolonged TFA treatment. A number of soft acid (TFA, thalium (III) trifluoroacetate/TFA) labile groups, or TFA stable but thalium (III) trifluoroacetate/TFA labile groups, or soft acid stable groups are used to protect Cystine.

The two most widely used protection strategies are the Boc/Bzl- and the Fmoc/tBu-strategies. In Boc/Bzl, Boc is used for amino protection and the side-chains of the various amino acids are protected using Bzl- or cHex-based protecting groups. A Boc group is stable under catalytic hydrogenation conditions and is used orthogonally along with a Z group for protection of many side chain groups. In Fmoc/tBu, Fmoc is used for amino protection and the side-chains are protected with tBu-based protecting groups.

Alternatively, the peptide of the invention is produced by the recombinant expression of nucleic acid encoding the amino acid sequence of said peptide. The appropriate nucleotide sequence of said nucleic acid is readily derived from the amino acid sequence data provided herein, using the genetic code in combination with codon preference tables for the organism in which expression of the peptide is to be carried out Such methods are well known to those skilled in the art. Accordingly, a further embodiment of the invention clearly extends to an isolated nucleic acid comprising a nucleotide sequence that encodes a peptide of the invention having an amino acid sequence as disclosed herein in any one of SEQ ID NOs: 22-318.

Once the appropriate nucleotide sequence encoding the peptide epitope has been determined, nucleic acid encoding the epitopes described herein is produced by standard oligonucleotide synthesis. Preferably, the oligonucleotide is synthesized with linker or adaptor sequences at the 5'- and 3'-ends to facilitate subsequent cloning into a suitable vector system using standard techniques. For expressing a peptide by recombinant means, the nucleic acid encoding said peptide is placed in operable connection with a promoter or other regulatory sequence capable of regulating expression in a cell-free system or cellular system.

Placing a nucleic acid molecule under the regulatory control of, i.e., "in operable connection with", a promoter sequence means positioning said molecule such that expression is controlled by the promoter sequence, generally by positioning the promoter 5' (upstream) of the peptide-encoding sequence.

The prerequisite for producing intact polypeptides and peptides in bacteria such as E. coli is the use of a strong promoter with an effective ribosome binding site. Typical promoters suitable for expression in bacterial cells such as E. coli include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in E. coli are well-known in the art and are described, for example, in Ausubel et al (In: Current Protocols in Molecular Biology. Wiley Interscience, ISBN 047150338, 1987) or Sambrook et al (In: Molecular cloning, A laboratory manual, second edition, Cold Spring Harbor Laboratory, Cold Spring Harbor, N.Y., 1989). Numerous plasmids with suitable promoter sequences for expression in bacteria and efficient ribosome binding sites have been described, such as for example, pKC30 ($\lambda_L$: Shimatake and Rosenberg, Nature 292, 128, 1981); pKK173-3 (tac: Amann and Brosius, Gene 40, 183, 1985), pET-3 (T7: Studier and Moffat, J. Mol. Bio. 189, 113, 1986); the pBAD/TOPO or pBAD/Thio-TOPO series of vectors containing an arabinose-inducible promoter (Invitrogen, Carlsbad, Calif.), the latter of which is designed to also produce fusion proteins with thioredoxin to enhance solubility of the expressed protein; the pFLEX series of expression vectors (Pfizer Inc., CT, USA); or the pQE series of expression vectors (Qiagen, CA), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (eg. 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., Mol. Cell. Biol., 11, 1785, 1991). The vector pcDNA 3.1 myc-His (Invitrogen) is particularly preferred for expressing a secreted form of the peptide of the invention or a derivative thereof in 293T cells, wherein the expressed peptide or protein can be purified free of conspecific proteins, using standard affinity techniques that employ a Nickel column to bind the protein via the His tag.

A wide range of additional host/vector systems suitable for expressing the peptide of the invention or an immunological derivative thereof are available publicly, and described, for example, in Sambrook et al (In: Molecular cloning, A laboratory manual, second edition, Cold Spring Harbor Laboratory, Cold Spring Harbor, N.Y., 1989).

Means for introducing the nucleic acid encoding the peptide or a gene construct comprising same into a cell for expression are well-known to those skilled in the art The technique used for a given organism depends on the known successful techniques. Means for introducing recombinant DNA into animal cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

2. Isolated HCMV Polyepitopes

A second aspect the present invention provides an immunologically active polyepitope peptide comprising two or more of the cytotoxic T-lymphocyte (CTL) epitopes of the invention described herein above.

The number of CTL epitopes contained within a single polyepitope peptide can be readily determined by those skilled in the art.

In the case of synthetic peptides, the maximum number of CTL epitopes to be included in a single polyepitope peptide is constrained by the efficiency of peptide synthesis, and, in general, a peptide of up to 400 amino acids, preferably up to 350 amino acids, more preferably up to 300 amino acids, even more preferably up to 250 or 200 or 0.150 or 100 or 50 amino acids in length is readily synthesized. This means that as many as about 45 distinct CTL epitopes of the present invention are readily included in a synthetic polyepitope peptide. As will be known to those skilled in the art, the efficiency of peptide synthesis is enhanced for shorter peptides. In a particularly preferred embodiment of the invention, a synthetic polyepitope peptide comprises about 30-35 of the CTL epitopes described herein.

For recombinant polyepitope peptides expressed in isolated cells that have been transfected with an expression vector comprising nucleic acid encoding the polyepitope peptide, a much larger number of distinct CTL epitopes can be included in a single polyepitope peptide. As will be known to those skilled in the art, nucleic acid manipulations can be readily performed on nucleic acid consisting of up to several kilobases of nucleotides. Methods for recombinant peptide production are described in detail herein above and in the general texts referred to at page 2 and incorporated herein by reference.

For synthetic nucleic acid encoding the polyepitope of the invention, synthetic oligonucleotides of up to about 50-110 nucleotides in length, each with a coding capacity of about 3-4 contiguous CTL epitopes are readily produced at high efficiency, and these can be cloned in tandem in a suitable vector without undue experimentation to provide the requisite number of contiguous CTL epitopes.

Preferably, the polyepitope peptide of the invention comprises about 5-10 CTL epitopes, more preferably about 10-15 CTL epitopes, even more preferably about 15-20 CTL epitopes, still even more preferably about 20-25 CTL epitopes and still even more preferably about 25-30 CTL epitopes. In a particularly preferred embodiment exemplified herein, there is provided an isolated polyepitope peptide comprising 26 or 27 distinct CTL epitopes of the invention.

As will be known to those skilled in the art of producing polyepitopes, it is not necessary to introduce any spacing between the individual epitope monomers of a polyepitope, or alternatively, between the peptide moiety and any lipid moiety introduced to the epitope or polyepitope.

Preferably, the polyepitope of the invention is not restricted to a single MHC Class I haplotype. Even more preferably, polyepitopes are restricted to a sufficient number of MHC Class I molecules to provide coverage for a significant proportion of the general population irrespective of racial origin or ethnicity. Those skilled in the art will readily be in a position to determine the number of individual HCMV CTL epitopes required to provide coverage of any given population from the HLA specificity data provided herein.

Preferably, a polyepitope peptide at least comprises amino acid sequences that are restricted to MHC Class I alleles selected from the group consisting of: HLA A1, HLA A2, HLA A3, HLA A11, HLA A23, HLA A24, HLA A26, HLA A29, HLA A30, HLA A68, HLA B7, HLA B8, HLA B27, HLA B35, HLA B41, HLA B44, HLA B57, and HLA B58. Those skilled in the art will readily be able to achieve such a broad restriction based upon the HLA restriction data provided herein for the epitopes of the invention and those epitopes of the prior art, the only proviso being that at least one CTL epitope of said polyepitope is other than an epitope selected from the group consisting of SEQ ID Nos: 1-21.

More preferably, the polyepitope peptide is restricted MHC Class I alleles selected from the group consisting of: HLA A1, HLA A2, HLA A3, HLA A11, HLA A23, HLA A24, HLA A26, HLA A30, HLA A68, HLA B7, HLA B8, HLA B27, HLA B35, HLA B41, HLA B44, HLA B57 and HLA B58. Such a broad HLA restriction is readily achieved using CTL epitopes having amino acid sequences selected from the group consisting of: SEQ ID NO: 13 (YSEHPTFTSQY; HLA A1); SEQ ID NO: 165 (VTEHDTLLY; HLA A1); SEQ ID NO: 5 (NLVPMVATV; HLA A2); SEQ ID NO: 101 (VLEETSVML; HLA A2); SEQ ID NO: 7 (RIFAELEGV); HLA A2); SEQ ID NO: 254 (IIYTRNHEV; HLA A2); SEQ ID No: 135 (IMREFNSYK; HLA A3); SEQ ID NO: 21 (TTVYPPSSTAK; HLA A3); SEQ ID No: 1 (SVLGPISGHVLK; HLA A11); SEQ ID NO: 116 (AYAQKIFKIL; HLA A23/A24/A30); SEQ ID NO: 33 (QYDPVAALF; HLA A24); SEQ ID NO: 2 (FTSQYRIQGKL; HLA A26); SEQ ID NO: 3 (FVFPTKDVALR; HLA A68); SEQ ID NO: 15 (DIYRIFAEL; HLA A26); SEQ ID NO: 3 (FVFPTKDVALR; HLA A68); SEQ ID NO: 134 (NVRRSWEEL; HLA B7); SEQ ID NO: 41 (QARLTVSGL; HLA B7); SEQ ID NO: 8 (TPRVTGGGAM; HLA B7); SEQ ID NO: 109 (KARAKKDEL; HLA B7/B8); SEQ ID NO: 113 (QIKVRVDMV; HLA B8); SEQ ID NO: 112 (ELRRKMMYM; HLA B8); SEQ ID NO: 42 (RRRHRQDAL); HLA B8); SEQ ID No: 162 (ARVYEIKCR; HLA B27); SEQ ID NO: 66 (CPSQEPMSIYVY; HLA B35); SEQ ID NO: 4 (FPTKDVAL; HLA B35); SEQ ID NO: 55 (IPSINVHHY; HLA B35); SEQ ID No: 260 (FEQPTETPP; HLA B41); SEQ ID NO: 189 (YAYIYTTYL; HLA B41); SEQ ID No: 56 (QEFFWDANDIY; HLA B44); SEQ ID NO: 170 (YEQHKITSY; HLA B44); SEQ ID NO: 51 (QEPMSIYVY; HLA B44); SEQ ID NO: 47 (SEHPTFTSQY; HLA B44); and SEQ ID NO: 63 (QAIRETVEL; HLA B57/B58), subject to the proviso that at least one of said sequences in the polyepitope peptide is other than a sequence selected from the group consisting of SEQ ID NO: 1 (SVLGPISGHVLK; HLA A11); SEQ ID NO: 2 (FTSQYRIQGKL; HLA A24); SEQ ID NO: 3 (FVFPTKDVALR; HLA A68); SEQ ID NO: 4 (FPTKDVAL; HLA B35); SEQ ID NO: 5 (NLVPMVATV; HLA B7); SEQ ID NO: 7 (RIFAELEGV; HLA A2); SEQ ID NO: 8 (TPRVTGGGAM; HLA B7); SEQ ID NO: 13 (YSEHPTFTSQY; HLA A1); SEQ ID NO: 15 (DIYRIFAEL; HLA A26); SEQ ID NO: 21 (TTVYPPSSTAK; HLA A3); and SEQ ID NO: 55 (IPSINVHHY).

Still more preferably, the polyepitope peptide is restricted MHC Class I alleles selected from the group consisting of: HLA A1, HLA A2, HLA A3, HLA A23, HLA A24, HLA A26, HLA A30, HLA B7, HLA B8, HLA B27, HLA B35, HLA B41, HLA B44, HLA B57 and HLA B58. Such a broad HLA restriction is readily achieved using CTL epitopes having amino acid sequences selected from the group consisting of: SEQ ID NO: 165 (VTEHDTLLY; HLA A1); SEQ ID NO: 101 (VLEETSVML; HLA A2); SEQ ID NO: 254 (IIYTRNHEV; HLA A2); SEQ ID NO: 135 (IMREFNSYK; HLA A3); SEQ ID NO: 116 (AYAQKIFKIL; HLA A23/A24/A30); SEQ ID NO: 33 (QYDPVAALF; HLA A24); SEQ ID NO: 37 (YVKYVYESF; HLA 26); SEQ ID NO: 134 (NVRRSWEEL; HLA B7); SEQ ID NO: 132 (KARDHLAVL; HLA 7); SEQ ID NO: 41 (QARLTVSGL; HLA B7); SEQ ID NO: 109 (KARAKKDEL; HLA B7/B8); SEQ ID NO: 113 (QIKVRVDMV; HLA B8); SEQ ID NO: 112 (ELRRKMMYM; HLA B8); SEQ ID NO: 42 (RRRHRQDAL; HLA B8); SEQ ID NO: 162 (ARVYEIKCR; HLA B27); SEQ ID NO: 66 (CPSQEPMSIYVY; HLA B35); SEQ ID NO: 260 (FEQPTETPP; HLA B41); SEQ ID NO: 189 (YAYIYTTYL; HLA B41); SEQ ID NO: 56 (QEFFWDANDIY; HLA B44); SEQ ID NO: 170 (YEQHKITSY; HLA B44); SEQ ID NO: 51 (QEPMSIYVY; HLA B44); SEQ ID NO: 47 (SEHPTFTSQY; HLA B44); and SEQ ID NO: 63 (QAIRETVEL; HLA B57/B58).

As with single epitopes, the polyepitopes of the invention preferably display HLA supertype specificity and/or preferably comprise one or more CD4+determinants sufficient to facilitate a T-helper function in a human subject infected with HCMV. Preferably, the polyepitope peptide will comprise at least one epitope having HLA supertype specificity, and more preferably two or three or four or five such epitopes. Preferably, a polyepitope peptide having HLA supertype specificity comprises an amino acid sequence selected from the group consisting of SEQ ID NO: 116; SEQ ID NO: 117; SEQ ID NO: 109; SEQ ID NO: 195; SEQ ID NO: 57; SEQ ID NO: 69; SEQ ID NO: 63; SEQ ID NO: 80; and SEQ ID NO: 81.

In a particularly preferred embodiment of the invention there is provided a polyepitope peptide having an amino acid sequence selected from the group consisting of: SEQ ID NO: 309; SEQ ID NO: 310; SEQ ID NO: 311; SEQ ID NO: 312; SEQ ID NO: 313; SEQ ID NO: 314; SEQ ID NO: 315; SEQ ID NO: 316; SEQ ID NO: 317; and SEQ ID NO: 318.

This aspect of the invention clearly encompasses a derivative or functionally equivalent variant of the polyepitope peptide.

As used herein, the term "derivative or functionally equivalent variant of the polyepitope peptide" shall be taken to include a derivative or functionally equivalent variant of any one or more CTL epitopes contained within said polyepitope peptide, or a derivative or variant as described herein above and applied to a polyepitope peptide (i.e. a sequence variant or lipopeptide of a polyepitope peptide or a polyepitope peptide having additional B cell epitopes or T-helper epitopes conjugated thereto).

The present invention clearly contemplates derivatives of the subject epitopes or polyepitopes that comprise a spacer molecule, such as, for example, a spacer that comprises carbon or an amino acid residue. Serine dimers, trimers, tetramers, etc, are particularly preferred for this purpose. Conveniently, a spacer comprising one or more conformation-stabilizing alpha-alkylamino acids (e.g. Aib) is used to prevent the alpha-helix from being destabilized. Spacers of the type X-(Ala-Aib-Ala-Aib-Ala)$_a$-Y wherein n is an integer being 2 or 4, and X and Y are protective groups, hydrogen, hydroxyl, or amino groups are particularly preferred. Preferably, such spacers are added to a lipid structure prior to its addition to the peptide, and include a terminal protected amino acid residue to facilitate the later conjugation of the modified lipoamino acid to the polypeptide.

3. Vaccine Compositions

Another aspect of the invention provides a composition for eliciting a cellular immune response in a human subject against HCMV, said composition comprising an effective amount of one or more immunologically active peptides of the invention (ie. single epitopes or polyepitopes) or a derivative or functionally equivalent variant thereof in combination with a pharmaceutically acceptable carrier, excipient, diluent and/or an adjuvant.

As used herein, the term "effective amount" means a sufficient amount of the subject peptide to produce HCMV-specific T cell activation and preferably to elicit cell mediated immunity in the subject.

The vaccine compositions of the invention may be subunit vaccines comprising the immunologically active peptides or a lipopeptide derived therefrom.

For subunit vaccines, the peptide epitope or polyepitope of the invention or derivative or variant thereof is conveniently formulated in a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills in the art.

Optionally, the vaccine formulation will also include a carrier. Although not strictly necessary to achieve antibody production, the use of a molecular weight carrier molecule is clearly encompassed by the present invention. Commonly used carrier molecules are bovine serum albumin (BSA), keyhole limpet hemocyanin (KLH), ovalbumin, mouse serum albumin, rabbit serum albumin and the like. Synthetic carriers also are used and are readily available. Means for conjugating peptides to carrier proteins are also well known in the art and include glutaraldehyde, m-maleimidobencoyl-N-hydroxysuccinimide ester, carbodiimide and bis-biazotized benzidine.

In certain situations, it may also be desirable to formulate the peptide or derivative or variant thereof with an adjuvant to enhance the immune response to the CTL epitope. Again, this is strictly not essential. Such adjuvants include all acceptable immunostimulatory compounds such as, for example, a cytokine, toxin, or synthetic composition. Exemplary adjuvants include squalene or other oil of animal origin; a block copolymer; detergent, such as Tween-80 or other nonionic detergent; oils, such as, for example, Drakeol or Marcol; vegetable oil such as, for example, peanut oil; *Corynebacterium*-derived adjuvant such as, for example, *C. parvum*; *Propionibacterium*-derived adjuvant such as, for example, P. acne; *Mycobacterium*-derived adjuvant, such as, for example, *M. bovis*; poxvirus protein, such as, for example, derived from *Vaccinia*; virus component, such as, for example, Cholera toxin; cytokine (monokine or interleukin) such as, for example, IL-1, IL-2, or IL-12; tumor necrosis factor (TNF); interferon (IFN) such as, for example, IFN-γ; BCG; aluminum hydroxide; synthetic glycopeptides, such as a muramyl dipeptide or derivative thereof, including N-acetyl-muramyl-L-threonyl-D-isoglutamine (thur-MDP), N-acetyl-normuramyl-L-alanyl-D-isoglutamine (CGP 11637, referred to as nor-MDP), or N-acetylmuramyl-L-alanyl-D-isoglutarninyl-L-alanine-2-(1'-2'-dipalmitoyl-sn-glycero-3-hydroxyphosphoryloxy)-ethylamine (CGP) 1983A, (referred to as MTP-PE); Avridine; lipid A or derivative thereof, such as, for example, monophosphoryl lipid A; dextran sulfate; DEAE-Dextran optionally combined with aluminum phosphate; carboxypolymethylene, such as, for example, Carbopol'EMA; acrylic copolymer emulsion such as, for example, Neocyl A640 (U.S. Pat. No. 5,047,238); MPL; RIBI, which contains three components extracted from bacteria; trehalose dimycolate; cell wall extract or skeleton, such as, for example, a combination of MPL and TDM and CWS in a 2% squalene/Tween 80 emulsion; or a saponified adjuvant composition comprising a saponin or a fraction thereof, such as, for example, QuilA, ISCOMATRIX, or ISCOM in combination with one or more of the adjuvants described herein or other known adjuvant.

A particularly preferred adjuvant comprises an ISCOM and/or ISCOMATRIX (CSL Limited, Parkville, Australia) to enhance the effective immune response obtained using the inventive epitope or polyepitope, and preferably, to enhance the induction of a cytotoxic T cell response in a human subject. ISCOM and ISCOMATRIX can enhance the cellular and humoral immune responses to the peptides described herein.

ISCOMATRIX are ISCOM particles that do not have an incorporated or associated antigen. An ISCOMATRIX adjuvant comprises saponins derived from the bark of *Quillaia saponaria* molina complexed with lipids, such as, for example, cholesterol and phospholipids. Under defined conditions, this complex can form particles having an average diameter of 40 nm. The immune stimulatory properties of this adjuvant are ideally suited to applications which require cell mediated immune responses. Accordingly, ISCOMATRIX particles provide both adjuvant and antigen delivery properties.

When antigens are incorporated into an ISCOMATRIX particle, or associated with a pre-formed ISCOMATRIX particle, an ISCOM is produced. An ISCOM can be prepared using Quil A (a semi-purified preparation of saponins) or purified saponin fractions. Preferred saponin preparations include, for example, ISCOPREP703 (CSL Limited) comprising a mixture of the purified saponin fractions.

In addition to adjuvants, it may be desirable to co-administer biologic response modifiers (BRM) with the peptide or variant or derivative to down regulate suppressor T cell activity. Exemplary BRM's include, but are not limited to, Cimetidine (CIM; 1200 mg/d) (Smith/Kline, PA, USA); Indomethacin (IND; 150 mg/d) (Lederle, NJ, USA); or low-dose Cyclophosphamide (CYP; 75, 150 or 300 mg/m.sup.2) (Johnson/Mead, NJ, USA).

Preferred vehicles for administration of the vaccine formulation include liposomes. Liposomes are microscopic vesicles that consist of one or more lipid bilayers surrounding aqueous compartments. (Bakker-Woudenberg et al., *Eur. J. Clin. Microbiol. Infect. Dis.* 12(Suppl. 1), S61 (1993); and Kim, *Drugs* 46, 618 (1993)). Liposomes are similar in composition to cellular membranes and as a result, liposomes generally are administered safely and are biodegradable.

Techniques for preparation of liposomes and the formulation (e.g., encapsulation) of various molecules, including peptides and oligonucleotides, with liposomes are well known to the skilled artisan.

Depending on the method of preparation, liposomes may be unilamellar or multilamellar, and can vary in size with diameters ranging from 0.02 μm to greater than 10 μm. A variety of agents are encapsulated in liposomes. Hydrophobic agents partition in the bilayers and hydrophilic agents partition within the inner aqueous space(s) (Machy et al., LIPOSOMES IN CELL BIOLOGY AND PHARMACOLOGY (John Libbey 1987), and Ostro et al., *American J. Hosp. Pharm.* 46, 1576, 1989).

Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446, 368

(1985)). In the present context, the peptide or derivative or variant thereof can be localized on the surface of the liposome, to facilitate antigen presentation without disruption of the liposome or endocytosis. Irrespective of the mechanism or delivery, however, the result is the intracellular disposition of the associated peptide or derivative or variant thereof.

Liposomal vectors may be anionic or cationic. Anionic liposomal vectors include pH sensitive liposomes which disrupt or fuse with the endosomal membrane following endocytosis and endosome acidification. Cationic liposomes are preferred for mediating mammalian cell transfection in vitro, or general delivery of nucleic acids, but are used for delivery of other therapeutics, such as peptides.

Cationic liposome preparations are made by conventional methodologies (Feigner et al, *Proc. Nat'l Acad. Sci USA* 84, 7413 (1987); Schreier, Liposome Res. 2, 145 (1992)). Commercial preparations, such as Lipofectin (Life Technologies, Inc., Gaithersburg, Md. USA), are readily available. The amount of liposomes to be administered are optimized based on a dose response curve. Feigner et al., supra.

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these liposomes are well known in the art. (See COLLOIDAL DRUG DELIVERY SYSTEMS, vol. 66, J. Kreuter, ed., Marcel Dekker, Inc. 1994).

Other forms of delivery particle, for example, microspheres and the like, also are contemplated for delivery of the peptide epitopes or polyepitopes.

Guidance in preparing suitable formulations and pharmaceutically effective vehicles, are found, for example, in REMINGTON'S PHARMACEUTICAL SCIENCES, chapters 83-92, pages 1519-1714 (Mack Publishing Company 1990) (Remington's), which are hereby incorporated by reference.

Alternatively, nucleic acid-based vaccines are produced that comprise nucleic acid, such as, for example, DNA or RNA, encoding the immunologically active peptide epitope or polyepitope and cloned into a suitable vector (eg. vaccinia, canarypox, adenovirus, or other eukaryotic virus vector).

Alternatively, the peptide is administered in the form of a cellular vaccine via the administration of autologous or allogeneic APCs or dendritic cells that have been treated in vitro so as to present the peptide on their surface.

4. Methods of Enhancing HCMV-Specific Immunity

Another aspect of the present invention provides a method of enhancing the HCMV-specific cell mediated immunity of a human subject comprising administering at least one immunologically active epitope peptide or polyepitope peptide of the invention or a derivative or a functionally equivalent variant of said peptide or a vaccine composition comprising said peptide or variant or derivative for a time and under conditions sufficient to activate a CTL and/or a CTL precursor of said subject.

By "CTL precursor" is meant a naive T cell (ie. a T cell that expresses one or more T cell receptors on its surface and is capable of proliferating and differentiating into a memory T cell or effector T cell).

Preferably, the peptide or vaccine is administered to a subject harboring a latent or active HCMV infection, or is otherwise immune suppressed or immune compromised, such as, for example, a transplant recipient, or is at risk of complications arising from HCMV infection, such as, for example, a female subject having reproductive capacity or a pregnant female. Preferably, the transplant recipient is a bone marrow transplant (BMT) recipient.

In the present context, the term "activate" means that the ability of a T cell to recognize and lyse a cell harboring HCMV is enhanced, or that the ability of a T cell to recognize a T cell epitope of an antigen of HCMV is enhanced, either transiently or in a sustained manner. The term "activate" shall also be taken to include a reactivation of a T cell population following activation of a latent HCMV infection or following re-infection with HCMV or following immunization of a previously-infected subject with a peptide or composition of the invention.

Those skilled in the art are aware that optimum T cell activation requires cognate recognition of antigen/MHC by the T cell receptor (TcR), and a co-stimulation involving the ligation of a variety of cell surface molecules on the T cell with those on an antigen presenting cell (APC). The costimulatory interactions CD28/B7, CD40UCD40 and OX40/OX40L are preferred, but not essential for T cell activation. Other costimulation pathways may operate.

Standard methods are used to determine whether or not CTL activation has occurred in the subject, such as, for example, using cytotoxicity assays, ELISPOT, or determining IFN-γ production in PBMC of the subject, essentially as described herein.

Preferably, the peptide or derivative or variant or vaccine composition is administered for a time and under conditions sufficient to elicit or enhance the expansion of CD8$^+$ T cells.

Besides supporting humoral immunity, CD4$^+$ T-helper cells function in CMI as producers of cytokines, which mediate delayed-type hypersensitivity and support CTLs and which as such are critical components of the CMI responses to intracellular pathogens. For example, major histocompatibility complex (MHC)-restricted CTL responses are supported by Th1 cells. In some cases, CD4$^+$ T-helper cells may also be required to secrete sufficient cytokine, such as, for example IL-2, to thereby facilitate the expansion of CD8$^+$ T cells or to interact with the APC thereby rendering it more competent to activate CD8$^+$ T cells. In such circumstances, the use of a 20-mer peptide comprising both CD4+ and CD8$^+$ epitopes, or alternatively, the use of a CD8$^+$ epitope of the invention in combination with a known permissive CD4$^+$ epitope, is preferred.

Still more preferably, the peptide or derivative or variant or vaccine composition is administered for a time and under conditions sufficient for HCMV-specific cell mediated immunity (CMI) to be enhanced in the subject.

By "HCMV-specific CMI" is meant that the activated and clonally expanded CTLs are MHC-restricted and specific for a CTL epitope of the invention. CTLs are classified based on antigen specificity and MHC restriction, (ie., non-specific CTLs and antigen-specific, MHC-restricted CTLs). Non-specific CTLs are composed of various cell types, including NK cells and antibody-dependent cytotoxicity, and can function very early in the immune response to decrease pathogen load, while antigen-specific responses are still being established. In contrast, MHC-restricted CTLs achieve optimal activity later than non-specific CTL, generally before antibody production. Antigen-specific CTLs inhibit or reduce the spread of HCMV and preferably terminate infection.

CTL activation, clonal expansion, or CMI can be induced systemically or compartmentally localized. In the case of compartmentally localized effects, it is preferred to utilize a vaccine composition suitable formulated for administration to that compartment. On the other hand, there are no such stringent requirements for inducing CTL activation, expansion or CMI systemically in the subject.

The effective amount of peptide to be administered, either solus or in a vaccine composition to elicit CTL activation, clonal expansion or CMI varies upon the nature of the immunogenic epitope, the route of administration, the weight, age, sex, or general health of the subject immunized, and the nature of the CTL response sought. All such variables are empirically determined by art-recognized means.

The peptide, optionally formulated with any suitable or desired carrier, adjuvant, BRM, or pharmaceutically acceptable excipient, is conveniently administered in the form of an injectable composition. Injection may be intranasal, intramuscular, sub-cutaneous, intravenous, intradermal, intraperitoneal, or by other known route. For intravenous injection, it is desirable to include one or more fluid and nutrient replenishers.

The optimum dose to be administered and the preferred route for administration are established using animal models, such as, for example, by injecting a mouse, rat, rabbit, guinea pig, dog, horse, cow, goat or pig, with a formulation comprising the peptide, and then monitoring the CTL immune response to the epitope using any conventional assay as described in the Examples.

The use of HLA A2/K$^b$ transgenic mice carrying a chimeric human-mouse Class I major histocompatibility complex (MHC) locus composed of the α1 and α2 domains of the human HLA A*0201 allele and the α3 domain of the mouse H-2 K$^b$ Class I molecules (Vitiello et al., *J. Exp. Med.* 173, 1007, 1991) is particularly preferred for testing CTL responses to the vaccine compositions of the invention comprising HLA A2-restricted peptide epitopes or polyepitopes in vivo.

In a related embodiment, the invention provides a method of enhancing the HCMV-specific cell mediated immunity of a human subject, said method comprising contacting ex vivo a T cell obtained from a human subject with an immunologically active peptide comprising a CTL epitope of a HCMV antigen or a derivative or variant thereof or a vaccine composition comprising said peptide or derivative or variant for a time and under conditions sufficient to confer HCMV activity on said T cells.

In a preferred embodiment, the invention provides a method of enhancing the HCMV-specific cell mediated immunity of a human subject, said method comprising:
(i) contacting ex vivo a T cell obtained from a human subject with an immunologically active peptide comprising a CTL epitope of a HCMV antigen or a derivative or variant thereof or a vaccine composition comprising said peptide or derivative or variant for a time and under conditions sufficient to confer HCMV activity on said T cells; and
(ii) introducing the activated T cells autologously to the subject or allogeneically to another human subject.

The T cell may be a CTL or CTL precursor cell.

The human subject from whom the T cell is obtained may be the same subject or a different subject to the subject being treated. The subject being treated can be any human subject carrying a latent or active HCMV infection or at risk of HCMV infection or reactivation of HCMV infection (eg. a female having reproductive capacity or a pregnant female or a transplant patent, including a bone marrow transplant patient) or a person who is otherwise in need of obtaining vaccination against HCMV or desirous of obtaining vaccination against HCMV.

Such adoptive transfer is preferably carried out and HCMV reactivity assayed essentially as described by Einsele et al., *Blood* 99, 3916-3922, 2002, which procedures are incorporated herein by reference.

By "HCMV activity" is meant that the T cell is rendered capable of being activated as defined herein above (ie. the T cell will recognize and lyze a cell harboring HCMV or able to recognize a T cell epitope of an antigen of HCMV, either transiently or in a sustained manner). Accordingly, it is particularly preferred for the T cell to be a CTL precursor which by the process of the invention is rendered able to recognize and lyze a cell harboring HCMV or able to recognize a T cell epitope of an antigen of HCMV, either transiently or in a sustained manner.

For such an ex vivo application, the T cell is preferably contained in a biological sample obtained from a human subject, such as, for example, a biopsy specimen comprising a primary or central lymphoid organ (eg. bone marrow or thymus) or a secondary or peripheral lymphoid organ (eg. blood, PBMC or a buffy coat fraction derived therefrom).

Preferably, the T cell or specimen comprising the T cell was obtained previously from a human subject, such as, for example, by a consulting physician who has referred the specimen to a pathology laboratory for analysis.

Preferably, the subject method further comprises obtaining a sample comprising the T cell of the subject, and more preferably, obtaining said sample from said subject.

Another aspect of the invention provides a method of providing or enhancing immunity against HCMV in an uninfected human subject comprising administering to said subject an immunologically active peptide comprising a CTL epitope of a HCMV antigen or a derivative or variant thereof or a vaccine composition comprising said peptide or derivative or variant for a time and under conditions sufficient to provide immunological memory against a future infection by HCMV.

In a related embodiment, the invention provides a method of enhancing or conferring immunity against HCMV in an uninfected human subject comprising contacting ex vivo a T cell obtained from said subject with an immunologically active peptide comprising a CTL epitope of a HCMV antigen or a derivative or variant thereof or a vaccine composition comprising said peptide or derivative or variant for a time and under conditions sufficient to confer HCMV reactivity on said T cells.

Accordingly, this aspect of the invention provides for the administration of a prophylactic vaccine to the subject, wherein the active substituent of said vaccine (i.e. the epitope or polyepitope of the invention) induces immunological memory via memory T cells in an uninfected individual. The preferred embodiments of vaccination protocols described herein for enhancing the HCMV-specific cell mediated immunity of a human subject apply mutatis mutandis to the induction of immunological memory against HCMV in a human subject.

5. Diagnostic Applications

A further aspect of the invention provides a method for determining whether or not a subject has been previously infected with HCMV, said method comprising contacting ex vivo a T cell obtained from the subject with an antigen presenting cell (APC) primed with an immunologically active peptide comprising a CTL epitope of a HCMV antigen or a derivative or variant thereof or a vaccine composition comprising said peptide or derivative or variant and determining the activation of a CTL or precursor CTL, wherein said activation of a CTL or precursor CTL indicates that the subject has been previously infected with HCMV.

The process of the subject method is also useful for monitoring the degree of immunity in an individual suffering from an HCMV infection or harboring a latent HCMV infection. Accordingly, the subject method is useful for both a quantitative analysis (ie. the degree of immunity) and a qualitative analysis (ie. infected versus non-infected) of HCMV-specific T cell immunity.

In a related embodiment, the invention provides a method for determining the level of HCMV-specific cell mediated immunity in a human subject, said method comprising contacting ex vivo a T cell obtained from the subject with an antigen presenting cell (APC) primed with an immunologically active peptide comprising a CTL epitope of a HCMV antigen or a derivative or variant thereof or a vaccine composition comprising said peptide or derivative or variant and determining the level of activation of a CTL or precursor CTL, wherein the level of activation of a CTL or precursor CTL is correlated to the level of HCMV-specific cell mediated immunity of the subject.

The human subject from whom the T cell is obtained may be the same subject or a different subject to the subject being diagnosed. The subject being diagnosed can be any human subject carrying a latent or active HCMV infection or at risk of HCMV infection or reactivation of HCMV infection (eg. a female having reproductive capacity or a pregnant female or a transplant patient, including a bone marrow transplant patient) or a person who is otherwise in need of obtaining a determination of their HCMV status or desirous of obtaining their HCMV status.

For such an ex vivo application, the T cell is preferably contained in a biological sample obtained from a human subject, such as, for example, a biopsy specimen comprising a primary or central lymphoid organ (eg. bone marrow or thymus) or a secondary or peripheral lymphoid organ (eg. blood, PBMC or a buffy coat fraction derived therefrom).

Preferably, the T cell or specimen comprising the T cell was obtained previously from a human subject, such as, for example, by a consulting physician who has referred the specimen to a pathology laboratory for analysis.

Preferably, the subject method further comprises obtaining a sample comprising the T cell of the subject, and more preferably, obtaining said sample from said subject.

For determining the activation of a CTL or precursor CTL or the level of HCMV-specific cell mediated immunity in a human subject, standard methods for assaying the number of T cells in a specimen that are HCMV-specific, or for determining the ability of T cells in a specimen to become activated in a HCMV-specific manner, can be used. Preferred assay formats include a cytotoxicity assay, assay for IFN-γ production, such as, for example, the standard chromium release assay, or ELISPOT assay as described herein.

MHC class 1 Tetramer assays can also be utilized, particularly for the HCMV epitope-specific quantitation of $CD8^+$ T cells (Altman et al., *Science* 274, 94-96, 1996; Ogg et al., *Curr Opin Immunol.* 10, 393-396, 1998). To produce tetramers, the carboxyl terminus of an MHC molecule, such as, for example, the HLA A2 heavy chain, is associated with a specific peptide epitope or polyepitope, and treated so as to form a tetramer complex having bound thereto a suitable reporter molecule, preferably a fluorochrome such as, for example, fluoroscein isothiocyanate (FITC), phycoerythrin, phycocyanin or allophycocyanin. Tetramer formation is achieved, for example, by producing the MHC-peptide fusion protein as a biotinylated molecule and then mixing the biotinylated MHC-peptide with deglycosylated avidin that has been labeled with a fluorophore, at a molar ratio of 4:1. The Tetramers produced bind to a distinct set of $CD8^+$ T cell receptors (TcRs) on a subset of $CD8^+$ T cells derived from the subject (eg in whole blood or a PBMC sample), to which the peptide is HLA restricted. There is no requirement for in vitro T cell activation or expansion. Following binding, and washing of the T cells to remove unbound or non-specifically bound Tetramer, the number of $CD8^+$ cells binding specifically to the HLA-peptide Tetramer is readily quantified by standard flow cytometry methods, such as, for example, using a FACSCalibur Flow cytometer (Becton Dickinson). The Tetramers can also be attached to paramagnetic particles or magnetic beads to facilitate removal of non-specifically bound reporter and cell sorting. Such particles are readily available from commercial sources (eg. Beckman Coulter, Inc., San Diego, Calif., USA) Tetramer staining does not kill the labeled cells; therefore cell integrity is maintained for further analysis. MHC Tetramers enable the accurate quantitative analyses of specific cellular immune responses, even for extremely rare events that occur at less than 1% of $CD8^+$T cells (Bodinier et al., *Nature Med.* 6, 707-710, 2000; Ogg et al., *Curr Opin Immunol.* 10, 393-396, 1998).

The total number of $CD8^+$ cells in a sample can also be determined readily, such as, for example, by incubating the sample with a monoclonal antibody against CD8 conjugated to a different reporter molecule to that used for detecting the Tetramer. Such antibodies are readily available (eg. Becton Dickinson). The relative intensifies of the signals from the two reporter molecules used allows quantification of both the total number of $CD8^+$ cells and Tetramer-bound T cells and a determination of the proportion of total T cells bound to the Tetramer.

Cytokine assays can also be used to determine the activation of a CTL or precursor CTL or the level of HCMV-specific cell mediated immunity in a human subject. In such assays, a cytokine such as, for example, IL-2, is detected or production of a cytokine is determined as an indicator of the level of HCMV antigen-reactive T cells. As explained herein above, $CD4^+$ T-helper cells function in CMI as producers of cytokines, such as, for example IL-2, to facilitate the expansion of $CD8^+$ T cells or to interact with the APC thereby rendering it more competent to activate $CD8^+$ T cells. Accordingly, cytokine production is an indirect measure of T cell activation.

Preferably, the cytokine assay format used for determining the level of a cytokine or cytokine production is essentially as described by Petrovsky and Harrison, *J. Immunol. Methods* 186, 37-46, 1995, which assay reference is incorporated herein.

Preferably, the cytokine assay is performed on whole blood or PBMC or buffy coat.

6. Production of HCMV-Specific T Cells for Therapeutic/Diagnostic applications

Another aspect of the present invention relates to a method of producing an HCMV-specific CTL comprising contacting a T cell with an isolated peptide of the present invention or an APC primed with an isolated peptide of the invention, culturing the T cell and selecting T cells that proliferate.

By "HCMV-specific CTL" is meant a T cell or precursor T cell that is capable of recognizing a CTL epitope of HCMV, or a polyepitope comprising said epitope, or lyzing a human cell infected with HCMV.

The T cell may be a human or non-human cell, such as, for exmaple, an effector T cell or memory T cell or CTL precursor. The T cell includes (a) a cell possessing MHC class I molecules capable of recognizing the peptide epitope or polyepitope and (b) cells capable of being converted to CTLs having the potential of cells (a).

The CTLs are produced in vivo or ex vivo. For in vivo CTL production, the peptide or composition comprising same is administered to an animal for a time and under conditions sufficient for HCMV-specific CTLs to be produced. For ex vivo production, cells that have been removed from the animal body are contacted with the peptide or an APC that presents the peptide or an autologous primed LCL.

Preferably, monoclonal or polyclonal HCMV-specific CTLs are generated by stimulating PBMCs from healthy seropositive donors with autologous LCLs that have been previously primed or sensitized using an isolated epitope peptide or polyepitope peptide of the invention, or a vaccine composition of the invention comprising said epitope peptide or polyepitope peptide. In a particularly preferred embodiment, a recombinant virus expressing an HCMV antigen or an epitope peptide or a polyepitope peptide, such as, for example a recombinant vaccinia virus, is used to prime the LCL. Means for sensitizing LCLs will be well known to those skilled in the art.

In the present context, "sensitize" includes, for example, the transfection or transformation of an LCL with nucleic acid encoding said peptide (eg. in the form of a virus subgenomic fragment or synthetic nucleic acid cloned into a suitable expression vector, vaccine vector, etc), and the contacting of an LCL with an isolated peptide, or antigen or virus protein.

In a particularly preferred embodiment, T-cell clones from individual donors are generated by a process essentially as described in Example 9.

Non-human animal cells are suitable for use in diagnostic applications, such as, for example, for binding to specific peptide epitope or peptide polyepitopes to determine the HLA specificity or binding efficiency of said peptide. As will be apparent to those skilled in the art, such CTL clones are thus useful for assaying newly synthesized CTL epitopes, including any variant sequences of the epitopes disclosed herein, such as, for example, by MHC class 1 Tetramer assay, cytotoxicity assay, assay for IFN-γ production (eg. chromium release assay), cytokine assay, ELISPOT, etc.

In the case of human cells, the CTLs produced in this manner are then used for adoptive transfer to humans (e.g. by introducing them into the same or a different subject) as part of a therapeutic regime, or for diagnostic applications.

Optionally, the T cell is contacted with peptide in the presence of a cytokine, such as, for example, IL-2.

The present invention clearly extends to the T cell clones produced using a novel immunologically active peptide described herein, and to the use of such T cell clones in any diagnostic, prophylactic or therapeutic procedures for monitoring HCMV infection, latency of HCMV infection, the likelihood of HCMV infection in a human subject, such as, for example, before, during or following organ transplantation (eg. BMT), or during pregnancy.

In order that the nature of the present invention may be more clearly understood preferred forms will now be described with reference to the following non-limiting Examples.

EXAMPLE 1

Materials and Methods

1. Establishment and Maintenance of Cell Lines

Epstein Barr virus-transformed lymphoblastoid cell lines (LCLs) were established from HCMV seropositive donors by exogenous virus transformation of peripheral B cells using the B95.8 (Klein et al., *Intervirology* 3, 232-244, 1974) and QIMR-WIL (Pope et al., *Int J Cancer* 4, 255-260, 1969) virus isolates. In addition, the peptide transporter (TAP)-negative B x T hybrid cell line 174×CEM.T2 (referred to as T2) (Salter et al, *EMBO J.* 5, 943, 1986) was used for MHC stabilization assays. All cell lines were routinely maintained in RPMI 1640 supplemented with 2 mM L-glutamine, 100 IU/ml penicillin and 100 µg/ml streptomycin plus 10% foetal calf serum (FCS) (growth medium).

To generate phytohaemagglutinin (PHA) blasts, peripheral blood mononuclear cells (PBMC) were stimulated with PHA (Commonwealth Serum Laboratories, Melbourne, Australia) and after 3 days of culture, growth medium containing MLA 144 supernatant and highly purified recombinant human IL-2 (rIL-2) was added (Khanna et al., *J. Exp Med* 176, 169, 1992). PHA blasts were propagated by twice-weekly replacement of rIL-2 and MLA supernatant (no further PHA added) for up to 6 weeks.

T2 cells transfected with individual HLA class I antigens were used for MHC stabilization assays (see below). T2 cells expressing HLA B35, HLA B7 and HLA B27 have been described elsewhere (Takiguchi et al, *Int. Immunol.* 6, 1345, 1994; Smith and Lutz, *J. Immunol.* 156, 3755, 1996; and Zweerink et al., *J. Immunol.* 150, 1763, 1993). T2 cells expressing HLA A3, HLA A24 and HLA B8 were established by transfecting expression vectors encoding individual class I alleles as described previously (Khanna et al., *Eur. J. Immunol.* 29, 1587, 1999). Briefly, cDNAs for these HLA class I alleles were amplified using sequence-specific primers and cloned into an EGFP-N1 expression vector (Clontech). T2 cells were transfected with these recombinant expression vectors and cultured in growth medium supplemented with G418 (800 µg/ml) for three weeks. Green fluorescence protein (GFP)-positive cells were sorted using FACS vantage and purified cells were maintained in growth medium supplemented with G418 (800 µg/ml). HLA class I expression on these transfectants was confirmed by using HLA allele-specific antibodies.

2. Epitope Prediction and Peptide Synthesis

Predictive algorithms were used to predict putative HLA class 1-restricted CTL epitopes from within the amino acid sequences of HCMV antigens pp28, pp50, pp65, pp150, pp71, gH, gB, IE-1, IE-2, US2, US3, US6, US11 and UL18. The algorithms used were: (i) the epitope prediction algorithm in the SYFPEITHI database of MHC ligands and peptide motifs that bind to MHC Class I molecules of the University of Tuebingen, Germany (Rammensee et al., *Immunogenetics* 50, 213, 1999); and (ii) HLA Peptide Binding Predictions algorithm of the Bioinformatics and Molecular Analysis Section (BIMAS) of the National Institutes of Health of the government of the United States of America (Parker et al, *J. Immunol* 152, 163, 1994). These algorithms were used to identify potential epitopes for HLA A1, A2, A3, A24, A26, B7, B8, B27, B35, and B44 alleles. Each peptide was assigned a score on the basis of the strength of the interaction between the MHC molecule and the peptide. Peptides that ranked higher than 24 in the SYFPEITHI program predictions and peptides that scored greater 100 from the BIMAS program predictions were synthesized using the Merrifield solid phase method (Valerio et al, *Anal. Biochem* 197, 168, 1991), or purchased from Chiron Mimotopes (Melbourne, Australia). In addition, sets of overlapping peptides (20-mer peptides derived from the full-length pp65, gB, gH, pp150, IE-1 and IE-2 antigens, wherein each member of each set overlaps with another member of the same set by 10 amino acid residues) were also synthesised. All peptides were dissolved in 10% (v/v) dimethyl sulfoxide (DMSO) and diluted in serum-free RPMI 1640 medium for use in assays which tested for their ability to bind MHC molecules and induce both the production of IFN-γ ELISPOT and CTL activity in donor PBMC and T cell clones.

3. MHC Stabilization Assay

The ability of synthetic peptides to stabilize MHC molecules on the surface of the T2 cell line was measured by indirect immunofluorescence (Burrows et al, *J Virol* 70, 4829, 1966). T2 cells ($2 \times 10^5$) were incubated in serum-free AIM-V medium (GibcoBRL, Invitrogen™, Melbourne, Australia) in the presence of 5 μM of peptide for 1 hr at 37° C. and 5% $CO_2$ in a humidified atmosphere. These were then incubated for a further 14-16 hrs at 26° C., after which time the cells were returned to 37° C. for 2 hrs prior to immunofluorescent staining. Cells were washed free of unbound peptide with growth medium prior to the addition of primary antibody. Anti-HLA allele-specific monoclonal antibody was added to the T2 cells and incubated at 4° C. for 30 min. HLA-specific antibodies used in this study were MA2.1 (HLA A2-specific, ATCC Accession No. HB54), SFR8-B6 (HLA Bw6-specific, ATCC Accession No. HB152), TU109 (HLA Bw4-specific; Muller et al., *Hum Immunol* 14, 333-349, 1989). After washing with growth medium, these cells were incubated with FITC- or PE-labelled anti-mouse Ig-specific antibody (Silenus, AMRAD, Australia) at 4° C. for 30 min. Finally, cells were washed and resuspended in 500 μl of cold PBS supplemented with 1% FCS. A sample of T2 cells was incubated with AIM-V medium alone at 26° C. for 14-16 hrs and served as a negative control. The second negative control comprised a sample of T2 cells that had been cultured in growth medium without peptide at 37° C. Fluorescence intensities were then measured with a FACScan or FACSclaibur (BD Biosciences, San Jose, Calif.). MHC Stabilization Efficiency (MSE) for each peptide was calculated as the percent enhancement of average fluorescence relative to the fluorescence determined for the negative control sample.

4. ELISPOT Assay

ELISPOT assay was used to assess whether stimulation of PBMC from a large panel of seropositive donors with HCMV peptides could induce IFN-γ expression in T cells. Briefly, a 96-well nitrocellulose plate (Multiscreen, Millipore) was coated overnight at 4° C. with mouse monoclonal antibody anti-IFN-γ IgG1 (10 μg/ml; Mabtech Nacka, Sweden). The plate was then washed six times in Phosphate Buffered Saline (PBS) and blocked for 1 hour at 37° C. with PBS supplemented with 5% FCS. The blocking solution was removed and PBMC from healthy HCMV seropositive donors were added at a concentration of $2.5 \times 10^5$ cells per well in growth medium. These cells were incubated for 18 h at 37° C. in a 5% $CO_2$ atmosphere in the presence of synthetic peptides from HCMV antigens (10 μg/ml). After incubation, the plate was washed three times with PBS supplemented with 0.05% Tween, followed by three washes with PBS alone. Biotinylated anti-IFN-γ (Mabtech, Nacka Sweden) detection antibody was added to each well at a final concentration of 1 μg/ml in PBS. The plates were incubated at room temperature in the dark for 4 h and then washed, as described above. Streptavidin-Alkaline phosphatase (Sigma) was added to each well at a final concentration of 1 μg/ml in PBS and incubated at room temperature in the dark for 2 h. After a final wash with PBS, the substrate, 5-bromo-4-chloro-3-indolyl phosphate and nitro blue tetrazolium, was added to each well and the plates incubated for 30 min at RT. Cells that produced IFN-γ in response to the presence of peptide were detected as purple spots on the nitrocellulose membrane of each well. The spots were counted automatically using a closed-circuit camera (CCD) and ImagePro image analysis software or automated ELISPOT reader (AID, Germany). The T cell precursor frequency for each peptide was based on the total number of PBMC in the well and the number of peptide-specific spots per well, over an average of 3 wells. The number of peptide-specific spots was also calculated by subtracting the negative control values, which consisted of PBMC without peptide (an average of 3 wells), from the test wells.

5. Enrichment of $CD4^+/CD8^+$ T cells for ELISPO T Assay

To determine whether a particular 20-mer peptide contained either a $CD4^+$- or $CD8^+$-restricted epitope, or both, $CD4^+/CD8^+$ cell depletion ELISPOT assays were performed on PBMC from healthy virus carriers. For any one experiment, three populations of cells were used: a) $CD8^+$-depleted PBMC, b) $CD4^+$-depleted PBMC, and c) non-depleted PBMC. These populations of cells were tested concurrently with the same peptides in a conventional ELISPOT assay as described herein above. DYNABEADS M-450 (Dynal, Oslo, Norway) that bound specifically to $CD4^+$- or $CD8^+$ cells were used to perform the depletion essentially according to manufacturers instructions. Beads were washed twice in cold PBS supplemented with 2% FCS using magnetic isolation. The requisite number of cells was resuspended in cold PBS supplemented with 2% FCS, added to the beads and then incubated at 4° C., in the dark, for 30 mins ($CD8^+$ beads) or 60 mins ($CD4^+$ beads). Populations were depleted of $CD4^+$ or $CD8^+$ cells using magnetic separation. After depletion, the non-attached cells were removed and washed once in growth medium, counted and used in conventional ELISPOT assay. Depleted cells were used at $1.7 \times 10^5$ cells per well and the non-depleted population was used at the standard $2.5 \times 10^5$ cells per well. After the depletion step, each respective cell population was assessed for the purity of $CD4^+$ and $CD8^+$ T cells by three-colour flow cytometry. Samples of depleted cell populations were stained with anti-CD3 antibody directly conjugated to fluorescein isothiocyanate (FITC), anti-CD4 antibody conjugated with phycoerythrin (PE) fluorochrome, and anti-CD8 antibody conjugated with Tricolor fluorochrome (described below). The percent of $CD3^+/CD4^+$ cells present within the $CD8^+$-depleted population and the percent of $CD3^+/CD8^+$ cells present within the $CD4^+$-depleted populations were assessed on FACSCalibur cytometer (Becton Dickinson). The purity of each population was greater than 90% and the results from the ELISPOT assays are expressed as the percentage of CD4+ or $CD8^+$ cells within the depleted populations that responded toward each peptide by producing IFN-γ.

6. Intracellular Cytokine Staining

PBMCs were incubated at 37° C. in RPMI+10% FCS with and without 10 μg/ml peptides for 6 hours. Golgiplug™ (Pharmingen, San Diego, Calif., USA) was added to the samples according to manufacturer's instructions during the second hour of incubation and cells activated with 25 ng/ml phorbol 12-myristidate 13-acetate (PMA; Sigma-Aldrich Co, St. Louis Mo.) and 1 μg/ml iomomycin (Sigma) acted as a positive control. Following the incubation, $1 \times 10^6$ cells/sample were washed and resuspended in staining buffer consisting of PBS with GolgiPlug™, 3% FCS and sodium azide. Cells were then stained with FITC conjugated anti-CD3-FITC (UCHT1, Immunotech, Marseille, France), and either Tricolor (TRI) conjugated anti-CD4 (S3.5, Caltag, Burlingame, Calif.) or anti-CD8 (3B5, Caltag) for 30 minutes, 4° C. in the dark. The cells were fixed for 20 min at 4° C. with Cytofix/Cytoperm™ (BD Biosciences) and resuspended in Perm/Wash™ permeabilization buffer (BD Biosciences) according to manufacturers protocol. Fixed cells were stained with phycoerythrin (PE) conjugated anti-human IFN-γ (B27, Pharmingen) for 30 min at 4° C. in the dark. As a negative control, cells were stained with appropriate isotype matched control antibodies. Cells were washed twice in permeabilization buffer and resuspended in staining buffer before analysis by three-colour flow cytometry on a FACSCalibur cytometer (BD Biosciences). All data analysis was carried out using FlowJo software (Tree Star, Inc. San Carlos, CA).

7. Generation of Polyclonal and Clonal HCMV-specific CTLs

To generate polyclonal CTLs, $2 \times 10^6$ PBMC from HCMV seropositive healthy donors were co-cultivated for seven days with $1 \times 10^6$ autologous PBMC sensitized with synthetic peptides (20 μg/ml). On day 7, these lymphocytes were restimulated with peptide-sensitized autologous LCLs. After 10 days of culture in growth medium supplemented with rIL-2 (20 U/ml) and 30% TCGF, the cells were used as polyclonal effectors in a standard $^{51}$Cr-release assay against peptide-sensitized autologous PHA blasts or LCLs (Burrows et al., *Eur. J. Immunol* 22, 191, 1992).

To generate HCMV-specific CTL clones, PBMC ($10^6$/ml) were cultivated with peptide sensitized autologous PBMC (responder to stimulator ratio of 2:1) in 2 ml culture wells (Linbro) for 3 days in growth medium. CTL clones, generated by seeding in 0.35% agarose, were established and maintained in growth medium containing rIL2 (Burrows et al, *Eur. J. Immunol.* 22, 191, 1992) and were restimulated once weekly with γ-irradiated peptide-sensitized autologous LCLs. These CTL clones were screened on a panel of target cells either sensitized with synthetic peptides or infected with recombinant vaccinia virus encoding individual HCMV antigens (see below).

8. Vaccinia Virus Recombinants

Recombinant vaccinia constructs encoding HCMV antigens and a control vaccinia virus construct made by insertion of the pSCI1 vector alone and negative for thymidine kinase (Vacc.TK⁻) are publicly available (Riddell et al., *Rev. Infect. Dis.* 13 *Suppl.* 11, S966-S973, 1991; Browne et al, *Nature* 347, 770, 1990; and Britt et al., *J. Virol* 64, 1079, 1990). Target cells were infected with recombinant vaccinia virus at a multiplicity of infection (MOI) of 10:1 for 1 h at 37° C., as described by Khanna et al, *J. Exp. Med.* 176, 169, 1992 and Khanna et al, *Immunol* 74, 504, 1991. After overnight infection, cells were washed with growth medium and processed for CTL assays (Khanna et al, *J. Immunol. Meth.* 164, 41, 1993).

9. Cytotoxicity Assays

Target cells were either infected with recombinant vaccinia viruses or pre-sensitized with synthetic peptide epitopes and then incubated with $^{51}$Cr for 90 min. Following incubation, these cells were washed in growth medium and used as targets in a standard 4-6 h $^{51}$Cr-release assay (Burrows et al., *Eur J. Immunol* 22, 191, 1992).

EXAMPLE 2

HLA class I Epitope Prediction and HLA Binding Peptides from HCMV Antigens

HLA class I-restricted CTL epitopes were identified using two computer-based algorithms as described in Example 1. These algorithms predict 8, 9 or 10-mer amino acid sequences that are likely to bind successfully to MHC class I molecules (HLA A1, A2, A3, A24, A26, B7, B8, B27, B35 and B44) based on the half-time dissociation of the interaction. Peptides that ranked higher than 24 in the SYFPEITHI program and/or peptides that scored greater than 100 from the BIMAS program are listed in Table 1.

The peptides listed in Table 1 were used to screen healthy, seropositive donors. All peptides predicted to bind HLA class I alleles were also analysed for their capacity to bind to HLA class I MHC molecules and stabilize their expression on the surface of T2 cells transfected with individual HLA alleles. Representative data for the HLA A2 stabilization are shown in FIGS. 1*a* through 1*i*. A summary of MHC stabilization data is also provided in Table 1. HCMV peptides inducing a significant enhancement of relative fluorescence intensity compared to the negative controls (i.e. greater than mean+3 S.E.M) for each HLA class I allele were considered to be positive. Predictive peptides for HLA B44 and A26 were not tested in these assays, as T2 transfectants for these alleles were not available for this study. Data indicate that a large number of peptides predicted by a bioinformatics approach also showed strong HLA Class I binding.

EXAMPLE 3

ELISPOT Assay on HLA A2 Predictive Peptides

To determine whether memory CTL responses against the predictive HCMV potential epitopes could be detected in healthy seropositive virus carriers, we used the ELISPOT assay, which allows rapid identification of CTL epitopes without prolonged in vitro culture. PBMC isolated from a cohort of HLA A2-positive healthy virus carriers (Table 2) were stimulated with the peptides that gave a positive result in HLA binding assays (Example 2), and those cells that produced IFN-γ were detected.

Figure 2A:
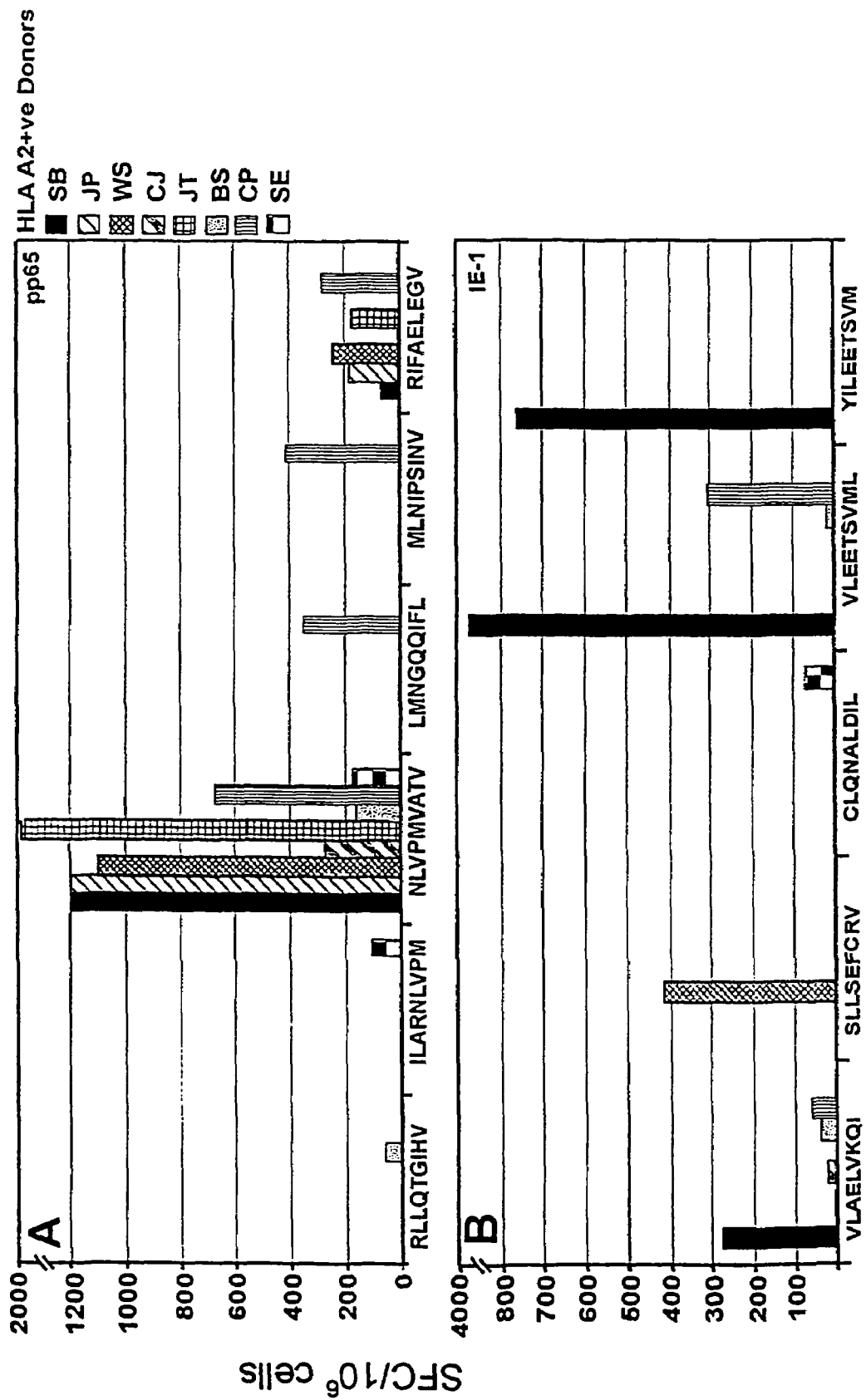
FIG. 2a is a graphical representation showing the ex vivo functional analysis of HCMV-specific CTL responses to HCMV pp65-derived peptides or HCMV IE-1-derived peptides in a cohort of eight HLA A2-positive healthy seropositive individuals. CTL epitope peptides derived from HCMV pp65 (panel A) or HCMV IE-1 (panel B) were tested using ELISPOT assays. HCMV pp65 peptides had the amino acid sequences indicated on the x-axis of panel A (i.e. SEQ ID NOs: 10, 54, 5, 53, 6, and 7 respectively, from left to right of the figure). HCMV IE-1 peptides had the amino acid sequences indicated on the x-axis of panel B (i.e. SEQ ID NOs: 97, 96, 102, 101, and 18 respectively, from left to right of the figure). Peripheral blood mononuclear cells (PBMC) from healthy seropositve individuals were stimulated with individual synthetic peptides (10 μg/ml) from these antigens and IFN-γ production was measured in ELISPOT assays as described in the Material and Methods section. The results are expressed as spot forming cells (SFC) per $10^6$ PBMC on the ordinate.
Figure 2B:
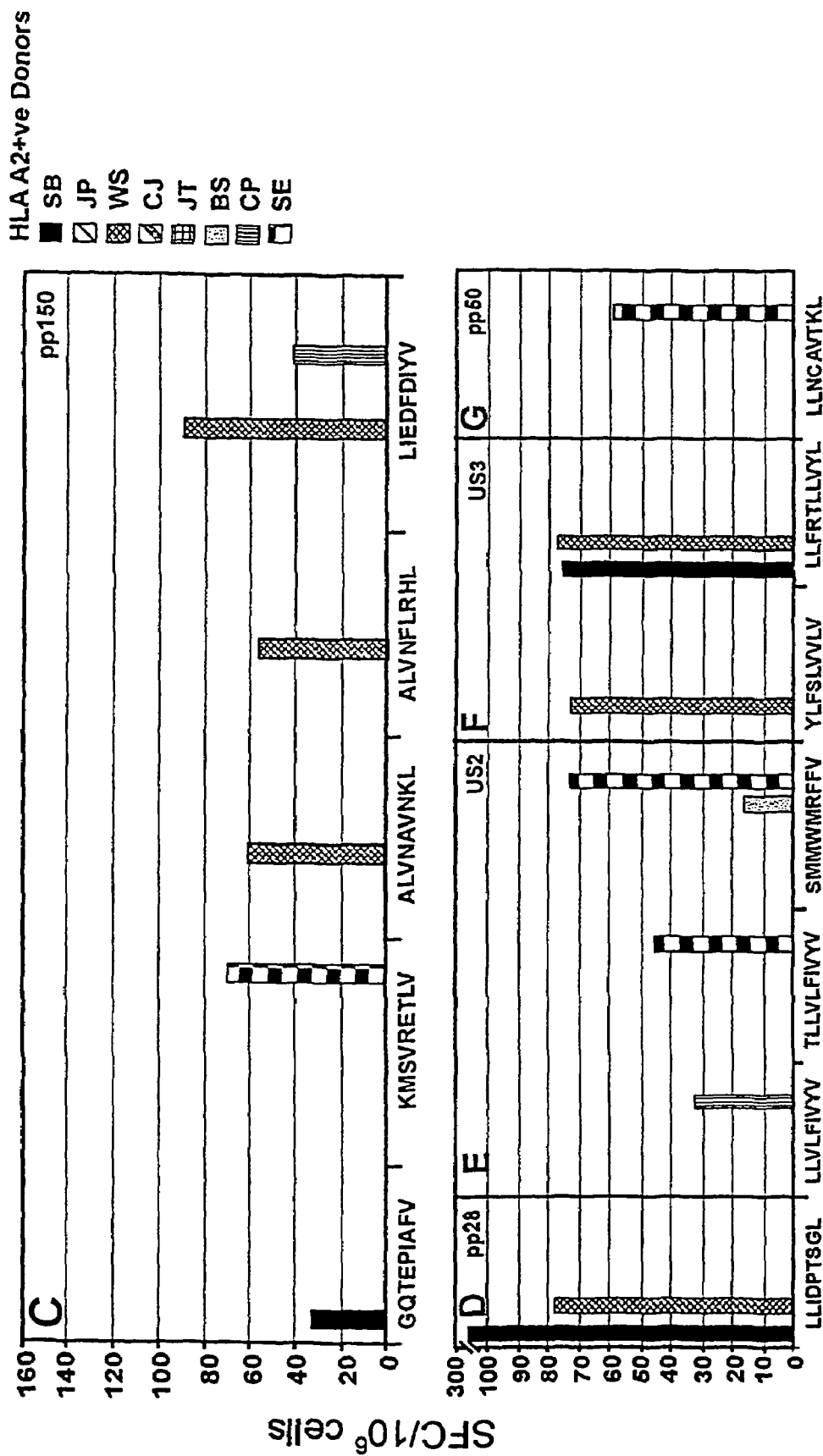
FIG. 2b is a graphical representation showing the ex vivo functional analysis of HCMV-specific CTL responses to HCMV pp150-derived peptides (panel C), pp28-derived peptides (panel D), US2-derived peptides (panel E), US3-derived peptides (panel F), or pp50-derived peptides (panel G), in a cohort of eight HLA A2-positive healthy seropositive individuals. CTL epitope peptides were tested using ELISPOT assays as described in the legend to FIG. 2a. Data are shown as described in the legend to FIG. 2a. HCMV pp150 peptides had the amino acid sequences indicated on the x-axis of panel C (i.e. SEQ ID NOs: 122, 141, 143, 144, and 140 respectively, from left to right of the figure). The HCMV pp28 peptide had the amino acid sequence indicated on the x-axis of panel D (i.e. SEQ ID NO: 150). HCMV US2 peptides had the amino acid sequences indicated on the x-axis of panel E (i.e. SEQ ID NOs: 294, 296 and 295 respectively, from left to right of the figure). HCMV US3 peptides had the amino acid sequences indicated on the x-axis of panel F (i.e. SEQ ID NOs: 298 and 300 respectively, from left to right of the figure). The HCMV pp50 peptide had the amino acid sequence indicated on the x-axis of panel G (i.e. SEQ ID NO: 163).
Figure 2C:
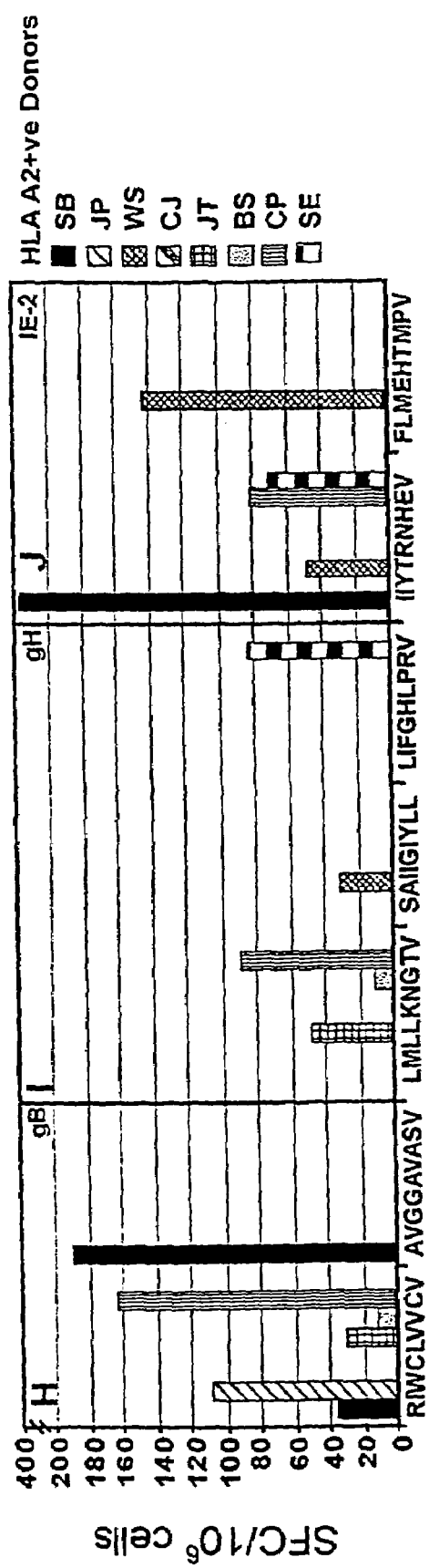
FIG. 2c is a graphical representation showing the ex vivo functional analysis of HCMV-specific CTL responses to HCMV gB-derived peptides (panel H), gH-derived peptides (panel 1), or IE-2-derived peptides (panel J), in a cohort of eight HLA A2-positive healthy seropositive individuals. CTL epitope peptides were tested using ELISPOT assays as described in the legend to FIG. 2a. Data are shown as described in the legend to FIG. 2a. HCMV gB peptides had the amino acid sequences indicated on the x-axis of panel H (i.e. SEQ ID NOs: 181 and 187 respectively, from left to right of the figure). The HCMV gH peptides had the amino acid sequences indicated on the x-axis of panel I (i.e. SEQ ID NOs: 206, 216, and 202 respectively, from left to right of the figure). HCMV IE-2 peptides had the amino acid sequences indicated on the x-axis of panel J (i.e. SEQ ID NOs: 254 and 251 respectively, from left to right of the figure).

Representative data on the ELISPOT assays HLA A2 binding peptides are shown in FIGS. 2*a* through 2*c* for peptides derived from HCMV pp65, IE-1, pp150, pp28, US2, US3, pp50, gB, gH, and IE-2.

Overall, the T cell responses for HLA A2-restricted epitopes in ELISPOT assays indicated an interesting hierarchy between the different antigens of HCMV. As reported by Gyulai et al, *J. Infect. Dis.* 181, 1537-1546, 2000, pp65 was clearly the most immunodominant antigen recognised by all the healthy virus carriers (FIG. 2*a*). The majority of donors recognised two or more epitopes within the pp65 antigen. A range of precursor CTL frequencies for the pp65 epitopes were evident among the different donors (FIG. 2*a*), ranging from 29 SFC/$10^6$ PBMC to 3752 SFC/$10^6$ PBMC.

A known peptide epitope from pp65 having the sequence NLVPMVATV (SEQ ID NO: 5) was the only epitope recognized by every donor tested in this study. Another commonly recognized known epitope from pp65 has the sequence RIFAELEGV (SEQ ID NO: 7) which was recognized by 5 of the 8 donors tested. For pp65 epitopes, the average precursor frequency was highest for NLVPMVATV (SEQ ID NO: 5), followed by LMNGQQIFL (SEQ ID NO: 53), RIFAELEGV (SEQ ID NO: 7) and MLNIPSINV (SEQ ID NO: 6) respectively. Of these, the epitope having the sequence set forth in SEQ ID NO: 53 has not been described previously. Occasional subdominant responses to other epitopes, such as, for example, RLLQTGIHV (SEQ ID NO: 10) and ILARNLVPM (SEQ ID NO: 54) within pp65 were also detected by two different donors.

IE-1 was considered to be the second most immunodominant antigen after pp65, followed by pp150, gB, gH, IE-2, US2, pp28, US3 and pp50. Six of the eight HLA A2-positive donors showed CTL reactivity to at least one CTL epitope within IE-1 (FIG. 2b). Interestingly, one of most dominant CTL responses to any epitope was identified within IE-1 (VLEETSVML; SEQ ID NO: 101). This epitope showed a precursor frequency of 3752 SFC/10$^6$ PBMC in the donor SB. This epitope was recognized more efficiently by three donors than a similar, previously-described epitope having the sequence YILEETSVM (SEQ ID NO: 18; Retière et al, *J. Virol* 74, 3948-3952, 2000). Other novel epitopes identified from IE-1 had the sequences VLAELVKQI (SEQ ID NO: 97), SLLSEFCRV (SEQ ID NO: 96) and CLQNALDIL (SEQ ID NO: 102) showed comparably lower frequency. CTL frequencies to epitopes within gB, gH, pp28, pp50, US2, US3, US11, IE-2 and pp150 were generally very low, although CTL epitopes within gB and gH were more frequently recognized by healthy virus carriers when compared to pp150, pp28, US2, US3, US11 and pp50. Moreover, the IE-2, US2, US3 and US11 antigens were identified for the first time as targets for T cell responses. Although only four HLA A2-positive healthy virus carriers were identified as potential responders to the epitopes within these four antigens, further screening for additional epitopes restricted through other HLA class I alleles identified a number of other epitopes within these antigens (See below).

A comparison of overall T cell reactivity to all tested antigens amongst the cohort of healthy virus carriers indicated that CTL responses were generally not constrained to a single HCMV antigen. The majority of the HLA A2-positive donors tested in our study showed a broad range of CTL responses to multiple antigens. Donors SB and CP showed the broadest range of CTL reactivity, and recognized seven of the ten antigens tested in our study. Moreover, both of these donors recognized a greater number of epitopes (11/30) than any other donor tested in our study (FIGS. 2a through 2c). On average, CTL responses from our panel of HLA A2 healthy virus carriers were directed towards 6-7 different epitopes. These results strongly suggest that broadly directed CTL responses to multiple epitopes are required to efficiently control HCMV replication. Broad T cell reactivity enables an individual to clear the HCMV more efficiently than a narrowly focused CTL response to a single antigen, or a limited number of eptiopes. These observations highlight the importance of designing a HCMV vaccine that combines, in one single regimen, all those antigens that might provide protection.

EXAMPLE 4

T Cell Response to Other HLA class I Predictive HCMV Peptides

We tested epitopes that were restricted for HLA A1, A3, A24, A26, B7, B8, B27, B35 and B44 in ELISPOT assays, to determine whether memory T cell responses could be detected in healthy HLA-matched virus carriers. PBMC from a cohort of healthy virus carriers (Table 2) were stimulated with individual peptides and the cells that produced IFN-γ were detected. CTL epitopes that were restricted through either HLA A1, A3, A24, A26, B7, B8 or B27, were identified.

Figure 3A:
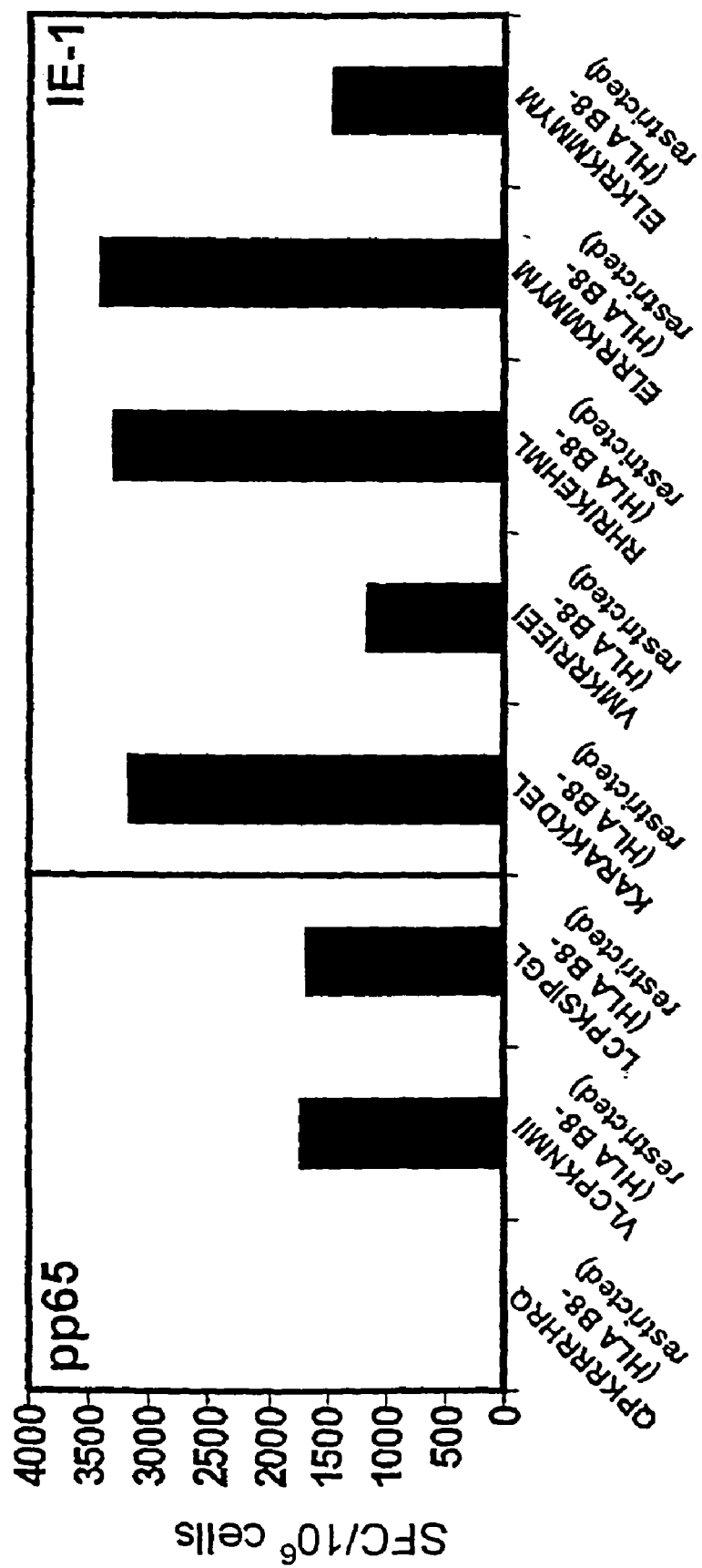
FIG. 3a is a graphical representation showing ex vivo functional analysis of HCMV-specific T cell responses against HLA B8-restricted CTL epitopes derived from HCMV pp65 (left panel) or HCMV IE-1 (right panel) antigens. Peptide epitopes were tested using ELISPOT assays. PBMC from healthy seropositve individuals were stimulated with individual synthetic peptides from these antigens and IFN-γ production was measured in ELISPOT assay as described herein. Peptides and their HLA restrictions are indicated on the x-axis. The HCMV pp65 peptides tested had the amino acid sequences indicated (ie. SEQ ID NOs: 43, 14, and 44 respectively, from the left of the figure). The HCMV IE-1 peptides tested had the amino acid sequences indicated (ie. SEQ ID NOs: 109, 110, 111, 112, and 114 respectively, from the left of the figure). T cell responses, as indicated by spot forming cells (SFC) per $10^6$ PBMC are indicated on the ordinate.
Figure 3B:
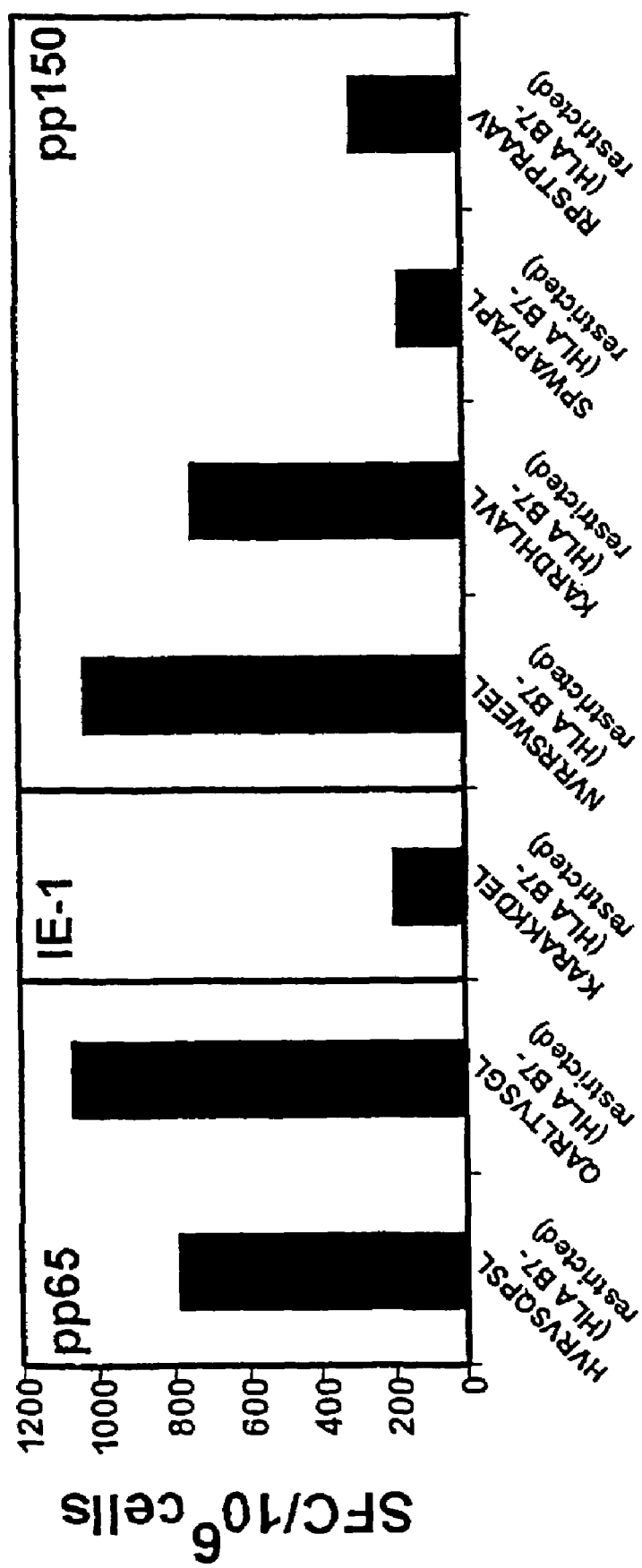
FIG. 3b is a graphical representation showing ex vivo functional analysis of HCMV-specific T cell responses against HLA B7-restricted CTL epitopes derived from HCMV pp65 (left panel), IE-1 (middle panel), or HCMV pp150 (right panel) antigens. Peptide epitopes were tested using ELISPOT assays. PBMC from healthy seropositve individuals were stimulated with individual synthetic peptides from these antigens and IFN-γ production was measured in ELISPOT assay as described herein. Peptides and their HLA restrictions are indicated on the x-axis. The HCMV pp65 peptides tested had the amino acid sequences indicated (ie. SEQ ID NOs: 40 and 41 respectively, from the left of the figure). The HCMV IE-1 peptide tested had the amino acid sequence indicated (ie. SEQ ID NO: 109). The HCMV pp150 peptides tested had the amino acid sequences indicated (ie. SEQ ID NOs: 134, 132, 131, and 130 respectively, from the left of the figure). T cell responses, as indicated by spot forming cells (SFC) per $10^6$ PBMC are indicated on the ordinate.
Figure 3C:
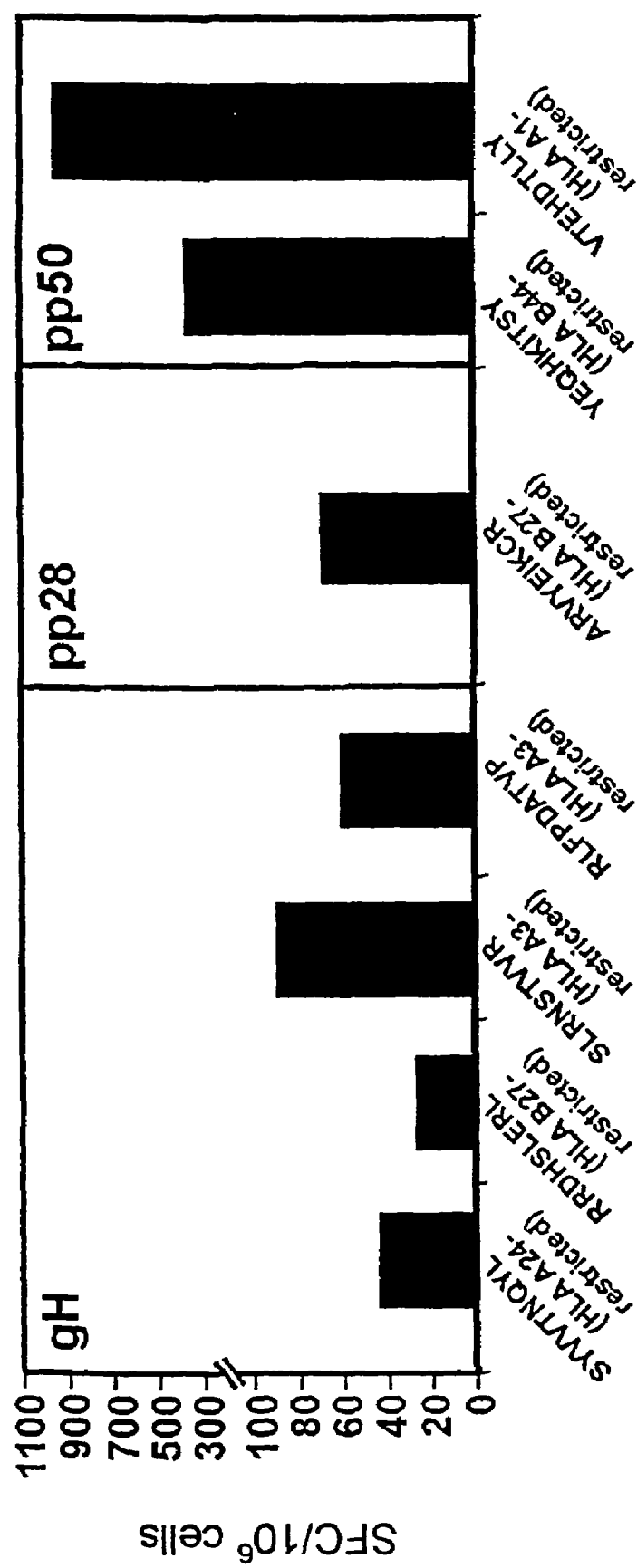
FIG. 3c is a graphical representation showing ex vivo functional analysis of HCMV-specific T cell responses against CTL epitopes that have HLA A24, HLA B27, HLA A3, HLA B44 or HLA A1 restrictions, said CTL epitopes being derived from HCMV gH (left panel), pp28 (middle panel), or HCMV pp50 (right panel) antigens. Peptide epitopes were tested using ELISPOT assays. PBMC from healthy seropositve individuals were stimulated with individual synthetic peptides from these antigens and IFN-γ production was measured in ELISPOT assay as described herein. Peptides and their HLA restrictions are indicated on the x-axis. The HCMV gH peptides tested had the amino acid sequences indicated (ie. SEQ ID NOs: 227, 243, 217, and 220 respectively, from the left of the figure). The HCMV pp28 peptide tested was HLA B27-restricted and had the amino acid sequence indicated (ie. SEQ ID NO: 162). The HCMV pp50 peptides tested had the amino acid sequences indicated (ie. SEQ ID NOs: 170 and 165 respectively, from the left of the figure). T cell responses, as indicated by spot forming cells (SFC) per $10^6$ PBMC are indicated on the ordinate.

Representative data showing ELISPOT responses for each of these alleles are shown in FIGS. 3a through 3c. As in the case of HLA A2-restricted CTL responses, both pp65 and IE-1 were clearly the most immunodominant antigens (FIG. 3a). Surprisingly, CTL responses to IE-1 epitopes in some individuals constituted 5-10% of their total CD8$^+$ T cell population (data not shown). Other antigens such as pp150, gH, pp28, pp50, IE-2 and UL18 were also identified as potential targets for class I-restricted CTL response (FIGS. 3b, 3c). Although pp28 and pp50 have been identified as potential targets of CTL response, this is the first report which maps multiple CTL epitopes restricted through HLA A1, A2 and B27.

Of particular interest was a HLA A1-restricted CTL epitope from pp50 having the sequence VTEHDTTLY (SEQ ID NO: 165) which was consistently recognized as one of the most dominant responses in all (i.e. 6/6) HLA A1-positive healthy virus carriers. Furthermore, the frequency and intensity of this response was comparable to the CTL response measured to NLVPMVATV (SEQ ID NO: 5) epitope in HLA A2-positive donors. Novel epitopes were also mapped within the IE-2 and UL18 antigens.

A comprehensive list of all epitopes identified using the ELISPOT assay is presented in Table 3.

EXAMPLE 5

Analysis of HCMV-Specific CTL Responses Using Cytotxicity Assays

To further confirm the CTL epitopes identified by ELISPOT assays, we generated polyclonal and clonal CTL lines specific for these epitopes. PBMC from the healthy seropositive donors were stimulated with synthetic peptide epitopes, and the CTL clones or polyclonal lines that were established and tested in standard $^{51}$Cr-release assays.

Figure 4A:
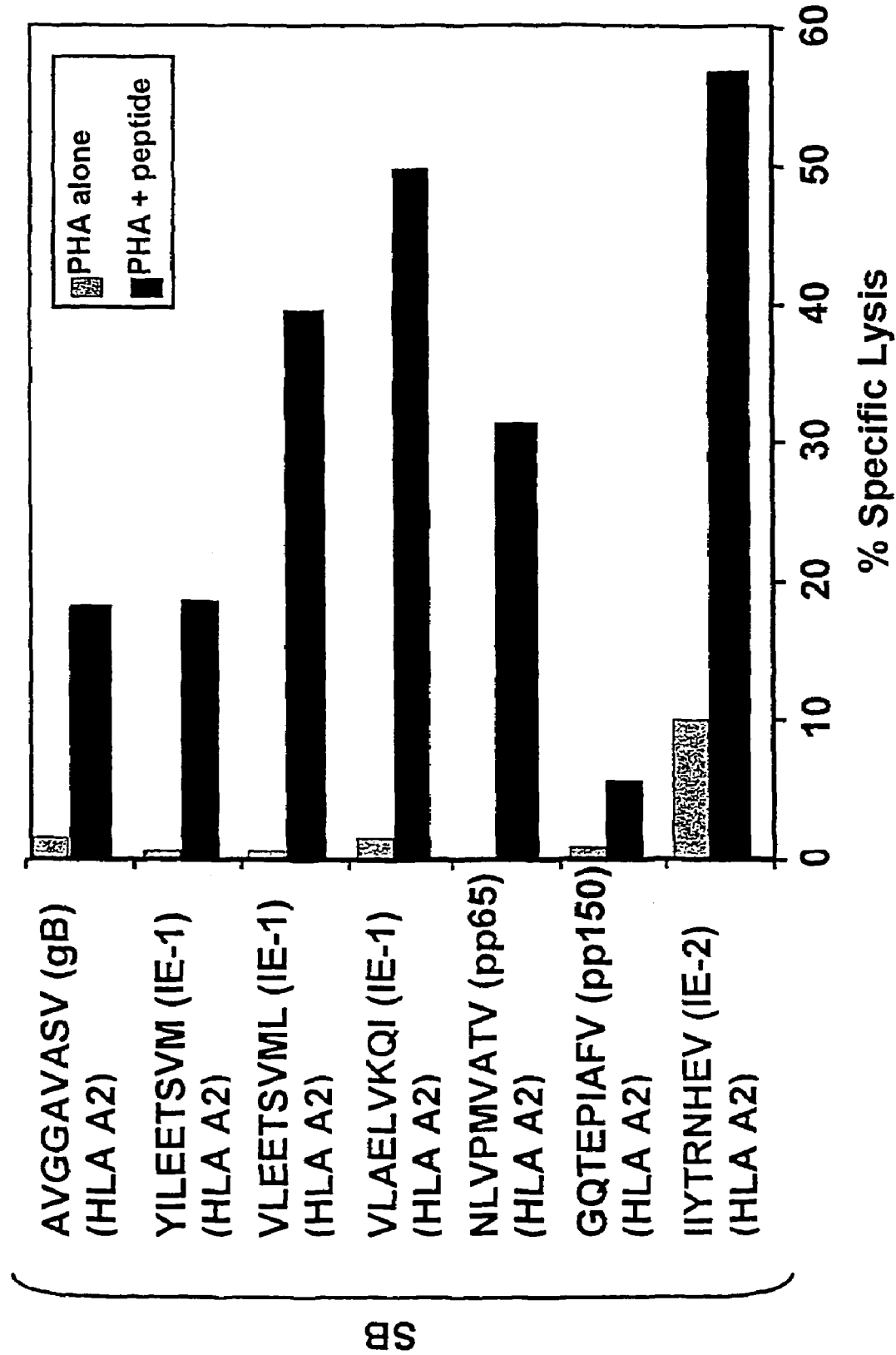
FIG. 4a is a graphical representation showing the recognition of HLA A2-restricted HCMV CTL epitopes by CTLs from a healthy seropositive donor designated SB. PBMC from the donor were co-cultivated with peptide-sensitized (20 μg/ml) autologous PBMC at a ratio of 2:1 for 7 days. On day 7, the cultures were restimulated with autologous γ-irradiated EBV-transformed LCLs sensitized with peptide epitopes. On day 10, these T cell lines were used as polyclonal effectors in a standard $^{51}$Cr-release assay against peptide sensitized autologous phytohaemagglutinin (PHA) blasts. An effector:target ratio of 10:1 was used in these assays. Percent specific lysis is indicated on the x-axis. Complete CTL epitope sequences (i.e. SEQ ID NOs: 187, 18, 101, 97, 5, 122, and 254 respectively, from the top to the bottom of the figure), antigens from which the peptides were derived (ie. gB, IE-1, IE-1, IE-1, pp65, pp150 and IE-2 respectively, from the top to the bottom of the figure), and the HLA restriction (HLA A2) for each epitope is shown on the Y-axis. The responding donor is also indicated (SB).
Figure 4B:
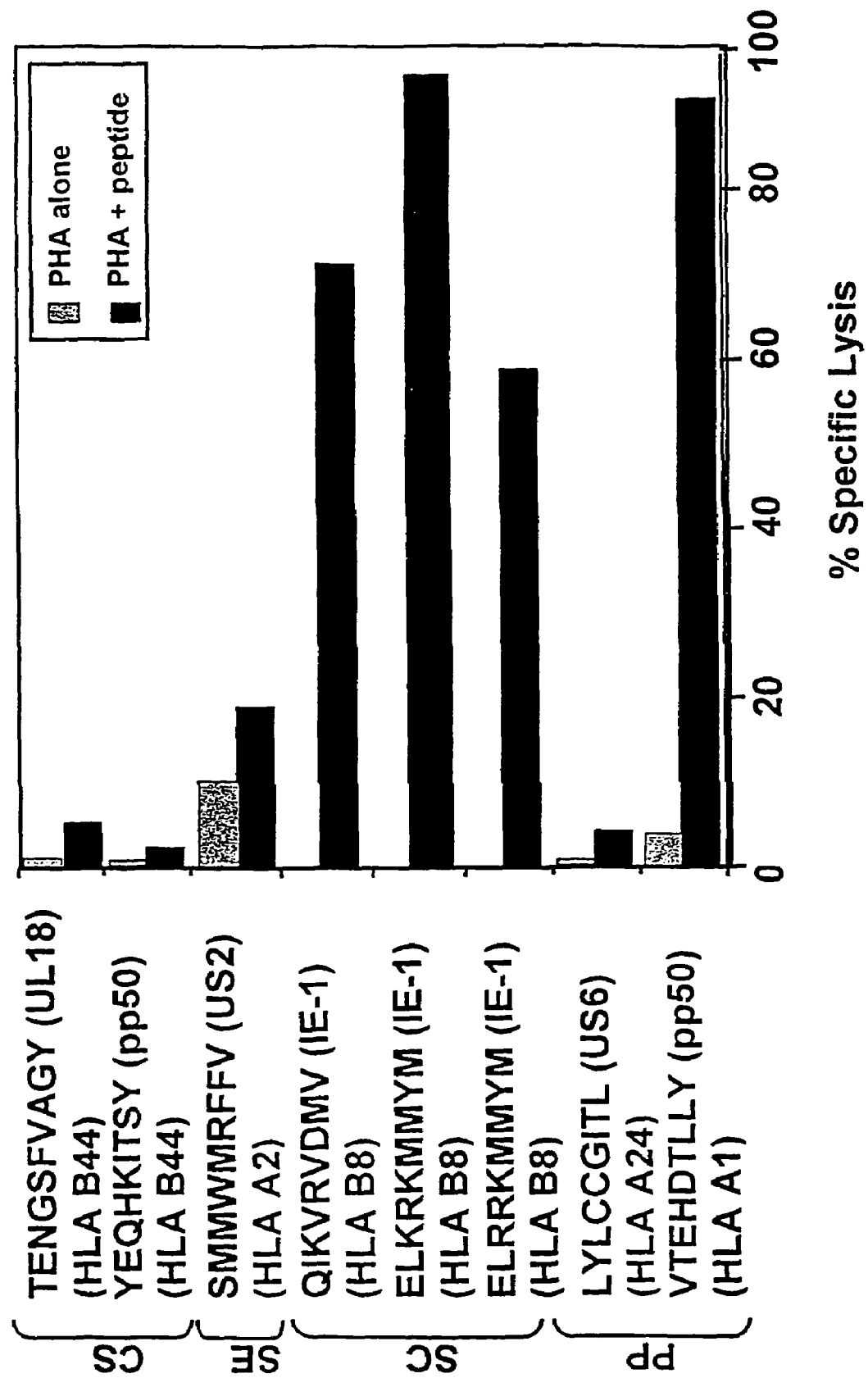
FIG. 4b is a graphical representation showing the recognition of HCMV CTL epitopes by CTLs from four healthy seropositive donors designated CS, SE, SC and PP. PBMC from each donor were co-cultivated with peptide-sensitized (20 μg/ml) autologous PBMC, restimulated with autologous γ-irradiated EBV-transformed LCLs sensitized with peptide epitopes, and $^{51}$Cr-release assays performed as described in the legend to FIG. 4a. Percent specific lysis is indicated on the x-axis. Complete CTL epitope sequences (i.e. SEQ ID NOs: 292, 295, 113, 114, 112, 303, and 165 respectively, from the top to the bottom of the figure), antigens from which the peptides were derived (i.e. UL18, pp50, US2, IE-1, IE-1, IE-1, US6 and pp50 respectively, from the top to the bottom of the figure), and the HLA restrictions (HLA B44, HLA B44, HLA A2, HLA B8, HLA B8, HLA B8, HLA A24, and HLA A1 respectively, from the top to the bottom of the figure) for each epitope is shown on the Y-axis. The responding donors are also indicated (i.e. CS, SE, SC, and PP) for each peptide.

Representative data from the polyclonal CTL lines established from the donors SB, PP, CS, SE and SC are shown in FIGS. 4a and 4b. For the donor SB (FIG. 4a), seven representative HLA class I-restricted epitopes from IE-2, pp150, pp65, IE-1 and gB antigens were assessed. Six of these seven epitopes recalled strong CTL responses, and a lower CTL activity was observed in the polyclonal CTL line established against the polyepitope having the sequence GQTEPIAFV (SEQ ID NO: 122).

Similarly, CTL lines established from other donors (PP, CS, SE and SC) also showed strong cytolytic activity against peptide sensitized autologous PHA blasts (FIG. 4b).

The overall strength of CTL activity observed in these assays generally correlated with the number IFN-γ-producing cells detected. For example, the VLEETSVML (SEQ ID NO: 101) epitope from the HCMV IE-1 antigen, was the most dominant epitope for the donor SB in the ELISPOT assays (Table 3), and showed strong CTL activity in the cytotoxicity assays (FIG. 4a).

A series of CTL clones were established to further characterize these epitopes. Representative data from four different epitopes are presented in FIGS. 5a through 5d.

Of particular interest was the CTL clone specific for the VLEETSVML (SEQ ID NO: 101) epitope derived from the HCMV IE-1 antigen. Retière et al, *J. Virol* 74, 3948-3952, 2000 have identified another HCMV IE-1 HLA A2-restricted epitope (YILEETSVM; SEQ ID NO: 18) having a similar, albeit non-identical sequence to this epitope. To determine whether the CTL responses to these epitopes are similar, we titrated these peptides and compared the cytotoxic activity in a standard $^{51}$Cr-release assay. The data presented in FIG. 5a clearly show a lack of significant cross-recognition between these epitopes. These observations have also been confirmed by polyclonal CTL lines established from other HLA A2-positive donors (data not shown). Thus, VLEETSVML (SEQ ID NO: 101) and YILEETSVM (SEQ ID NO: 18) represent distinct CTL epitopes.

Figure 5A:
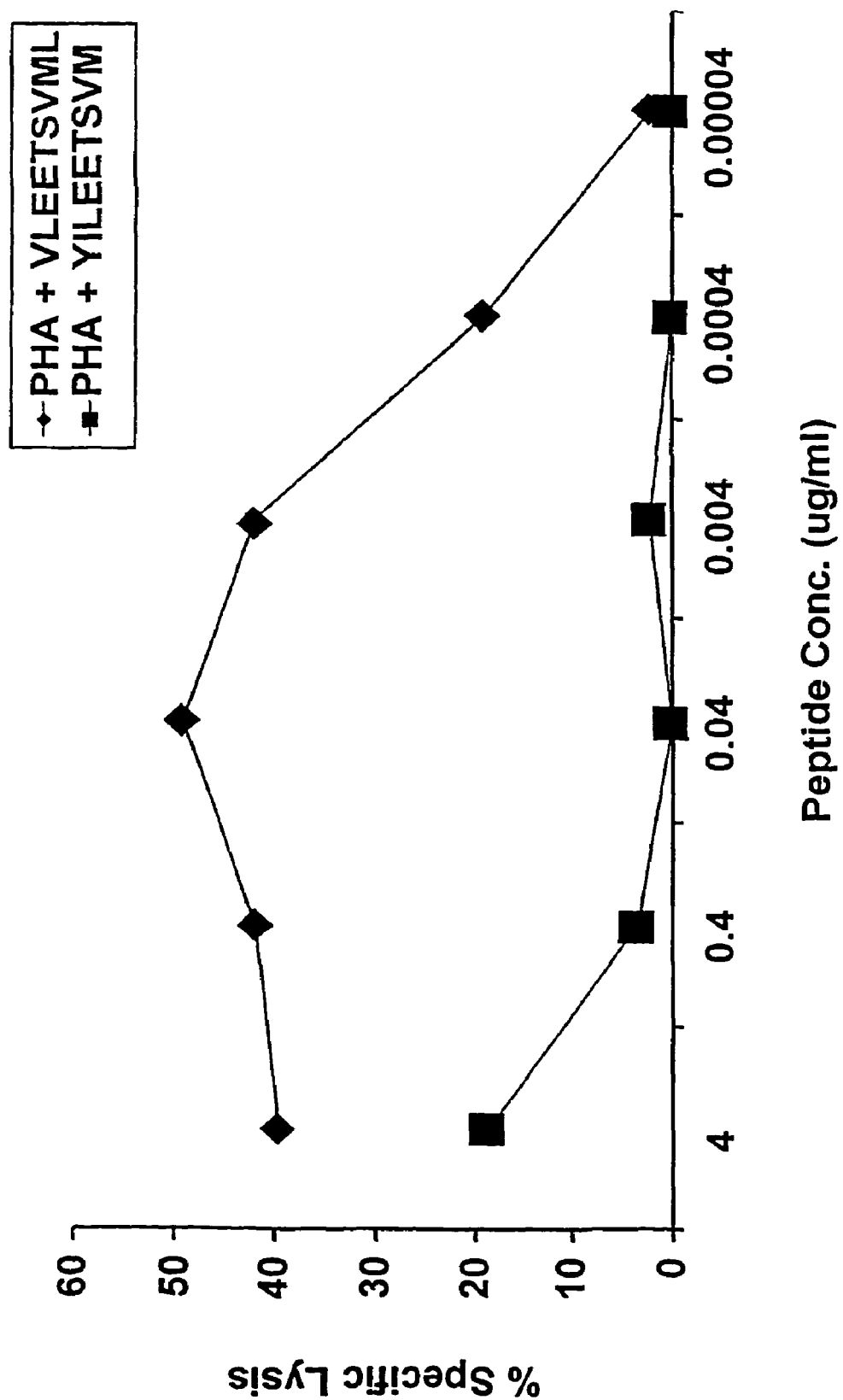
FIG. 5a is a graphical representation showing the percent specific lysis at different concentrations of HCMV CTL epitopes, using virus-specific CTL clones from healthy virus carriers. CTL clones from healthy virus carriers were isolated as described herein and incubated with a peptide epitope derived from HCMV IE-1 and having HLA A2 restriction, and consisting of the sequence VLEETSVML (SEQ ID NO: 101; ♦), or the sequence YILEETSVM (SEQ ID NO: 18; ■). CTL clones specific for each peptide epitope were tested against autologous PHA blasts presensitized with varying concentrations of synthetic peptide α-axis).
Figure 5B:
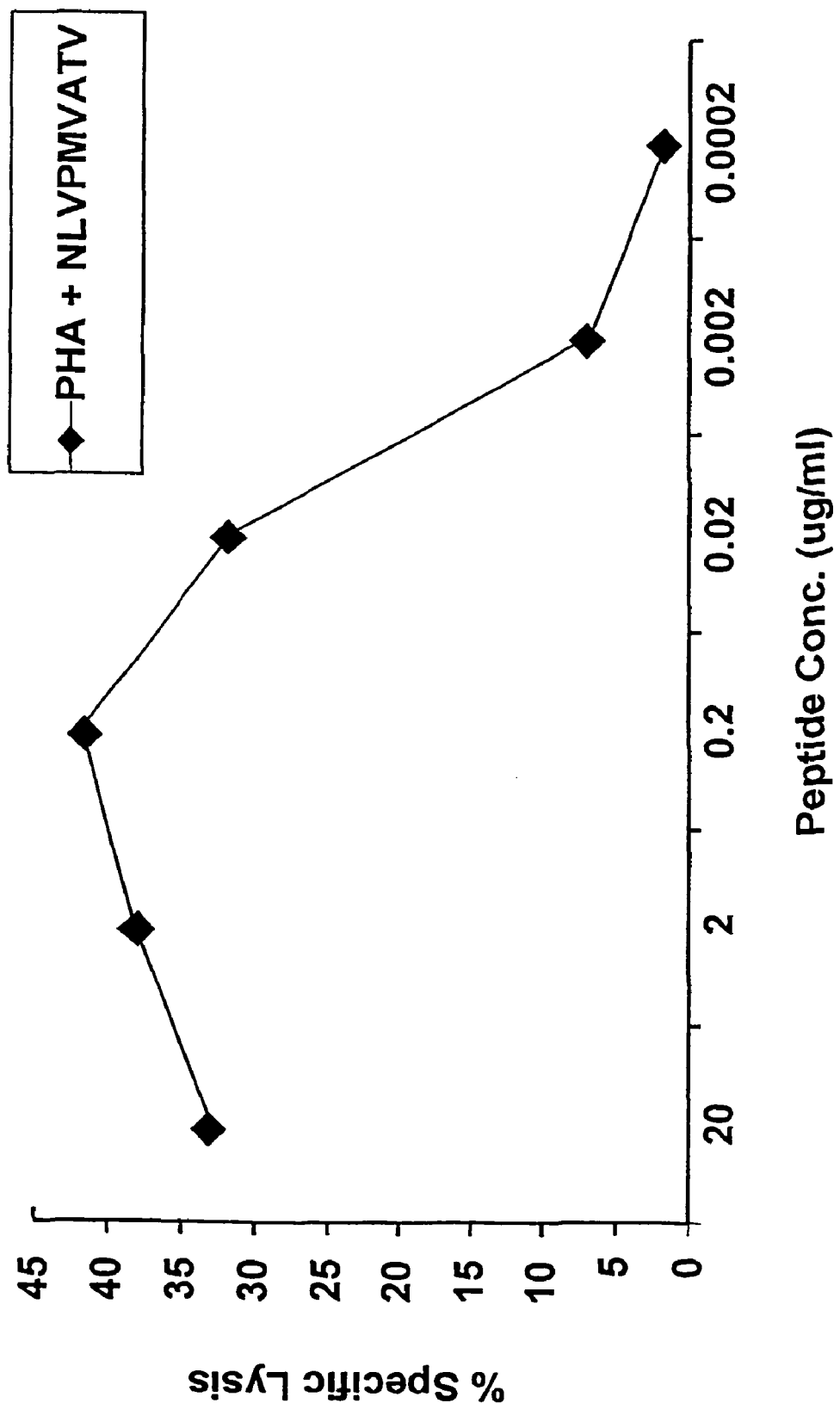
FIG. 5b is a graphical representation showing the percent specific lysis at different concentrations of a HLA A2-restricted HCMV pp65-derived CTL epitope having the amino acid sequence NLVPMATV (SEQ ID NO: 5), using virus-specific CTL clones from healthy virus carriers. CTL clones from healthy virus carriers were isolated as described herein and incubated with the peptide. CTL clones specific for the peptide epitope were tested against autologous PHA blasts presensitized with varying concentrations of synthetic peptide (x-axis). Results are expressed as percent specific lysis.
Figure 5C:
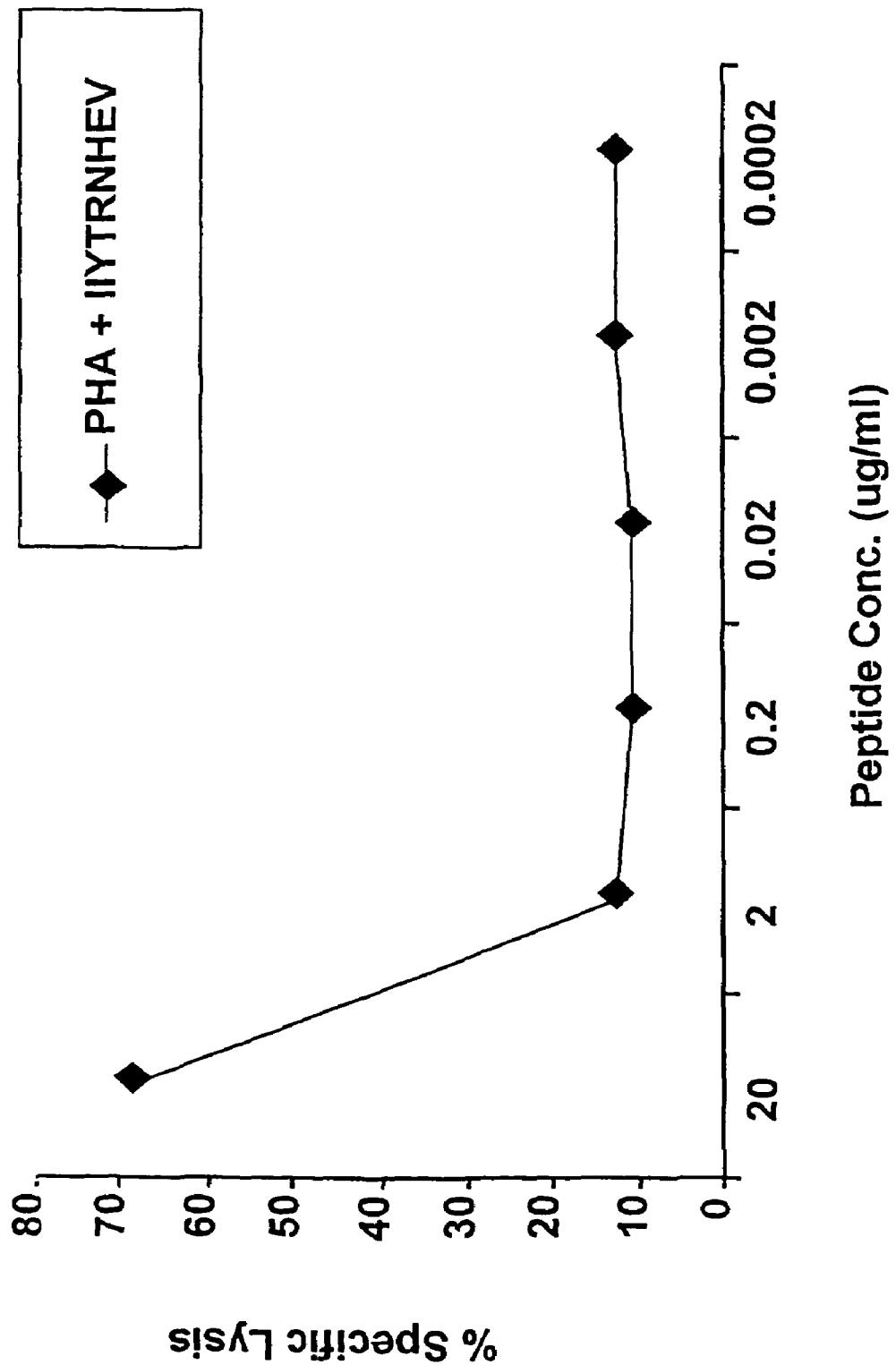
FIG. 5c is a graphical representation showing the percent specific lysis at different concentrations of a HLA A2-restricted HCMV IE-2-derived CTL epitope having the amino acid sequence IIYTRNHEV (SEQ ID NO: 254), using virus-specific CTL clones from healthy virus carriers. CTL clones from healthy virus carriers were isolated as described herein and incubated with the peptide. CTL clones specific for the peptide epitope were tested against autologous PHA blasts presensitized with varying concentrations of synthetic peptide (x-axis). Results are expressed as percent specific lysis.
Figure 5D:
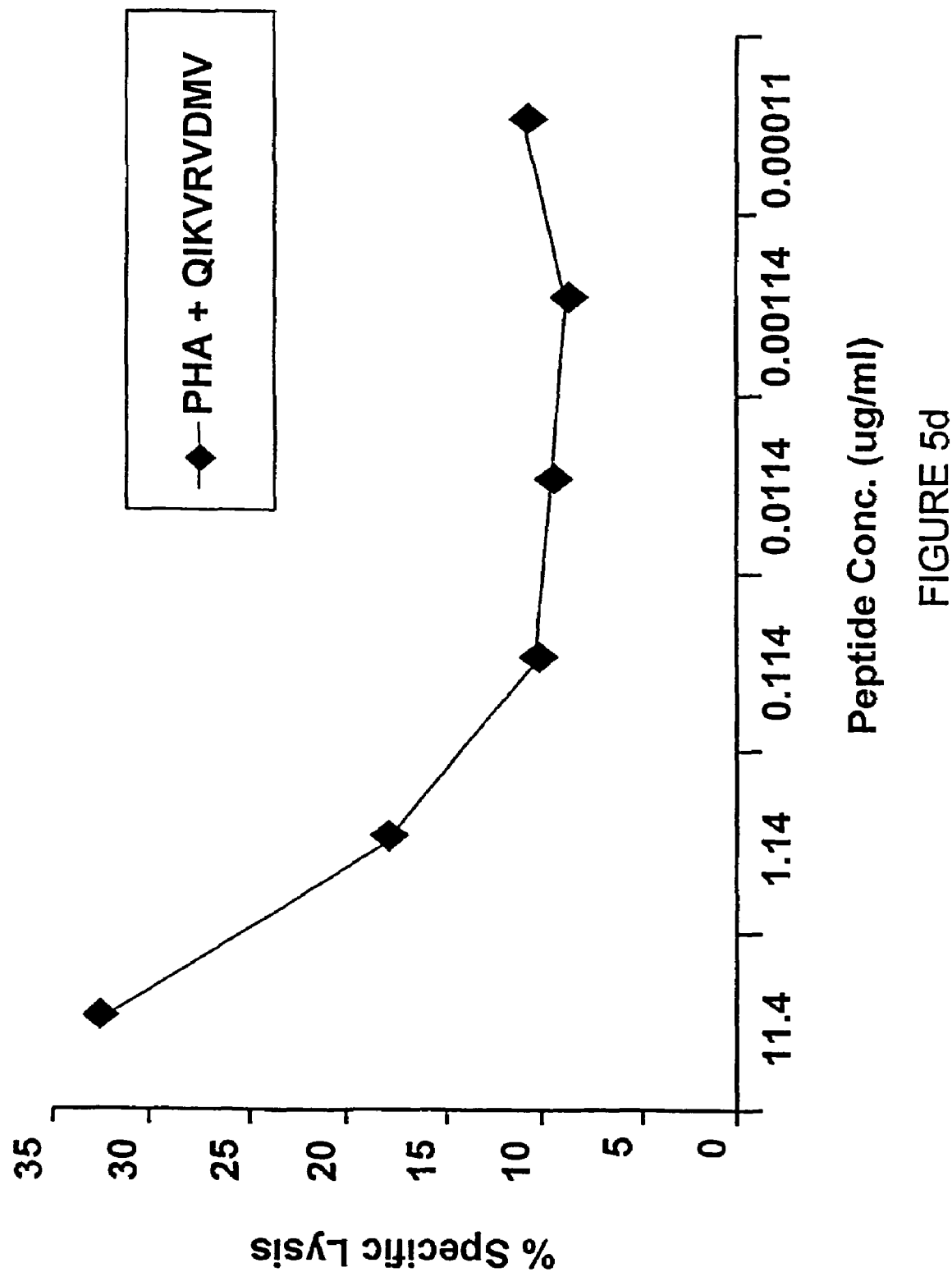
FIG. 5d is a graphical representation showing the percent specific lysis at different concentrations of a HLA B8-restricted HCMV IE-1-derived CTL epitope having the amino acid sequence QIKVRVDMV (SEQ ID NO: 113), using virus-specific CTL clones from healthy virus carriers. CTL clones from healthy virus carriers were isolated as described herein and incubated with the peptide. CTL clones specific for the peptide epitope were tested against autologous PHA blasts presensitized with varying concentrations of synthetic peptide (x-axis). Results are expressed as percent specific lysis.

Other CTL clones tested in this study were specific for the HLA A2-restricted pp65 epitope NLVPMVATV (SEQ ID NO: 5) as shown in FIG. 5b; the HLA A2-restricted IE-2 epitope IIYTRNHEV (SEQ ID NO: 254; FIG. 5c), or the HLA B8-restricted IE-1 epitope QIKVRVDMV (SEQ ID NO: 113; FIG. 5d). A comparison of the overall CTL reactivity of clones specific for IIYTRNHEV (SEQ ID NO: 254) revealed that this epitope was generally poorly recognized at limiting concentrations (FIG. 5c). The peptide concentration required for half maximal lysis for the IIYTRNHEV (SEQ ID NO: 254) epitope was almost 100-500 fold more than the NLVPMVATV (SEQ ID NO: 5) and VLEETSVML (SEQ ID NO: 101) epitopes respectively. An identical pattern of peptide titration was also seen with another five different CTL clones specific for the epitope IIYTRNHEV (SEQ ID NO: 254) (data not shown).

EXAMPLE 6

CTL Recognition of Recombinant Vaccinia Encoded HCMV Antigens

Figure 6:
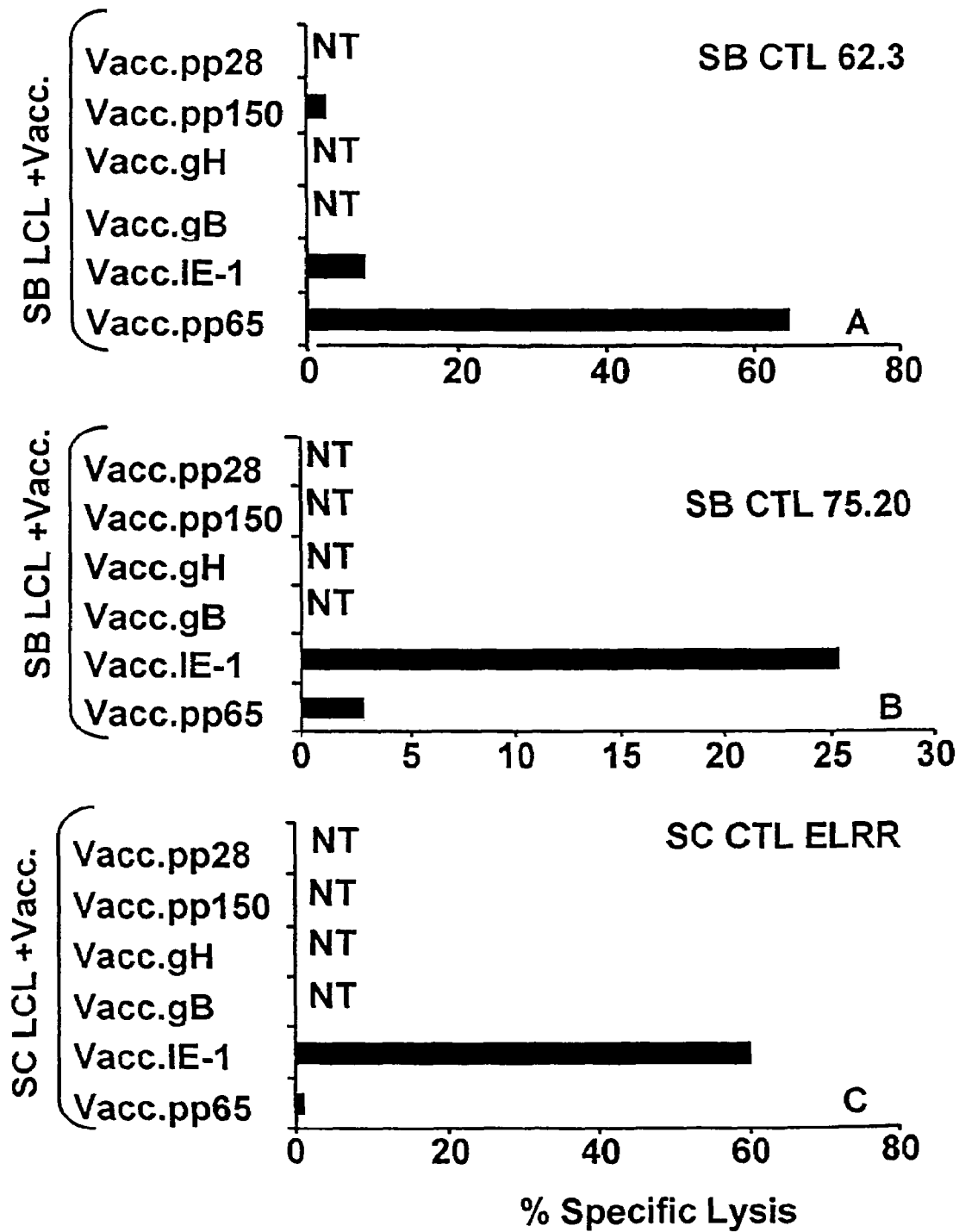
FIG. 6 is a graphical representation showing specific lysis by HCMV-specific CTLs from healthy HCMV seropositive donors designated SB (top panel marked SB CTL 62.3 and middle panel marked SB CTL 75.20) or SC (lower panel marked SC CTL ELRR) of autologous LCLs infected with recombinant vaccinia virus expressing the HCMV antigens pp65 (Vacc.pp65), IE-1 (Vacc.IE-1), gB (Vacc.gB), gH (Vacc.gH), pp150 (Vacc.pp150) or pp28 (Vacc.pp28). LCLs were infected with vaccinia constructs for 12-14 h at a multiplicity of infection (MOI) of 10:1, and processed for standard $^{51}$Cr-release assay. Results are expressed as percent specific lysis observed in a standard 4 h chromium-release assay. An effector to target ratio of 5:1 was used throughout the assay.
Figure 7A:
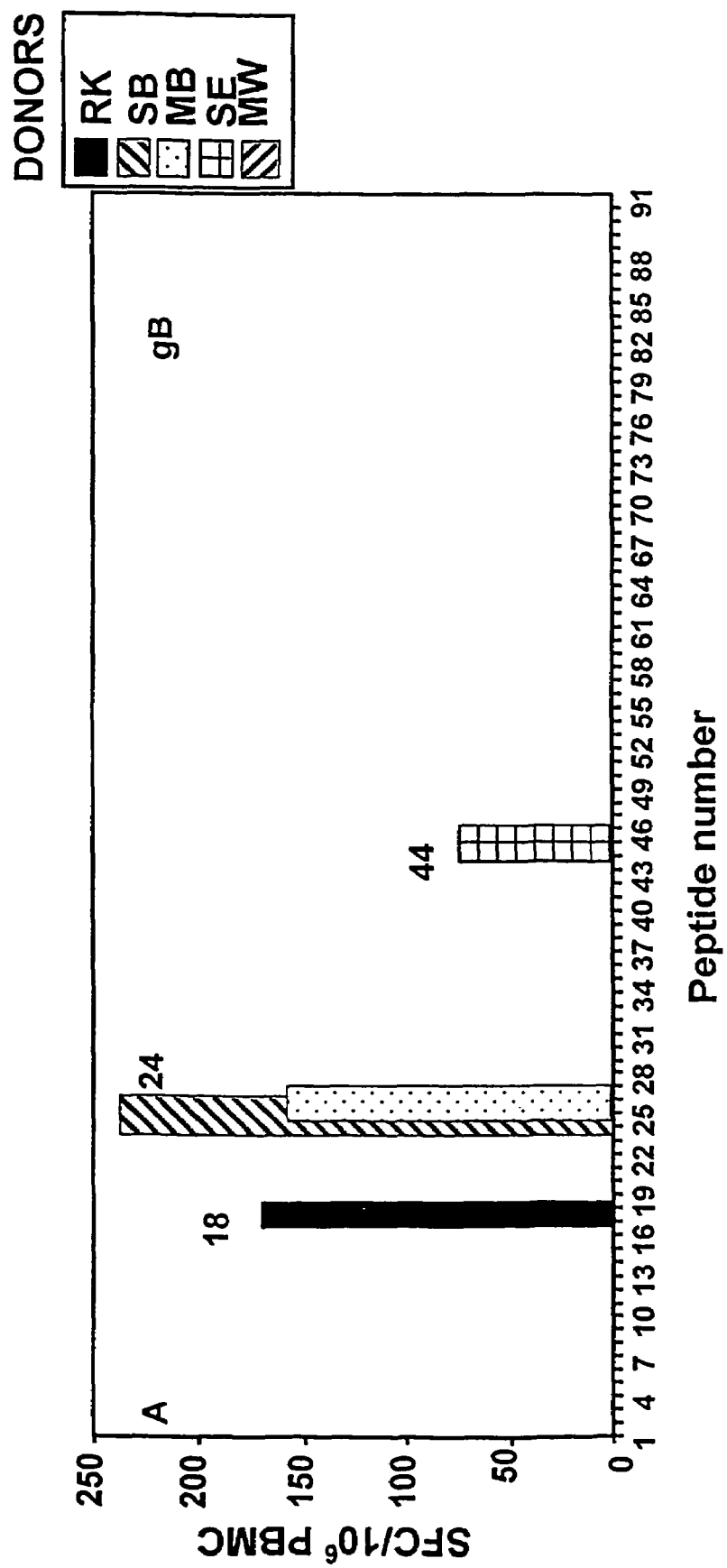
FIG. 7a is a graphical representation showing ex vivo HCMV-specific T cell responses against overlapping sets of peptides derived from HCMV antigen gB. A set of 92 overlapping peptides was tested in a cohort of five unrelated healthy HCMV carriers designated RK (filled), SB (forward hatching), MB (stippled), SE (cross-hatched) and MW (back hatched), using ELISPOT assays. PBMC from these donors were stimulated with individual synthetic peptides and IFN-γ production was measured in ELISPOT assay as described herein. The results are expressed on the ordinate as spot forming cells (SFC) per $10^6$ PBMC. Peptide number is indicated on the x-axis and at the top of each column.
Figure 7B:
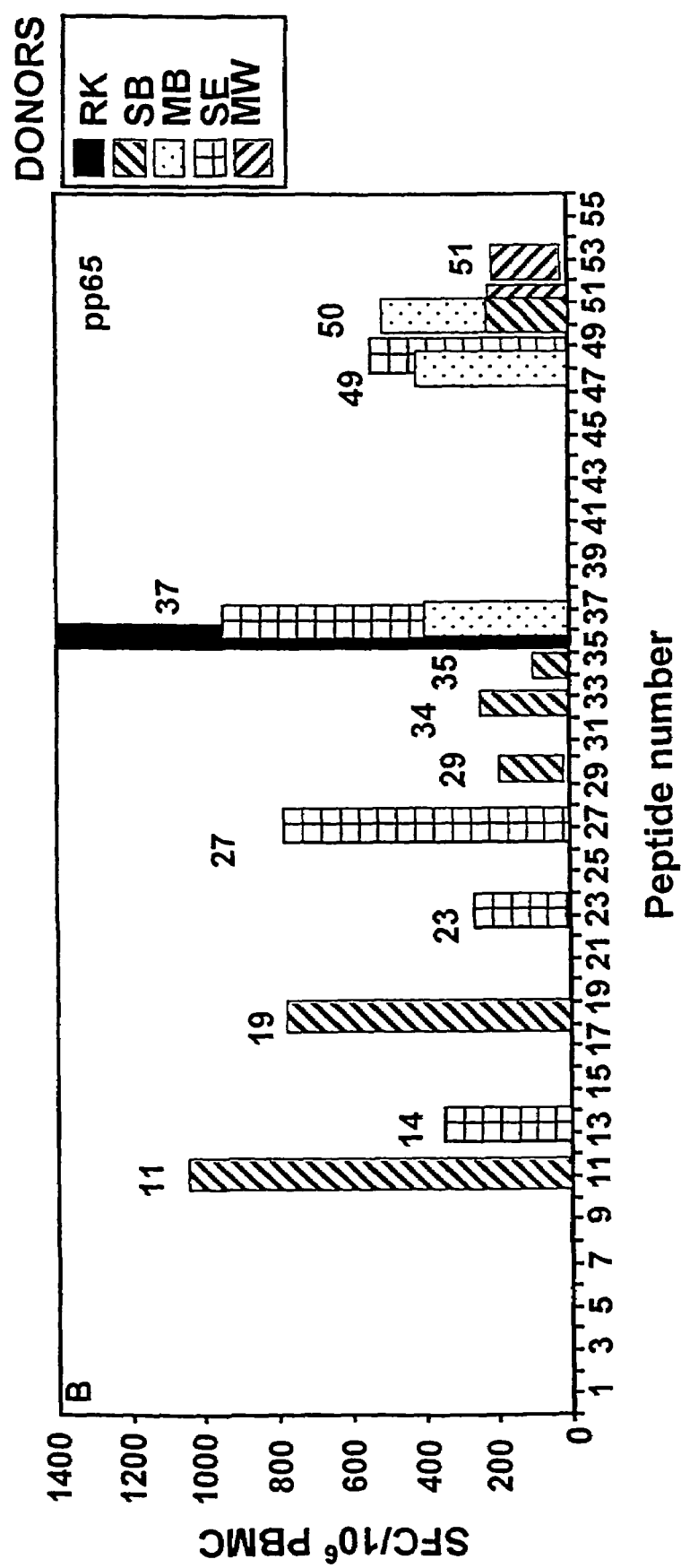
Figure 7C:
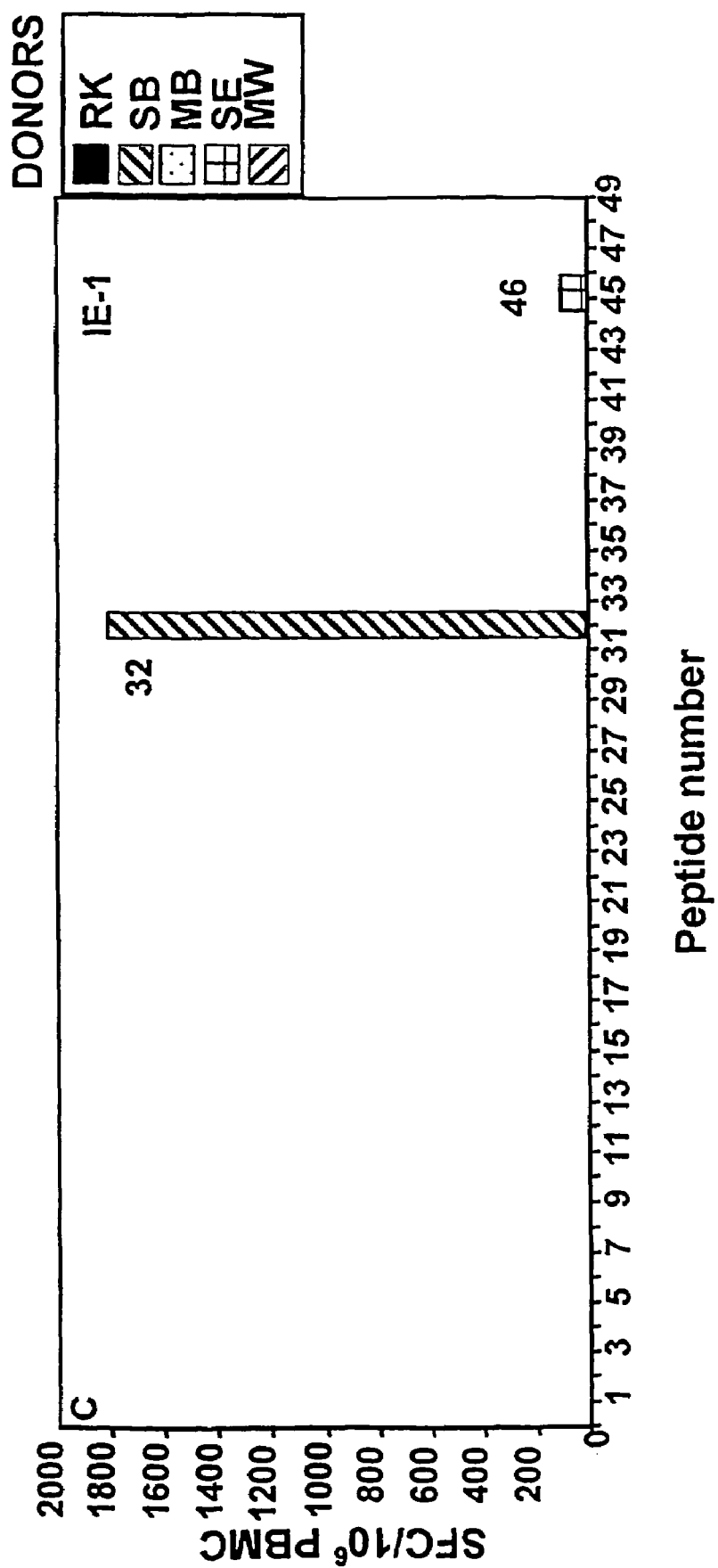
Figure 7D:
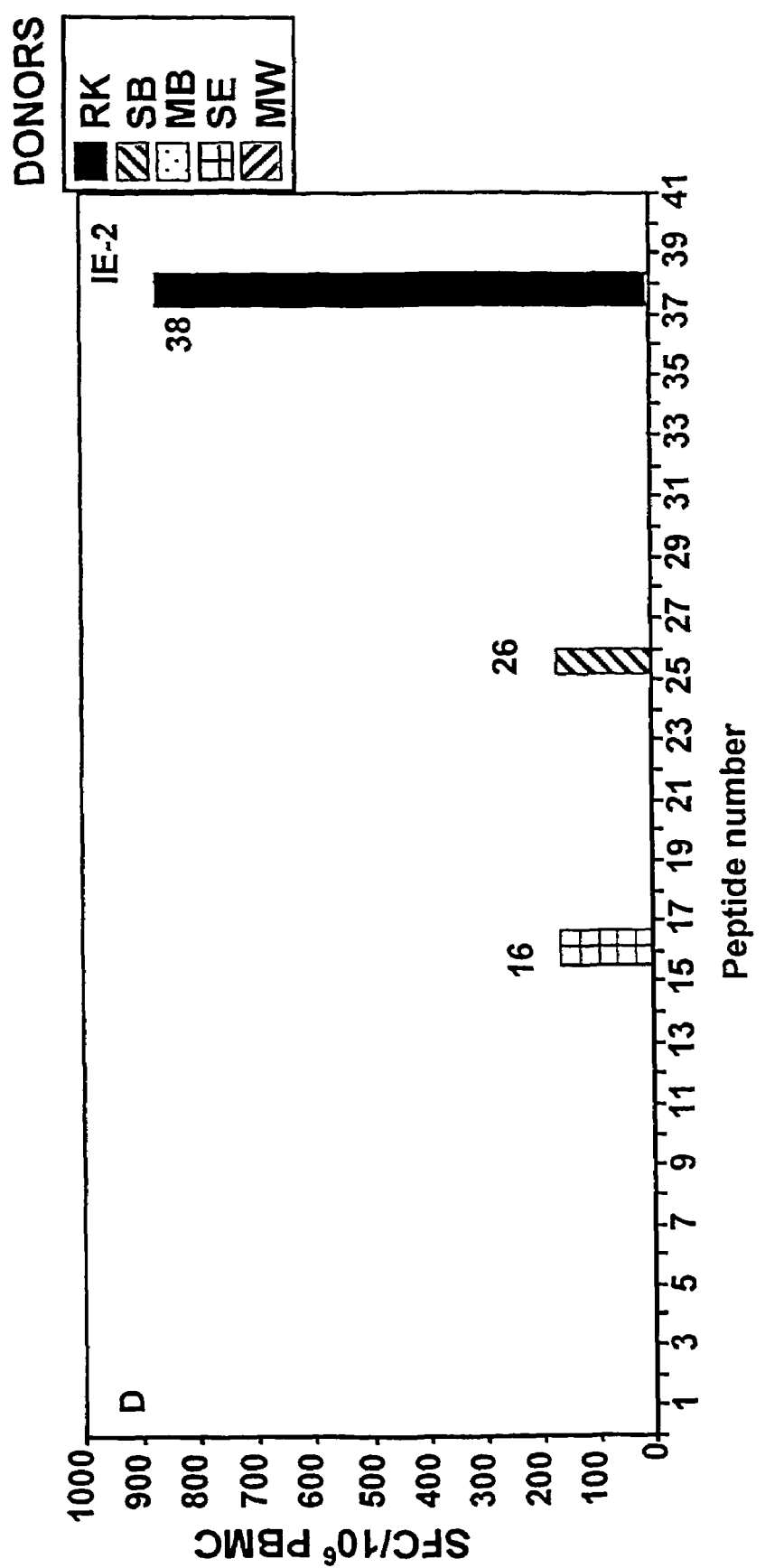
Figure 7E:
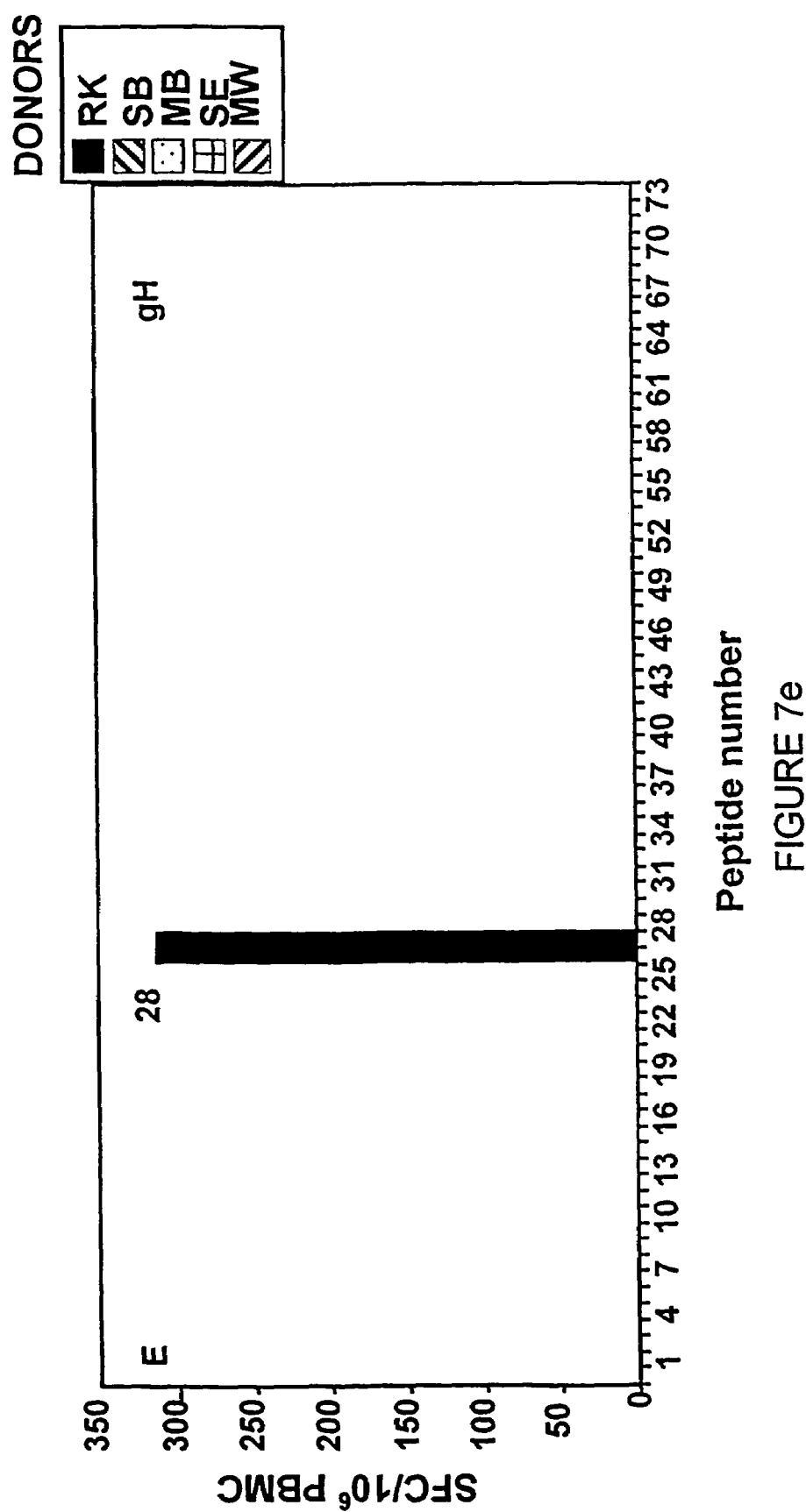
Figure 7F:
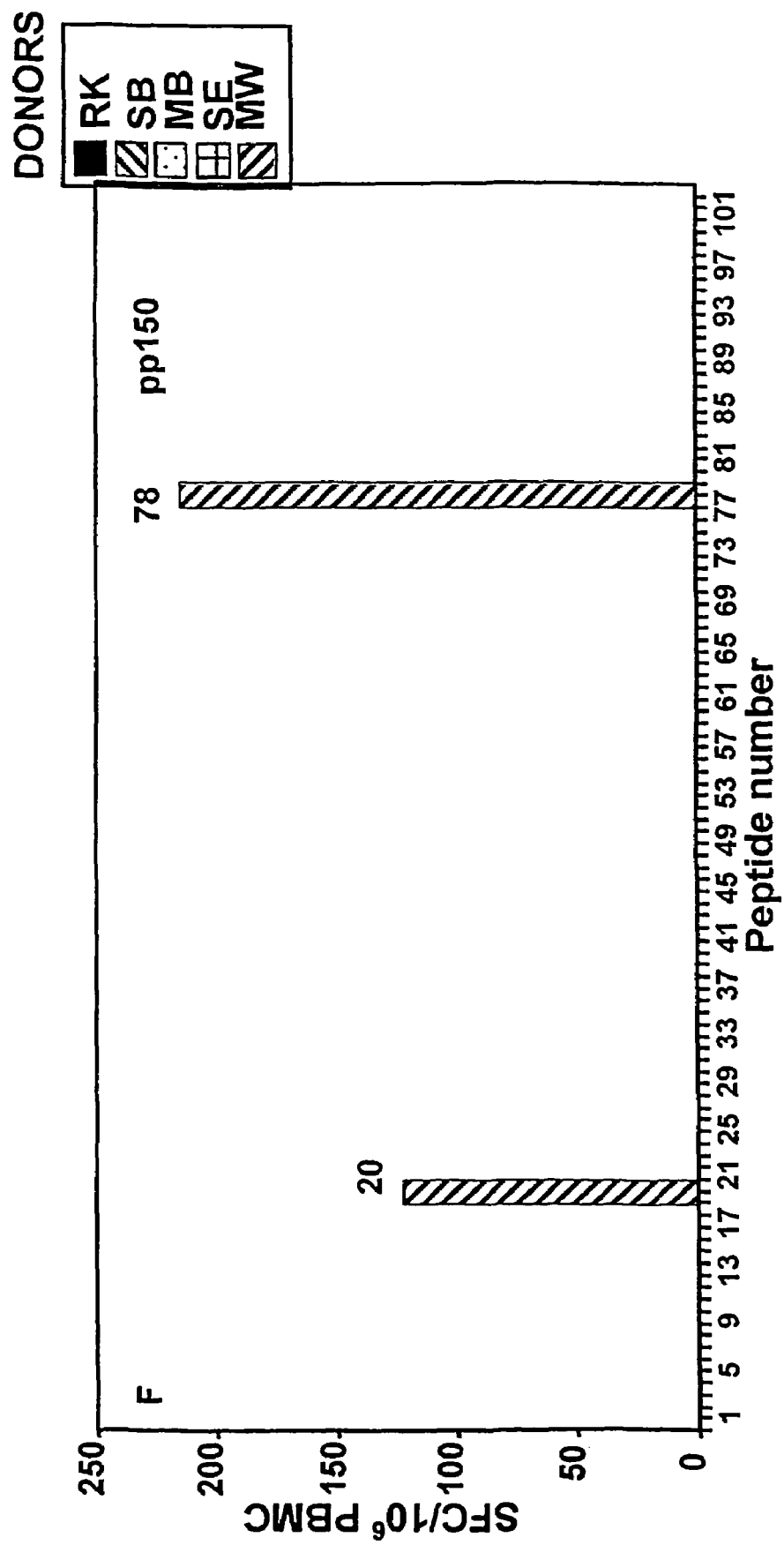

The data presented herein clearly show that the epitopes predicted by computer-based algorithms, and subsequently tested by ELISPOT assays, were indeed able to recall a strong T cell response. To demonstrate that these CTL effectors were also able to recognize target cells expressing full-length HCMV antigens, we isolated more than 100 clonal or polyclonal T cell lines from a cohort of 14 healthy HCMV immune donors using the stimulation protocol described herein above. Those CTL lines showing strong reactivity towards the peptide-sensitized targets were tested against autologous LCLs infected with recombinant vaccinia vectors that expressed the HCMV antigens pp28, pp65, pp150, gH, gB, or IE-1. The reactivities of two different CTL clones from donors SB and a polyclonal CTL line from the donor SC are shown in FIG. 6. One of these clones recognized target cells infected with recombinant vaccinia encoding pp65 (referred to as Vacc.pp65; top panel of FIG. 6). The remaining two CTL lines recognized Vacc.IE-1 infected target cells (middle and lower panels of FIG. 6). Similarly, CTL clones/lines specific for other CTL epitopes showing strong peptide-specific reactivity efficiently recognized recombinant vaccinia-infected targets (data not shown). These results demonstrate that the CTL epitopes mapped using the strategy described herein represent the overall repertoire of CTL responses to HCMV, and that these epitopes are efficiently processed endogenously by virus-infected cells.

EXAMPLE 7

ELISPOT and CTL Assays Using Overlapping Peptides from HCMV Antigens

Previous studies from both our laboratory and other groups have indicated that, although computer-based algorithms can be successfully employed to map a large panel of novel epitopes, this approach is limited by the availability of the specific motifs for individual HLA alleles. Moreover, class I-restricted epitopes that do not conform to the constraints laid out by the computer-based algorithms, with respect to the length of the epitope and the potential MHC-binding anchor residues, are often not selected by such predictive methods. To overcome these potential limitations, we selected six of the most dominant HCMV antigens (gB, gH, IE-1, IE-2, pp150 and pp65), and synthesized complete sets of overlapping peptides (20 amino acids long, each member overlapping with another member of the same set by 10 amino acids) spanning the full length of each antigen. Thus, a total of 450 peptides were produced. ELISPOT assays were used to determine whether ex vivo memory T cell responses could be detected in a cohort of 14 healthy virus carriers (Table 2). PBMC were stimulated with individual peptides and the cells that produced IFN-γ were detected. Representative data from a subset of five healthy virus carriers are shown in FIGS. 7a through 7f. Strong ELISPOT responses to multiple peptides from different HCMV antigens were detected. Consistent with our earlier analysis, peptides from pp65 were the most frequently recognized epitopes in ELISPOT assays. The analysis with 20-mer peptides also indicated that the IE-2 antigen was more often recognized when compared to IE-1, gB, gH and pp150.

The overall repertoire of T cell responses to HCMV was not constrained to a single antigen. In every responding donor, two or more antigens were consistently recognized as targets for CTL control. In spite of the diversity of these responses, a dominant response to one or two epitopes was always evident in responding donors.

Figure 8:
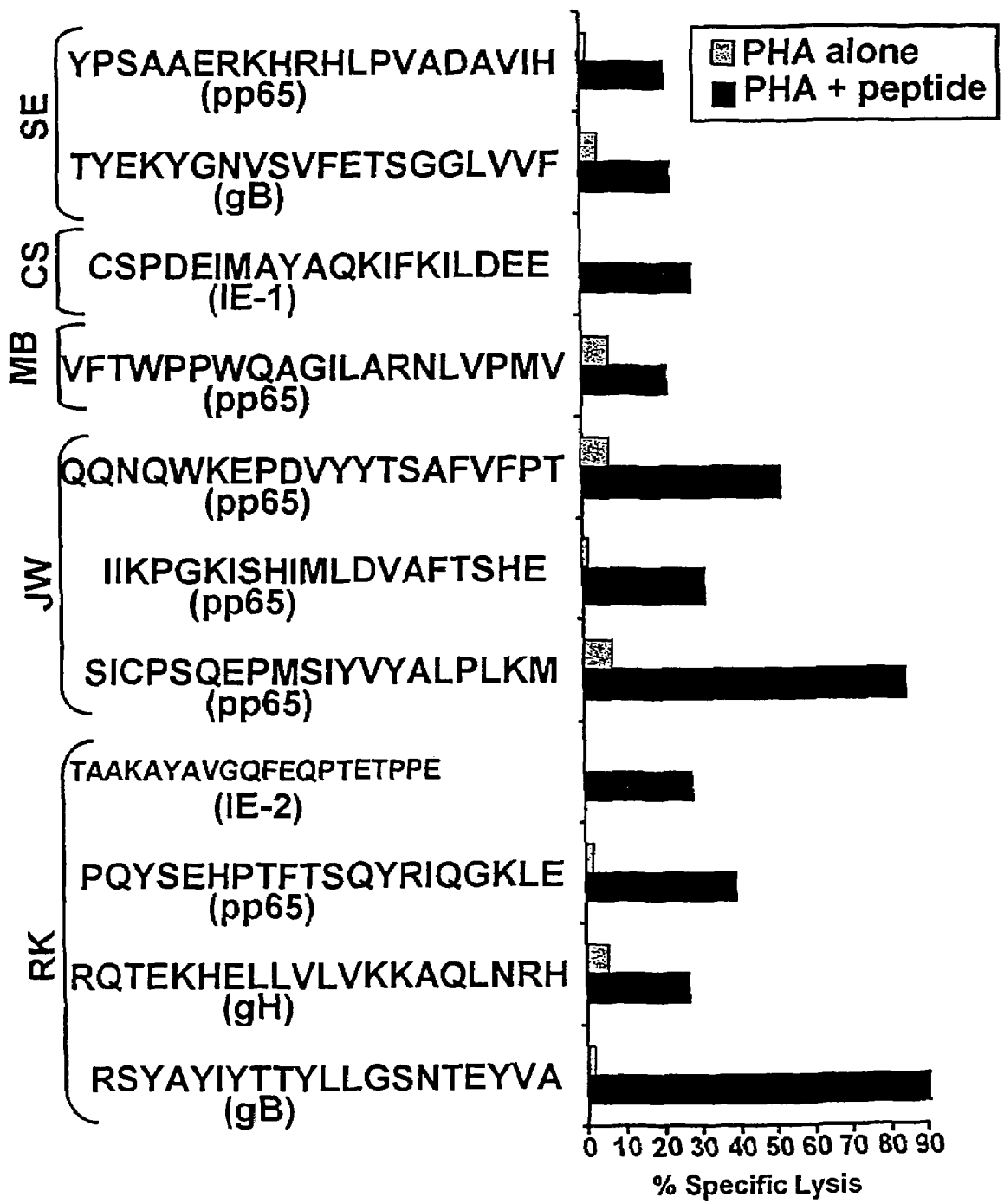
FIG. 8 is a graphical representation showing the CTL recognition of 20-mer peptides from HCMV antigens by polyclonal effectors from healthy seropositive donors. PBMC from healthy HCMV seropositive donors designated RK, JW, MB, CS and SE were co-cultivated for 7 days with autologous PBMC sensitized with each specific peptide epitope (20 μg/ml) at a ratio of 2:1. Peptides tested had the amino acid sequences indicated on the ordinate (i.e. SEQ ID NOs: 75, 193, 117, 72, 92, 77, 90, 269, 70, 249, and 192 respectively, from the top to the bottom of the figure). On day 7, these cultures were restimulated with autologous γ-irradiated EBV-transformed LCLs sensitized with peptide epitopes. On day 10, these T cell lines were used as polyclonal effectors in a standard $^{51}$Cr-release assay against peptide-sensitized autologous PHA blasts. An effector:target ratio of 10:1 was used in these assays. Results are expressed on the x-axis as percent specific lysis.

In addition to the identification of the epitopes by ELISPOT, their validity was further confirmed by specifically stimulating T cells with peptides to generate polyclonal and clonal CTL lines. Data from one such analysis based on six different donors (RK, JW, MB, CS, SB and SE) are presented in FIG. 8.

Figure 9:
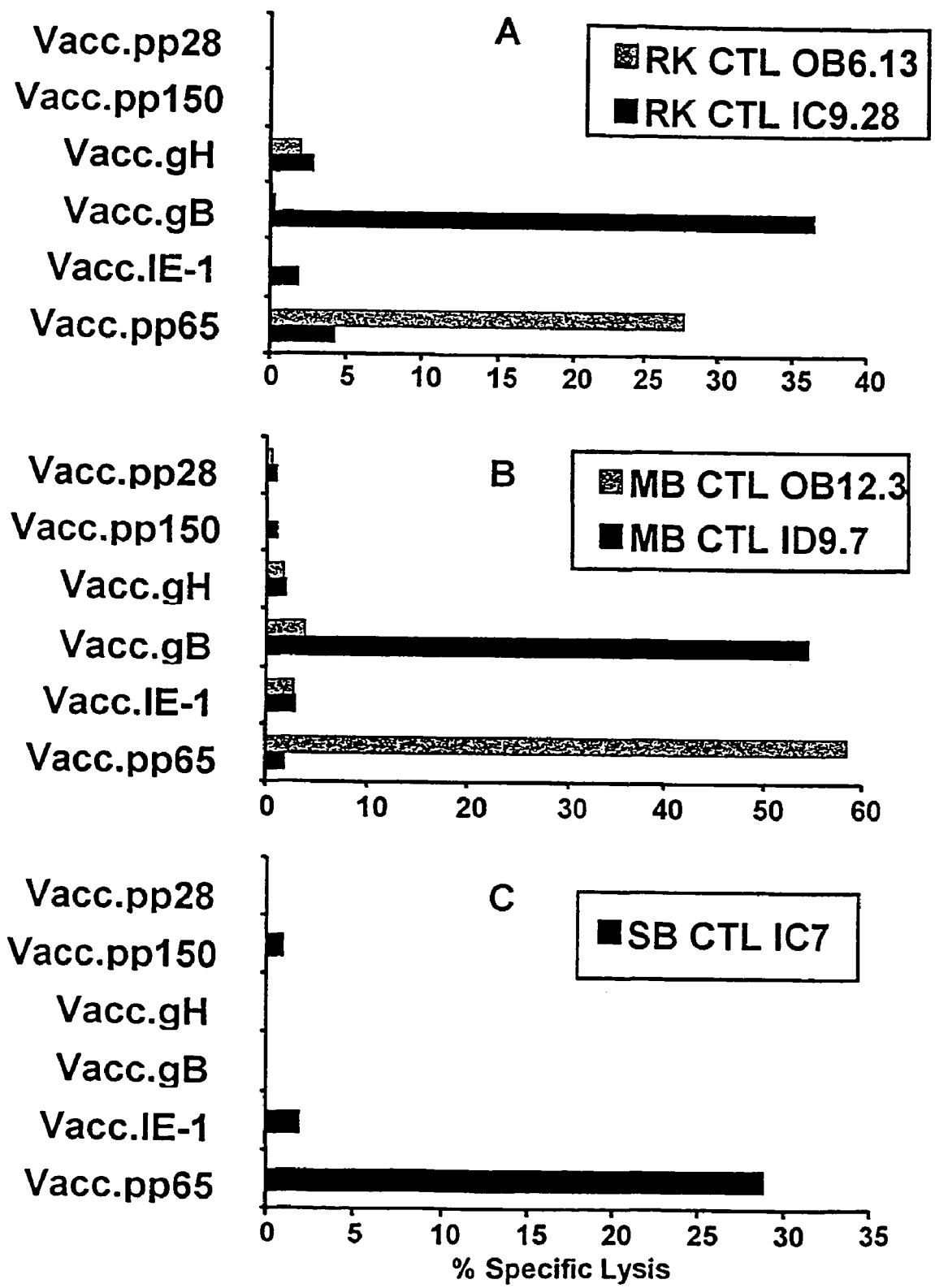
FIG. 9 is a graphical representation showing the function of HCMV-specific CTL clones derived from healthy HCMV seropositive donors designated RK (ie. panel A; clones RK.CTL OB6.13 and RK CTL 1C9.28), MB (ie. panel B; clones MB CTL OB12.3 and MB CTL 1D9.7), and SB (ie. panel C; clone SB CTL 1C7) generated by in vitro stimulation with 20-mer peptides. Clones were tested on autologous LCLs infected with recombinant vaccinia virus encoding individual HCMV antigens (Vacc.pp28, Vacc.pp150, Vacc.gH, Vacc.gB, Vacc.IE-1 and Vacc.pp65 respectively, from top to bottom in each panel). LCLs were infected with vaccinia constructs for 12-14 h (MOI of 10:1) and processed for standard $^{51}$Cr-release assay. Results are expressed on the x-axis as percent specific lysis observed in a standard 4 h chromium-release assay. An effector to target ratio of 5:1 was used throughout the assay.

The antigen specificity of the effectors generated was subsequently confirmed using autologous LCLs targets infected with recombinant vaccinia virus that expressed individual HCMV antigens in a $^{51}$Cr-release assay. Data presented in FIG. 9, show that CTL clones from donor RK (panel A) and MB (panel B) recognized Vacc.gB (OB6.13, OB12.3) and Vacc.pp65 (1C9.28, ID9.7), respectively, while a polyclonal line from donor SB (panel C) recognized Vacc.pp65 (IC7 CTL).

The analysis of overlapping 20-mer peptides identified numerous novel sequences from HCMV proteins that were not identified using predictive algorithms. This highlights the need to combine both approaches to comprehensively map CTL epitopes within virally-encoded antigens.

Figure 10A:
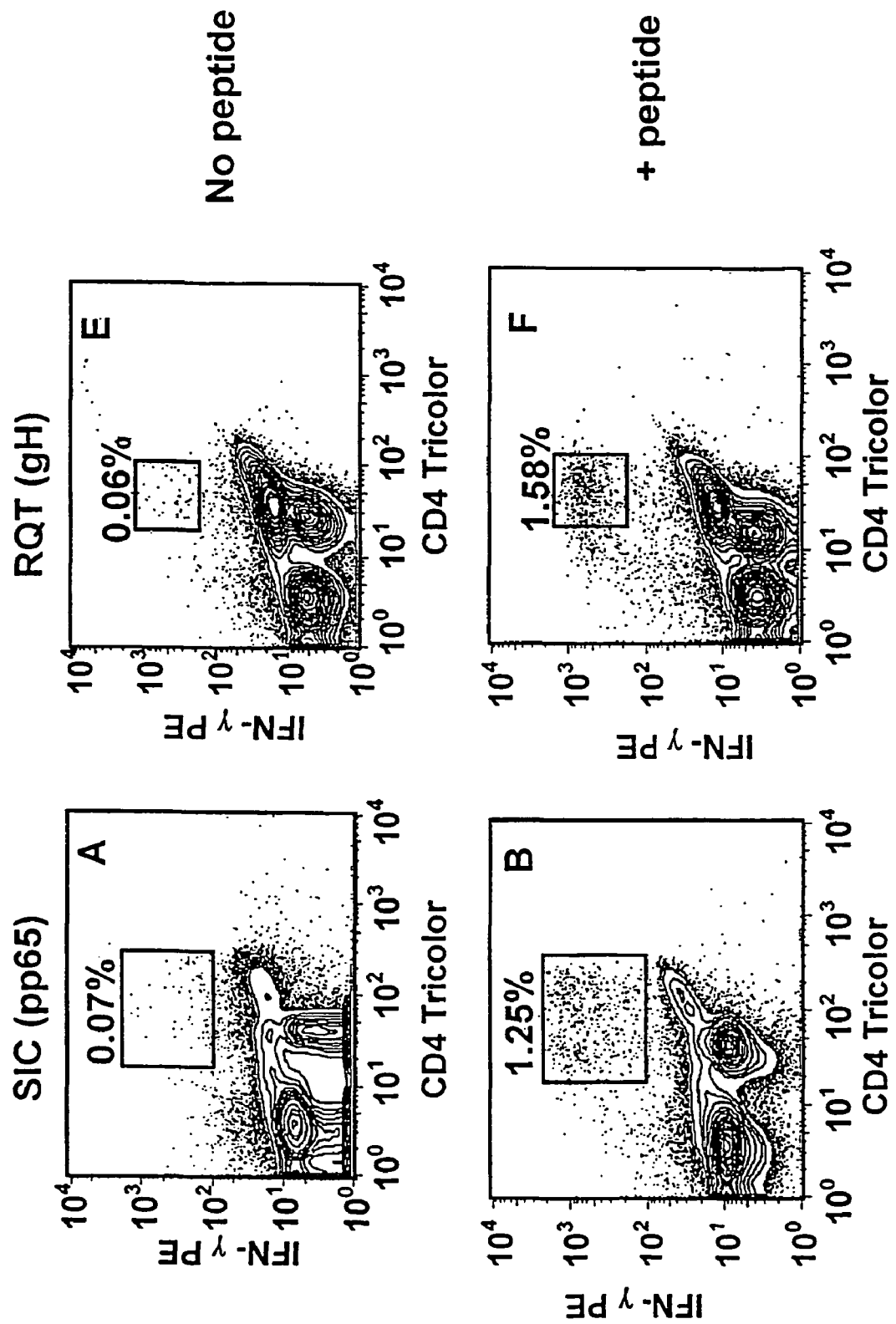
FIG. 10a is a representation showing IFN-γ secretion by CD4$^+$ T cell populations in the absence of peptide (panels marked "No peptide") or in response 20-mer peptides derived from HCMV pp65 or HCMV gH antigens (panels marked "+ peptide"). The 20-mer peptides were a pp65-derived 20-mer peptide having the sequence SICPSQEPMSIYVYALPLKM (SEQ ID NO: 90; designated SIC in the figure; left panel) and to an gH-derived 20-mer peptide having the sequence RQTEKHELLVLVKKAQLNRH (SEQ ID NO: 249; designated RQT in the figure; right panel). Cells were progressively gated by forward- and side-scatter for lymphocytes and CD3+ for T cells. Gated populations are plotted on probability contour plots as CD4-staining (horizontal axis) versus IFN-γ-staining (vertical axis). Frequencies of antigen-specific CD4+ and IFN-γ-positive cells (within total CD4+ T cells) are shown above each box.
Figure 10B:
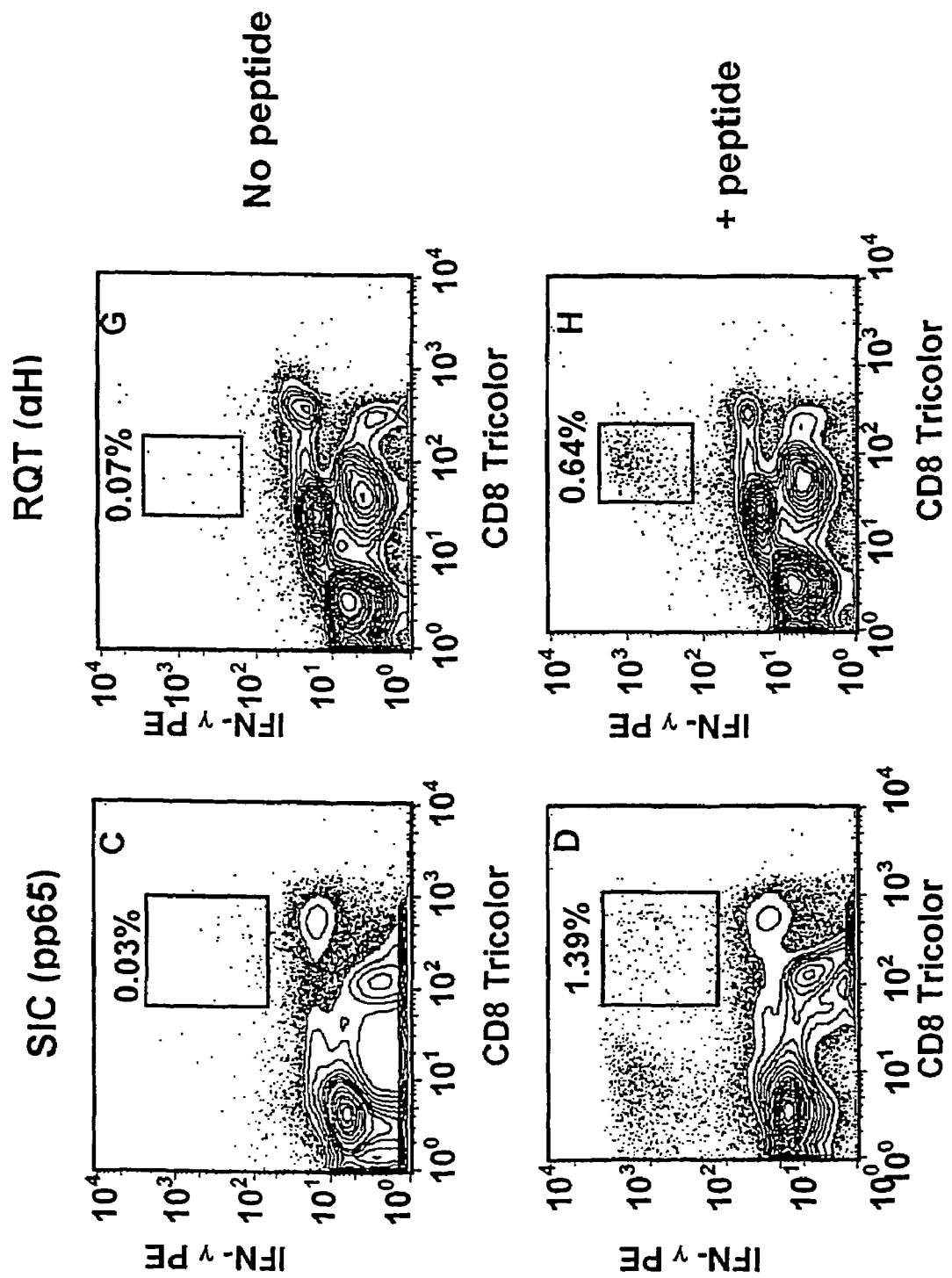
FIG. 10b is a representation showing IFN-γ secretion by CD8+ T cell populations in the absence of peptide (panels marked "No peptide") or in response 20-mer peptides derived from HCMV pp65 or HCMV gH antigens (panels marked "+ peptide"). The 20-mer peptides were a pp65-derived 20-mer peptide having the sequence SICPSQEPMSIYVYALPLKM (SEQ ID NO: 90; designated SIC in the figure; left panel) and to an gH-derived 20-mer peptide having the sequence RQTEKHELLVLVKKAQLNRH (SEQ ID NO: 249; designated RQT in the figure; right panel). Cells were progressively gated by forward- and side-scatter for lymphocytes and CD3+ for T cells. Gated populations are plotted on probability contour plots as CD8-staining (horizontal axis) versus IFN-γ-staining (vertical axis). Frequencies of antigen-specific CD8+ and IFN-γ-positive cells (within total CD8+ T cells) are shown above each box.

When using 20-mer peptides to map epitopes by ELISPOT, it is possible that some responses may be MHC class-II restricted, and not necessarily restricted through HLA class I alleles. It was evident throughout this study that some epitopes identified using ELISPOT could not be confirmed using cytotoxicity analysis. In this instance, we investigated the existence of a class II-restricted epitope within 20-mer sequences using both intracellular IFN-γ staining techniques and IFN-γ ELISPOT. PBMC were co-stained with CD4, CD8, CD3 and IFN-γ after stimulation with various 20-mer peptides, and the proportion of CD4$^+$ and CD8$^+$ populations that responded to the peptide were analysed by flow cytometry (FIGS. 10a through 10b).

For IFN-γ ELISPOT assays, populations of both CD4$^+$ T cell-depleted and CD8$^+$ T cell-depleted PBMC were prepared, stimulated with 20-mer peptides and the number of CD4$^+$ or CD8$^+$ T cells that responded to the peptide by producing IFN-γ was evaluated. Both of these techniques proved valuable in characterising the presence of MHC class II-restricted epitopes from HCMV antigens.

In addition, MHC class II-restricted epitopes were identified from 20-mer sequences thought to contain only an MHC class I-restricted epitope. For example, the HCMV pp65 peptide SICPSQEPMSIYVYALPLKM (SEQ ID NO: 90) (referred to as SIC in FIGS. 10a and 10b) stimulated the production of IFN-γ in 3178 cells per 10⁶ PBMC from donor JW (see Table 4). However, substantial IFN-γ production was also detected in the CD3⁺/CD4⁺ population of PBMC from the same donor following intracellular IFN-γ analysis. Moreover, the percentage of the CD3+/CD4+cells that responded to the 20-mer sequence (1.18%) was comparable to the percentage of CD3⁺/CD8⁺ population of cells that responded (1.36%). This indicated that, not only did this sequence contain a class I-restricted CTL epitope, but also an MHC class II-restricted epitope. A second 20-mer peptide, that proved difficult to characterise as a CD8⁺ CTL epitope, was also found to contain a class II-restricted epitope. Repeated attempts to generate both polyclonal and clonal cytotoxic T cell lines specific for the gH peptide having the sequence RQTEKHELLV-LVKKAQLNRH (SEQ ID NO: 249) were unsuccessful. The results from flow cytometric analysis of intracellular IFN-γ production showed that 1.52% of CD3⁺/CD4⁺ T cells produced IFN-γ in response to this peptide, whereas only 0.57% of the CD3⁺/CD8⁺ population did so (FIGS. 10a and 10b). Therefore, the peptide set forth in SEQ ID NO: 249 induced a more substantial response from CD4⁺ T cells than from CD8⁺ T cells.

Where the precursor frequency of the cells responding to 20-mer peptides was too low to be detected by flow cytometry, IFN-γ ELISPOT assays were performed using CD4⁺ T cell- and CD8⁺ T cell-depleted populations of PBMC. This technique allowed both the visualisation and enumeration of the number cells producing IFN-γ in response to a given peptide. Detailed results from the CD4⁺/CD8⁺ analysis of 20-mer peptides are presented in Table 4. The use of both of these techniques has highlighted the presence of MHC class II-restricted epitopes not only within the conventional HCMV target antigens gB and gH (Plotkin et al., *Pediatr. Infect. Dis. J.* 18, 313, 1999; and Britt et al., *Intervirol.* 39, 401, 1996), but within other HCMV antigens as well. This finding may have important implications for the future design of vaccine candidates that prime both cytotoxic and helper immune responses for protection against HCMV.

Figure 11A:
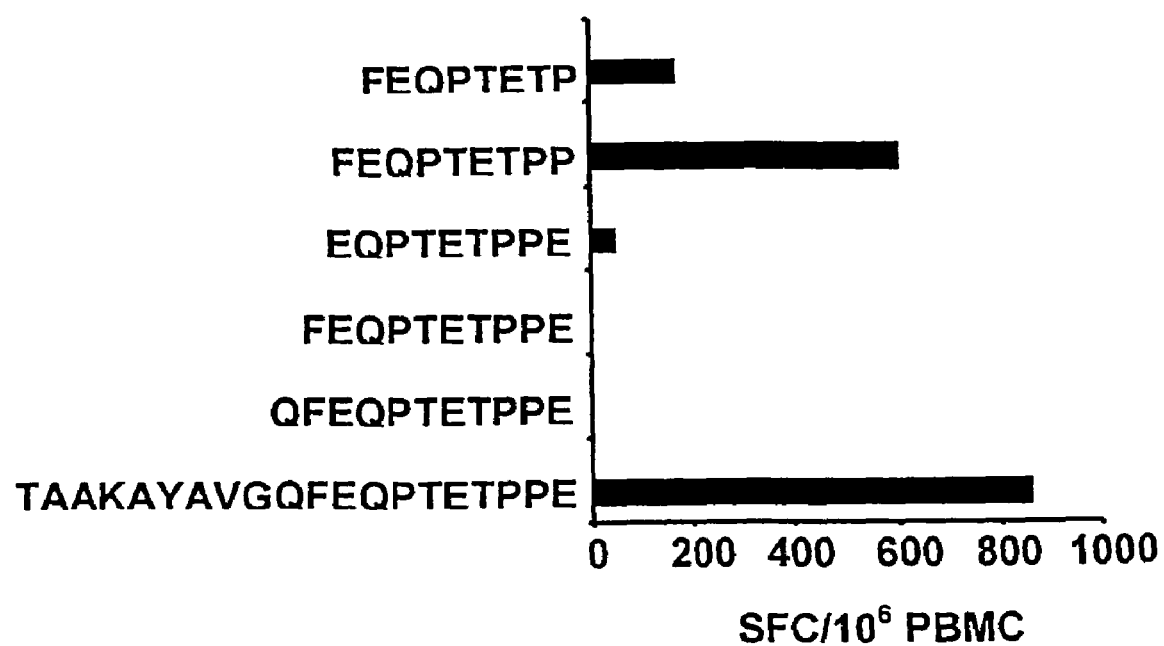
FIG. 11a is a graphical representation showing the mapping of minimal epitope sequences using ELISPOT assay. PBMC from a healthy seropositive donor designated RK were stimulated with overlapping peptides derived from HCMV IE-2 antigen, and IFN-γ production was measured in ELISPOT assays as described herein. Peptides tested had the amino acid sequence FEQPTETP (SEQ ID NO: 261), FEQPTETPP (SEQ ID NO: 260), EQPTETPPE (SEQ ID NO: 263), FEQPTETPPE (SEQ ID NO: 262), QFEQPTETPPE (SEQ ID NO: 264), or TAAKAYAVGQFEQPTETPPE (SEQ ID NO: 269). Data are expressed as spot forming cells (SFC) per $10^6$ PBMC.
Figure 11B:
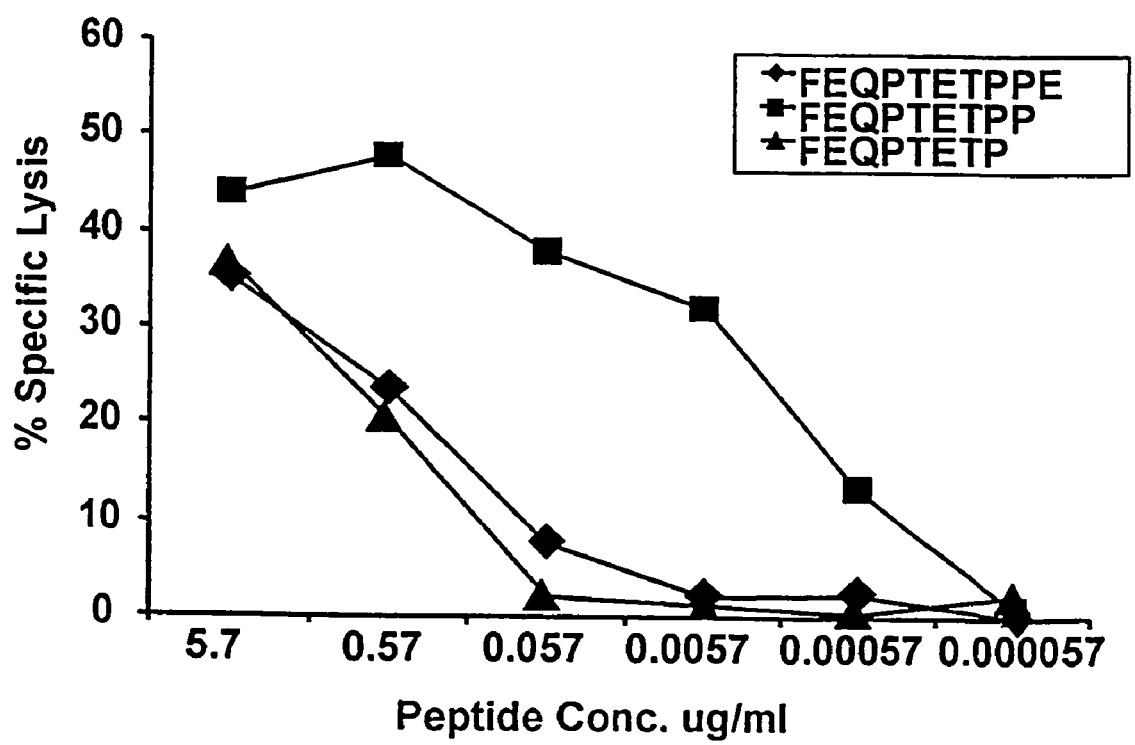
FIG. 11b is a graphical representation showing the mapping of minimal epitope sequences using a CTL assay. A CTL clone specific for the HCMV IE-2-derived peptide having the amino acid sequence TMKAYAVGQFEQPTETPPE (SEQ ID NO: 269) was tested against autologous PHA blast pre-sensitized with varying concentrations of overlapping synthetic peptides having the amino acid sequences FEQPTETPPE (SEQ ID NO: 262; ♦), FEQPTETPP (SEQ ID NO: 260; ■), or FEQPTETP (SEQ ID NO: 261; ▲). Peptide concentration is indicated on the x-axis. Percent specific lysis is indicated on the ordinate.

To identify the minimal sequences within the 20-mer peptides mapped by ELISPOT assays, overlapping 12-mer and/or 9-mer peptides were synthesized and tested in the ELISPOT and/or CTL assays. Data from one representative study are shown in FIGS. 11a and 11b. As shown above in Table 4, ELISPOT assays on 20-mer peptides indicated a strong response to the overlapping peptides TAAKAYAVGQFEQPTETPPE (SEQ ID NO: 269) and FEQPTETPPEDLDTLSLAIE (SEQ ID NO: 270) by donor RK, which was subsequently confirmed by in vitro cytotoxicity assays (Table 4). Both assays indicated that the sequence FEQPTETPP (SEQ ID NO: 260) was the minimal sequence required to induce strong lytic activity by T cells from the donor RK (FIGS. 11a and 11b).

A summary of this analysis is presented in Table 4.

Figure 12A:
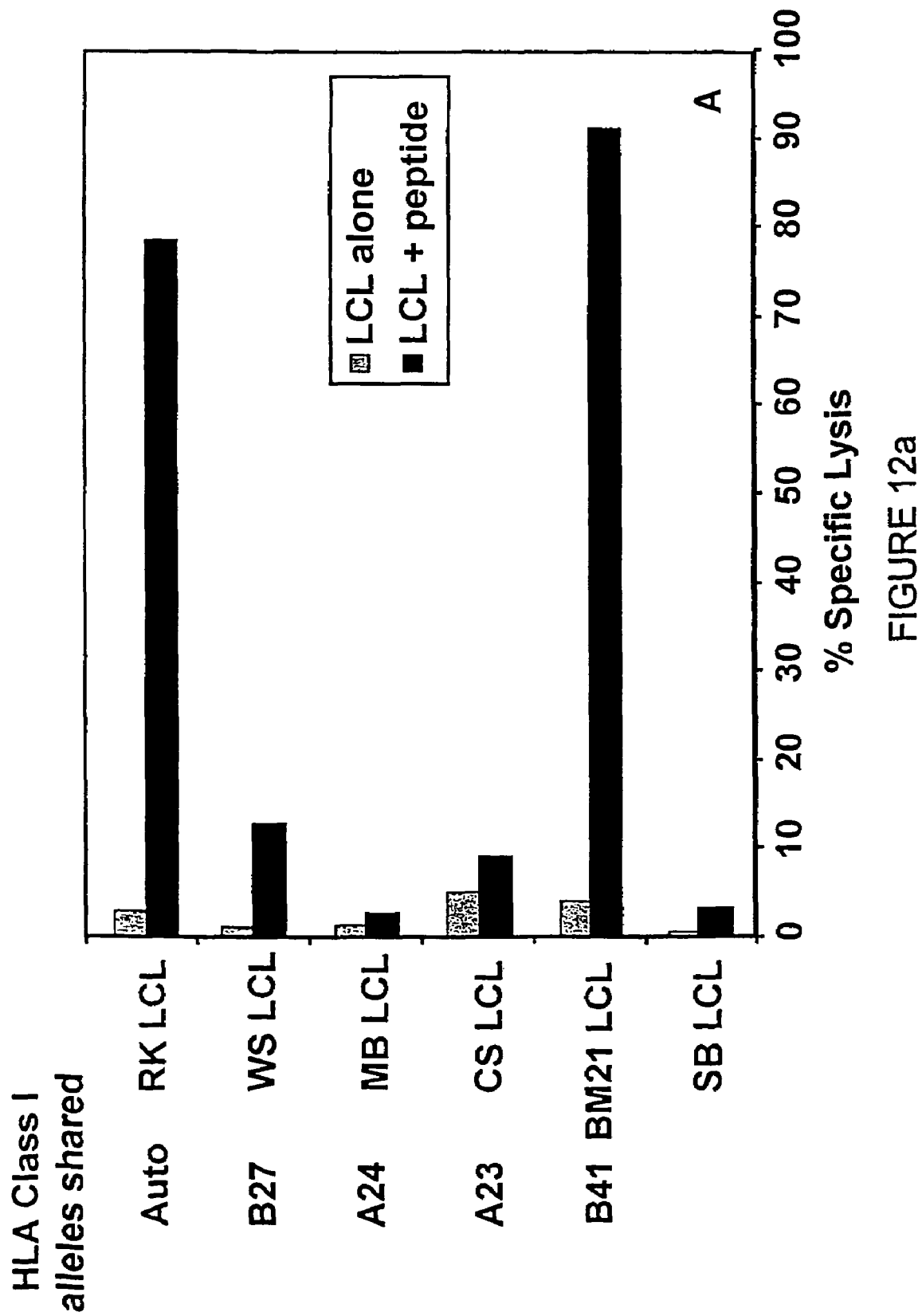
FIG. 12a is a graphical representation showing HLA class I restriction analysis of HCMV CTL epitopes derived from the HCMV IE-2 antigen against a HLA B41-restricted CTL line from a healthy seropositive donor designated RK. The CTL clone from donor RK was exposed to peptide-sensitized autologous LCLs from donor RK (Auto RK LCL) or to allogeneic LCLs from healthy seropositive donors designated WS (ie, WS LCL), MB (ie, MB LCL), CS (ie, CS LCL), BM21 (ie, BM21 LCL) or SB (ie, SB LCL) in a standard $^{51}$Cr-release assay. HLA class I alleles shared by individual LCLs with the donor RK (from whom the CTL line was established) are shown on the Y-axis. Data are shown as percent specific lysis on the x-axis.
Figure 12B:
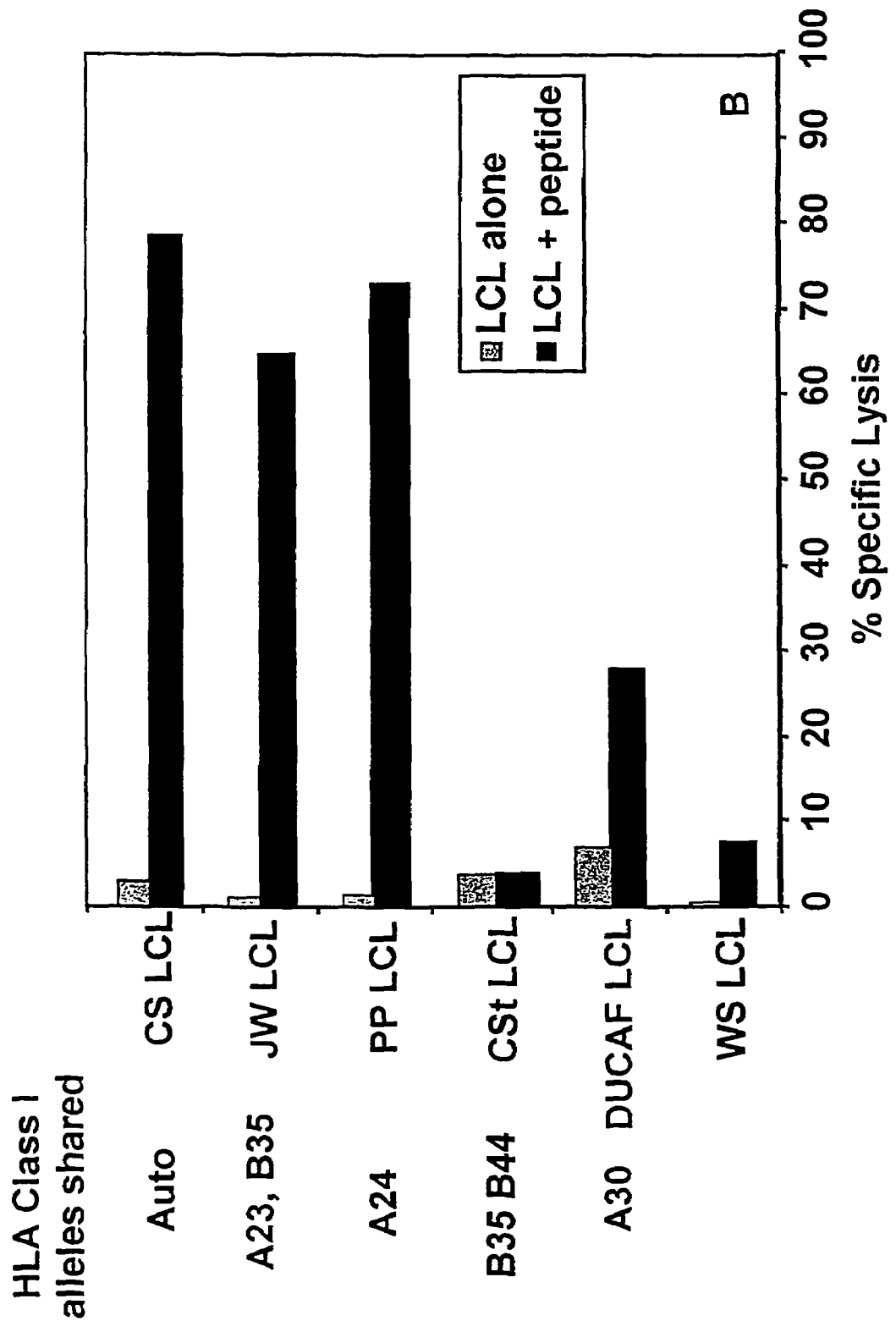
FIG. 12b is a graphical representation showing HLA class I restriction analysis of HCMV CTL epitopes derived from the HCMV IE-1 antigen against a CTL line from a healthy seropositive donor designated CS that recognizes peptide coated target cells expressing HLA A23, HLA A24 and HLA A30. The CTL clone from donor CS was exposed to peptide-sensitized autologous LCLs (Auto CS LCL), or to allogeneic LCLs from healthy seropositive donors designated JW (ie, JW LCL), PP (ie, PP LCL), CSt (ie, CSt LCL), DUCAF (ie, DUCAF LCL) or WS (ie, WS LCL) in a standard $^{51}$Cr-release assay. HLA class I alleles shared by individual LCLs with the donor CS (from whom the CTL line was established) are shown on the Y-axis. Data are shown as percent specific lysis on the x-axis.

The HLA class I-restriction of CTL epitopes was determined by comparing the lysis of peptide-sensitized autologous PHA blasts or LCLs and peptide-sensitized allogeneic PHA blasts or LCLs sharing one or more alleles. For example, HLA restriction analysis for CTL lines specific for epitopes within IE-2 and IE-1 antigens are presented in FIGS. 12a and 12b. An IE-2-specific CTL line from donor RK recognized the HLA B41-positive target cells, indicating that this epitope was restricted through HLA B41 allele (FIG. 12a). Of interest, was the reactivity of an IE-1-specific CTL line from donor CS, which recognized both HLA A23, A24 and A30-positive target cells sensitized with synthetic peptide epitope (FIG. 12b). These data suggests that this IE-1 epitope can efficiently bind multiple HLA A24 supertype alleles (Sette and Sidney, *Immunogenetics* 50, 201, 1999).

An overall summary of HLA restriction analysis for the 20-mer sequences is presented in Table 4.

EXAMPLE 8

Polyepitope peptides

In accordance with the procedures described herein, peptides comprising multiple HCMV epitopes were designed that are specific for the same or different HLA Class I restriction elements. The epitopes were designed so as to maximize the population coverage achieved by vaccination therewith. Accordingly, CTL epitopes that are restricted by frequently expressed HLA alleles (see Tables 1, 3 and 4) were preferred for inclusion in such polyepitope vaccines, and epitopes from both immunodominant pp65 IE-1, and pp150 proteins, as well as from subdominant antigens were included. The amino acid sequences of ten (10) representative polyepitope peptides are presented in SEQ ID NOs: 309-319.

EXAMPLE 9

Generation of CTLs

1. Generation of Polyclonal CTLs

Polyclonal CTL effectors are generated by stimulating PBMCs from healthy seropositive donors with autologous HCMV-transformed lymphoblastoid cell lines (LCLs) on days 0 and 7.

2. Agar Cloning of T-Cells.

T-cell clones from individual donors are generated as follows. PBMC's are isolated and suspended in medium at a concentration of 2×10⁶ cells in 24 well plates (Costar, Cambridge, Mass.). Peptide-sensitized PBMC from the same donor are added to each of these wells at either 10⁶ cells/well. After three days, cells are dispersed and seeded in 3.5 cm diameter culture dishes in 0.35% (w/v) agarose (Seaplaque, FMC Corp., Rockland, Me.) containing RPMI 1640, 20% 2×RPMI 1640, 20% FCS, 16% MLA supernatant and 50 U/ml recombinant IL-2 (rIL-2). Colonies appear within the agar after five days. These are identified under the inverted microscope (25× magnification) as clusters or chains of discrete cells. These colonies are harvested under the microscope in a laminar flow cabinet by suction into a Gilson pipette. Harvested colonies are dispersed into T-cell growth medium (RPMI 1640, 20% FCS, 30% MLA supernatant and 20 U/ml rIL-2) and transferred to a 96 well microtitre tray containing peptide sensitized γ-irradiated LCLs from the same donor (10³ cells/well). These colonies continue to be expanded and are stored in liquid nitrogen (approximately 5×10⁶ cells/ampoule).

EXAMPLE 10

Diagnostic Procedures Using CTL Clones

1. Screening CTL Clones for Reactivity Against HCMV Vaccinia Virus Recombinant

LCLs are infected with recombinant vaccinia viruses at a multiplicity of infection of 10:1 for 1 hour at 37° C. After 14-16 hours, cells are washed with basic culture medium and incubated with ⁵¹Cr for 90 minutes, washed three times and used as targets in a standard 4-6 hour chromium release assay as described below.

2. Peptide Screen

A standard 4-6 h chromium release assay is performed on either polyclonal T-cell effectors or T-cell clones, to assess specificity for the peptide epitope. Briefly, washed $^{51}$Cr (Amersham International, England) labeled (60 minutes, 37° C.) target cells (autologous PHA blasts) are added ($10^4$ cells/well in 40 μl) to 10 μl of peptide (final concentration 10 μM) in a U-well 96 well plate (Nunc, Denmark). After a 30 minute incubation at 37° C., between 104 and 50.×$10^4$ effector T-cell (cloned or bulk CTLs), in triplicate, are then added per well in 150 μl, to obtain a final effector to target ratio of 10:1 or 5:1. Two controls are added; (i) media and target (background release) and (ii) targets (total release) for addition of SDS, preferably 100 μl 0.5% SDS. The plate is then centrifuged at 500 rpm for five minutes and incubated at 37° C. for five hours. Following incubation, 20 μl supernatants are removed for gamma counting. Results are expressed as % specific lysis calculated as:

$$\frac{\text{mean counts (experimental wells)} - \text{mean counts (control wells)}}{\text{total counts for SDS solubilization} - \text{mean counts (control wells)}}.$$

TABLE 1

List of HLA class I-restricted predictive CTL epitopes from HCMV proteins and MHC stabilization efficiency

|  |  | (HLA) | MSE* |
|---|---|---|---|
| pp28 | | | |
| LLIDPTSGL | (SED ID NO: 150) | (A2) | + |
| LLVEPCARV | (SED ID NO: 151) | (A2) | ++ |
| LLLIVTPVV | (SED ID NO: 152) | (A2) | ++ |
| FLLSHDAAL | (SED ID NO: 153) | (A2) | ++ |
| PLREYLADL | (SED ID NO: 154) | (A2) | − |
| GLLGASMDL | (SED ID NO: 155) | (A2) | − |
| LVEPCARVY | (SED ID NO: 156) | (A1/A3) | NT/++ |
| GIKHEGLVK | (SED ID NO: 157) | (A3) | +++ |
| ELLAGGRVF | (SED ID NO: 158) | (A3) | − |
| RLLDLAPNY | (SED ID NO: 159) | (A3) | +++ |
| ELLGRLNVY | (SED ID NO: 160) | (A3) | − |
| CRYKYLRKK | (SED ID NO: 161) | (B27) | − |
| ARVYEIKCR | (SED ID NO: 162) | (B27) | − |
| pp50 | | | |
| LLNCAVTKL | (SED ID NO: 163) | (A2) | ++ |
| QLRSVIRAL | (SED ID NO: 164) | (A2) | − |
| VTEHDTLLY | (SED ID NO: 165) | (A1) | NT |
| RGDPFDKNY | (SED ID NO: 166) | (A1) | NT |
| GLDRNSGNY | (SED ID NO: 167) | (A1) | NT |
| TLLNCAVTK | (SED ID NO: 168) | (A3) | +++ |
| TVRSHCVSK | (SED ID NO: 169) | (A3) | +++ |
| TRVKRNVKK | (SED ID NO: 171) | (B27) | − |

TABLE 1-continued

List of HLA class I-restricted predictive CTL epitopes from HCMV proteins and MHC stabilization efficiency

|  |  | (HLA) | MSE* |
|---|---|---|---|
| YEQHKITSY | (SED ID NO: 170) | (B44) | NT |
| SEDSVTFEF | (SED ID NO: 172) | (B44) | NT |
| TRLSEPPTL | (SED ID NO: 173) | (B27) | NT |
| US3 | | | |
| YLFSLVVLV | (SED ID NO: 298) | (A2) | + |
| TLLVYLFSL | (SED ID NO: 299) | (A2) | ++ |
| LLFRTLLVYL | (SED ID NO: 300) | (A2) | +++ |
| VYLFSLVVL | (SED ID NO: 301) | (A24) | − |
| IE-2 | | | |
| FLMEHTMPV | (SED ID NO: 251) | (A2) | ++ |
| LMQKFPKQV | (SED ID NO: 252) | (A2) | + |
| NLALSTPFL | (SED ID NO: 253) | (A2) | ++ |
| IIYTRNHEV | (SED ID NO: 254) | (A2) | + |
| LLGALNLCL | (SED ID NO: 256) | (A2) | ++ |
| KPEPDFTIQY | (SED ID NO: 257) | (A1) | NT |
| IIYTRNHEVK | (SED ID NO: 255) | (A3) | +++ |
| IMKDKNTPF | (SED ID NO: 258) | (B8) | +++ |
| PRKKKSKRI | (SED ID NO: 259) | (B8) | − |
| pp71 | | | |
| QLLIPKSFTL | (SED ID NO: 174) | (A2) | − |
| TLVIPSWHV | (SED ID NO: 175) | (A2) | ++ |
| LLIPKSFTL | (SED ID NO: 176) | (A2) | − |
| DLVPLTVSV | (SED ID NO: 177) | (A2) | + |
| CSDPNTYIHK | (SED ID NO: 178) | (A1) | NT |
| EYIVQIQNAF | (SED ID NO: 179) | (A24) | +++ |
| AEVVARHNPY | (SED ID NO: 180) | (B44) | NT |
| pp150 | | | |
| GQTEPIAFV | (SED ID NO: 122) | (A2) | + |
| KMSVRETLV | (SED ID NO: 141) | (A2) | ++ |
| FLGARSPSL | (SED ID NO: 142) | (A2) | ++ |
| ALVNAVNKL | (SED ID NO: 143) | (A2) | ++ |
| ALVNFLRHL | (SED ID NO: 144) | (A2) | ++ |
| NILQKIEKI | (SED ID NO: 145) | (A2) | + |
| LIEDFDIYV | (SED ID NO: 140) | (A2) | ++ |
| PLIPTTAVI | (SED ID NO: 139) | (A2) | − |
| RIEENLEGV | (SED ID NO: 138) | (A2) | + |

TABLE 1-continued

List of HLA class I-restricted predictive CTL epitopes from HCMV proteins and MHC stabilization efficiency

| | | (HLA) | MSE* |
|---|---|---|---|
| NVRRSWEEL | (SED ID NO: 134) | (B7) | ++ |
| WPRERAWAL | (SED ID NO: 133) | (B7/B8) | +++/++ |
| KARDHLAVL | (SED ID NO: 132) | (B7) | +++ |
| SPWAPTAPL | (SED ID NO: 131) | (B7) | +++ |
| RPSTPRAAV | (SED ID NO: 130) | (A1) | NT |
| UL18 | | | |
| GEINITFIHY | (SED ID NO: 291) | (B44) | NT |
| TENGSFVAGY | (SED ID NO: 292) | (B44) | NT |
| TMWCLTLFV | (SED ID NO: 293) | (A2) | ++ |
| LELEIALGY | (SEQ ID NO: 308) | (B44) | NT |
| US6 | | | |
| LYLCCGITL | (SED ID NO: 303) | (A24) | − |
| pp65 | | | |
| SQEPMSIYVY | (SED ID NO: 22) | (A1) | NT |
| ATVQGQNLKY | (SED ID NO: 23) | (A1) | NT |
| IRETVELRQY | (SED ID NO: 24) | (A1) | NT |
| IGDQYVKVY | (SED ID NO: 25) | (A1) | NT |
| TVQGQNLKY | (SED ID NO: 26) | (A1) | NT |
| YRIQGKLEY | (SED ID NO: 27) | (A1) | NT |
| QVIGDQYVK | (SED ID NO: 28) | (A3) | ++ |
| LLLQRGPQY | (SED ID NO: 29) | (A3) | +++ |
| RVTGGGAMA | (SED ID NO: 30) | (A3) | − |
| GVMTRGRLK | (SED ID NO: 31) | (A3) | +++ |
| VYALPLKML | (SED ID NO: 32) | (A24) | − |
| QYDPVAALF | (SED ID NO: 33) | (A24) | − |
| VYYTSAFVF | (SED ID NO: 34) | (A24) | − |
| DIYRIFAEL | (SED ID NO: 15) | (A24) | NT |
| DVPSGKLFM | (SED ID NO: 35) | (A26) | NT |
| DIDLLLQRG | (SED ID NO: 36) | (A26) | NT |
| YVKVYLESF | (SED ID NO: 37) | (A26) | NT |
| TVQGQNLKY | (SED ID NO: 38) | (A26) | NT |
| EPMSIYVYAL | (SED ID NO: 39) | (B7) | + |
| HVRVSQPSL | (SED ID NO: 40) | (B7) | ++ |
| QARLTVSGL | (SED ID NO: 41) | (B7) | +++ |
| RRRHRQDAL | (SED ID NO: 42) | (B27/B8) | ++/+ |
| QPKRRRHRQ | (SED ID NO: 43) | (B8) | − |
| LCPKSIPGL | (SED ID NO: 44) | (B8) | − |

TABLE 1-continued

List of HLA class I-restricted predictive CTL epitopes from HCMV proteins and MHC stabilization efficiency

| | | (HLA) | MSE* |
|---|---|---|---|
| VLCPKNMII | (SED ID NO: 14) | (B8) | − |
| YRIQGKLEY | (SED ID NO: 27) | (B27) | − |
| SEHPTFTSQY | (SED ID NO: 47) | (B44) | NT |
| CEDVPSGKLF | (SED ID NO: 48) | (B44) | NT |
| NEIHNPAVF | (SED ID NO: 49) | (B44) | NT |
| RETVELRQY | (SED ID NO: 50) | (B44) | NT |
| QEPMSIYVY | (SED ID NO: 51) | (B44) | NT |
| QMWQARLTV | (SED ID NO: 52) | (A2) | + |
| ALFFFDIDL | (SED ID NO: 12) | (A2) | ++ |
| RLLQTGIHV | (SED ID NO: 10) | (A2) | ++ |
| NLVPMVATV | (SED ID NO: 5) | (A2) | ++ |
| LMNGQQIFL | (SED ID NO: 53) | (A2) | ++ |
| MLNIPSINV | (SED ID NO: 6) | (A2) | ++ |
| RIFAELEGV | (SED ID NO: 7) | (A2) | ++ |
| ILARNLVPM | (SED ID NO: 54) | (A2) | ++ |
| VIGDQYVKV | (SED ID NO: 11) | (A2) | ++ |
| TPRVTGGGAM | (SED ID NO: 8) | (B7) | |
| RPHERNGFTVL | (SED ID NO: 9) | (B7) | |
| gH | | | |
| YLMDELRYV | (SEQ ID NO: 196) | (A2) | ++ |
| YLTVFTVYL | (SEQ ID NO: 197) | (A2) | ++ |
| TLTEDFFVV | (SEQ ID NO: 198) | (A2) | ++ |
| LLMMSVYAL | (SEQ ID NO: 199) | (A2) | ++ |
| YLLYRMLKT | (SEQ ID NO: 200) | (A2) | − |
| ILFDGHDLL | (SEQ ID NO: 201) | (A2) | +++ |
| LIFGHLPRV | (SEQ ID NO: 202) | (A2) | ++ |
| SLVRLVYIL | (SEQ ID NO: 203) | (A2) | + |
| LLYPTAVDL | (SEQ ID NO: 204) | (A2) | +++ |
| ALDPYNEVV | (SEQ ID NO: 205) | (A2) | +++ |
| LMLLKNGTV | (SEQ ID NO: 206) | (A2) | − |
| SAIIGIYLL | (SEQ ID NO: 207) | (A2) | − |
| ITSLVRLVY | (SEQ ID NO: 208) | (A1) | NT |
| HHEYLSDLY | (SEQ ID NO: 209) | (A1) | NT |
| AIIGIYLLY | (SEQ ID NO: 210) | (A1/A3) | NT/+++ |
| QTEKHELLV | (SEQ ID NO: 211) | (A1) | NT |
| ATDSRLLMM | (SEQ ID NO: 212) | (A1) | NT |

TABLE 1-continued

List of HLA class I-restricted predictive CTL epitopes from HCMV proteins and MHC stabilization efficiency

| | | (HLA) | MSE* |
|---|---|---|---|
| FLDAALDFNY | (SEQ ID NO: 213) | (A1) | NT |
| DTQGVINIMY | (SEQ ID NO: 214) | (A1) | NT |
| LRENTTQCTY | (SEQ ID NO: 215) | (A1) | NT |
| SAIIGIYLLY | (SEQ ID NO: 216) | (A1) | NT |
| SLRNSTVVR | (SEQ ID NO: 217) | (A3) | +++ |
| ALALFAAAR | (SEQ ID NO: 218) | (A3) | − |
| QLNRHSYLK | (SEQ ID NO: 219) | (A3) | +++ |
| RLFPDATVP | (SEQ ID NO: 220) | (A3) | − |
| RLNTYALVSK | (SEQ ID NO: 221) | (A3) | +++ |
| LVRLVYILSK | (SEQ ID NO: 222) | (A3) | +++ |
| YLMDELRYVK | (SEQ ID NO: 223) | (A3) | − |
| ELYLMGSLVH | (SEQ ID NO: 224) | (A3) | − |
| ALTVSEHVSY | (SEQ ID NO: 225) | (A3) | ++ |
| NYLDLSALL | (SEQ ID NO: 226) | (A24) | − |
| SYVVTNQYL | (SEQ ID NO: 227) | (A24) | − |
| SYLKDSDFL | (SEQ ID NO: 228) | (A24) | − |
| TYALVSKDL | (SEQ ID NO: 229) | (A24) | − |
| SYRSFSQQL | (SEQ ID NO: 230) | (A24) | − |
| TYGRPIRFL | (SEQ ID NO: 231) | (A24) | − |
| YYVFHMPRCL | (SEQ ID NO: 232) | (A24) | − |
| MYMHDSDDVL | (SEQ ID NO: 233) | (A24) | − |
| ETFPDLFCL | (SEQ ID NO: 234) | (A26) | NT |
| DLTETLERY | (SEQ ID NO: 235) | (A26) | NT |
| SPRTHYLML | (SEQ ID NO: 236) | (B7) | +++ |
| FPDLFCLPL | (SEQ ID NO: 237) | (B7) | +++ |
| SPRTHYLMLL | (SEQ ID NO: 238) | (B7) | +++ |
| MPRCLFAGPL | (SEQ ID NO: 239) | (B7) | +++ |
| TPMLLIFGHL | (SEQ ID NO: 240) | (B7) | ++ |
| APYQRDNFIL | (SEQ ID NO: 241) | (B7) | +++ |
| GRCQMLDRR | (SEQ ID NO: 242) | (B27) | − |
| RRDHSLERL | (SEQ ID NO: 243) | (B27) | − |
| SEALDPHAF | (SEQ ID NO: 244) | (B44) | NT |
| RENTTQCTY | (SEQ ID NO: 245) | (B44) | NT |
| DDVLFALDPY | (SEQ ID NO: 246) | (B44) | NT |

IE-1

| | | (HLA) | MSE* |
|---|---|---|---|
| SLLSEFCRV | (SEQ ID NO: 96) | (A2) | +++ |
| VLAELVKQI | (SEQ ID NO: 97) | (A2) | ++ |

TABLE 1-continued

List of HLA class I-restricted predictive CTL epitopes from HCMV proteins and MHC stabilization efficiency

| | | (HLA) | MSE* |
|---|---|---|---|
| ILGADPLRV | (SEQ ID NO: 98) | (A2) | ++ |
| TMYGGISLL | (SEQ ID NO: 99) | (A2) | ++ |
| LLSEFCRVL | (SEQ ID NO: 100) | (A2) | ++ |
| VLEETSVML | (SEQ ID NO: 101) | (A2) | ++ |
| YILEETSVM | (SEQ ID NO: 18) | (A2) | ++ |
| CLQNALDIL | (SEQ ID NO: 102) | (A2) | ++ |
| ILDEERDKV | (SEQ ID NO: 103) | (A2) | ++ |
| IKEHMLKKY | (SEQ ID NO: 104) | (A1) | NT |
| DEEEAIVAY | (SEQ ID NO: 105) | (A1) | NT |
| CVETMCNEY | (SEQ ID NO: 19) | (A1) | NT |
| KLGGALQAK | (SEQ ID NO: 106) | (A3) | +++ |
| QYILGADPL | (SEQ ID NO: 107) | (A24) | +++ |
| KYTQTEEKF | (SEQ ID NO: 108) | (A24) | − |
| KARAKKDEL | (SEQ ID NO: 109) | (B7/B8) | −/− |
| VMKRRIEEI | (SEQ ID NO: 110) | (B8) | + |
| RHRIKEHML | (SEQ ID NO: 111) | (B8) | − |
| ELRRKMMYM | (SEQ ID NO: 112) | (B8) | ++ |
| QIKVRVDMV | (SEQ ID NO: 113) | (B8) | + |
| ELKRKMMYM | (SEQ ID NO: 114) | (B8) | − |
| RRKMMYMCY | (SEQ ID NO: 115) | (B27) | + |
| RRIEEICMK | (SEQ ID NO: 20) | (B27) | − |

US2

| | | (HLA) | MSE* |
|---|---|---|---|
| LLVLFIVYV | (SEQ ID NO: 294) | (A2) | − |
| SMMWMRFFV | (SEQ ID NO: 295) | (A2) | ++ |
| TLLVLFIVYV | (SEQ ID NO: 296) | (A2) | − |
| VYVTVDCNL | (SEQ ID NO: 297) | (A24) | − | gB

| | | (HLA) | MSE* |
|---|---|---|---|
| RIWCLVVCV | (SEQ ID NO: 181) | (A2) | − |
| QMLLALARL | (SEQ ID NO: 182) | (A2) | + |
| GLDDLMSGL | (SEQ ID NO: 183) | (A2) | ++ |
| IILVAIAVV | (SEQ ID NO: 184) | (A2) | + |
| DLDEGIMVV | (SEQ ID NO: 185) | (A2) | − |
| NLFPYLVSA | (SEQ ID NO: 186) | (A2) | ++ |
| AVGGAVASV | (SEQ ID NO: 187) | (A2) | − |
| YINRALAQI | (SEQ ID NO: 188) | (A2) | ++ |
| CYSRPVVIF | (SED ID NO: 137) | (A24) | − |

TABLE 1-continued

List of HLA class I-restricted predictive CTL epitopes from HCMV proteins and MHC stabilization efficiency

|  |  | (HLA) | MSE* |
|---|---|---|---|
| KMTATFLSK | (SED ID NO: 136) | (A3) | +++ |
| IMREFNSYK | (SED ID NO: 135) | (A3) | +++ |
| VKESPGRCY | (SED ID NO: 129) | (A1) | NT |
| LDEGIMVVY | (SED ID NO: 128) | (A1) | NT |
| ATSTGDVVY | (SED ID NO: 127) | (A1) | NT |
| NTDFRVLEL | (SED ID NO: 126) | (A1) | NT |
| AYIYTTYLL | (SED ID NO: 125) | (A24) | - |
| SYENKTMQL | (SED ID NO: 124) | (A24) | - |
| AYEYVDYLF | (SED ID NO: 123) | (A24) | - |
| US11 |  |  |  |
| YYVECEPRC | (SED ID NO: 302) | (A24) | NT |
| TLFDEPPPLV | (SEQ ID NO: 304) | (A2) | NT |
| TPRVYYQTL | (SEQ ID NO: 305) | (B7) | +++ |
| APVAGSMPEL | (SEQ ID NO: 306) | (B7) | +++ |
| SESLVAKRY | (SEQ ID NO: 307) | (B44) | NT |

*MSE: MHC stabilization efficiency was assessed using T2 cells transfected with individual HLA class I alleles. The levels of HLA in the presence of peptide are expressed relative to expression on T2 cells in the absence of peptide at 26° C.: +++ = 200-300%, ++ = 100-199%, + = 51-99%, - = 0-50%, relative increase in HLA expression.
NT: Not tested

TABLE 2

HLA Antigen (class I) type of the HCMV-immune Donors included in this study

| Donor | HLA Typing |
|---|---|
| MB | A1 A24 B8 B58 |
| SB | A2 B35 B57 |
| SC | A1 B8 |
| JDu | A31 A33 B35 B58 |
| JDa | A28 A31 B27 B18 |
| JG | A1 A2 B7 B37 |
| TD | A24 A26 B15 B62 |
| RE | A11 A24 B35 B60 |
| SE | A2 A29 B44 B60 |
| TF | A2 A24 B40 B60 |
| PH | A1 A2 B8 B44 |
| CJ | A2 A3 B8 B60 |
| RK | A23 A24 B27 B41 |
| TK | A3 A25 B35 B44 |
| MM | A1 A3 B50 B57 |
| PP | A1 A24 B8 B14 |
| CP | A2 A32 B7 B50 |
| JP | A2 A28 B8 B62 |
| CR | A1 A3 B35 B57 |
| BS | A2 A11 B13 B27 |
| CS | A3 A23 B35 B44 |
| WS | A2 A32 B27 B60 |
| JT | A2 A32 B44 B62 |
| JW | A23 A32 B35 B49 |
| MW | A1 A3 B8 B35 |
| TC | A1 A11 B8 B35 |
| CSt | A2 A26 B44 B35 |

TABLE 3

Comprehensive List Of HLA Class I-Restricted CTL Epitopes From HCMV Antigens Mapped By ELISPOT And CTL Assays

| Antigen | Peptide Sequence |  | Donor(s) and ELISPOT Responses (SFC/10⁶ PBMC) | HLA Restriction | CTL Response* |
|---|---|---|---|---|---|
| gB | RIWCLVVCV | (SEQ ID NO: 181) | JP(108), CP(105) | HLA A2 | ND |
|  | AVGGAVASV | (SEQ ID NO: 187) | SB(192) | HLA A2 | Y |
|  | IMREFNSYK | (SED ID NO: 135) | MB(202) | HLA A3 | NT |
|  | VKESPGRCY | (SED ID NO: 129) | TC(51) | HLA A1 | NT |
|  | LDEGIMVVY | (SED ID NO: 128) | TC(239) | HLA A1 | NT |
|  | ATSTGDVVY | (SED ID NO: 127) | TC(239) | HLA A1 | NT |
|  | NTDFRVLEL | (SED ID NO: 126) | TC(1631) | HLA A1 | NT |
| gH | LIFGHLPRV | (SEQ ID NO: 202) | SE(84) | HLA A2 | NT |
|  | LMLLKNGTV | (SEQ ID NO: 206) | CJ(80) | HLA A2 | NT |
| IE-1 | SLLSEFCRV | (SEQ ID NO: 96) | WS(471) | HLA A2 | ND |
|  | VLAELVKQI | (SEQ ID NO: 97) | SB(276) | HLA A2 | Y |
|  | VLEETSVML | (SEQ ID NO: 101) | SB(3752), CP(245) | HLA A2 | Y |

TABLE 3-continued

Comprehensive List Of HLA Class I-Restricted CTL Epitopes From HCMV Antigens Mapped By ELISPOT And CTL Assays

| Antigen | Peptide Sequence | | Donor(s) and ELISPOT Responses (SFC/10⁶ PBMC) | HLA Restriction | CTL Response* |
|---|---|---|---|---|---|
| | YILEETSVM | (SEQ ID NO: 18) | SB(764) | HLA A2 | ND |
| | CLQNALDIL | (SEQ ID NO: 102) | SE(490) | HLA A2 | NT |
| | KARAKKDEL | (SEQ ID NO: 109) | MB(231), PH(235) | HLA B7/B8 | ND |
| | QIKVRVDMV | (SEQ ID NO: 113) | SC(2848), JP(475), PH(2425), TC(2251) | HLA B8 | Y |
| | ELRRKMMYM | (SEQ ID NO: 112) | SC(1243), JP(145), PH(430), TC(4999) | HLA B8 | Y |
| | ELKRKMMYM | (SEQ ID NO: 114) | SC(1000), MW(1992), PH(300), PP(100), TC(4999) | HLA B8 | Y |
| | IKEHMLKKY | (SEQ ID NO: 104) | TC(4232) | HLA A1 | NT |
| | DEEEAIVAY | (SEQ ID NO: 105) | TC(3903) | HLA A1 | NT |
| | CVETMCNEY | (SEQ ID NO: 19) | TC(4187) | HLA A1 | NT |
| IE-2 | IIYTRNHEV | (SED ID NO: 254) | SB(369), CP(80), SE(137) | HLA A2 | Y |
| | FLMEHTMPV | (SED ID NO: 251) | WS(137) | HLA A2 | NT |
| pp28 | LLIDPTSGL | (SED ID NO: 150) | SB(270), NS(77) | HLA A2 | NT |
| | ARVYEIKCR | (SED ID NO: 162) | RK(148) | HLA B27 | Y |
| pp50 | LLNCAVTKL | (SED ID NO: 163) | SE(59) | HLA A2 | NT |
| | VTEHDTLLY | (SED ID NO: 165) | MB(925), SC(902), MW(975), PP(230), PH(1290), TC(2531), JG(1070) | HLA A1 | Y |
| | YEQHKITSY | (SED ID NO: 170) | CS(67) | HLA B44 | ND |
| | RGDPFDKNY | (SED ID NO: 166) | JG(720), TC(2739) | HLA A1 | NT |
| | GLDRNSGNY | (SED ID NO: 167) | MW(345), TC(507) | HLA A1 | NT |
| pp150 | KMSVRETLV | (SED ID NO: 141) | SE(69) | HLA A2 | NT |
| | ALVNAVNKL | (SED ID NO: 143) | WS(60) | HLA A2 | NT |
| | ALVNFLRHL | (SED ID NO: 144) | WS(57) | HLA A2 | NT |
| | LIEDFDIYV | (SED ID NO: 140) | WS(88) | HLA A2 | NT |
| | NVRRSWEEL | (SED ID NO: 134) | MB(1431), CS(274) | HLA B7 | ND |
| | KARDHLAVL | (SED ID NO: 132) | MB(975) | HLA B7 | ND |
| | SPWAPTAPL | (SED ID NO: 131) | MB(180) | HLA B7 | ND |
| | RPSTPRAAV | (SED ID NO: 130) | MB(306) | HLA B7 | ND |
| | WPRERAWAL | (SED ID NO: 133) | TC(67) | HLA B8 | NT |
| pp65 | RLLQTGIHV | (SED ID NO: 10) | BS(57) | HLA A2 | ND |
| | NLVPMVATV | (SED ID NO: 5) | SB(1202), JP(1201), WS(1102), CJ(271), JT(1195), BS(161), CP(671), SE(170) CP(356), WS(335) | HLA A2 | Y |
| | LMNGQQIFL | (SED ID NO: 53) | CP(217), WS(751) | HLA A2 HLA | ND |

TABLE 3-continued

Comprehensive List Of HLA Class I-Restricted CTL Epitopes From HCMV Antigens Mapped By ELISPOT And CTL Assays

| Antigen | Peptide Sequence | | Donor(s) and ELISPOT Responses (SFC/$10^6$ PBMC) | HLA Restriction | CTL Response* |
|---|---|---|---|---|---|
| | MLNIPSINV | (SED ID NO: 6) | SB(65), JP(178), A2 | HLA A2 | ND |
| | RIFAELEGV | (SED ID NO: 7) | WS(236), JT(170), CP(275) | | ND |
| pp65 | ILARNLVPM | (SED ID NO: 54) | SE(170) | HLA A2 | ND |
| | HVRVSQPSL | (SED ID NO: 40) | MB(783) | HLA B7 | ND |
| | QARLTVSGL | (SED ID NO: 41) | MB(1116) | HLA B7 | ND |
| | IGDQYVKVY | (SED ID NO: 25) | PH(565), TC(67) | HLA A1 | NT |
| | TVQGQNLKY | (SED ID NO: 26) | PH(385), TC(251) | HLA A1 | NT |
| | YRIQGKLEY | (SED ID NO: 27) | TC(307) | HLA 1/B27 | NT |
| | FPTKDVAL | (SED ID NO: 4) | MW(445) | HLA B35 | Y |
| | RRRHRQDAL | (SED ID NO: 42) | PH(215), TC(71) | HLA B8 | NT |
| | YSEHPTFTSQY | (SED ID NO: 13) | MW(310), TC(359) | HLA-A1 | NT |
| US2 | SMMWMRFFV | (SEQ ID NO: 295) | SE(393) | HLA A2 | Y |
| | TLLVLFIVYV | (SEQ ID NO: 296) | SE(46) | HLA A2 | NT |
| | LLVLFIVYV | (SEQ ID NO: 294) | WS(92) | HLA A2 | NT |
| US3 | YLFSLVVLV | (SED ID NO: 298) | WS(73) | HLA A2 | NT |
| | LLFRTLLVYL | (SEQ ID NO: 300) | SB(76), WS(77) | HLA A2 | ND |
| UL18 | TENGSFVAGY | (SEQ ID NO: 292) | CS(283) | B44 | ND |

**CTL response for each of the peptide was detected by using the protocol described in the "Material and Methods" section.
Y: Yes;
NT: Not tested;
ND: Not detected

TABLE 4

Summary Of ELISPOT Analysis Based On Overlapping 20mer Peptides From HCMV Antigens

| Antigen | Peptide Sequence | Donor(s) and ELISPOT (SFC/$10^6$ PBMC) | Responding cells (% CD4/% CD8) | Minimal sequence defined | HLA Restriction | CTL response* |
|---|---|---|---|---|---|---|
| gB | RSYAYIYTTYLLGSNTEYVA (SEQ ID NO: 192) | RK(170) | RK(0.39/0.58) | YAYIYTTYL (SEQ ID NO: 189) | HLA B41 | Y |
| | TYEKYGNVSVFETSGGLVVF (SEQ ID NO: 193) | SE(75) | SE(0/0.097) | VFETSGGLVV (SEQ ID NO: 190) | HLA A29 | Y |
| | FETSGGLVVFWQGIKQKSLV (SEQ ID NO: 194) | MB(23), SB(185) | NT | | | ND |
| | MQLIPDDYSNTHSTRYVTVK (SEQ ID NO: 195) | MB(238), MB(302), SB(157) | MB(0.06/0.03) | DDYSNTHSTRYV (SEQ ID NO: 191) | HLA DR7 | Y |
| gH | RQTEKHELLVLVKKAQLNRH (SEQ ID NO: 249) | RK(313) | RK(1.52/0.57) | HELLVLVKKAQL (SEQ ID NO: 247) | HLA DR* | Y |
| | ALTVSEHVSYVVTNQYLIKG (SEQ ID NO: 250) | MB(23) | NT | LTVSEHVSYVVT (SEQ ID NO: 248) | | NT |
| IE-1 | CSPDEIMAYAQKIFKILDEE (SEQ ID NO: 117) | CS(1532) | CS(0.53/0.4) | AYAQKIFKIL (SEQ ID NO: 116) | HLA A23, A24 & A30 | Y |

TABLE 4-continued

Summary Of ELISPOT Analysis Based On Overlapping 20mer Peptides From HCMV Antigens

| Antigen | Peptide Sequence | Donor(s) and ELISPOT (SFC/10$^6$ PBMC) | Responding cells (% CD4/% CD8) | Minimal sequence defined | HLA Restriction | CTL response* |
|---|---|---|---|---|---|---|
| | SEPVSEIEEVAPEEEEDGAE (SEQ ID NO: 118) | SE(200) | SE(0/0.097) | VLEETSVML (SEQ ID NO: 101) | — | NT |
| | VLCCYVLEETSVMLAKRPLI (SEQ ID NO: 119) | SB(2171) | NT | | HLA A2 | Y |
| | RRKMMYMCYRNIEFFTKNSA (SEQ ID NO: 120) | CP(632) | NT | | — | NT |
| | NIEFFTKNSAFPKTTNGCSQ (SEQ ID NO: 121) | CP(1767) | NT | | — | ND |
| IE-2 | TAAKAYAVGQFEQPTETPPE (SEQ ID NO: 269) | RK(859), SB(326) | RK(0.2/0.35) | FEQPTETPP (SEQ ID NO: 260) | HLA B41 | Y |
| | FEQPTETPPEDLDTLSLAIE (SEQ ID NO: 270) | RK(791) | RK(0.2/0.35) | FEQPTETPP (SEQ ID NO: 260) | HLA B41 | Y |
| | MLPLIKQEDIKPEPDFTIQY (SEQ ID NO: 271) | SB(132) | NT | | — | NT |
| | THQLCPRSSDYRNMIIHAAT (SEQ ID NO: 272) | SC(173), TC(124) | NT | SDYNMIIHA (SEQ ID NO: 265) | HLA A1/B8 | ND |
| | YRNMIIHAATPVDLLGALNL (SEQ ID NO: 273) | SC(229), JW(132), TC(137) | NT | YRNMIIHAAT (SEQ ID NO: 266) | HLA A1/B8/B35 HLA A2 | ND |
| | TGPRKKKSKRISELDNEKVR (SEQ ID NO: 274) | SB(148), SE(162) | SB(0.02/0.02) | | | ND |
| IE-2 | PVDLLGALNLCLPLMQKFPK (SEQ ID NO: 275) | SC(111), TC(169) | NT | CLPLMQKFP (SEQ ID NO: 267) | HLA A1/B8 | ND |
| | IQIIYTRNHEVKSEVDAVRC (SEQ ID NO: 276) | SE(203), SB(288) | SE(0/0.19) | IIYTRNHEVK (SEQ ID NO: 255) | HLA A2 | Y |
| | VKSEVDAVRCRLGTMCNLAL (SEQ ID NO: 277) | SE(253), SB(320) | SE(0/0.06) | | HLA A2 | NT |
| | RVKIDEVSRMFRNTNRSLEY (SEQ ID NO: 278) | SC(306), TC(194) | NT | IDEVSRMFRNTNRS (SEQ ID NO: 268) | HLA A1/B8 | NT |
| | SSSSSSCSSASDSESESEEM (SEQ ID NO: 279) | JW(125), TC(93) | JW(0/0.01), TC(0/0.05) | | HLA B35 | ND |
| | ASSPSTGSGTPRBTSPTHPL (SEQ ID NO: 280) | JW(95) | NT | | — | NT |
| | PRVTSPTHPLSQMNHPPLPD (SEQ ID NO: 281) | JW(52), TC(96) | NT | | HLA B35 | NT |
| | PLGRPDEDSSSSSSSSCSSA (SEQ ID NO: 282) | TC(46) | NT | | — | NT |
| | SDSESESEEMKCSSGGGASV (SEQ ID NO: 283) | TC(147) | TC(0.01/0.22) | | — | NT |
| | KCSSGGGASVTSSHHGRGGF (SEQ ID NO: 284) | TC(54) | NT | | — | NT |
| IE-2 | CTPNVQTRRGRVKIDEVSRM (SEQ ID NO: 285) | TC(89) | NT | | — | NT |
| | FRNTNRSLEYKNLPFTIPSM (SEQ ID NO: 286) | TC(187) | TC(0/0.25) | | — | NT |
| | HQVLDEAIKACKTMQVNNKG (SEQ ID NO: 287) | TC(234) | TC(0/0.18) | | — | NT |
| | CKTMQVNNKGIQIIYTRNHE (SEQ ID NO: 288) | TC(154) | TC(0/0.14) | | — | NT |

TABLE 4-continued

Summary Of ELISPOT Analysis Based On Overlapping 20mer Peptides From HCMV Antigens

| Antigen | Peptide Sequence | Donor(s) and ELISPOT (SFC/$10^6$ PBMC) | Responding cells (% CD4/% CD8) | Minimal sequence defined | HLA Restriction | CTL response* |
|---|---|---|---|---|---|---|
| | KAAWSLKELHTHQLCPRSSD (SEQ ID NO: 289) | TC(162) | TC(0/0.08) | — | — | NT |
| | CLPLMQKFPKQVMVRIFSTN (SEQ ID NO: 290) | TC(256) | TC(0/0.15) | CLPLMQKFP (SEQ ID NO: 267) | — | NT |
| pp150 | WPRERAWALKNPHLAYNPFR (SEQ ID NO: 147) | RE(83) | RE(0.03/0.27) | ERAWALKNPHLA (SEQ ID NO: 146) | — | Y |
| | STSQKPVLGKRVATPHASAR (SEQ ID NO: 148) | MW(215) | NT | — | — | ND |
| | HANTALVNAVNKLVYTGRLI (SEQ ID NO: 149) | MW(122) | NT | — | — | ND |
| pp65 | LNIPSINVHHYPSAAERKHR (SEQ ID NO: 67) | RE(285), TC(222) | NT | IPSINVHHY (SEQ ID NO: 55) | HLA B35 | Y |
| | ATVQGQNLKYQEFFWDANDI (SEQ ID NO: 68) | CS(226), PP(202), SC(687) MW(189), RE(25) | RE(0.03/0) | QEFFWDANDIY (SEQ ID NO: 56) | HLA B44 | Y |
| | QEFFWDANDIYRIFAELEGV (SEQ ID NO: 69) | CS(107) | NT | QEFFWDANDI (SEQ ID NO: 57) | HLA B44 | Y |
| | | RE(30), PP(295), SC(704) | NT | QEFFWDANDI (SEQ ID NO: 57) | HLA A1/A24 | Y |
| | PQYSEHPTFTSQYRIQGKLE (SEQ ID NO: 70) | RK(1393), SE(980), MB(413) | RK(1.69/0.96) | FTSQYRIQGKL (SEQ ID NO: 2) | HLA A24 | Y |
| | | MB(0.05/0) SE(0/0.87) | | YSEHPTFTSQY (SEQ ID NO: 13) | HLA A1 | NT |
| | SQYRIQGKLEYRHTWDRHDE (SEQ ID NO: 71) | SE(1203) | SE(0/2.0) | QYRIQGKLE (SEQ ID NO: 58) | — | Y |
| | VFTWPPWQAGILARNLVPMV (SEQ ID NO: 72) | SE(533), MB(420) | SE(0/0.45) | ILARNLVPMV (SEQ ID NO: 16) | HLA A2 | Y |
| | ILARNLVPMVATVQGQNLKY (SEQ ID NO: 73) | MB(500), SB(216), MW(229) | NT | NLVPMVATV (SEQ ID NO: 5) | HLA A2 | Y |
| | DQYVKVYLESFCEDVPSGKL (SEQ ID NO: 74) | SE(265) | SE(0/0.23) | — | — | ND |
| pp65 | YPSAAERKHRHLPVADAVIH (SEQ ID NO: 75) | SE(350) | SE(0/0.313) | RKHRHLPVADAV (SEQ ID NO: 59) | — | Y |
| | QYDPVAALFFFDIDLLLQRG (SEQ ID NO: 76) | SB(97) | SB(0.22/0.03) | DPVAALFFF (SEQ ID NO: 60) | HLA B35 | Y |
| | IIKPGKISHIMLDVAFTSHE (SEQ ID NO: 77) | SC(691), PP(177), SB(155), JW(370) | JW(0.04/0.05) SB(0.02/0.03) | PGKISHIMLDVA (SEQ ID NO: 61) | HLA B35 | Y |
| | AHELVCSMENTRATKMQVIG (SEQ ID NO: 78) | MM(169), SB(231) | SB(0.04/0.01) | TRATKMQVI (SEQ ID NO: 62) | HLA B57 | ND |
| | TRATKMQVIGDQYVKVYLES (SEQ ID NO: 79) | MM(139), SB(346) | SB(0.09/0.01) | TRATKMQVI (SEQ ID NO: 62) | HLA B57 | ND |
| | MNGQQIFLEVQAIRETVELR (SEQ ID NO: 80) | MM(277) JD(2985) | JD(0.26/0.48) | QAIRETVEL (SEQ ID NO: 63) | HLA B57 & B58 HLA B57 & B58 | Y |
| | QAIRETVELRQYDPVAALFF (SEQ ID NO: 81) | MM(102), SB(241), JD(2593) | JD(0.28/0.33) | QAIRETVEL (SEQ ID NO: 63) | — | Y |
| | LTVSGLAWTRQQNQWKEPDV (SEQ ID NO: 82) | SC(695) | NT | — | HLA B8 | NT |
| | WQPAAQPKRRRHRQDALPGP (SEQ ID NO: 83) | SC(615) | NT | RRRHRQDAL (SEQ ID NO: 42) | — | ND |

TABLE 4-continued

Summary Of ELISPOT Analysis Based On Overlapping 20mer Peptides From HCMV Antigens

| Antigen | Peptide Sequence | Donor(s) and ELISPOT (SFC/10⁶ PBMC) | Responding cells (% CD4/% CD8) | Minimal sequence defined | HLA Restriction | CTL response* |
|---|---|---|---|---|---|---|
| | YRHTWDRHDEGAAQGDDDVW (SEQ ID NO: 84) | SC(295) | NT | YHRTWDRHEGA (SEQ ID NO: 64) | — | ND |
| pp65 | TSAGRKRKSASSATACTSGV (SEQ ID NO: 85) | SC(138) | NT | — | — | NT |
| | HRQDALPGPCIASTPKKHRG (SEQ ID NO: 86) | SC(109) | NT | — | — | NT |
| | YYTSAFVFPTKDVALRHVVC (SEQ ID NO: 87) | JD(358), SB(775), JW(858) | JD(0.05/0.04) | FPTKDVAL (SEQ ID NO: 4) | HLA B35 | Y |
| | VTTERKTPRVTGGGAMAGAS (SEQ ID NO: 88) | JW(285), SC(322), JD(319) | JW(0.17/0.24) | — | — | ND |
| | QPFMRPHERNGFTVLCPKNM (SEQ ID NO: 89) | SE(783) | JD(0.05/0) | FMRPHERNGFTV (SEQ ID NO: 65) | — | ND |
| | SICPSQEPMSIYVYALPLKM (SEQ ID NO: 90) | SB(1044), JW(3178), SB(76) | JW(1.18/1.36) | CPSQEPMSIYVY (SEQ ID NO: 66) | HLA B35 | Y |
| | IYVYALPLKMLNIPSINVHH (SEQ ID NO: 91) | | NT | — | — | NT |
| | QQNQWKEPDVYYTSAFVFPT (SEQ ID NO: 92) | JW(600) | JW(0/0.03) | — | — | Y |
| | GAAQGDDDVWTSGSDSDEEL (SEQ ID NO: 93) | JW(248) | JW(0/0.01) | — | — | ND |
| | TGGGAMAGASTSAGRKRKSA (SEQ ID NO: 94) | JW(441) | JW(0.01/0.01) | — | — | ND |
| pp65 | KDVALRHVVCAHELVCSMEN (SEQ ID NO: 95) | TC(50) | NT | — | — | NT |

*CTL response for each of the peptide was detected by using the protocol described in the "Material and Methods" section.
Y: Yes;
NT: Not tested;
ND: Not detected

We claim:

1. An isolated peptide comprising a cytotoxic T-lymphocyte (CTL) epitope of a pp50 antigen of a cytomegalovirus of humans (HCMV) wherein said peptide consists of the amino acid sequence set forth in SEQ ID NO:165.

2. The isolated peptide of claim 1 wherein said peptide binds to a MHC Class I cell expressing CD8+.

3. The isolated peptide of claim 2 wherein said peptide binds to a CD8+ cell expressing an HLA A1 allele.

4. A method of enhancing the HCMV-specific cell mediated immunity of a human subject, said method comprising contacting ex vivo a T cell obtained from a human subject with an effective amount of the isolated peptide of claim 1 sufficient to confer HCMV reactivity on said T cells.

5. A method of providing or enhancing immunity against HCMV in an uninfected human subject comprising administering to said subject an effective amount of the isolated peptide of claim 1 sufficient to provide immunological memory against a future infection by HCMV.

6. A method of providing or enhancing immunity against HCMV in an uninfected human subject, said method comprising contacting ex vivo a T cell obtained from a human subject with an effective amount of the isolated peptide of claim 1 sufficient to confer HCMV reactivity on said T cells.

7. A method for determining whether or not a subject has been previously infected with HCMV, said method comprising contacting ex vivo a T cell obtained from the subject with an antigen presenting cell (APC) primed with the isolated peptide of claim 1 and determining the activation of a CTL or precursor CTL, wherein said activation of a CTL or precursor CTL indicates that the subject has been previously infected with HCMV.

8. A method for determining the level of HCMV-specific cell mediated immunity in a human subject, said method comprising contacting ex vivo a T cell obtained from the subject with an antigen presenting cell (APC) primed with the isolated peptide of claim 1 and determining the level of activation of a CTL or precursor CTL, wherein the level of activation of a CTL or precursor CTL is correlated to the level of HCMV-specific cell mediated immunity of the subject.

9. A method of producing an HCMV-specific CTL comprising: (i) contacting a T cell with the isolated peptide of claim 1 or an antigen presenting cell (APC) primed with said peptide or an autologous lymphoblastoid cell line (LCL) primed with said peptide; (ii) culturing the T cell; and (iii) selecting T cells that proliferate.

10. A method of enhancing the HCMV-specific cell mediated immunity of a human subject comprising administering an effective amount of the isolated peptide of claim 1 sufficient to activate a CTL or a CTL precursor of said subject.

* * * * *

SEQUENCE LISTING

<160> NUMBER OF SEQ ID NOS: 318

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 1

Ser Val Leu Gly Pro Ile Ser Gly His Val Leu Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

```
<400> SEQUENCE: 2

Phe Thr Ser Gln Tyr Arg Ile Gln Gly Lys Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 3

Phe Val Phe Pro Thr Lys Asp Val Ala Leu Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 4

Phe Pro Thr Lys Asp Val Ala Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 5

Asn Leu Val Pro Met Val Ala Thr Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 6

Met Leu Asn Ile Pro Ser Ile Asn Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 7

Arg Ile Phe Ala Glu Leu Glu Gly Val
1               5

<210> SEQ ID NO 8
<211> LENGTH: 11
```

```
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 8

Thr Pro Arg Val Thr Gly Gly Gly Ala Met
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 9

Arg Pro His Glu Arg Asn Gly Phe Thr Val Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 10

Arg Leu Leu Gln Thr Gly Ile His Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 11

Val Ile Gly Asp Gln Tyr Val Lys Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 12

Ala Leu Phe Phe Phe Asp Ile Asp Leu
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 13

Tyr Ser Glu His Pro Thr Phe Thr Ser Gln Tyr
```

```
1               5              10
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 14

Val Leu Cys Pro Lys Asn Met Ile Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 15

Asp Ile Tyr Arg Ile Phe Ala Glu Leu
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 16

Ile Leu Ala Arg Asn Leu Val Pro Met Val
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 17

Glu Phe Phe Trp Asp Ala Asn Asp Ile Tyr
1               5                   10

<210> SEQ ID NO 18
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human
      cytomegalovirus pp65 CTL epitope peptide

<400> SEQUENCE: 18

Tyr Ile Leu Glu Glu Thr Ser Val Met
1               5

<210> SEQ ID NO 19
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 19

Cys Val Glu Thr Met Cys Asn Glu Tyr
1               5

<210> SEQ ID NO 20
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human
      cytomegalovirus pp65 CTL epitope peptide

<400> SEQUENCE: 20

Arg Arg Ile Glu Glu Ile Cys Met Lys
1               5

<210> SEQ ID NO 21
<211> LENGTH: 11
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 21

Thr Thr Val Tyr Pro Pro Ser Ser Thr Ala Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 22

Ser Gln Glu Pro Met Ser Ile Tyr Val Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 23

Ala Thr Val Gln Gly Gln Asn Leu Lys Tyr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 24

Ile Arg Glu Thr Val Glu Leu Arg Gln Tyr
1               5                   10

<210> SEQ ID NO 25

```
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 25

Ile Gly Asp Gln Tyr Val Lys Val Tyr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 26

Thr Val Gln Gly Gln Asn Leu Lys Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 27

Tyr Arg Ile Gln Gly Lys Leu Glu Tyr
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 28

Gln Val Ile Gly Asp Gln Tyr Val Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 29

Leu Leu Leu Gln Arg Gly Pro Gln Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 30
```

-continued

```
Arg Val Thr Gly Gly Gly Ala Met Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 31

Gly Val Met Thr Arg Gly Arg Leu Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 32

Val Tyr Ala Leu Pro Leu Lys Met Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 33

Gln Tyr Asp Pro Val Ala Ala Leu Phe
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 34

Val Tyr Tyr Thr Ser Ala Phe Val Phe
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 35

Asp Val Pro Ser Gly Lys Leu Phe Met
1               5

<210> SEQ ID NO 36
<211> LENGTH: 9
<212> TYPE: PRT
<213> ORGANISM: Artificial Sequence
<220> FEATURE:
```

```
<223> OTHER INFORMATION: Description of Artificial Sequence:  human
      cytomegalovirus pp65 CTL epitope peptide

<400> SEQUENCE: 36

Asp Ile Asp Leu Leu Leu Gln Arg Gly
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 37

Tyr Val Lys Val Tyr Leu Glu Ser Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 38

Thr Val Gln Gly Gln Asn Leu Lys Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 39

Glu Pro Met Ser Ile Tyr Val Tyr Ala Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 40

His Val Arg Val Ser Gln Pro Ser Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 41

Gln Ala Arg Leu Thr Val Ser Gly Leu
1               5
```

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 42

Arg Arg Arg His Arg Gln Asp Ala Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 43

Gln Pro Lys Arg Arg Arg His Arg Gln
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 44

Leu Cys Pro Lys Ser Ile Pro Gly Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 45

Tyr Arg Ile Gln Gly Lys Leu Glu Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 46

Tyr Ser Glu His Pro Thr Phe Thr Ser Gln Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 47

```
Ser Glu His Pro Thr Phe Thr Ser Gln Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 48

Cys Glu Asp Val Pro Ser Gly Lys Leu Phe
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 49

Asn Glu Ile His Asn Pro Ala Val Phe
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 50

Arg Glu Thr Val Glu Leu Arg Gln Tyr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 51

Gln Glu Pro Met Ser Ile Tyr Val Tyr
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 52

Gln Met Trp Gln Ala Arg Leu Thr Val
1               5

<210> SEQ ID NO 53
<211> LENGTH: 9
<212> TYPE: PRT
<213> ORGANISM: Artificial Sequence
```

```
<220> FEATURE:
<223> OTHER INFORMATION: Description of Artificial Sequence:  human
      cytomegalovirus pp65 CTL epitope peptide

<400> SEQUENCE: 53

Leu Met Asn Gly Gln Gln Ile Phe Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 54

Ile Leu Ala Arg Asn Leu Val Pro Met
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 55

Ile Pro Ser Ile Asn Val His His Tyr
1               5

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 56

Gln Glu Phe Phe Trp Asp Ala Asn Asp Ile Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 57

Gln Glu Phe Phe Trp Asp Ala Asn Asp Ile
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 58

Gln Tyr Arg Ile Gln Gly Lys Leu Glu
1               5
```

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 59

Arg Lys His Arg His Leu Pro Val Ala Asp Ala Val
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 60

Asp Pro Val Ala Ala Leu Phe Phe Phe
1               5

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 61

Pro Gly Lys Ile Ser His Ile Met Leu Asp Val Ala
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 62

Thr Arg Ala Thr Lys Met Gln Val Ile
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 63

Gln Ala Ile Arg Glu Thr Val Glu Leu
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide -continued

<400> SEQUENCE: 64

Tyr His Arg Thr Trp Asp Arg His Glu Gly Ala
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 65

Phe Met Arg Pro His Glu Arg Asn Gly Phe Thr Val
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 66

Cys Pro Ser Gln Glu Pro Met Ser Ile Tyr Val Tyr
1               5                   10

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 67

Leu Asn Ile Pro Ser Ile Asn Val His His Tyr Pro Ser Ala Ala Glu
1               5                   10                  15

Arg Lys His Arg
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 68

Ala Thr Val Gln Gly Gln Asn Leu Lys Tyr Gln Glu Phe Phe Trp Asp
1               5                   10                  15

Ala Asn Asp Ile
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 69

Gln Glu Phe Phe Trp Asp Ala Asn Asp Ile Tyr Arg Ile Phe Ala Glu

```
1               5                  10                  15

Leu Glu Gly Val
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 70

Pro Gln Tyr Ser Glu His Pro Thr Phe Thr Ser Gln Tyr Arg Ile Gln
1               5                  10                  15

Gly Lys Leu Glu
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 71

Ser Gln Tyr Arg Ile Gln Gly Lys Leu Glu Tyr Arg His Thr Trp Asp
1               5                  10                  15

Arg His Asp Glu
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 72

Val Phe Thr Trp Pro Pro Trp Gln Ala Gly Ile Leu Ala Arg Asn Leu
1               5                  10                  15

Val Pro Met Val
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 73

Ile Leu Ala Arg Asn Leu Val Pro Met Val Ala Thr Val Gln Gly Gln
1               5                  10                  15

Asn Leu Lys Tyr
            20

<210> SEQ ID NO 74
<211> LENGTH: 20
<212> TYPE: PRT
<213> ORGANISM: Artificial Sequence
<220> FEATURE:
```

```
<223> OTHER INFORMATION: Description of Artificial Sequence:  human
      cytomegalovirus pp65 CTL epitope peptide

<400> SEQUENCE: 74

Asp Gln Tyr Val Lys Val Tyr Leu Glu Ser Phe Cys Glu Asp Val Pro
1               5                   10                  15

Ser Gly Lys Leu
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 75

Tyr Pro Ser Ala Ala Glu Arg Lys His Arg His Leu Pro Val Ala Asp
1               5                   10                  15

Ala Val Ile His
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 76

Gln Tyr Asp Pro Val Ala Ala Leu Phe Phe Phe Asp Ile Asp Leu Leu
1               5                   10                  15

Leu Gln Arg Gly
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 77

Ile Ile Lys Pro Gly Lys Ile Ser His Ile Met Leu Asp Val Ala Phe
1               5                   10                  15

Thr Ser His Glu
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 78

Ala His Glu Leu Val Cys Ser Met Glu Asn Thr Arg Ala Thr Lys Met
1               5                   10                  15

Gln Val Ile Gly
            20
```

```
<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 79

Thr Arg Ala Thr Lys Met Gln Val Ile Gly Asp Gln Tyr Val Lys Val
1               5                   10                  15

Tyr Leu Glu Ser
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 80

Met Asn Gly Gln Gln Ile Phe Leu Glu Val Gln Ala Ile Arg Glu Thr
1               5                   10                  15

Val Glu Leu Arg
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 81

Gln Ala Ile Arg Glu Thr Val Glu Leu Arg Gln Tyr Asp Pro Val Ala
1               5                   10                  15

Ala Leu Phe Phe
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 82

Leu Thr Val Ser Gly Leu Ala Trp Thr Arg Gln Gln Asn Gln Trp Lys
1               5                   10                  15

Glu Pro Asp Val
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 83
```

```
Trp Gln Pro Ala Ala Gln Pro Lys Arg Arg His Arg Gln Asp Ala
1               5                   10                  15

Leu Pro Gly Pro
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 84

Tyr Arg His Thr Trp Asp Arg His Asp Glu Gly Ala Ala Gln Gly Asp
1               5                   10                  15

Asp Asp Val Trp
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 85

Thr Ser Ala Gly Arg Lys Arg Lys Ser Ala Ser Ser Ala Thr Ala Cys
1               5                   10                  15

Thr Ser Gly Val
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 86

His Arg Gln Asp Ala Leu Pro Gly Pro Cys Ile Ala Ser Thr Pro Lys
1               5                   10                  15

Lys His Arg Gly
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 87

Tyr Tyr Thr Ser Ala Phe Val Phe Pro Thr Lys Asp Val Ala Leu Arg
1               5                   10                  15

His Val Val Cys
            20

<210> SEQ ID NO 88
<211> LENGTH: 20
<212> TYPE: PRT
<213> ORGANISM: Artificial Sequence
```

```
<220> FEATURE:
<223> OTHER INFORMATION: Description of Artificial Sequence:  human
      cytomegalovirus pp65 CTL epitope peptide

<400> SEQUENCE: 88

Val Thr Thr Glu Arg Lys Thr Pro Arg Val Thr Gly Gly Gly Ala Met
1               5                   10                  15

Ala Gly Ala Ser
            20

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 89

Gln Pro Phe Met Arg Pro His Glu Arg Asn Gly Phe Thr Val Leu Cys
1               5                   10                  15

Pro Lys Asn Met
            20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 90

Ser Ile Cys Pro Ser Gln Glu Pro Met Ser Ile Tyr Val Tyr Ala Leu
1               5                   10                  15

Pro Leu Lys Met
            20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 91

Ile Tyr Val Tyr Ala Leu Pro Leu Lys Met Leu Asn Ile Pro Ser Ile
1               5                   10                  15

Asn Val His His
            20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence:  human
      cytomegalovirus pp65 CTL epitope peptide

<400> SEQUENCE: 92

Gln Gln Asn Gln Trp Lys Glu Pro Asp Val Tyr Tyr Thr Ser Ala Phe
1               5                   10                  15

Val Phe Pro Thr
            20
```

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 93

Gly Ala Ala Gln Gly Asp Asp Asp Val Trp Thr Ser Gly Ser Asp Ser
1               5                   10                  15

Asp Glu Glu Leu
            20

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 94

Thr Gly Gly Gly Ala Met Ala Gly Ala Ser Thr Ser Ala Gly Arg Lys
1               5                   10                  15

Arg Lys Ser Ala
            20

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: human
      cytomegalovirus pp65 CTL epitope peptide

<400> SEQUENCE: 95

Lys Asp Val Ala Leu Arg His Val Val Cys Ala His Glu Leu Val Cys
1               5                   10                  15

Ser Met Glu Asn
            20

<210> SEQ ID NO 96
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human
      cytomegalovirus pp65 CTL epitope peptide

<400> SEQUENCE: 96

Ser Leu Leu Ser Glu Phe Cys Arg Val
1               5

<210> SEQ ID NO 97
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human
      cytomegalovirus pp65 CTL epitope peptide

<400> SEQUENCE: 97

Val Leu Ala Glu Leu Val Lys Gln Ile
1               5

```
<210> SEQ ID NO 98
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 98

Ile Leu Gly Ala Asp Pro Leu Arg Val
1               5

<210> SEQ ID NO 99
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 99

Thr Met Tyr Gly Gly Ile Ser Leu Leu
1               5

<210> SEQ ID NO 100
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 100

Leu Leu Ser Glu Phe Cys Arg Val Leu
1               5

<210> SEQ ID NO 101
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 101

Val Leu Glu Glu Thr Ser Val Met Leu
1               5

<210> SEQ ID NO 102
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 102

Cys Leu Gln Asn Ala Leu Asp Ile Leu
1               5

<210> SEQ ID NO 103
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide
```

-continued

```
<400> SEQUENCE: 103

Ile Leu Asp Glu Glu Arg Asp Lys Val
1               5

<210> SEQ ID NO 104
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 104

Ile Lys Glu His Met Leu Lys Lys Tyr
1               5

<210> SEQ ID NO 105
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 105

Asp Glu Glu Glu Ala Ile Val Ala Tyr
1               5

<210> SEQ ID NO 106
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 106

Lys Leu Gly Gly Ala Leu Gln Ala Lys
1               5

<210> SEQ ID NO 107
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 107

Gln Tyr Ile Leu Gly Ala Asp Pro Leu
1               5

<210> SEQ ID NO 108
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 108

Lys Tyr Thr Gln Thr Glu Glu Lys Phe
1               5

<210> SEQ ID NO 109
<211> LENGTH: 9
```

```
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 109

Lys Ala Arg Ala Lys Lys Asp Glu Leu
1               5

<210> SEQ ID NO 110
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 110

Val Met Lys Arg Arg Ile Glu Glu Ile
1               5

<210> SEQ ID NO 111
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 111

Arg His Arg Ile Lys Glu His Met Leu
1               5

<210> SEQ ID NO 112
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 112

Glu Leu Arg Arg Lys Met Met Tyr Met
1               5

<210> SEQ ID NO 113
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 113

Gln Ile Lys Val Arg Val Asp Met Val
1               5

<210> SEQ ID NO 114
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence:  human
      cytomegalovirus pp65 CTL epitope peptide

<400> SEQUENCE: 114

Glu Leu Lys Arg Lys Met Met Tyr Met
```

<210> SEQ ID NO 115
<211> LENGTH: 9
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 115

Arg Arg Lys Met Met Tyr Met Cys Tyr
1               5

<210> SEQ ID NO 116
<211> LENGTH: 10
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 116

Ala Tyr Ala Gln Lys Ile Phe Lys Ile Leu
1               5                   10

<210> SEQ ID NO 117
<211> LENGTH: 20
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 117

Cys Ser Pro Asp Glu Ile Met Ala Tyr Ala Gln Lys Ile Phe Lys Ile
1               5                   10                  15

Leu Asp Glu Glu
            20

<210> SEQ ID NO 118
<211> LENGTH: 20
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 118

Ser Glu Pro Val Ser Glu Ile Glu Glu Val Ala Pro Glu Glu Glu Glu
1               5                   10                  15

Asp Gly Ala Glu
            20

<210> SEQ ID NO 119
<211> LENGTH: 20
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 119

Val Leu Cys Cys Tyr Val Leu Glu Glu Thr Ser Val Met Leu Ala Lys
1               5                   10                  15

Arg Pro Leu Ile

<210> SEQ ID NO 120
<211> LENGTH: 20
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 120

Arg Arg Lys Met Met Tyr Met Cys Tyr Arg Asn Ile Glu Phe Phe Thr
1               5                   10                  15

Lys Asn Ser Ala
            20

<210> SEQ ID NO 121
<211> LENGTH: 20
<212> TYPE: PRT
<213> ORGANISM: human cytomegalovirus IE1 CTL epitope peptide
<220> FEATURE:
<223> OTHER INFORMATION: Description of Artificial Sequence: human cytomegalovirus pp65 CTL epitope peptide

<400> SEQUENCE: 121

Asn Ile Glu Phe Phe Thr Lys Asn Ser Ala Phe Pro Lys Thr Thr Asn
1               5                   10                  15

Gly Cys Ser Gln
            20

<210> SEQ ID NO 122
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 122

Gly Gln Thr Glu Pro Ile Ala Phe Val
1               5

<210> SEQ ID NO 123
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human cytomegalovirus pp65 CTL epitope peptide

<400> SEQUENCE: 123

Ala Tyr Glu Tyr Val Asp Tyr Leu Phe
1               5

<210> SEQ ID NO 124
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human cytomegalovirus pp65 CTL epitope peptide

<400> SEQUENCE: 124

Ser Tyr Glu Asn Lys Thr Met Gln Leu
1               5

<210> SEQ ID NO 125
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 125

Ala Tyr Ile Tyr Thr Thr Tyr Leu Leu
1               5

<210> SEQ ID NO 126
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 126

Asn Thr Asp Phe Arg Val Leu Glu Leu
1               5

<210> SEQ ID NO 127
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 127

Ala Thr Ser Thr Gly Asp Val Val Tyr
1               5

<210> SEQ ID NO 128
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 128

Leu Asp Glu Gly Ile Met Val Val Tyr
1               5

<210> SEQ ID NO 129
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 129

Val Lys Glu Ser Pro Gly Arg Cys Tyr
1               5

<210> SEQ ID NO 130
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 130

-continued

Arg Pro Ser Thr Pro Arg Ala Ala Val
1               5

<210> SEQ ID NO 131
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 131

Ser Pro Trp Ala Pro Thr Ala Pro Leu
1               5

<210> SEQ ID NO 132
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 132

Lys Ala Arg Asp His Leu Ala Val Leu
1               5

<210> SEQ ID NO 133
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 133

Trp Pro Arg Glu Arg Ala Trp Ala Leu
1               5

<210> SEQ ID NO 134
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human
      cytomegalovirus pp65 CTL epitope peptide

<400> SEQUENCE: 134

Asn Val Arg Arg Ser Trp Glu Glu Leu
1               5

<210> SEQ ID NO 135
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 135

Ile Met Arg Glu Phe Asn Ser Tyr Lys
1               5

<210> SEQ ID NO 136
<211> LENGTH: 9
<212> TYPE: PRT
<213> ORGANISM: human cytomegalovirus gB CTL epitope peptide

```
<220> FEATURE:
<223> OTHER INFORMATION: Description of Artificial Sequence:  human
      cytomegalovirus pp65 CTL epitope peptide

<400> SEQUENCE: 136

Lys Met Thr Ala Thr Phe Leu Ser Lys
1               5

<210> SEQ ID NO 137
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence:  human
      cytomegalovirus pp65 CTL epitope peptide

<400> SEQUENCE: 137

Cys Tyr Ser Arg Pro Val Val Ile Phe
1               5

<210> SEQ ID NO 138
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 138

Arg Ile Glu Glu Asn Leu Glu Gly Val
1               5

<210> SEQ ID NO 139
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 139

Pro Leu Ile Pro Thr Thr Ala Val Ile
1               5

<210> SEQ ID NO 140
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 140

Leu Ile Glu Asp Phe Asp Ile Tyr Val
1               5

<210> SEQ ID NO 141
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 141

Lys Met Ser Val Arg Glu Thr Leu Val
1               5
```

<210> SEQ ID NO 142
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 142

Phe Leu Gly Ala Arg Ser Pro Ser Leu
1               5

<210> SEQ ID NO 143
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 143

Ala Leu Val Asn Ala Val Asn Lys Leu
1               5

<210> SEQ ID NO 144
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 144

Ala Leu Val Asn Phe Leu Arg His Leu
1               5

<210> SEQ ID NO 145
<211> LENGTH: 9
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 145

Asn Ile Leu Gln Lys Ile Glu Lys Ile
1               5

<210> SEQ ID NO 146
<211> LENGTH: 12
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

<400> SEQUENCE: 146

Glu Arg Ala Trp Ala Leu Lys Asn Pro His Leu Ala
1               5                   10

<210> SEQ ID NO 147
<211> LENGTH: 20
<212> TYPE: PRT
<213> ORGANISM: human cytomegalovirus pp150 CTL epitope peptide
<220> FEATURE:
<223> OTHER INFORMATION: Description of Artificial Sequence: human cytomegalovirus pp65 CTL epitope peptide

```
<400> SEQUENCE: 147

Trp Pro Arg Glu Arg Ala Trp Ala Leu Lys Asn Pro His Leu Ala Tyr
1               5                   10                  15

Asn Pro Phe Arg
            20

<210> SEQ ID NO 148
<211> LENGTH: 20
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 148

Ser Thr Ser Gln Lys Pro Val Leu Gly Lys Arg Val Ala Thr Pro His
1               5                   10                  15

Ala Ser Ala Arg
            20

<210> SEQ ID NO 149
<211> LENGTH: 20
<212> TYPE: PRT
<213> ORGANISM: human cytomegalovirus pp150 CTL epitope peptide
<220> FEATURE:
<223> OTHER INFORMATION: Description of Artificial Sequence:  human
      cytomegalovirus pp65 CTL epitope peptide

<400> SEQUENCE: 149

His Ala Asn Thr Ala Leu Val Asn Ala Val Asn Lys Leu Val Tyr Thr
1               5                   10                  15

Gly Arg Leu Ile
            20

<210> SEQ ID NO 150
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 150

Leu Leu Ile Asp Pro Thr Ser Gly Leu
1               5

<210> SEQ ID NO 151
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 151

Leu Leu Val Glu Pro Cys Ala Arg Val
1               5

<210> SEQ ID NO 152
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide
```

-continued

```
<400> SEQUENCE: 152

Leu Leu Leu Ile Val Thr Pro Val Val
1               5

<210> SEQ ID NO 153
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 153

Phe Leu Leu Ser His Asp Ala Ala Leu
1               5

<210> SEQ ID NO 154
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 154

Pro Leu Arg Glu Tyr Leu Ala Asp Leu
1               5

<210> SEQ ID NO 155
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 155

Gly Leu Leu Gly Ala Ser Met Asp Leu
1               5

<210> SEQ ID NO 156
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 156

Leu Val Glu Pro Cys Ala Arg Val Tyr
1               5

<210> SEQ ID NO 157
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence:  human
      cytomegalovirus pp65 CTL epitope peptide

<400> SEQUENCE: 157

Gly Ile Lys His Glu Gly Leu Val Lys
1               5

<210> SEQ ID NO 158
<211> LENGTH: 9
<212> TYPE: PRT
```

<210> SEQ ID NO 158 (context continues)
<213> ORGANISM: human cytomegalovirus pp28 CTL epitope peptide
<220> FEATURE:
<223> OTHER INFORMATION: Description of Artificial Sequence: human
      cytomegalovirus pp65 CTL epitope peptide

<400> SEQUENCE: 158

Glu Leu Leu Ala Gly Gly Arg Val Phe
1               5

<210> SEQ ID NO 159
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence: human
      cytomegalovirus pp65 CTL epitope peptide

<400> SEQUENCE: 159

Arg Leu Leu Asp Leu Ala Pro Asn Tyr
1               5

<210> SEQ ID NO 160
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence: human
      cytomegalovirus pp65 CTL epitope peptide

<400> SEQUENCE: 160

Glu Leu Leu Gly Arg Leu Asn Val Tyr
1               5

<210> SEQ ID NO 161
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence: human
      cytomegalovirus pp65 CTL epitope peptide

<400> SEQUENCE: 161

Cys Arg Tyr Lys Tyr Leu Arg Lys Lys
1               5

<210> SEQ ID NO 162
<211> LENGTH: 9
<212> TYPE: PRT
<213> ORGANISM: human cytomegalovirus pp28 CTL epitope peptide
<220> FEATURE:
<223> OTHER INFORMATION: Description of Artificial Sequence: human
      cytomegalovirus pp65 CTL epitope peptide

<400> SEQUENCE: 162

Ala Arg Val Tyr Glu Ile Lys Cys Arg
1               5

<210> SEQ ID NO 163
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human
      cytomegalovirus pp65 CTL epitope peptide

<400> SEQUENCE: 163

Leu Leu Asn Cys Ala Val Thr Lys Leu
1               5

<210> SEQ ID NO 164
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide

<400> SEQUENCE: 164

Gln Leu Arg Ser Val Ile Arg Ala Leu
1               5

<210> SEQ ID NO 165
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide

<400> SEQUENCE: 165

Val Thr Glu His Asp Thr Leu Leu Tyr
1               5

<210> SEQ ID NO 166
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide

<400> SEQUENCE: 166

Arg Gly Asp Pro Phe Asp Lys Asn Tyr
1               5

<210> SEQ ID NO 167
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide

<400> SEQUENCE: 167

Gly Leu Asp Arg Asn Ser Gly Asn Tyr
1               5

<210> SEQ ID NO 168
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide

<400> SEQUENCE: 168

Thr Leu Leu Asn Cys Ala Val Thr Lys
1               5

<210> SEQ ID NO 169
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human cytomegalovirus pp65 CTL epitope peptide -continued

<400> SEQUENCE: 169

Thr Val Arg Ser His Cys Val Ser Lys
1               5

<210> SEQ ID NO 170
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human
      cytomegalovirus pp65 CTL epitope peptide

<400> SEQUENCE: 170

Tyr Glu Gln His Lys Ile Thr Ser Tyr
1               5

<210> SEQ ID NO 171
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human
      cytomegalovirus pp65 CTL epitope peptide

<400> SEQUENCE: 171

Thr Arg Val Lys Arg Asn Val Lys Lys
1               5

<210> SEQ ID NO 172
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human
      cytomegalovirus pp65 CTL epitope peptide

<400> SEQUENCE: 172

Ser Glu Asp Ser Val Thr Phe Glu Phe
1               5

<210> SEQ ID NO 173
<211> LENGTH: 9
<212> TYPE: PRT
<213> ORGANISM: human cytomegalovirus pp50 CTL epitope peptide
<220> FEATURE:
<223> OTHER INFORMATION: Description of Artificial Sequence: human
      cytomegalovirus pp65 CTL epitope peptide

<400> SEQUENCE: 173

Thr Arg Leu Ser Glu Pro Pro Thr Leu
1               5

<210> SEQ ID NO 174
<211> LENGTH: 10
<212> TYPE: PRT
<213> ORGANISM: human cytomegalovirus pp71 CTL epitope peptide
<220> FEATURE:
<223> OTHER INFORMATION: Description of Artificial Sequence: human
      cytomegalovirus pp65 CTL epitope peptide

<400> SEQUENCE: 174

Gln Leu Leu Ile Pro Lys Ser Phe Thr Leu
1               5                   10

<210> SEQ ID NO 175
<211> LENGTH: 9

```
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 175

Thr Leu Val Ile Pro Ser Trp His Val
1               5

<210> SEQ ID NO 176
<211> LENGTH: 9
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 176

Leu Leu Ile Pro Lys Ser Phe Thr Leu
1               5

<210> SEQ ID NO 177
<211> LENGTH: 9
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 177

Asp Leu Val Pro Leu Thr Val Ser Val
1               5

<210> SEQ ID NO 178
<211> LENGTH: 10
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 178

Cys Ser Asp Pro Asn Thr Tyr Ile His Lys
1               5                   10

<210> SEQ ID NO 179
<211> LENGTH: 10
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 179

Glu Tyr Ile Val Gln Ile Gln Asn Ala Phe
1               5                   10

<210> SEQ ID NO 180
<211> LENGTH: 10
<212> TYPE: PRT
<213> ORGANISM: human cytomegalovirus pp71 CTL epitope peptide
<220> FEATURE:
<223> OTHER INFORMATION: Description of Artificial Sequence:  human
      cytomegalovirus pp65 CTL epitope peptide

<400> SEQUENCE: 180

Ala Glu Val Val Ala Arg His Asn Pro Tyr
```

<210> SEQ ID NO 181
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 181

Arg Ile Trp Cys Leu Val Val Cys Val
1               5

<210> SEQ ID NO 182
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 182

Gln Met Leu Leu Ala Leu Ala Arg Leu
1               5

<210> SEQ ID NO 183
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 183

Gly Leu Asp Asp Leu Met Ser Gly Leu
1               5

<210> SEQ ID NO 184
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 184

Ile Ile Leu Val Ala Ile Ala Val Val
1               5

<210> SEQ ID NO 185
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 185

Asp Leu Asp Glu Gly Ile Met Val Val
1               5

<210> SEQ ID NO 186
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human cytomegalovirus pp65 CTL epitope peptide

<400> SEQUENCE: 186

Asn Leu Phe Pro Tyr Leu Val Ser Ala
1               5

<210> SEQ ID NO 187
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 187

Ala Val Gly Gly Ala Val Ala Ser Val
1               5

<210> SEQ ID NO 188
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 188

Tyr Ile Asn Arg Ala Leu Ala Gln Ile
1               5

<210> SEQ ID NO 189
<211> LENGTH: 9
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 189

Tyr Ala Tyr Ile Tyr Thr Thr Tyr Leu
1               5

<210> SEQ ID NO 190
<211> LENGTH: 10
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 190

Val Phe Glu Thr Ser Gly Gly Leu Val Val
1               5                   10

<210> SEQ ID NO 191
<211> LENGTH: 12
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 191

Asp Asp Tyr Ser Asn Thr His Ser Thr Arg Tyr Val
1               5                   10

<210> SEQ ID NO 192

```
<211> LENGTH: 20
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 192

Arg Ser Tyr Ala Tyr Ile Tyr Thr Thr Tyr Leu Leu Gly Ser Asn Thr
1               5                   10                  15

Glu Tyr Val Ala
            20

<210> SEQ ID NO 193
<211> LENGTH: 20
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 193

Thr Tyr Glu Lys Tyr Gly Asn Val Ser Val Phe Glu Thr Ser Gly Gly
1               5                   10                  15

Leu Val Val Phe
            20

<210> SEQ ID NO 194
<211> LENGTH: 20
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 194

Phe Glu Thr Ser Gly Gly Leu Val Val Phe Trp Gln Gly Ile Lys Gln
1               5                   10                  15

Lys Ser Leu Val
            20

<210> SEQ ID NO 195
<211> LENGTH: 20
<212> TYPE: PRT
<213> ORGANISM: human cytomegalovirus gB CTL epitope peptide
<220> FEATURE:
<223> OTHER INFORMATION: Description of Artificial Sequence: human
      cytomegalovirus pp65 CTL epitope peptide

<400> SEQUENCE: 195

Met Gln Leu Ile Pro Asp Asp Tyr Ser Asn Thr His Ser Thr Arg Tyr
1               5                   10                  15

Val Thr Val Lys
            20

<210> SEQ ID NO 196
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 196

Tyr Leu Met Asp Glu Leu Arg Tyr Val
1               5
```

```
<210> SEQ ID NO 197
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 197

Tyr Leu Thr Val Phe Thr Val Tyr Leu
1               5

<210> SEQ ID NO 198
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 198

Thr Leu Thr Glu Asp Phe Phe Val Val
1               5

<210> SEQ ID NO 199
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 199

Leu Leu Met Met Ser Val Tyr Ala Leu
1               5

<210> SEQ ID NO 200
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 200

Tyr Leu Leu Tyr Arg Met Leu Lys Thr
1               5

<210> SEQ ID NO 201
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 201

Ile Leu Phe Asp Gly His Asp Leu Leu
1               5

<210> SEQ ID NO 202
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide
```

<400> SEQUENCE: 202

Leu Ile Phe Gly His Leu Pro Arg Val
1               5

<210> SEQ ID NO 203
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 203

Ser Leu Val Arg Leu Val Tyr Ile Leu
1               5

<210> SEQ ID NO 204
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 204

Leu Leu Tyr Pro Thr Ala Val Asp Leu
1               5

<210> SEQ ID NO 205
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 205

Ala Leu Asp Pro Tyr Asn Glu Val Val
1               5

<210> SEQ ID NO 206
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 206

Leu Met Leu Leu Lys Asn Gly Thr Val
1               5

<210> SEQ ID NO 207
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 207

Ser Ala Ile Ile Gly Ile Tyr Leu Leu
1               5

<210> SEQ ID NO 208
<211> LENGTH: 9

```
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 208

Ile Thr Ser Leu Val Arg Leu Val Tyr
1               5

<210> SEQ ID NO 209
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 209

His His Glu Tyr Leu Ser Asp Leu Tyr
1               5

<210> SEQ ID NO 210
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 210

Ala Ile Ile Gly Ile Tyr Leu Leu Tyr
1               5

<210> SEQ ID NO 211
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 211

Gln Thr Glu Lys His Glu Leu Leu Val
1               5

<210> SEQ ID NO 212
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 212

Ala Thr Asp Ser Arg Leu Leu Met Met
1               5

<210> SEQ ID NO 213
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 213

Phe Leu Asp Ala Ala Leu Asp Phe Asn Tyr
```

-continued

```
1               5                   10

<210> SEQ ID NO 214
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 214

Asp Thr Gln Gly Val Ile Asn Ile Met Tyr
1               5                   10

<210> SEQ ID NO 215
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 215

Leu Arg Glu Asn Thr Thr Gln Cys Thr Tyr
1               5                   10

<210> SEQ ID NO 216
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 216

Ser Ala Ile Ile Gly Ile Tyr Leu Leu Tyr
1               5                   10

<210> SEQ ID NO 217
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 217

Ser Leu Arg Asn Ser Thr Val Val Arg
1               5

<210> SEQ ID NO 218
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 218

Ala Leu Ala Leu Phe Ala Ala Ala Arg
1               5

<210> SEQ ID NO 219
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
```

-continued cytomegalovirus pp65 CTL epitope peptide

<400> SEQUENCE: 219

Gln Leu Asn Arg His Ser Tyr Leu Lys
1               5

<210> SEQ ID NO 220
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 220

Arg Leu Phe Pro Asp Ala Thr Val Pro
1               5

<210> SEQ ID NO 221
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 221

Arg Leu Asn Thr Tyr Ala Leu Val Ser Lys
1               5                   10

<210> SEQ ID NO 222
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 222

Leu Val Arg Leu Val Tyr Ile Leu Ser Lys
1               5                   10

<210> SEQ ID NO 223
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 223

Tyr Leu Met Asp Glu Leu Arg Tyr Val Lys
1               5                   10

<210> SEQ ID NO 224
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 224

Glu Leu Tyr Leu Met Gly Ser Leu Val His
1               5                   10

<210> SEQ ID NO 225

```
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 225

Ala Leu Thr Val Ser Glu His Val Ser Tyr
1               5                   10

<210> SEQ ID NO 226
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 226

Asn Tyr Leu Asp Leu Ser Ala Leu Leu
1               5

<210> SEQ ID NO 227
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 227

Ser Tyr Val Val Thr Asn Gln Tyr Leu
1               5

<210> SEQ ID NO 228
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 228

Ser Tyr Leu Lys Asp Ser Asp Phe Leu
1               5

<210> SEQ ID NO 229
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 229

Thr Tyr Ala Leu Val Ser Lys Asp Leu
1               5

<210> SEQ ID NO 230
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 230
```

```
Ser Tyr Arg Ser Phe Ser Gln Gln Leu
1               5

<210> SEQ ID NO 231
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 231

Thr Tyr Gly Arg Pro Ile Arg Phe Leu
1               5

<210> SEQ ID NO 232
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 232

Tyr Tyr Val Phe His Met Pro Arg Cys Leu
1               5                   10

<210> SEQ ID NO 233
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 233

Met Tyr Met His Asp Ser Asp Asp Val Leu
1               5                   10

<210> SEQ ID NO 234
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 234

Glu Thr Phe Pro Asp Leu Phe Cys Leu
1               5

<210> SEQ ID NO 235
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence:  human
      cytomegalovirus pp65 CTL epitope peptide

<400> SEQUENCE: 235

Asp Leu Thr Glu Thr Leu Glu Arg Tyr
1               5

<210> SEQ ID NO 236
<211> LENGTH: 9
<212> TYPE: PRT
<213> ORGANISM: human cytomegalovirus gH CTL epitope peptide
<220> FEATURE:
```

```
<223> OTHER INFORMATION: Description of Artificial Sequence: human
      cytomegalovirus pp65 CTL epitope peptide

<400> SEQUENCE: 236

Ser Pro Arg Thr His Tyr Leu Met Leu
1               5

<210> SEQ ID NO 237
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 237

Phe Pro Asp Leu Phe Cys Leu Pro Leu
1               5

<210> SEQ ID NO 238
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 238

Ser Pro Arg Thr His Tyr Leu Met Leu Leu
1               5                   10

<210> SEQ ID NO 239
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 239

Met Pro Arg Cys Leu Phe Ala Gly Pro Leu
1               5                   10

<210> SEQ ID NO 240
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 240

Thr Pro Met Leu Leu Ile Phe Gly His Leu
1               5                   10

<210> SEQ ID NO 241
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 241

Ala Pro Tyr Gln Arg Asp Asn Phe Ile Leu
1               5                   10
```

```
<210> SEQ ID NO 242
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 242

Gly Arg Cys Gln Met Leu Asp Arg Arg
1               5

<210> SEQ ID NO 243
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 243

Arg Arg Asp His Ser Leu Glu Arg Leu
1               5

<210> SEQ ID NO 244
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 244

Ser Glu Ala Leu Asp Pro His Ala Phe
1               5

<210> SEQ ID NO 245
<211> LENGTH: 9
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 245

Arg Glu Asn Thr Thr Gln Cys Thr Tyr
1               5

<210> SEQ ID NO 246
<211> LENGTH: 10
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 246

Asp Asp Val Leu Phe Ala Leu Asp Pro Tyr
1               5                   10

<210> SEQ ID NO 247
<211> LENGTH: 12
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 247
```

```
His Glu Leu Leu Val Leu Val Lys Lys Ala Gln Leu
1               5                   10
```

<210> SEQ ID NO 248
<211> LENGTH: 12
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 248

```
Leu Thr Val Ser Glu His Val Ser Tyr Val Val Thr
1               5                   10
```

<210> SEQ ID NO 249
<211> LENGTH: 20
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 249

```
Arg Gln Thr Glu Lys His Glu Leu Leu Val Leu Val Lys Lys Ala Gln
1               5                   10                  15

Leu Asn Arg His
            20
```

<210> SEQ ID NO 250
<211> LENGTH: 20
<212> TYPE: PRT
<213> ORGANISM: human cytomegalovirus gH CTL epitope peptide
<220> FEATURE:
<223> OTHER INFORMATION: Description of Artificial Sequence: human
      cytomegalovirus pp65 CTL epitope peptide

<400> SEQUENCE: 250

```
Ala Leu Thr Val Ser Glu His Val Ser Tyr Val Val Thr Asn Gln Tyr
1               5                   10                  15

Leu Ile Lys Gly
            20
```

<210> SEQ ID NO 251
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human
      cytomegalovirus pp65 CTL epitope peptide

<400> SEQUENCE: 251

```
Phe Leu Met Glu His Thr Met Pro Val
1               5
```

<210> SEQ ID NO 252
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human
      cytomegalovirus pp65 CTL epitope peptide

<400> SEQUENCE: 252

```
Leu Met Gln Lys Phe Pro Lys Gln Val
1               5
```

<210> SEQ ID NO 253
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide

<400> SEQUENCE: 253

Asn Leu Ala Leu Ser Thr Pro Phe Leu
1               5

<210> SEQ ID NO 254
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide

<400> SEQUENCE: 254

Ile Ile Tyr Thr Arg Asn His Glu Val
1               5

<210> SEQ ID NO 255
<211> LENGTH: 10
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide

<400> SEQUENCE: 255

Ile Ile Tyr Thr Arg Asn His Glu Val Lys
1               5                   10

<210> SEQ ID NO 256
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide

<400> SEQUENCE: 256

Leu Leu Gly Ala Leu Asn Leu Cys Leu
1               5

<210> SEQ ID NO 257
<211> LENGTH: 10
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide

<400> SEQUENCE: 257

Lys Pro Glu Pro Asp Phe Thr Ile Gln Tyr
1               5                   10

<210> SEQ ID NO 258
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence: human cytomegalovirus pp65 CTL epitope peptide -continued

```
<400> SEQUENCE: 258

Ile Met Lys Asp Lys Asn Thr Pro Phe
1               5

<210> SEQ ID NO 259
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 259

Pro Arg Lys Lys Lys Ser Lys Arg Ile
1               5

<210> SEQ ID NO 260
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 260

Phe Glu Gln Pro Thr Glu Thr Pro Pro
1               5

<210> SEQ ID NO 261
<211> LENGTH: 8
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 261

Phe Glu Gln Pro Thr Glu Thr Pro
1               5

<210> SEQ ID NO 262
<211> LENGTH: 10
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 262

Phe Glu Gln Pro Thr Glu Thr Pro Pro Glu
1               5                   10

<210> SEQ ID NO 263
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 263

Glu Gln Pro Thr Glu Thr Pro Pro Glu
1               5

<210> SEQ ID NO 264
<211> LENGTH: 11
```

-continued

```
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 264

Gln Phe Glu Gln Pro Thr Glu Thr Pro Pro Glu
1               5                   10

<210> SEQ ID NO 265
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 265

Ser Asp Tyr Asn Met Ile Ile His Ala
1               5

<210> SEQ ID NO 266
<211> LENGTH: 10
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 266

Tyr Arg Asn Met Ile Ile His Ala Ala Thr
1               5                   10

<210> SEQ ID NO 267
<211> LENGTH: 9
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 267

Cys Leu Pro Leu Met Gln Lys Phe Pro
1               5

<210> SEQ ID NO 268
<211> LENGTH: 14
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 268

Ile Asp Glu Val Ser Arg Met Phe Arg Asn Thr Asn Arg Ser
1               5                   10

<210> SEQ ID NO 269
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 269

Thr Ala Ala Lys Ala Tyr Ala Val Gly Gln Phe Glu Gln Pro Thr Glu
```

-continued

```
1               5                   10                  15

Thr Pro Pro Glu
            20

<210> SEQ ID NO 270
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 270

Phe Glu Gln Pro Thr Glu Thr Pro Pro Glu Asp Leu Asp Thr Leu Ser
1               5                   10                  15

Leu Ala Ile Glu
            20

<210> SEQ ID NO 271
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 271

Met Leu Pro Leu Ile Lys Gln Glu Asp Ile Lys Pro Glu Pro Asp Phe
1               5                   10                  15

Thr Ile Gln Tyr
            20

<210> SEQ ID NO 272
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 272

Thr His Gln Leu Cys Pro Arg Ser Ser Asp Tyr Arg Asn Met Ile Ile
1               5                   10                  15

His Ala Ala Thr
            20

<210> SEQ ID NO 273
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 273

Tyr Arg Asn Met Ile Ile His Ala Ala Thr Pro Val Asp Leu Leu Gly
1               5                   10                  15

Ala Leu Asn Leu
            20

<210> SEQ ID NO 274
<211> LENGTH: 20
<212> TYPE: PRT
<213> ORGANISM: human cytomegalovirus IE2 CTL epitope peptide
<220> FEATURE:
```

<223> OTHER INFORMATION: Description of Artificial Sequence: human
cytomegalovirus pp65 CTL epitope peptide

<400> SEQUENCE: 274

Thr Gly Pro Arg Lys Lys Ser Lys Arg Ile Ser Glu Leu Asp Asn
1               5                   10                  15

Glu Lys Val Arg
            20

<210> SEQ ID NO 275
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence: human
cytomegalovirus pp65 CTL epitope peptide

<400> SEQUENCE: 275

Pro Val Asp Leu Leu Gly Ala Leu Asn Leu Cys Leu Pro Leu Met Gln
1               5                   10                  15

Lys Phe Pro Lys
            20

<210> SEQ ID NO 276
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence: human
cytomegalovirus pp65 CTL epitope peptide

<400> SEQUENCE: 276

Ile Gln Ile Ile Tyr Thr Arg Asn His Glu Val Lys Ser Glu Val Asp
1               5                   10                  15

Ala Val Arg Cys
            20

<210> SEQ ID NO 277
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence: human
cytomegalovirus pp65 CTL epitope peptide

<400> SEQUENCE: 277

Val Lys Ser Glu Val Asp Ala Val Arg Cys Arg Leu Gly Thr Met Cys
1               5                   10                  15

Asn Leu Ala Leu
            20

<210> SEQ ID NO 278
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence: human
cytomegalovirus pp65 CTL epitope peptide

<400> SEQUENCE: 278

Arg Val Lys Ile Asp Glu Val Ser Arg Met Phe Arg Asn Thr Asn Arg
1               5                   10                  15

Ser Leu Glu Tyr
            20

```
<210> SEQ ID NO 279
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 279

Ser Ser Ser Ser Ser Ser Cys Ser Ser Ala Ser Asp Ser Glu Ser Glu
1               5                   10                  15

Ser Glu Glu Met
            20

<210> SEQ ID NO 280
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 280

Ala Ser Ser Pro Ser Thr Gly Ser Gly Thr Pro Arg Asx Thr Ser Pro
1               5                   10                  15

Thr His Pro Leu
            20

<210> SEQ ID NO 281
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 281

Pro Arg Val Thr Ser Pro Thr His Pro Leu Ser Gln Met Asn His Pro
1               5                   10                  15

Pro Leu Pro Asp
            20

<210> SEQ ID NO 282
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 282

Pro Leu Gly Arg Pro Asp Glu Asp Ser Ser Ser Ser Ser Ser Ser Ser
1               5                   10                  15

Cys Ser Ser Ala
            20

<210> SEQ ID NO 283
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 283
```

Ser Asp Ser Glu Ser Glu Ser Glu Glu Met Lys Cys Ser Ser Gly Gly
1               5                   10                  15

Gly Ala Ser Val
            20

<210> SEQ ID NO 284
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 284

Lys Cys Ser Ser Gly Gly Gly Ala Ser Val Thr Ser Ser His His Gly
1               5                   10                  15

Arg Gly Gly Phe
            20

<210> SEQ ID NO 285
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 285

Cys Thr Pro Asn Val Gln Thr Arg Arg Gly Arg Val Lys Ile Asp Glu
1               5                   10                  15

Val Ser Arg Met
            20

<210> SEQ ID NO 286
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 286

Phe Arg Asn Thr Asn Arg Ser Leu Glu Tyr Lys Asn Leu Pro Phe Thr
1               5                   10                  15

Ile Pro Ser Met
            20

<210> SEQ ID NO 287
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 287

His Gln Val Leu Asp Glu Ala Ile Lys Ala Cys Lys Thr Met Gln Val
1               5                   10                  15

Asn Asn Lys Gly
            20

<210> SEQ ID NO 288
<211> LENGTH: 20
<212> TYPE: PRT
<213> ORGANISM: human cytomegalovirus IE2 CTL epitope peptide

```
<220> FEATURE:
<223> OTHER INFORMATION: Description of Artificial Sequence:  human
      cytomegalovirus pp65 CTL epitope peptide

<400> SEQUENCE: 288

Cys Lys Thr Met Gln Val Asn Asn Lys Gly Ile Gln Ile Ile Tyr Thr
1               5                   10                  15

Arg Asn His Glu
            20

<210> SEQ ID NO 289
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 289

Lys Ala Ala Trp Ser Leu Lys Glu Leu His Thr His Gln Leu Cys Pro
1               5                   10                  15

Arg Ser Ser Asp
            20

<210> SEQ ID NO 290
<211> LENGTH: 20
<212> TYPE: PRT
<213> ORGANISM: human cytomegalovirus IE2 CTL epitope peptide
<220> FEATURE:
<223> OTHER INFORMATION: Description of Artificial Sequence:  human
      cytomegalovirus pp65 CTL epitope peptide

<400> SEQUENCE: 290

Cys Leu Pro Leu Met Gln Lys Phe Pro Lys Gln Val Met Val Arg Ile
1               5                   10                  15

Phe Ser Thr Asn
            20

<210> SEQ ID NO 291
<211> LENGTH: 10
<212> TYPE: PRT
<213> ORGANISM: human cytomegalovirus UL18 CTL epitope peptide
<220> FEATURE:
<223> OTHER INFORMATION: Description of Artificial Sequence:  human
      cytomegalovirus pp65 CTL epitope peptide

<400> SEQUENCE: 291

Gly Glu Ile Asn Ile Thr Phe Ile His Tyr
1               5                   10

<210> SEQ ID NO 292
<211> LENGTH: 10
<212> TYPE: PRT
<213> ORGANISM: human cytomegalovirus UL18 CTL epitope peptide
<220> FEATURE:
<223> OTHER INFORMATION: Description of Artificial Sequence:  human
      cytomegalovirus pp65 CTL epitope peptide

<400> SEQUENCE: 292

Thr Glu Asn Gly Ser Phe Val Ala Gly Tyr
1               5                   10

<210> SEQ ID NO 293
<211> LENGTH: 9
<212> TYPE: PRT
<213> ORGANISM: human cytomegalovirus UL18 CTL epitope peptide
```

```
<220> FEATURE:
<223> OTHER INFORMATION: Description of Artificial Sequence:  human
      cytomegalovirus pp65 CTL epitope peptide

<400> SEQUENCE: 293

Thr Met Trp Cys Leu Thr Leu Phe Val
1               5

<210> SEQ ID NO 294
<211> LENGTH: 9
<212> TYPE: PRT
<213> ORGANISM: human cytomegalovirus US2 CTL epitope peptide
<220> FEATURE:
<223> OTHER INFORMATION: Description of Artificial Sequence:  human
      cytomegalovirus pp65 CTL epitope peptide

<400> SEQUENCE: 294

Leu Leu Val Leu Phe Ile Val Tyr Val
1               5

<210> SEQ ID NO 295
<211> LENGTH: 9
<212> TYPE: PRT
<213> ORGANISM: human cytomegalovirus US2 CTL epitope peptide
<220> FEATURE:
<223> OTHER INFORMATION: Description of Artificial Sequence:  human
      cytomegalovirus pp65 CTL epitope peptide

<400> SEQUENCE: 295

Ser Met Met Trp Met Arg Phe Phe Val
1               5

<210> SEQ ID NO 296
<211> LENGTH: 10
<212> TYPE: PRT
<213> ORGANISM: human cytomegalovirus US2 CTL epitope peptide
<220> FEATURE:
<223> OTHER INFORMATION: Description of Artificial Sequence:  human
      cytomegalovirus pp65 CTL epitope peptide

<400> SEQUENCE: 296

Thr Leu Leu Val Leu Phe Ile Val Tyr Val
1               5                   10

<210> SEQ ID NO 297
<211> LENGTH: 9
<212> TYPE: PRT
<213> ORGANISM: human cytomegalovirus US2 CTL epitope peptide
<220> FEATURE:
<223> OTHER INFORMATION: Description of Artificial Sequence:  human
      cytomegalovirus pp65 CTL epitope peptide

<400> SEQUENCE: 297

Val Tyr Val Thr Val Asp Cys Asn Leu
1               5

<210> SEQ ID NO 298
<211> LENGTH: 9
<212> TYPE: PRT
<213> ORGANISM: human cytomegalovirus US3 CTL epitope peptide
<220> FEATURE:
<223> OTHER INFORMATION: Description of Artificial Sequence:  human
      cytomegalovirus pp65 CTL epitope peptide

<400> SEQUENCE: 298

Tyr Leu Phe Ser Leu Val Val Leu Val
1               5
```

<210> SEQ ID NO 299
<211> LENGTH: 9
<212> TYPE: PRT
<213> ORGANISM: human cytomegalovirus US3 CTL epitope peptide
<220> FEATURE:
<223> OTHER INFORMATION: Description of Artificial Sequence: human cytomegalovirus pp65 CTL epitope peptide

<400> SEQUENCE: 299

Thr Leu Leu Val Tyr Leu Phe Ser Leu
1               5

<210> SEQ ID NO 300
<211> LENGTH: 10
<212> TYPE: PRT
<213> ORGANISM: human cytomegalovirus US3 CTL epitope peptide
<220> FEATURE:
<223> OTHER INFORMATION: Description of Artificial Sequence: human cytomegalovirus pp65 CTL epitope peptide

<400> SEQUENCE: 300

Leu Leu Phe Arg Thr Leu Leu Val Tyr Leu
1               5                   10

<210> SEQ ID NO 301
<211> LENGTH: 9
<212> TYPE: PRT
<213> ORGANISM: human cytomegalovirus US3 CTL epitope peptide
<220> FEATURE:
<223> OTHER INFORMATION: Description of Artificial Sequence: human cytomegalovirus pp65 CTL epitope peptide

<400> SEQUENCE: 301

Val Tyr Leu Phe Ser Leu Val Val Leu
1               5

<210> SEQ ID NO 302
<211> LENGTH: 9
<212> TYPE: PRT
<213> ORGANISM: human cytomegalovirus US11 CTL epitope peptide
<220> FEATURE:
<223> OTHER INFORMATION: Description of Artificial Sequence: human cytomegalovirus pp65 CTL epitope peptide

<400> SEQUENCE: 302

Tyr Tyr Val Glu Cys Glu Pro Arg Cys
1               5

<210> SEQ ID NO 303
<211> LENGTH: 9
<212> TYPE: PRT
<213> ORGANISM: human cytomegalovirus US6 CTL epitope peptide
<220> FEATURE:
<223> OTHER INFORMATION: Description of Artificial Sequence: human cytomegalovirus pp65 CTL epitope peptide

<400> SEQUENCE: 303

Leu Tyr Leu Cys Cys Gly Ile Thr Leu
1               5

<210> SEQ ID NO 304
<211> LENGTH: 10
<212> TYPE: PRT
<213> ORGANISM: human cytomegalovirus US11 CTL epitope peptide
<220> FEATURE:
<223> OTHER INFORMATION: Description of Artificial Sequence: human cytomegalovirus pp65 CTL epitope peptide

```
<400> SEQUENCE: 304

Thr Leu Phe Asp Glu Pro Pro Pro Leu Val
1               5                   10

<210> SEQ ID NO 305
<211> LENGTH: 9
<212> TYPE: PRT
<213> ORGANISM: human cytomegalovirus US11 CTL epitope peptide
<220> FEATURE:
<223> OTHER INFORMATION: Description of Artificial Sequence:  human
      cytomegalovirus pp65 CTL epitope peptide

<400> SEQUENCE: 305

Thr Pro Arg Val Tyr Tyr Gln Thr Leu
1               5

<210> SEQ ID NO 306
<211> LENGTH: 10
<212> TYPE: PRT
<213> ORGANISM: human cytomegalovirus US11 CTL epitope peptide
<220> FEATURE:
<223> OTHER INFORMATION: Description of Artificial Sequence:  human
      cytomegalovirus pp65 CTL epitope peptide

<400> SEQUENCE: 306

Ala Pro Val Ala Gly Ser Met Pro Glu Leu
1               5                   10

<210> SEQ ID NO 307
<211> LENGTH: 9
<212> TYPE: PRT
<213> ORGANISM: human cytomegalovirus US11 CTL epitope peptide
<220> FEATURE:
<223> OTHER INFORMATION: Description of Artificial Sequence:  human
      cytomegalovirus pp65 CTL epitope peptide

<400> SEQUENCE: 307

Ser Glu Ser Leu Val Ala Lys Arg Tyr
1               5

<210> SEQ ID NO 308
<211> LENGTH: 9
<212> TYPE: PRT
<213> ORGANISM: human cytomegalovirus UL18 CTL epitope peptide
<220> FEATURE:
<223> OTHER INFORMATION: Description of Artificial Sequence:  human
      cytomegalovirus pp65 CTL epitope peptide

<400> SEQUENCE: 308

Leu Glu Leu Glu Ile Ala Leu Gly Tyr
1               5

<210> SEQ ID NO 309
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 309

Val Thr Glu His Asp Thr Leu Leu Tyr Asn Leu Val Pro Met Val Ala
1               5                   10                  15

Thr Val Val Leu Glu Glu Thr Ser Val Met Leu Arg Ile Phe Ala Glu
            20                  25                  30

Leu Glu Gly Val Ile Ile Tyr Thr Arg Asn His Glu Val Ile Met Arg
```

-continued

```
                35                  40                  45
Glu Phe Asn Ser Tyr Lys Ala Tyr Ala Gln Lys Ile Phe Lys Ile Leu
 50                  55                  60

Gln Tyr Asp Pro Val Ala Ala Leu Phe Tyr Val Lys Tyr Val Tyr Glu
 65                  70                  75                  80

Ser Phe Asp Ile Tyr Arg Ile Phe Ala Glu Leu Asn Val Arg Arg Ser
                 85                  90                  95

Trp Glu Glu Leu Lys Ala Arg Asp His Leu Ala Val Leu Gln Ala Arg
                100                 105                 110

Leu Thr Val Ser Gly Leu Lys Ala Arg Ala Lys Asp Glu Leu Gln
            115                 120                 125

Ile Lys Val Arg Val Asp Met Val Glu Leu Lys Arg Lys Met Met Tyr
130                 135                 140

Met Arg Arg Arg His Arg Gln Asp Ala Leu Ala Arg Val Tyr Glu Ile
145                 150                 155                 160

Lys Cys Arg Cys Pro Ser Gln Glu Pro Met Ser Ile Tyr Val Tyr Phe
                165                 170                 175

Glu Gln Pro Thr Glu Thr Pro Pro Tyr Ala Tyr Ile Tyr Thr Thr Tyr
                180                 185                 190

Leu Gln Glu Phe Phe Trp Asp Ala Asn Asp Ile Tyr Tyr Glu Gln His
            195                 200                 205

Lys Ile Thr Ser Tyr Gln Glu Pro Met Ser Ile Tyr Val Tyr Ser Glu
        210                 215                 220

His Pro Thr Phe Thr Ser Gln Tyr Gln Ala Ile Arg Glu Thr Val Glu
225                 230                 235                 240

Leu

<210> SEQ ID NO 310
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 310

Asn Val Arg Arg Ser Trp Glu Glu Leu Val Thr Glu His Asp Thr Leu
 1               5                  10                  15

Leu Tyr Ala Tyr Ala Gln Lys Ile Phe Lys Ile Leu Asn Leu Val Pro
                20                  25                  30

Met Val Ala Thr Val Leu Glu Glu Thr Ser Val Met Leu Gln Glu
             35                  40                  45

Pro Met Ser Ile Tyr Val Tyr Ser Glu His Pro Thr Phe Thr Ser Gln
 50                  55                  60

Tyr Gln Ile Lys Val Arg Val Asp Met Val Glu Leu Lys Arg Lys Met
 65                  70                  75                  80

Met Tyr Met Arg Ile Phe Ala Glu Leu Glu Gly Val Ile Ile Tyr Thr
                 85                  90                  95

Arg Asn His Glu Val Tyr Glu Gln His Lys Ile Thr Ser Tyr Gln Ala
                100                 105                 110

Ile Arg Glu Thr Val Glu Leu Ile Met Arg Glu Phe Asn Ser Tyr Lys
            115                 120                 125

Cys Pro Ser Gln Glu Pro Met Ser Ile Tyr Val Tyr Gln Tyr Asp Pro
        130                 135                 140

Val Ala Ala Leu Phe Lys Ala Arg Asp His Leu Ala Val Leu Tyr Val
```

```
            145                 150                 155                 160
Lys Tyr Val Tyr Glu Ser Phe Asp Ile Tyr Arg Ile Phe Ala Glu Leu
                    165                 170                 175

Phe Glu Gln Pro Thr Glu Thr Pro Pro Tyr Ala Tyr Ile Tyr Thr Thr
                180                 185                 190

Tyr Leu Gln Ala Arg Leu Thr Val Ser Gly Leu Lys Ala Arg Ala Lys
                195                 200                 205

Lys Asp Glu Leu Arg Arg Arg His Arg Gln Asp Ala Leu Ala Arg Val
                210                 215                 220

Tyr Glu Ile Lys Cys Arg Gln Glu Phe Phe Trp Asp Ala Asn Asp Ile
225                 230                 235                 240

Tyr

<210> SEQ ID NO 311
<211> LENGTH: 250
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 311

Tyr Val Lys Tyr Val Tyr Glu Ser Phe Asn Leu Val Pro Met Val Ala
1               5                   10                  15

Thr Val Gln Ile Lys Val Arg Val Asp Met Val Val Leu Glu Glu Thr
                20                  25                  30

Ser Val Met Leu Lys Ala Arg Asp His Leu Ala Val Leu Ala Tyr Ala
                35                  40                  45

Gln Lys Ile Phe Lys Ile Leu Val Thr Glu His Asp Thr Leu Leu Tyr
    50                  55                  60

Tyr Ala Tyr Ile Tyr Thr Thr Tyr Leu Gln Glu Phe Phe Trp Asp Ala
65                  70                  75                  80

Asn Asp Ile Tyr Gln Glu Pro Met Ser Ile Tyr Val Tyr Arg Ile Phe
                85                  90                  95

Ala Glu Leu Glu Gly Val Ile Ile Tyr Thr Arg Asn His Glu Val Ile
                100                 105                 110

Met Arg Glu Phe Asn Ser Tyr Lys Ser Glu His Pro Thr Phe Thr Ser
                115                 120                 125

Gln Tyr Gln Ala Arg Leu Thr Val Ser Gly Leu Gln Tyr Asp Pro Val
    130                 135                 140

Ala Ala Leu Phe Tyr Glu Gln His Lys Ile Thr Ser Tyr Gln Ala Ile
145                 150                 155                 160

Arg Glu Thr Val Glu Leu Tyr Val Lys Tyr Val Tyr Glu Ser Phe Asp
                165                 170                 175

Ile Tyr Arg Ile Phe Ala Glu Leu Asn Val Arg Arg Ser Trp Glu Glu
                180                 185                 190

Leu Lys Ala Arg Ala Lys Lys Asp Glu Leu Glu Leu Lys Arg Lys Met
                195                 200                 205

Met Tyr Met Arg Arg Arg His Arg Gln Asp Ala Leu Ala Arg Val Tyr
                210                 215                 220

Glu Ile Lys Cys Arg Cys Pro Ser Gln Glu Pro Met Ser Ile Tyr Val
225                 230                 235                 240

Tyr Phe Glu Gln Pro Thr Glu Thr Pro Pro
                245                 250
```

```
<210> SEQ ID NO 312
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 312

Asn Val Arg Arg Ser Trp Glu Glu Leu Lys Ala Arg Asp His Leu Ala
1               5                   10                  15

Val Leu Gln Ala Arg Leu Thr Val Ser Gly Leu Lys Ala Arg Ala Lys
            20                  25                  30

Lys Asp Glu Leu Gln Ile Lys Val Arg Val Asp Met Val Glu Leu Lys
        35                  40                  45

Arg Lys Met Met Tyr Met Arg Arg His Arg Gln Asp Ala Leu Ala
    50                  55                  60

Arg Val Tyr Glu Ile Lys Cys Arg Cys Pro Ser Gln Glu Pro Met Ser
65                  70                  75                  80

Ile Tyr Val Tyr Phe Glu Gln Pro Thr Glu Thr Pro Pro Tyr Ala Tyr
                85                  90                  95

Ile Tyr Thr Thr Tyr Leu Gln Glu Phe Phe Trp Asp Ala Asn Asp Ile
            100                 105                 110

Tyr Tyr Glu Gln His Lys Ile Thr Ser Tyr Gln Glu Pro Met Ser Ile
        115                 120                 125

Tyr Val Tyr Ser Glu His Pro Thr Phe Thr Ser Gln Tyr Gln Ala Ile
    130                 135                 140

Arg Glu Thr Val Glu Leu Val Thr Glu His Asp Thr Leu Leu Tyr Asn
145                 150                 155                 160

Leu Val Pro Met Val Ala Thr Val Val Leu Glu Thr Ser Val Met
                165                 170                 175

Leu Arg Ile Phe Ala Glu Leu Glu Gly Val Ile Ile Tyr Thr Arg Asn
            180                 185                 190

His Glu Val Ile Met Arg Glu Phe Asn Ser Tyr Lys Ala Tyr Ala Gln
        195                 200                 205

Lys Ile Phe Lys Ile Leu Gln Tyr Asp Pro Val Ala Ala Leu Phe Tyr
    210                 215                 220

Val Lys Tyr Val Tyr Glu Ser Phe Asp Ile Tyr Arg Ile Phe Ala Glu
225                 230                 235                 240

Leu

<210> SEQ ID NO 313
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 313

Cys Pro Ser Gln Glu Pro Met Ser Ile Tyr Val Tyr Phe Glu Gln Pro
1               5                   10                  15

Thr Glu Thr Pro Pro Tyr Ala Tyr Ile Tyr Thr Thr Tyr Leu Gln Glu
            20                  25                  30

Phe Phe Trp Asp Ala Asn Asp Ile Tyr Tyr Glu Gln His Lys Ile Thr
        35                  40                  45

Ser Tyr Gln Glu Pro Met Ser Ile Tyr Val Tyr Ser Glu His Pro Thr
    50                  55                  60
```

```
Phe Thr Ser Gln Tyr Val Thr Glu His Asp Thr Leu Leu Tyr Asn Leu
 65                  70                  75                  80

Val Pro Met Val Ala Thr Val Val Leu Glu Glu Thr Ser Val Met Leu
                 85                  90                  95

Arg Ile Phe Ala Glu Leu Glu Gly Val Ile Ile Tyr Thr Arg Asn His
            100                 105                 110

Glu Val Ile Met Arg Glu Phe Asn Ser Tyr Lys Asn Val Arg Arg Ser
        115                 120                 125

Trp Glu Glu Leu Lys Ala Arg Asp His Leu Ala Val Leu Gln Ala Arg
    130                 135                 140

Leu Thr Val Ser Gly Leu Lys Ala Arg Ala Lys Lys Asp Glu Leu Gln
145                 150                 155                 160

Ile Lys Val Arg Val Asp Met Val Glu Leu Lys Arg Lys Met Met Tyr
                165                 170                 175

Met Arg Arg Arg His Arg Gln Asp Ala Leu Ala Arg Val Tyr Glu Ile
            180                 185                 190

Lys Cys Arg Ala Tyr Ala Gln Lys Ile Phe Lys Ile Leu Gln Tyr Asp
        195                 200                 205

Pro Val Ala Ala Leu Phe Tyr Val Lys Tyr Val Tyr Glu Ser Phe Asp
    210                 215                 220

Ile Tyr Arg Ile Phe Ala Glu Leu Gln Ala Ile Arg Glu Thr Val Glu
225                 230                 235                 240

Leu

<210> SEQ ID NO 314
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 314

Ala Tyr Ala Gln Lys Ile Phe Lys Ile Leu Asn Leu Val Pro Met Val
  1               5                  10                  15

Ala Thr Val Asn Val Arg Arg Ser Trp Glu Glu Leu Glu Leu Lys Arg
                 20                  25                  30

Lys Met Met Tyr Met Val Thr Glu His Asp Thr Leu Leu Tyr Phe Glu
            35                  40                  45

Gln Pro Thr Glu Thr Pro Pro Ala Arg Val Tyr Glu Ile Lys Cys Arg
        50                  55                  60

Arg Ile Phe Ala Glu Leu Glu Gly Val Val Leu Glu Glu Thr Ser Val
 65                  70                  75                  80

Met Leu Cys Pro Ser Gln Glu Pro Met Ser Ile Tyr Val Tyr Ile Ile
                 85                  90                  95

Tyr Thr Arg Asn His Glu Val Arg Arg His Arg Gln Asp Ala Leu
            100                 105                 110

Ile Met Arg Glu Phe Asn Ser Tyr Lys Gln Ile Lys Val Arg Val Asp
        115                 120                 125

Met Val Tyr Glu Gln His Lys Ile Thr Ser Tyr Gln Tyr Asp Pro Val
    130                 135                 140

Ala Ala Leu Phe Ser Glu His Pro Thr Phe Thr Ser Gln Tyr Gln Glu
145                 150                 155                 160

Phe Phe Trp Asp Ala Asn Asp Ile Tyr Tyr Val Lys Tyr Val Tyr Glu
                165                 170                 175
```

```
Ser Phe Asp Ile Tyr Arg Ile Phe Ala Glu Leu Lys Ala Arg Asp His
            180                 185                 190

Leu Ala Val Leu Gln Ala Arg Leu Thr Val Ser Gly Leu Lys Ala Arg
        195                 200                 205

Ala Lys Lys Asp Glu Leu Tyr Ala Tyr Ile Tyr Thr Thr Tyr Leu Gln
        210                 215                 220

Glu Pro Met Ser Ile Tyr Val Tyr Gln Ala Ile Arg Glu Thr Val Glu
225                 230                 235                 240

Leu

<210> SEQ ID NO 315
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 315

Tyr Glu Gln His Lys Ile Thr Ser Tyr Gln Glu Pro Met Ser Ile Tyr
1               5                   10                  15

Val Tyr Glu Leu Lys Arg Lys Met Met Tyr Met Arg Arg His Arg
            20                  25                  30

Gln Asp Ala Leu Ala Arg Val Tyr Glu Ile Lys Cys Arg Ala Tyr Ala
        35                  40                  45

Gln Lys Ile Phe Lys Ile Leu Gln Tyr Asp Pro Val Ala Ala Leu Phe
    50                  55                  60

Tyr Val Lys Tyr Val Tyr Glu Ser Phe Asp Ile Tyr Arg Ile Phe Ala
65                  70                  75                  80

Glu Leu Ser Glu His Pro Thr Phe Thr Ser Gln Tyr Gln Ala Ile Arg
                85                  90                  95

Glu Thr Val Glu Leu Asn Val Arg Arg Ser Trp Glu Leu Lys Ala
            100                 105                 110

Arg Ala Lys Lys Asp Glu Leu Val Thr Glu His Asp Thr Leu Leu Tyr
        115                 120                 125

Asn Leu Val Pro Met Val Ala Thr Val Val Leu Glu Glu Thr Ser Val
130                 135                 140

Met Leu Arg Ile Phe Ala Glu Leu Glu Gly Val Ile Ile Tyr Thr Arg
145                 150                 155                 160

Asn His Glu Val Ile Met Arg Glu Phe Asn Ser Tyr Lys Gln Ile Lys
                165                 170                 175

Val Arg Val Asp Met Val Phe Glu Gln Pro Thr Glu Thr Pro Pro Tyr
            180                 185                 190

Ala Tyr Ile Tyr Thr Thr Tyr Leu Gln Glu Phe Phe Trp Asp Ala Asn
        195                 200                 205

Asp Ile Tyr Lys Ala Arg Asp His Leu Ala Val Leu Gln Ala Arg Leu
    210                 215                 220

Thr Val Ser Gly Leu Cys Pro Ser Gln Glu Pro Met Ser Ile Tyr Val
225                 230                 235                 240

Tyr

<210> SEQ ID NO 316
<211> LENGTH: 241
<212> TYPE: PRT
<213> ORGANISM: artificial sequence
<220> FEATURE:
```

-continued

<223> OTHER INFORMATION: Description of Artificial Sequence: human
      cytomegalovirus pp65 CTL epitope peptide

<400> SEQUENCE: 316

Gln Ile Lys Val Arg Val Asp Met Val Ala Arg Val Tyr Glu Ile Lys
1               5                   10                  15

Cys Arg Asn Leu Val Pro Met Val Ala Thr Val Tyr Val Lys Tyr Val
            20                  25                  30

Tyr Glu Ser Phe Arg Ile Phe Ala Glu Leu Glu Gly Val Tyr Ala Tyr
        35                  40                  45

Ile Tyr Thr Thr Tyr Leu Ile Ile Tyr Thr Arg Asn His Glu Val Ile
    50                  55                  60

Met Arg Glu Phe Asn Ser Tyr Lys Ser Glu His Pro Thr Phe Thr Ser
65                  70                  75                  80

Gln Tyr Ala Tyr Ala Gln Lys Ile Phe Lys Ile Leu Gln Tyr Asp Pro
                85                  90                  95

Val Ala Ala Leu Phe Asp Ile Tyr Arg Ile Phe Ala Glu Leu Gln Glu
            100                 105                 110

Phe Phe Trp Asp Ala Asn Asp Ile Tyr Asn Val Arg Arg Ser Trp Glu
        115                 120                 125

Glu Leu Lys Ala Arg Asp His Leu Ala Val Leu Val Leu Glu Glu Thr
130                 135                 140

Ser Val Met Leu Gln Ala Arg Leu Thr Val Ser Gly Leu Lys Ala Arg
145                 150                 155                 160

Ala Lys Lys Asp Glu Leu Glu Leu Lys Arg Lys Met Met Tyr Met Val
                165                 170                 175

Thr Glu His Asp Thr Leu Leu Tyr Gln Glu Pro Met Ser Ile Tyr Val
            180                 185                 190

Tyr Arg Arg Arg His Arg Gln Asp Ala Leu Cys Pro Ser Gln Glu Pro
        195                 200                 205

Met Ser Ile Tyr Val Tyr Phe Glu Gln Pro Thr Glu Thr Pro Pro Tyr
    210                 215                 220

Glu Gln His Lys Ile Thr Ser Tyr Gln Ala Ile Arg Glu Thr Val Glu
225                 230                 235                 240

Leu

<210> SEQ ID NO 317
<211> LENGTH: 241
<212> TYPE: PRT
<213> ORGANISM: artificial sequence
<220> FEATURE:
<223> OTHER INFORMATION: Description of Artificial Sequence: human
      cytomegalovirus pp65 CTL epitope peptide

<400> SEQUENCE: 317

Asp Ile Tyr Arg Ile Phe Ala Glu Leu Cys Pro Ser Gln Glu Pro Met
1               5                   10                  15

Ser Ile Tyr Val Tyr Gln Ala Ile Arg Glu Thr Val Glu Leu Lys Ala
            20                  25                  30

Arg Asp His Leu Ala Val Leu Asn Leu Val Pro Met Val Ala Thr Val
        35                  40                  45

Tyr Val Lys Tyr Val Tyr Glu Ser Phe Val Leu Glu Glu Thr Ser Val
    50                  55                  60

Met Leu Asn Val Arg Arg Ser Trp Glu Glu Leu Ile Met Arg Glu Phe
65                  70                  75                  80

Asn Ser Tyr Lys Ala Tyr Ala Gln Lys Ile Phe Lys Ile Leu Glu Leu

```
                 85                  90                  95
Lys Arg Lys Met Met Tyr Met Gln Tyr Asp Pro Val Ala Ala Leu Phe
            100                 105                 110

Ser Glu His Pro Thr Phe Thr Ser Gln Tyr Gln Ala Arg Leu Thr Val
            115                 120                 125

Ser Gly Leu Lys Ala Arg Ala Lys Lys Asp Glu Leu Gln Ile Lys Val
            130                 135                 140

Arg Val Asp Met Val Arg Arg His Arg Gln Asp Ala Leu Ala Arg
145                 150                 155                 160

Val Tyr Glu Ile Lys Cys Arg Phe Glu Gln Pro Thr Glu Thr Pro Pro
                165                 170                 175

Tyr Ala Tyr Ile Tyr Thr Thr Tyr Leu Gln Glu Phe Phe Trp Asp Ala
            180                 185                 190

Asn Asp Ile Tyr Tyr Glu Gln His Lys Ile Thr Ser Tyr Val Thr Glu
            195                 200                 205

His Asp Thr Leu Leu Tyr Gln Glu Pro Met Ser Ile Tyr Val Tyr Arg
    210                 215                 220

Ile Phe Ala Glu Leu Glu Gly Val Ile Ile Tyr Thr Arg Asn His Glu
225                 230                 235                 240

Val

<210> SEQ ID NO 318
<211> LENGTH: 241
<212> TYPE: PRT
<213> ORGANISM: artificial sequence
<220> FEATURE:
<223> OTHER INFORMATION: Description of Artificial Sequence:  human
      cytomegalovirus pp65 CTL epitope peptide

<400> SEQUENCE: 318

Asn Leu Val Pro Met Val Ala Thr Val Gln Ala Arg Leu Thr Val Ser
1               5                   10                  15

Gly Leu Val Thr Glu His Asp Thr Leu Leu Tyr Tyr Ala Tyr Ile Tyr
            20                  25                  30

Thr Thr Tyr Leu Gln Glu Phe Phe Trp Asp Ala Asn Asp Ile Tyr Val
            35                  40                  45

Leu Glu Glu Thr Ser Val Met Leu Glu Leu Lys Arg Lys Met Met Tyr
        50                  55                  60

Met Arg Ile Phe Ala Glu Leu Glu Gly Val Gln Gln Pro Met Ser Ile
65                  70                  75                  80

Tyr Val Tyr Ile Ile Tyr Thr Arg Asn His Glu Val Ile Met Arg Glu
                85                  90                  95

Phe Asn Ser Tyr Lys Arg Arg His Arg Gln Asp Ala Leu Ala Tyr
            100                 105                 110

Ala Gln Lys Ile Phe Lys Ile Leu Ser Glu His Pro Thr Phe Thr Ser
            115                 120                 125

Gln Tyr Gln Tyr Asp Pro Val Ala Ala Leu Phe Tyr Val Lys Tyr Val
            130                 135                 140

Tyr Glu Ser Phe Asp Ile Tyr Arg Ile Phe Ala Glu Leu Asn Val Arg
145                 150                 155                 160

Arg Ser Trp Glu Glu Leu Lys Ala Arg Ala Lys Lys Asp Glu Leu Ala
                165                 170                 175

Arg Val Tyr Glu Ile Lys Cys Arg Cys Pro Ser Gln Glu Pro Met Ser
            180                 185                 190

Ile Tyr Val Tyr Phe Glu Gln Pro Thr Glu Thr Pro Pro Gln Ile Lys
```

-continued

```
            195                 200                 205
Val Arg Val Asp Met Val Tyr Glu Gln His Lys Ile Thr Ser Tyr Gln
    210                 215                 220

Ala Ile Arg Glu Thr Val Glu Leu Lys Ala Arg Asp His Leu Ala Val
225                 230                 235                 240

Leu
```